US009796964B2

(12) United States Patent
Mundorff et al.

(10) Patent No.: US 9,796,964 B2
(45) Date of Patent: *Oct. 24, 2017

(54) KETOREDUCTASE POLYPEPTIDES

(71) Applicant: Codexis, Inc., Redwood City, CA (US)

(72) Inventors: Emily Mundorff, Garden City, NY (US); Erik Jan De Vries, Livermore, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/211,505

(22) Filed: Jul. 15, 2016

(65) Prior Publication Data

US 2016/0376565 A1    Dec. 29, 2016

Related U.S. Application Data

(60) Continuation of application No. 14/824,766, filed on Aug. 12, 2015, now Pat. No. 9,422,530, which is a division of application No. 14/606,127, filed on Jan. 27, 2015, now Pat. No. 9,139,820, which is a division of application No. 13/764,596, filed on Feb. 11, 2013, now Pat. No. 8,956,840, which is a continuation of application No. 13/590,882, filed on Aug. 21, 2012, now Pat. No. 8,415,126, which is a division of application No. 12/545,034, filed on Aug. 20, 2009, now Pat. No. 8,273,554.

(60) Provisional application No. 61/092,807, filed on Aug. 29, 2008.

(51) Int. Cl.
| | |
|---|---|
| *C12N 9/02* | (2006.01) |
| *C12N 15/53* | (2006.01) |
| *C12P 17/00* | (2006.01) |
| *C12P 7/02* | (2006.01) |
| *C12N 9/04* | (2006.01) |
| *C12P 17/14* | (2006.01) |
| *C12P 41/00* | (2006.01) |
| *C12P 17/10* | (2006.01) |
| *C12N 15/75* | (2006.01) |
| *C12N 15/00* | (2006.01) |

(52) U.S. Cl.
CPC ............. *C12N 9/0006* (2013.01); *C12P 7/02* (2013.01); *C12P 17/10* (2013.01); *C12P 17/14* (2013.01); *C12P 41/002* (2013.01); *C12Y 101/01184* (2013.01); *C12N 15/00* (2013.01); *C12N 15/75* (2013.01); *Y02P 20/52* (2015.11)

(58) Field of Classification Search
CPC .. C12Y 101/01184; C12N 9/0006; C12P 7/02
USPC ............... 435/190, 189, 135, 320.1
See application file for complete search history.

(56) References Cited

U.S. PATENT DOCUMENTS

| | | |
|---|---|---|
| 5,064,761 A | 11/1991 | Schneider et al. |
| 5,200,335 A | 4/1993 | Hummel et al. |
| 5,225,339 A | 7/1993 | Wong et al. |
| 5,342,767 A | 8/1994 | Wong et al. |
| 5,385,833 A | 1/1995 | Bradshaw et al. |
| 5,427,933 A | 6/1995 | Chen et al. |
| 5,491,077 A | 2/1996 | Chartrain et al. |
| 5,538,867 A | 7/1996 | Durliat et al. |
| 5,559,030 A | 9/1996 | Matsuyama et al. |
| 5,618,707 A | 4/1997 | Homann et al. |
| 5,700,670 A | 12/1997 | Yamagishi et al. |
| 5,712,388 A | 1/1998 | Matsumoto et al. |
| 5,767,115 A | 6/1998 | Rosenblum et al. |
| 5,891,685 A | 4/1999 | Yamagishi et al. |
| 5,891,703 A | 4/1999 | Van Der Laan et al. |
| 6,033,823 A | 3/2000 | Van Der Laan et al. |
| 6,037,158 A | 3/2000 | Hummel et al. |
| 6,117,679 A | 9/2000 | Stemmer |
| 6,207,822 B1 | 3/2001 | Thiruvengadam et al. |
| 6,225,099 B1 | 5/2001 | Hummel et al. |
| 6,376,246 B1 | 4/2002 | Crameri et al. |
| 6,399,339 B1 | 6/2002 | Wolberg et al. |
| 6,413,750 B1 | 7/2002 | Hummel et al. |
| 6,495,023 B1 | 12/2002 | Zeikus et al. |
| 6,586,182 B1 | 7/2003 | Patten et al. |
| 6,627,757 B2 | 9/2003 | Fu et al. |

(Continued)

FOREIGN PATENT DOCUMENTS

| | | |
|---|---|---|
| EP | 0369691 B1 | 7/1994 |
| EP | 1 013 758 A1 | 6/2000 |

(Continued)

OTHER PUBLICATIONS

Amidjojo et al., 2005, "Asymmetric Synthesis of Tert-butyl (3R, 5S)6-chloro- dihydroxyhexanoate with *Lactobacillus kefir*," *Appl Microbiol Biotechnol.*, 69:9-15.

(Continued)

*Primary Examiner* — Robert Modesi
*Assistant Examiner* — Md. Younus Meah
(74) *Attorney, Agent, or Firm* — Codexis, Inc.

(57) ABSTRACT

The present disclosure provides engineered ketoreductase enzymes having improved properties as compared to a naturally occurring wild-type ketoreductase enzyme including the capability of reducing 5-((4S)-2-oxo-4-phenyl (1,3-oxazolidin-3-yl))-1-(4-fluorophenyl) pentane-1,5-dione to (4S)-3-[(5S)-5-(4-fluorophenyl)-5-hydroxypentanoyl]-4-phenyl-1,3-oxazolidin-2-one. Also provided are polynucleotides encoding the engineered ketoreductase enzymes, host cells capable of expressing the engineered ketoreductase enzymes, and methods of using the engineered ketoreductase enzymes to synthesize the intermediate (4S)-3-[(5S)-5-(4-fluorophenyl)-5-hydroxypentanoyl]-4-phenyl-1,3-oxazolidin-2-one in a process for making Ezetimibe.

2 Claims, 1 Drawing Sheet

(56) References Cited

U.S. PATENT DOCUMENTS

| | | | |
|---|---|---|---|
| 6,645,746 | B1 | 11/2003 | Kizaki et al. |
| 6,800,477 | B2 | 10/2004 | Patel et al. |
| 7,067,675 | B2 | 6/2006 | Reddy et al. |
| 7,083,962 | B2 | 8/2006 | Kimoto et al. |
| 8,273,554 | B2 | 9/2012 | Mundorff et al. |
| 8,415,126 | B2 | 4/2013 | Mundorff et al. |
| 8,956,840 | B2 | 2/2015 | Mundorff et al. |
| 9,139,820 | B2 | 9/2015 | Mundorff et al. |
| 2002/0061564 | A1 | 5/2002 | Rozzell |
| 2003/0054520 | A1 | 3/2003 | Bommanus et al. |
| 2003/0068811 | A1 | 4/2003 | Patel et al. |
| 2004/0214297 | A1 | 10/2004 | Davis et al. |
| 2004/0265978 | A1 | 12/2004 | Gupta et al. |
| 2005/0095619 | A1 | 5/2005 | Davis et al. |
| 2005/0124029 | A1 | 6/2005 | Van Der Laan et al. |
| 2006/0195947 | A1 | 8/2006 | Davis et al. |
| 2006/0286646 | A1 | 12/2006 | Patel et al. |
| 2007/0083055 | A1 | 4/2007 | Sturmer et al. |
| 2007/0243594 | A1 | 10/2007 | Gupta et al. |
| 2008/0220990 | A1 | 9/2008 | Fox |
| 2008/0248539 | A1 | 10/2008 | Giver et al. |
| 2008/0318295 | A1 | 12/2008 | Ching et al. |
| 2009/0093031 | A1 | 4/2009 | Liang et al. |
| 2009/0104671 | A1 | 4/2009 | Yasohara et al. |
| 2009/0155863 | A1 | 6/2009 | Liang et al. |
| 2009/0162909 | A1 | 6/2009 | Campopiano et al. |
| 2009/0191605 | A1 | 7/2009 | Liang et al. |
| 2009/0311762 | A1 | 12/2009 | Tschentscher et al. |
| 2009/0312196 | A1 | 12/2009 | Colbeck et al. |

FOREIGN PATENT DOCUMENTS

| | | |
|---|---|---|
| EP | 1176203 A1 | 1/2002 |
| EP | 1 179 595 A1 | 2/2002 |
| EP | 1908845 A1 | 9/2008 |
| WO | 95/22625 | 8/1995 |
| WO | 97/20078 | 6/1997 |
| WO | 97/35966 | 10/1997 |
| WO | 98/27230 | 6/1998 |
| WO | 00/42651 | 7/2000 |
| WO | WO 01/040450 A1 | 6/2001 |
| WO | WO 01/075767 A2 | 10/2001 |
| WO | WO 2002/086126 A2 | 10/2002 |
| WO | WO 2005/017135 A1 | 2/2005 |
| WO | WO 2005/018579 A2 | 3/2005 |
| WO | WO 2005/033094 A2 | 4/2005 |
| WO | WO 2005/054491 A1 | 6/2005 |
| WO | WO 2007/010944 A1 | 1/2007 |
| WO | WO 2007/012428 A1 | 2/2007 |
| WO | WO 2008/042876 A2 | 4/2008 |
| WO | WO 2008/103248 A1 | 8/2008 |

OTHER PUBLICATIONS

Baerga-Ortiz et al., 2006, "Directed Mutagenesis Alters the Stereochemistry of Catalysis by Isolated Ketoreductase Domains from the Erythromycin Polyketide Synthase," *Chem Biol.*, 13(3):277-85.

Bisel et al., 2007, "Stereochemical clarification of the enzyme-catalysed reduction of 2-acetylchromen-4-one," *Tetrahedron Asymmetry*, 18(9):1142-1144.

Bradshaw et al., 1992, "*Lactobacillus kefir*Alcohol Dehydrogenase: A Useful Catalyst for Synthesis," *J. Org. Chem.* 57(5):1532-1536.

Breyer-Pfaff et al., 1999, "High-affinity Stereoselective Reduction of the Enantiomers of Ketotifen and of Ketonic Nortriptyline Metabolites by Aldo-Keto Reductases from Human Liver," *Biochem. Pharmacol.*, 59:249-260.

Cha et al., 2002, "Stereochemical control in diastereoselective reduction of α-substituted-β-ketoesters using a reductase purified from Kluyveromyces marxianus," *Biotechnol. Lett*, 24:1695-1698.

Daussmann et al., 2006, "Oxidoreductases and Hydroxynitrilase Lyases: Complementary Enzymatic Technologies for Chiral Alcohols," *Eng Life Sci.*, 6(2):125-129.

Fuganti et al., 1993, "Microbial Generation of (2R,3S)- and (2S,3S)-Ethyl 2- Benzamidomethyl-3-hydroxybutyrate, a Key Intermediate in the Synthesis of (3S,1'R)-3-(1'-Hydroxyethyl)azetidin-2-one," *J Chem. Soc. Perkin Trans.* 1:2247-2249.

Genbank Accession No. 1NXQ_A dated Sep. 24, 2008.
Genbank Accession No. AB036927 dated Feb. 2, 2001.
Genbank Accession No. ABJ63353.1 dated Mar. 5, 2010.
Genbank Accession No. AJ544275 dated Feb 5, 2010.
Genbank Accession No. AAN73270 dated Nov. 3, 2003.
Genbank Accession No. AAP94029 dated Apr. 1, 2004.
Genbank Accession No. AF160799 dated Dec. 9, 1999.
Genbank Accession No. BAA24528.1 dated Jan. 28, 1998.
Genbank Accession No. CAD66648 dated Feb. 5, 2010.
Genbank Accession No. CP00046 dated Mar. 5, 2010.
Genbank Accession No. JC7338 dated Jun. 3, 2002.
Genbank Accession No. NO011476 dated May 17, 2010.
Genbank Accession No. NP010656.1 dated May 17, 2010.
Genbank Accession No. NP010159.1 dated May 17, 2010.
Genbank Accession No. NP014490.1 dated May 17, 2010.
Genbank Accession No. NP631415.1 dated Mar. 30, 2010.
Genbank Accession No. P41747 dated Apr. 20, 2010.
Genbank Accession No. Q07551 dated Apr. 20, 2010.
Genbank Accession No. Q9UUN9 dated Mar. 2, 2010.
Genbank Accession No. X64841.1 dated Jan. 8, 1997.
Genbank Accession No. ZP00318704.1 dated Jun. 17, 2004.
Genbank Accession No. ZP00202558.1 dated Oct. 4, 2004.

Goldberg et al., 2007, "Biocatalytic ketone reduction—a powerful tool for the production of chiral alcohols-part I: processes with isolated enzymes," *Appl Microbiol Biotechnol*, 76(2):237-248.

Groger et al., 2004, "Preparative asymmetric reduction of ketones in a biphasic medium with an (S)-alcohol dehydrogenase under in situ-cofactor-recycling with a formate dehydrogenase," *Tetrahedron* 60:633-640.

Honig et al., 1994, "Enzymatic Resolutions of Heterocyclic Alcohols," *Biocatalysis* 9:61-69.

Hummel et al., 1989, "Dehydrogenases for the synthesis of chiral compounds," *Eur. J. Biochem.* 184:1-13.

Hummel, 1990, "Reduction of acetophenone to R(+)-phenylethanol by a new alcohol dehydrogenase from Lactobacillus kefir," *Appl Microbiol Biotechnol*, 34(1): 15-19.

Hummel, 1999, "Large-scale applications of NAD(P)-dependent oxidoreductases: recent developments," *Trends Biotechnol.* 17(12):487-492.

Jornvall et al., 1995, "Short-chain dehydrogenase/reductases (SDR)," *Biochemistry* 34(18):6003-6013.

Kallberg et al., 2002, "Short-chain dehydrogenase/reductase (SDR) relationships: A large family with eight clusters common to human, animal, and plant genomes," *Protein Sci.* 11(3):636-641.

Kallberg et al., 2002, "Short-chain dehydrogenases/reductases (SDRs) Coenzyme-based functional assignments in completed genomes," *Eur. J. Biochem.* 269:4409-4417.

Kaluzna et al., 2005, "Ketoreductases: stereoselective catalysts for the facile synthesis of chiral alcohols," Tetrahedron: Asymmetry 16: 3682-3689.

Kataoka et al., 2003, "Novel bioreduction system for the production of chiral alcohols," Appl Microbiol Biotechnol 62:437-445.

Nakamura et al. 2003, "Recent developments in asymmetric reduction of ketones with biocatalysts," Tetrahedron: *Asymmetry* 14: 2659-2681.

Neifind et al., 2000, "Crystallization and preliminary characterization of crystals of R-alcohol dehydrogenase from *Lactobacillus brevis*," *Acta Crystallogr. D. Biol. Crystallogr.* 56:1696-1698.

Niefind et al., 2003, "The Crystal Structure of R-specific Alcohol Dehydrogenase from *Lactobacillus brevis* Suggests the Structural Basis of its Metal Dependency," *J Mol Bio.* 327(2):317-28.

Petrash et al., 2001, "Functional Genomic Studies of Aldo-keto Reductases," *Chem Biol Interact.*, 130-132(1-3):673-83.

Rodrigues et al., 2004, "Recent Advances in the Biocatalytic Asymmetric Reduction of Acetophenones and α,β-Unsaturated Carbonyl Compounds," *Food Technol. Biotechnol.* 42 (4) 295-303.

(56) References Cited

OTHER PUBLICATIONS

Santaniello et al., 1984, "Chiral Synthesis of a Component of Amanita muscaria, (—)-4-hydroxypyrrolidin-2-one, and Assessment of its Absolute Configuration," *J. Chem. Res., Synop.,* 132-133.

Schlieben et al., 2005, "Atomic Resolution Structures of R-specific Alcohol Dehydrogenase from *Lactobacillus brevis* Provide the Structural Bases of its Substrate and Cosubstrate Specificity," *J. Mol. Biol.* 349(4):801-13.

Stemmer et al., 1994, "DNA shuffling by random fragmentation and reassembly: in vitro recombination for molecular evolution," *Prod. Natl. Acad. Sci. USA* 91:10747-10751.

Sulzenbacher et al., 2004, "Crystal Structure of *E. coli* Alcohol Dehydrogenase YqhD: Evidence of a Covalently Modified Nadp Coenzyme," *Journal Mol. Biol.* 342:489-502.

Temino et al., 2005, "Entrapment of the alcohol dehydrogenase from *Lactobacillus kefir* in polyvinyl alcohol for the synthesis of chiral hydrophobic alcohols in organic solvents," *Enzyme Microb. Technol.,* 36(1):3-9.

Weckbecker et al., 2006, "Cloning, expression, and characterization of an (R)-specific alcohol dehydrogenase from *Lactobacillus kefir,*" *Biocatal. Biotransform.,* 24(5):380-389.

Wolberg et al., 2000, "Highly Regio- and Enantioselective Reduction of 3,5-Dioxocarboxylates," *Angew Chem. Int. Ed. Engl.* 39(23):4306-4308.

Wolberg, 2001, "Enzymatic Reduction of Hydrophobic beta, delta-Diketo Esters," *Synthesis* 937-942.

Xie et al., 2006, "Asymmetric Reduction of o-Chloroacetophenone with Candida pseudotropicalis 104," *Biotechnol. Prog.* 22:1301-1304.

Zhao et al., 1999, "Molecular evolution by staggered extension process (StEP) in vitro recombination," *Nature Biotech.* 16:258.

Zhu et al., 2005, "Evaluation of substituent effects on activity and enantioselectivity in the enzymatic reduction of aryl ketones," *Tetrahedron Asymm.* 16:1541-1546.

International Search Report of the International Searching Authority of PCT/US2009/054452 dated Feb. 25, 2010.

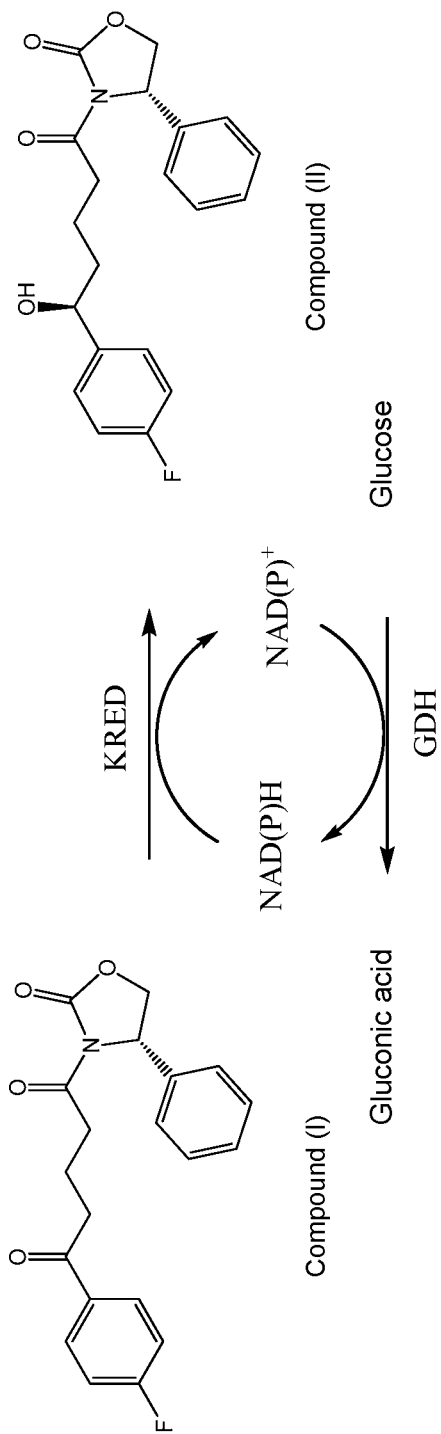

KETOREDUCTASE POLYPEPTIDES

CROSS REFERENCE TO RELATED APPLICATIONS

The present application is a Continuation of U.S. patent application Ser. No. 14/824,766, filed Aug. 12, 2015, U.S. Pat. No. 9,422,530 which is a Divisional of U.S. patent application Ser. No. 14/606,127, filed Jan. 27, 2015, now U.S. Pat. No. 9,139,520, which is a Divisional of U.S. patent application Ser. No. 13/764,596, filed Feb. 11, 2013, now U.S. Pat. No. 8,956,840, which claims priority to U.S. patent application Ser. No. 13/590,882, filed Aug. 21, 2012, which issued as U.S. Pat. No. 8,415,126 B2 on Apr. 9, 2013, and U.S. patent application Ser. No. 12/545,034, filed Aug. 20, 2009, which issued as U.S. Pat. No. 8,273,554 B2 on Sep. 25, 2012, and U.S. Provisional Appln. Ser. No. 61/092,807, filed Aug. 29, 2008, each of which is hereby incorporated by reference herein.

1. TECHNICAL FIELD

The present disclosure relates to engineered polypeptides and uses of the polypeptides for preparing the intermediate (4S)-3-[(5S)-5-(4-fluorophenyl)-5-hydroxypentanoyl]-4-phenyl-1,3-oxazolidin-2-one in a process for making Ezetimibe.

2. REFERENCE TO SEQUENCE LISTING, TABLE OR COMPUTER PROGRAM

The Sequence Listing concurrently submitted electronically under 37 C.F.R. §1.821 via EFS-Web in a computer readable form (CRF) as file name CX2-025USD1D3C1_Substitute_ST25.txt is herein incorporated by reference. The electronic copy of the Sequence Listing was created on Sep. 15, 2016, with a file size of 301 Kbytes.

3. BACKGROUND

Enzymes belonging to the ketoreductase (KRED) or carbonyl reductase class (EC1.1.1.184) are useful for the synthesis of optically active alcohols from the corresponding prostereoisomeric ketone substrates and by stereospecific reduction of corresponding racemic aldehyde and ketone substrates. KREDs typically convert a ketone or aldehyde substrate to the corresponding alcohol product, but may also catalyze the reverse reaction, oxidation of an alcohol substrate to the corresponding ketone/aldehyde product. The reduction of ketones and aldehydes and the oxidation of alcohols by enzymes such as KRED requires a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP) for the oxidation reaction. NADH and NADPH serve as electron donors, while NAD and NADP serve as electron acceptors. It is frequently observed that ketoreductases and alcohol dehydrogenases accept either the phosphorylated or the non-phosphorylated co-factor (in its oxidized and reduced state).

KRED enzymes can be found in a wide range of bacteria and yeasts (for reviews: Kraus and Waldman, Enzyme catalysis in organic synthesis Vols. 1&2.VCH Weinheim 1995; Faber, K., Biotransformations in organic chemistry, 4th Ed. Springer, Berlin Heidelberg New York. 2000; Hummel and Kula *Eur. J. Biochem.* 1989 184:1-13). Several KRED gene and enzyme sequences have been reported, e.g., *Candida magnoliae* (Genbank Acc. No. JC7338; GI:11360538) *Candida parapsilosis* (Genbank Acc. No. BAA24528.1; GI:2815409), *Sporobolomyces salmonicolor* (Genbank Acc. No. AF160799; GI:6539734).

In order to circumvent many chemical synthetic procedures for the production of key compounds, ketoreductases are being increasingly employed for the enzymatic conversion of different keto and aldehyde substrates to chiral alcohol products. These applications can employ whole cells expressing the ketoreductase for biocatalytic ketone reductions, or purified enzymes in those instances where presence of multiple ketoreductases in whole cells would adversely affect the stereopurity and yield of the desired product. For in vitro applications, a co-factor (NADH or NADPH) regenerating enzyme such as glucose dehydrogenase (GDH), formate dehydrogenase etc. is used in conjunction with the ketoreductase. Examples using ketoreductases to generate useful chemical compounds include asymmetric reduction of 4-chloroacetoacetate esters (Zhou, *J. Am. Chem. Soc.* 1983 105:5925-5926; Santaniello, *J. Chem. Res.* (S) 1984: 132-133; U.S. Pat. No. 5,559,030; U.S. Pat. No. 5,700,670 and U.S. Pat. No. 5,891,685), reduction of dioxocarboxylic acids (e.g., U.S. Pat. No. 6,399,339), reduction of tert-butyl (S) chloro-5-hydroxy-3-oxohexanoate (e.g., U.S. Pat. No. 6,645,746 and WO 01/40450), reduction pyrrolotriazine-based compounds (e.g., U.S. application No. 2006/0286646); reduction of substituted acetophenones (e.g., U.S. Pat. No. 6,800,477); and reduction of ketothiolanes (WO 2005/054491).

It is desirable to identify other ketoreductase enzymes that can be used to carry out conversion of various keto substrates to its corresponding chiral alcohol products.

4. SUMMARY

The present disclosure provides ketoreductase polypeptides capable of reducing 5-((4S)-2-oxo-4-phenyl (1,3-oxazolidin-3-yl))-1-(4-fluorophenyl) pentane-1,5-dione ("the substrate") to (4S)-3-[(5S)-5-(4-fluorophenyl)-5-hydroxypentanoyl]-4-phenyl-1,3-oxazolidin-2-one ("the product"), polynucleotides encoding such polypeptides, and methods for using the polypeptides. The ketoreductase polypeptides are also capable of reducing 1-(4-fluorophenyl)-3(R)-[3-oxo-3-(4-fluorophenyl)propyl)]-4(S)-(4-hydroxyphenyl)-2-azetidinone, to the corresponding stereoisomeric alcohol 1-(4-fluorophenyl)-3(R)-[3(S)-hydroxy-3(4-fluorophenyl)-propyl)]-4(S)-(4-hydroxyphenyl)-2-azetidinone.

In one aspect, the ketoreductase polypeptides described herein have an amino acid sequence that has one or more amino acid differences as compared to a reference amino acid sequence of a wild-type ketoreductase or an engineered ketoreductase that result in an improved property of the enzyme for the defined keto substrate. Generally, the engineered ketoreductase polypeptides have an improved property as compared to the naturally-occurring wild-type ketoreductase enzymes obtained from *Lactobacillus kefir* ("*L. kefir*"; SEQ ID NO:4), *Lactobacillus brevis* ("*L. brevis*"; SEQ ID NO:2), and *Lactobacillus minor* ("*L. minor*"; SEQ ID NO:158). In some embodiments, the polypeptides of the disclosure have an improved property as compared to another engineered polypeptide, such as SEQ ID NO: 8. Improvements in enzyme property include increases in enzyme activity, stereoselectivity, sterospecificity, thermostability, solvent stability, or reduced product inhibition. In the present disclosure, the ketoreductase polypeptides have at least the following amino acid sequence as compared to the amino acid sequence of SEQ ID NO:2, 4, or 158: the amino acid residue corresponding to X145 is a serine, and the amino acid residue corresponding to X190 is a cysteine. In some embodiments, as compared to the sequences of SEQ ID NO: 2, 4, or 158, the ketoreductase polypeptides have at least the following amino acid sequence differences: (1) the amino acid residue corresponding to X145 is a serine; the amino acid residue corresponding to residue X190 is a cysteine; and the amino acid residue corresponding to X96 is a glutamine. In some embodiments, as compared to the sequence of SEQ ID NO:2, 4, or 158, the ketoreductase polypeptides have at least the amino acid sequence as compared to the amino acid sequence of SEQ ID NO:2, 4, or 158: residue X145 is a serine; residue X190 is a cysteine, and residue X211 is an arginine.

In some embodiments, the ketoreductase polypeptides of the invention are improved as compared to SEQ ID NO:2, 4 or 158 with respect to their rate of enzymatic activity, i.e., their rate of converting the substrate to the product. In some embodiments, the ketoreductase polypeptides are capable of converting the substrate to the product at a rate that is at least 1.5-times, 2-times, 3-times, 4-times, 5-times, 10-times, 25-times, 50-times, 100-times, 150-times, 200-times, 400-times, 1000-times, 3000-times, 5000-times, 7000-times or more than 7000-times the rate exhibited by the enzyme of SEQ ID NO:2, 4 or 158.

In some embodiments, the ketoreductase polypeptide is capable of converting the substrate 5-((4S)-2-oxo-4-phenyl (1,3-oxazolidin-3-yl))-1-(4-fluorophenyl) pentane-1,5-dione to the product (4S)-3-[(5S)-5-(4-fluorophenyl)-5-hydroxy-pentanoyl]-4-phenyl-1,3-oxazolidin-2-one, at a rate that is improved over a reference polypeptide having the amino acid sequence of SEQ ID NO:8. In some embodiments, such ketoreductase polypeptides are also capable of converting the substrate to the product with a percent stereomeric excess of at least about 95%. In some embodiments, such ketoreductase polypeptides are also capable of converting the substrate to the product with a percent stereomeric excess of at least about 99%. Exemplary polypeptides with such properties include, but are not limited to, polypeptides which comprising amino acid sequences corresponding to SEQ ID NO: 42, 44, 46, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, and 126.

In some embodiments, the ketoreductase polypeptide is capable of converting the substrate 5-((4S)-2-oxo-4-phenyl (1,3-oxazolidin-3-yl))-1-(4-fluorophenyl) pentane-1,5-dione to the product (4S)-3-[(5S)-5-(4-fluorophenyl)-5-hydroxy-pentanoyl]-4-phenyl-1,3-oxazolidin-2-one, with a percent stereomeric excess of at least about 99% and at a rate that is at least about 5 times or more improved over a reference polypeptide having the amino acid sequence of SEQ ID NO:8. Exemplary polypeptides with such properties include, but are not limited to, polypeptides which comprise an amino acid sequence corresponding to SEQ ID NO: 42, 44, 46, 50, 52, 54, 56, 58, 60, 62, 64, 66, 68, 70, 72, 74, 76, 78, 80, 82, 84, 86, 88, 90, 92, 96, 98, 100, 102, 104, 106, 108, 110, 112, 114, 116, 118, 120, 122, 124, and 126.

In some embodiments, the ketoreductase polypeptide is capable of converting the substrate 5-((4S)-2-oxo-4-phenyl (1,3-oxazolidin-3-yl))-1-(4-fluorophenyl) pentane-1,5-dione to the product (4S)-3-[(5S)-5-(4-fluorophenyl)-5-hydroxy-pentanoyl]-4-phenyl-1,3-oxazolidin-2-one, with a percent stereomeric excess of at least about 99% and at a rate that is at least about 3000 to about 7000 times improved over a reference polypeptide having the amino acid sequence of SEQ ID NO:8. Exemplary polypeptides with such properties include, but are not limited to, polypeptides which comprise an amino acid sequence corresponding to SEQ ID NO: 44, 46, 50, 52, 54, 56, 58, 60, 62, 64, 66, 68, 72, 74, 78, 80, 82, 84, and 86.

In some embodiments, the ketoreductase polypeptide is capable of converting the substrate 5-((4S)-2-oxo-4-phenyl (1,3-oxazolidin-3-yl))-1-(4-fluorophenyl) pentane-1,5-dione to the product (4S)-3-[(5S)-5-(4-fluorophenyl)-5-hydroxy-pentanoyl]-4-phenyl-1,3-oxazolidin-2-one, with a percent stereomeric excess of at least about 99% and at a rate that is at least 7000 times improved over a reference polypeptide having the amino acid sequence of SEQ ID NO:8. Exemplary polypeptides with such properties include, but are not limited to, polypeptides which comprise amino acid sequences corresponding to SEQ ID NO: 102, 108, 120, 122, 124, and 126.

In some embodiments, the ketoreductase polypeptide is capable of converting at least about 95% of the substrate to the product in less than about 24 hours when carried out with greater than about 100 g/L of substrate and less than about 5 g/L of the polypeptide. Exemplary polypeptides that have this capability include, but are not limited to, polypeptides which comprise amino acid sequences corresponding to SEQ ID NO: 102, 108, 120, 122, 124, and 126.

In some embodiments, the ketoreductase polypeptide is highly stereoselective, wherein the polypeptide can reduce the substrate to the product in greater than about 99%, 99.1%, 99.2%, 99.3%, 99.4%, 99.5%, 99.6%, 99.7%, 99.8% or 99.9% stereomeric excess. Exemplary ketoreductase polypeptides with high stereoselectivity include, but are not limited to, the polypeptides comprising the amino acid sequences corresponding to SEQ ID NO: 42, 44, 46, 50, 52, 54, 56, 58, 60, 62, 64, 66, 68, 70, 72, 74, 76, 78, 80, 82, 84, 86, 88, 90, 92, 96, 98, 100, 102, 104, 106, 108, 110, 112, 114, 116, 118, 120, 122, 124, and 126.

In some embodiments, an improved ketoreductase polypeptide comprises an amino acid sequence that corresponds to the sequence formulas of SEQ ID NO:161, 162 or 163 (or a region thereof, such as residues 90-211). SEQ ID NO:162 is based on the amino acid sequence of the *Lactobacillus kefir* ketoreductase of SEQ ID NO:4. The sequence formula of SEQ ID NO:161 is based on the amino acid sequence of the *Lactobacillus brevis* ketoreductase (SEQ ID NO:2). The sequence formula of SEQ ID NO:163 is based on the amino acid sequence of the *Lactobacillus minor* ketoreductase (SEQ ID NO:158). SEQ ID NO:161, 162 or 163 specify that residue X145 is a polar residue and residue X190 is cysteine.

In some embodiments, an improved ketoreductase polypeptide of the disclosure is based on the sequence formulas of SEQ ID NO:161, 162 or 163 and can comprise an amino acid sequence that is at least about 85%, 86%, 87%, 88%, 89%, 90%, 91%, 92%, 93%, 94%, 95%, 96%, 97%, 98%, or 99% identical to the reference sequence of SEQ ID NO:128, 130, or 160, with the proviso that the ketoreductase amino acid sequence has at the residue corresponding to residue X145 a serine and at the amino acid residue corresponding to X190 a cysteine. In some embodiments, the ketoreductase polypeptides can have one or more amino acid residue differences as compared to SEQ ID NO:128, 130, or 160. These differences can be amino acid insertions, deletions, substitutions, or any combination of such changes. In some embodiments, the amino acid sequence differences can comprise non-conservative, conservative, as well as a combination of non-conservative and conservative amino acid substitutions. Various amino acid residue positions where such changes can be made are described herein.

In some embodiments, an improved ketoreductase polypeptide is based on the sequence formulas of SEQ ID NO:161, 162 or 163 and can comprise a region having an amino acid sequence that is at least about 85%, 86%, 87%, 88%, 89%, 90%, 91%, 92%, 93%, 94%, 95%, 96%, 97%, 98%, or 99% identical to a region or domain thereof, such as residues 90-211 of the reference sequence of SEQ ID NO:128, 130, or 160, with the proviso that the ketoreductase polypeptide amino acid sequence has at the residue corresponding to residue X145 a serine and at the amino acid residue corresponding to X190 a cysteine. In some embodiments, the amino acid sequence differences can comprise non-conservative, conservative, as well as a combination of non-conservative and conservative amino acid substitutions. Various amino acid residue positions where such changes can be made in the defined region are described herein.

In some embodiments, an improved ketoreductase comprises an amino acid sequence that is at least about 85%, 86%, 87%, 88%, 89%, 90%, 91%, 92%, 93%, 94%, 95%, 96%, 97%, 98%, or 99% identical to the amino acid sequence corresponding to SEQ ID NO: 8, 42, 44, 46, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, and 126, wherein the improved ketoreductase polypeptide amino acid sequence includes any one set of the specified amino acid substitution combinations presented in Tables 3 and 4. In some embodiments, these ketoreductase polypeptides can have mutations at other amino acid residues.

In another aspect, the present disclosure provides polynucleotides encoding the engineered ketoreductases described herein or polynucleotides that hybridize to such polynucleotides under highly stringent conditions. The polynucleotide can include promoters and other regulatory elements useful for expression of the encoded engineered ketoreductase, and can utilize codons optimized for specific desired expression systems. In some embodiments, the polynucleotides encode a ketoreductase polypeptides having at least the following amino acid sequence as compared to the amino acid sequence of SEQ ID NO:2, 4, or 158: the amino acid residue corresponding to X145 is a serine, and the amino acid residue corresponding to X190 is a cysteine. Exemplary polynucleotides include, but are not limited to, a polynucleotide sequence of SEQ ID NO: 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, and 125.

In another aspect, the present disclosure provides host cells comprising the polynucleotides and/or expression vectors described herein. The host cells may be *L. kefir* or *L. brevis*, or they may be a different organism, and as *E. coli*. The host cells can be used for the expression and isolation of the engineered ketoreductase enzymes described herein, or, alternatively, they can be used directly for the conversion of the substrate to the stereoisomeric product.

Whether carrying out the method with whole cells, cell extracts or purified ketoreductase enzymes, a single ketoreductase enzyme may be used or, alternatively, mixtures of two or more ketoreductase enzymes may be used.

The ketoreductase enzymes described herein are capable of catalyzing the reduction reaction of the keto group in the compound of structural formula (I), 5-((4S)-2-oxo-4-phenyl (1,3-oxazolidin-3-yl))-1-(4-fluorophenyl) pentane-1,5-dione ("the substrate"),

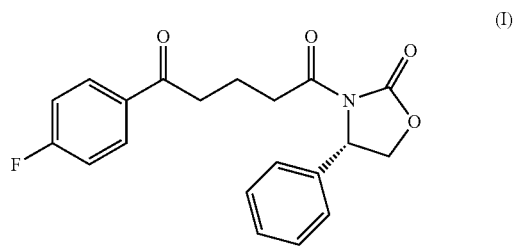 [SMILES: O=C(CCCC(=O)N1C(=O)OC[C@@H]1c1ccccc1)c1ccc(F)cc1]

to the corresponding stereoisomeric alcohol product of structural formula (II), (4S)-3-[(5S)-5-(4-fluorophenyl)-5-hydroxypentanoyl]-4-phenyl-1,3-oxazolidin-2-one ("the product"):

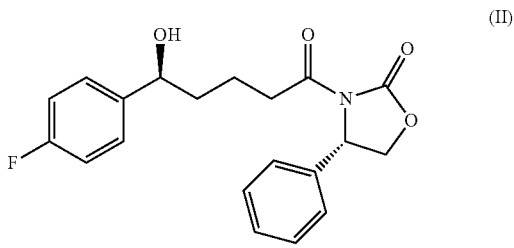 [SMILES: O=C(CCC[C@H](O)c1ccc(F)cc1)N1C(=O)OC[C@@H]1c1ccccc1]

In some embodiments, the method for reducing or converting the substrate having the structural formula (I) to the corresponding product of structural formula (II) comprises contacting or incubating the substrate with a ketoreductase polypeptide disclosed herein under reaction conditions suitable for reducing or converting the substrate to the product.

In some embodiment, the ketoreductase enzymes described herein are also capable of catalyzing the reduction reaction of the keto group in the compound of structural formula (III), 1-(4-fluorophenyl)-3(R)-[3-oxo-3-(4-fluorophenyl)propyl)]-4(S)-(4-hydroxyphenyl)-2-azetidinone,

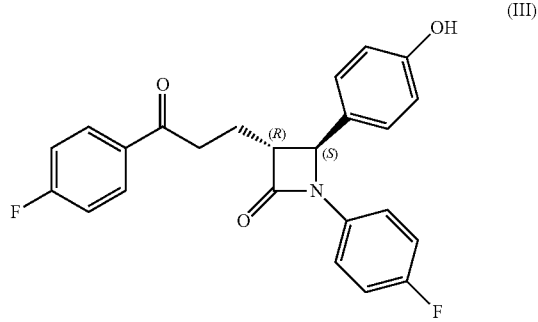

to the corresponding stereoisomeric alcohol product of structural formula (IV), 1-(4-fluorophenyl)-3(R)-[3(S)-hydroxy-3(4-fluorophenyl)-propyl)]-4(S)-(4-hydroxyphenyl)-2-azetidinone,

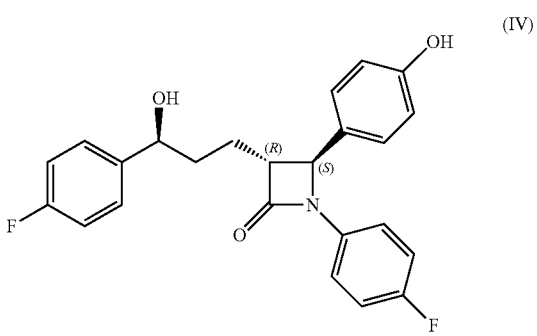

In some embodiments, the method for reducing the substrate having the structural formula (III) to the corresponding product of structural formula (IV) comprises contacting or incubating the compound of formula (III) with a ketoreductase polypeptide disclosed herein under reaction conditions suitable for reducing or converting the substrate of formula (III) to the product of formula (IV).

In some embodiments of this method for reducing the substrate to the product, the substrate is reduced to the product in greater than about 99% stereomeric excess, wherein the ketoreductase polypeptide comprises a sequence that corresponds to SEQ ID NO: SEQ ID NO: 42, 44, 46, 50, 52, 54, 56, 58, 60, 62, 64, 66, 68, 70, 72, 74, 76, 78, 80, 82, 84, 86, 88, 90, 92, 96, 98, 100, 102, 104, 106, 108, 110, 112, 114, 116, 118, 120, 122, 124, and 126.

In some embodiments of this method for reducing the substrate to the product, at least about 95% of the substrate is converted to the product in less than about 24 hours when carried out with greater than about 100 g/L of substrate and less than about 5 g/L of the polypeptide, wherein the polypeptide comprises an amino acid sequence corresponding to SEQ ID NO: 102, 108, 120, 122, 124, or 126.

5. BRIEF DESCRIPTION OF THE FIGURES

FIG. 1 illustrates the role of ketoreductases (KRED) in the conversion of the substrate compound of formula (I) to the corresponding product of formula (II). This reduction uses a KRED of the invention and a co-factor such as NADPH. A glucose dehydrogenase (GDH) is used to covert/recycle NADP$^+$ to NADPH. Glucose is converted to gluconic acid, which in turn is converted to its sodium salt (sodium gluconate) with the addition of sodium hydroxide.

6. DETAILED DESCRIPTION

6.1 Definitions

As used herein, the following terms are intended to have the following meanings.

"Ketoreductase" and "KRED" are used interchangeably herein to refer to a polypeptide having an enzymatic capability of reducing a carbonyl group to its corresponding alcohol. More specifically, the ketoreductase polypeptides of the invention are capable of stereoselectively reducing the compound of formula (I), supra to the corresponding product of formula (II), supra. The polypeptide typically utilizes a cofactor reduced nicotinamide adenine dinucleotide (NADH) or reduced nicotinamide adenine dinucleotide phosphate (NADPH) as the reducing agent.

Ketoreductases as used herein include naturally occurring (wild type) ketoreductases as well as non-naturally occurring engineered polypeptides generated by human manipulation.

"Coding sequence" refers to that portion of a nucleic acid (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, *Adv. Appl. Math.* 2:482, by the homology alignment algorithm of Needleman and Wunsch, 1970, *J. Mol. Biol.* 48:443, by the search for similarity method of Pearson and Lipman, 1988, *Proc. Natl. Acad. Sci. USA* 85:2444, by computerized implementations of these algorithms (GAP, BESTFIT, FASTA, and TFASTA in the GCG Wisconsin Software Package), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, *J. Mol. Biol.* 215: 403-410 and Altschul et al., 1977, *Nucleic Acids Res.* 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, *Proc Natl Acad Sci USA* 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptides are typically performed by comparing sequences of the two polynucleotides over a "comparison window" to identify and compare local regions of sequence similarity.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered ketoreductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereo selectivity is referred to as diastereoselectivity, the fraction (typically reported as a percentage) of one diastereomer in a mixture of two diasteromers, commonly alternatively reported as the diastereomeric excess (d.e.). Enantiomeric excess and diastereomeric excess are types of stereomeric excess.

"Highly stereoselective": refers to a ketoreductase polypeptide that is capable of converting or reducing the substrate to the corresponding (S)-product with at least about 99% stereomeric excess.

"Stereospecificity" refers to the preferential conversion in a chemical or enzymatic reaction of one stereoisomer over another. Stereospecificity can be partial, where the conversion of one stereoisomer is favored over the other, or it may be complete where only one stereoisomer is converted.

"Chemoselectivity" refers to the preferential formation in a chemical or enzymatic reaction of one product over another.

"Improved enzyme property" refers to a ketoreductase polypeptide that exhibits an improvement in any enzyme property as compared to a reference ketoreductase. For the engineered ketoreductase polypeptides described herein, the comparison is generally made to the wild-type ketoreductase enzyme, although in some embodiments, the reference ketoreductase can be another improved engineered ketoreductase. Enzyme properties for which improvement is desirable include, but are not limited to, enzymatic activity (which can be expressed in terms of percent conversion of the substrate), thermal stability, pH activity profile, cofactor requirements, refractoriness to inhibitors (e.g., product inhibition), stereospecificity, and stereoselectivity (including enantioselectivity).

"Increased enzymatic activity" refers to an improved property of the engineered ketoreductase polypeptides, which can be represented by an increase in specific activity (e.g., product produced/time/weight protein) or an increase in percent conversion of the substrate to the product (e.g., percent conversion of starting amount of substrate to product in a specified time period using a specified amount of KRED) as compared to the reference ketoreductase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.5 times the enzymatic activity of the corresponding wild-type ketoreductase enzyme, to as much as 2 times. 5 times, 10 times, 20 times, 25 times, 50 times, 75 times, 100 times, 150 times, 200 times, 500 times, 1000, times, 3000 times, 5000 times, 7000 times or more enzymatic activity than the naturally occurring ketoreductase or another engineered ketoreductase from which the ketoreductase polypeptides were derived. In specific embodiments, the engineered ketoreductase enzyme exhibits improved enzymatic activity in the range of 150 to 3000 times, 3000 to 7000 times, or more than 7000 times greater than that of the parent ketoreductase enzyme. It is understood by the skilled artisan that the activity of any enzyme is diffusion limited such that the catalytic turnover rate cannot exceed the diffusion rate of the substrate, including any required cofactors. The theoretical maximum of the diffusion limit, or $k_{cat}/K_m$, is generally about $10^8$ to $10^9$ ($M^{-1}s^{-1}$). Hence, any improvements in the enzyme activity of the ketoreductase will have an upper limit related to the diffusion rate of the substrates acted on by the ketoreductase enzyme. Ketoreductase activity can be measured by any one of standard assays used for measuring ketoreductase, such as a decrease in absorbance or fluorescence of NADPH due to its oxidation with the concomitant reduction of a ketone to an alcohol, or by product produced in a coupled assay. Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion": refers to the enzymatic reduction of the substrate to the corresponding product. "Percent conversion" refers to the percent of the substrate that is reduced to the product within a period of time under specified conditions. Thus, the "enzymatic activity" or "activity" of a ketoreductase polypeptide can be expressed as "percent conversion" of the substrate to the product.

"Thermostable" refers to a ketoreductase polypeptide that maintains similar activity (more than 60% to 80% for example) after exposure to elevated temperatures (e.g. 40-80° C.) for a period of time (e.g. 0.5-24 hrs) compared to the untreated enzyme.

"Solvent stable" refers to a ketoreductase polypeptide that maintains similar activity (more than e.g., 60% to 80%) after exposure to varying concentrations (e.g., 5-99%) of solvent (isopropyl alcohol, tetrahydrofuran, 2-methyltetrahydrofuran, acetone, toluene, butylacetate, methyl tert-butylether, etc.) for a period of time (e.g., 0.5-24 hrs) compared to the untreated enzyme.

"pH stable" refers to a ketoreductase polypeptide that maintains similar activity (more than e.g., 60% to 80%) after exposure to high or low pH (e.g., 4.5-6 or 8 to 12) for a period of time (e.g., 0.5-24 hrs) compared to the untreated enzyme.

"Thermo- and solvent stable" refers to a ketoreductase polypeptide that is both thermostable and solvent stable.

"Derived from" as used herein in the context of engineered ketoreductase enzymes, identifies the originating ketoreductase enzyme, and/or the gene encoding such ketoreductase enzyme, upon which the engineering was based. For example, the engineered ketoreductase enzyme of SEQ ID NO:158 was obtained by artificially evolving, over multiple generations the gene encoding the *Lactobacillus kefir* ketoreductase enzyme of SEQ ID NO:4. Thus, this engineered ketoreductase enzyme is "derived from" the wild-type ketoreductase of SEQ ID NO:4.

"Hydrophilic Amino Acid or Residue" refers to an amino acid or residue having a side chain exhibiting a hydrophobicity of less than zero according to the normalized consensus hydrophobicity scale of Eisenberg et al., 1984, *J. Mol. Biol.* 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

"Acidic Amino Acid or Residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic Amino Acid or Residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar Amino Acid or Residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Hydrophobic Amino Acid or Residue" refers to an amino acid or residue having a side chain exhibiting a hydrophobicity of greater than zero according to the normalized consensus hydrophobicity scale of Eisenberg et al., 1984, *J. Mol. Biol.* 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic Amino Acid or Residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

"Constrained amino acid or residue" refers to an amino acid or residue that has a constrained geometry. Herein, constrained residues include L-pro (P) and L-his (H). Histidine has a constrained geometry because it has a relatively small imidazole ring. Proline has a constrained geometry because it also has a five membered ring.

"Non-polar Amino Acid or Residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic Amino Acid or Residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine". The amino acid L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Small Amino Acid or Residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Hydroxyl-containing Amino Acid or Residue" refers to an amino acid containing a hydroxyl (—OH) moiety. Genetically-encoded hydroxyl-containing amino acids include L-Ser (S) L-Thr (T) and L-Tyr (Y).

"Conservative" amino acid substitutions or mutations refer to the interchangeability of residues having similar side chains, and thus typically involves substitution of the amino acid in the polypeptide with amino acids within the same or similar defined class of amino acids. However, as used herein, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. Table 1 below shows exemplary conservative substitutions.

TABLE 1

Conservative Substitutions

| Residue | Possible Conservative Mutations |
|---------|--------------------------------|
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar (N, Q, S, T) |
| Y, W, F | Other aromatic (Y, W, F) |
| C | None |

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered ketoreductase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered ketoreductase enzymes comprise insertions of one or more amino acids to the naturally occurring ketoreductase polypeptide as well as insertions of one or more amino acids to other improved ketoreductase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Different from" or "differs from" with respect to a designated reference sequence refers to difference of a given amino acid or polynucleotide sequence when aligned to the reference sequence. Generally, the differences can be determined when the two sequences are optimally aligned. Differences include insertions, deletions, or substitutions of amino acid residues in comparison to the reference sequence.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length ketoreductase polypeptide.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved ketoreductase enzymes may be present within a cell, present in the cellular medium, or prepared in various forms, such as lysates or isolated preparations. As such, in some embodiments, the improved ketoreductase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure ketoreductase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved ketoreductases polypeptide is a substantially pure polypeptide composition.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$ values for polynucleotides can be calculated using known methods for predicting melting temperatures (see, e.g., Baldino et al., *Methods Enzymology* 168:761-777; Bolton et al., 1962, *Proc. Natl. Acad. Sci. USA* 48:1390; Bresslauer et al., 1986, *Proc. Natl. Acad. Sci USA* 83:8893-8897; Freier et al., 1986, *Proc. Natl. Acad. Sci USA* 83:9373-9377; Kierzek et al., *Biochemistry* 25:7840-7846; Rychlik et al., 1990, *Nucleic Acids Res* 18:6409-6412 (erratum, 1991, *Nucleic Acids Res* 19:698); Sambrook et al., supra); Suggs et al., 1981, In *Developmental Biology Using Purified Genes* (Brown et al., eds.), pp. 683-693, Academic Press; and Wetmur, 1991, *Crit Rev Biochem Mol Biol* 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered ketoreductase enzyme of the present disclosure.

"Hybridization stringency" relates to such washing conditions of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA; with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$, as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the ketoreductases enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariat analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, Bioinformatics 14:372-73; Stenico et al., 1994, Nucleic Acids Res. 222437-46; Wright, F., 1990, Gene 87:23-29). Codon usage tables are available for a growing list of organisms (see for example, Wada et al., 1992, *Nucleic Acids Res.* 20:2111-2118; Nakamura et al., 2000, *Nucl. Acids Res.* 28:292; Duret, et al., supra; Henaut and Danchin, "*Escherichia coli* and *Salmonella*," 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., *Bioinformatics: Sequence and Genome Analysis*, Chapter 8, Cold Spring Harbor Laboratory Press, Cold Spring Harbor, N.Y., 2001; Uberbacher, E. C., 1996, *Methods Enzymol.* 266:259-281; Tiwari et al., 1997, *Comput. Appl. Biosci.* 13:263-270).

"Control sequence" is defined herein to include all components, which are necessary or advantageous for the expression of a polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed at a position relative to the coding sequence of the DNA sequence such that the control sequence directs the expression of a polynucleotide and/or polypeptide.

"Promoter sequence" is a nucleic acid sequence that is recognized by a host cell for expression of the coding region. The control sequence may comprise an appropriate promoter sequence. The promoter sequence contains transcriptional control sequences, which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Cofactor regeneration system" refers to a set of reactants that participate in a reaction that reduces the oxidized form of the cofactor (e.g., NADP+ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst that catalyzes the reduction of the oxidized form of the cofactor by the reductant. Cofactor regeneration systems to regenerate NADH or NADPH from NAD+ or NADP+, respectively, are known in the art and may be used in the methods described herein.

6.2 Ketoreductase Enzymes

The present disclosure provides engineered ketoreductase ("KRED") enzymes that are capable of stereoselectively reducing or converting the substrate 5-((4S)-2-oxo-4-phenyl (1,3-oxazolidin-3-yl))-1-(4-fluorophenyl) pentane-1,5-dione to the product (4S)-3-[(5S)-5-(4-fluorophenyl)-5-hydroxy-pentanoyl]-4-phenyl-1,3-oxazolidin-2-one and having an improved property when compared with the naturally-occurring, wild-type KRED enzyme of *L. kefir* (SEQ ID NO:4), *L. brevis* (SEQ ID NO:2), or *L. minor* (SEQ ID NO: 158), or when compared with other engineered ketoreductase enzymes (e.g. that of SEQ ID NO:8).

The engineered ketoreductase ("KRED") enzymes are also capable of stereoselectively reducing or converting the compound 1-(4-fluorophenyl)-3(R)-[3-oxo-3-(4-fluorophenyl)propyl)]-4(S)-(4-hydroxyphenyl)-2-azetidinone to the corresponding stereoisomeric alcohol product 1-(4-fluorophenyl)-3(R)-[3(S)-hydroxy-3(4-fluorophenyl)-propyl)]-4 (S)-(4-hydroxyphenyl)-2-azetidinone and having an improved property when compared with the naturally-occurring, wild-type KRED enzyme of *L. kefir* (SEQ ID NO:4), *L. brevis* (SEQ ID NO:2), or *L. minor* (SEQ ID NO:158) or when compared with other engineered ketoreductase enzymes (e.g. that of SEQ ID NO:8).

Enzyme properties for which improvement is desirable include, but are not limited to, enzymatic activity, thermal stability, pH activity profile, cofactor requirements, refractoriness to inhibitors (e.g., product inhibition), sterospecificity, stereoselectivity, and solvent stability. The improvements can relate to a single enzyme property, such as enzymatic activity, or a combination of different enzyme properties, such as enzymatic activity and stereoselectivity. For the polypeptides described herein, the amino acid sequence of the ketoreductase polypeptides have the requirement that: (1) the amino acid residue corresponding to residue position 145 of SEQ ID NO:2, 4, or 158 is serine and (2) the amino acid residue corresponding to residue position 190 of SEQ ID NO:2, 4, or 158 is cysteine.

In some embodiments, as noted above, the engineered ketoreductase with improved enzyme activity is described with reference to *Lactobacillus kefir* ketoreductase of SEQ ID NO:4, *Lactobacillus brevis* ketoreductase of SEQ ID NO:2, or *Lactobacillus minor* of SEQ ID NO:158. The amino acid residue position is determined in both ketoreductases beginning from the initiating methionine (M) residue (i.e., M represents residue position 1), although it will be understood by the skilled artisan that this initiating methionine residue may be removed by biological processing machinery, such as in a host cell or in vitro translation system, to generate a mature protein lacking the initiating methionine residue. The amino acid residue position at which a particular amino acid or amino acid change is present is sometimes describe in terms "Xn", or "position n", where n refers to the residue position. Where the amino acid residues at the same residue position differ between the ketoreductases, the different residues are denoted by an "/" with the arrangement being, for example, "*kefir* residue/*brevis* residue/mirror" A substitution mutation, which is a replacement of an amino acid residue in a corresponding residue of a reference sequence, for example the wildtype ketoreductases of SEQ ID NO:2, SEQ ID NO:4, or SEQ ID NO:158 with a different amino acid residue is denoted by the symbol "→".

Herein, mutations are sometimes described as a mutation "to a" type of amino acid. For example, residue 211 can be mutated "to a" basic residue. But the use of the phrase "to a" does not exclude mutations from one amino acid of a class to another amino acid of the same class. For example, residue 211 can be mutated from a lysine to an arginine.

The polynucleotide sequence encoding the naturally occurring ketoreductase of *Lactobacillus kefir* and *Lactobacillus brevis* (also referred to as "alcohol dehydrogenase" or "ADH"), and thus the corresponding amino acid sequences, are available from Genbank accession no. AAP94029 GI:33112056 for *Lactobacillus kefir*, Genbank accession no. CAD66648 GI:28400789 for *Lactobacillus brevis*, and U.S. Pat. Appl. No. 20040265978 or SEQ ID NO:158 for *Lactobacillus minor*.

In some embodiments, the ketoreductase polypeptides herein can have a number of modifications to the reference sequence (e.g., naturally occurring polypeptide or an engineered polypeptide) to result in an improved ketoreductase property. In such embodiments, the number of modifications to the amino acid sequence can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 20% of the total number of amino acids, or up to 30% of the total number of amino acids of the reference enzyme sequence. In some embodiments, the number of modifications to the naturally occurring polypeptide or an engineered polypeptide that produces an improved ketoreductase property may comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 modifications of the reference sequence. The modifications can comprise insertions, deletions, substitutions, or combinations thereof.

In some embodiments, the modifications comprise amino acid substitutions to the reference sequence. Substitutions that can produce an improved ketoreductase property may be at one or more amino acids, 2 or more amino acids, 3 or more amino acids, 4 or more amino acids, 5 or more amino acids, 6 or more amino acids, 8 or more amino acids, 10 or more amino acids, or 20 or more amino acids, up to 10% of the total number of amino acids, up to 20% of the total number of amino acids, or up to 30% of the total number of amino acids of the reference enzyme sequence. In some embodiments, the number of substitutions to the naturally occurring polypeptide or an engineered polypeptide that produces an improved ketoreductase property can comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acid substitutions of the reference sequence.

In some embodiments, the improved property, as compared to wild-type or another engineered polypeptide, of the ketoreductase polypeptide is with respect to an increase of its stereoselectivity i.e., herein, an increase in the stereomeric excess of the product, for reducing or converting the substrate 5-((4S)-2-oxo-4-phenyl (1,3-oxazolidin-3-yl))-1-(4-fluorophenyl) pentane-1,5-dione to the product (4S)-3-[(5S)-5-(4-fluorophenyl)-5-hydroxypentanoyl]-4-phenyl-1,3-oxazolidin-2-one. In some embodiments, the improved property of the ketoreductase polypeptide is with respect to an increase in its ability to convert or reduce a greater percentage of the substrate to the product. In some embodiments, the improved property of the ketoreductase polypeptide is with respect to an increase in its rate of conversion of the substrate to the product. This improvement in enzymatic activity can be manifested by the ability to use less of the improved polypeptide as compared to the wild-type or other reference sequence (for example, SEQ ID NO:8) to reduce or convert the same amount of product. In some embodiments, the improved property of the ketoreductase polypeptide is with respect to its stability or thermostability. In some embodiments, the ketoreductase polypeptide has more than one improved property.

In some embodiments, the ketoreductase polypeptide of the disclosure is capable of converting the substrate 5-((4S)-2-oxo-4-phenyl (1,3-oxazolidin-3-yl))-1-(4-fluorophenyl) pentane-1,5-dione to the product (4S)-3-[(5S)-5-(4-fluorophenyl)-5-hydroxypentanoyl]-4-phenyl-1,3-oxazolidin-2-one, with a percent stereomeric excess of at least about 90% and at a rate that is improved over the amino acid sequence of SEQ ID NO:8. Exemplary polypeptides with such properties include, but are not limited to, polypeptides which comprise an amino acid sequence corresponding to SEQ ID NO: 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, and 126. Because the reference polypeptide having the amino acid sequence of SEQ ID NO:8 is capable of converting the substrate to the product at a rate (for example, 4% of 1 g/L substrate converted to product in 24 hours with about 5 g/L of the KRED) and with a steroselectivity (94% stereomeric excess) that is improved over wild-type (SEQ ID NO:4), the polypeptides herein that are improved over SEQ ID NO:8 are also improved over wild-type.

In some embodiments, the ketoreductase polypeptide is capable of converting the substrate 5-((4S)-2-oxo-4-phenyl (1,3-oxazolidin-3-yl))-1-(4-fluorophenyl) pentane-1,5-dione to the product (4S)-3-[(5S)-5-(4-fluorophenyl)-5-hydroxypentanoyl]-4-phenyl-1,3-oxazolidin-2-one, with a percent stereomeric excess of at least about 99% and at a rate that is at least about 5 times improved over a reference polypeptide having the amino acid sequence of SEQ ID NO: 8. Exemplary polypeptides with such properties include, but are not limited to, polypeptides which comprise an amino acid sequence corresponding to SEQ ID NO: 42, 44, 46, 50, 52, 54, 56, 58, 60, 62, 64, 66, 68, 70, 72, 74, 76, 78, 80, 82, 84, 86, 88, 90, 92, 96, 98, 100, 102, 104, 106, 108, 110, 112, 114, 116, 118, 120, 122, 124, and 126.

In some embodiments, the ketoreductase polypeptide is capable of converting the substrate 5-((4S)-2-oxo-4-phenyl (1,3-oxazolidin-3-yl))-1-(4-fluorophenyl) pentane-1,5-dione to the product (4S)-3-[(5S)-5-(4-fluorophenyl)-5-hydroxypentanoyl]-4-phenyl-1,3-oxazolidin-2-one, with a percent stereomeric excess of at least about 99% and at a rate that is at least about 120 times or more improved over a reference polypeptide having the amino acid sequence of SEQ ID NO:8. Exemplary polypeptides with such properties include, but are not limited to, polypeptides which comprise an amino acid sequence corresponding to SEQ ID NO: 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, and 126.

In some embodiments, the ketoreductase polypeptide is capable of converting the substrate 5-((4S)-2-oxo-4-phenyl (1,3-oxazolidin-3-yl))-1-(4-fluorophenyl) pentane-1,5-dione to the product (4S)-3-[(5S)-5-(4-fluorophenyl)-5-hydroxypentanoyl]-4-phenyl-1,3-oxazolidin-2-one, with a percent stereomeric excess of at least about 99% and at a rate that is at least about 3000 times or more improved over a reference polypeptide having the amino acid sequence of SEQ ID NO:8. Exemplary polypeptides with such properties include, but are not limited to, polypeptides which comprise an amino acid sequence corresponding to SEQ ID NO: 76, 78, 80, 82, 84, 86, 88, 90, 92, 94, 96, 98, 100, 102, 104, 106, 108, 110, 112, 114, 116, 118, 120, 122, 124, and 126.

In some embodiments, the ketoreductase polypeptide is capable of converting the substrate 5-((4S)-2-oxo-4-phenyl (1,3-oxazolidin-3-yl))-1-(4-fluorophenyl) pentane-1,5-dione to the product (4S)-3-[(5S)-5-(4-fluorophenyl)-5-hydroxypentanoyl]-4-phenyl-1,3-oxazolidin-2-one, with a percent stereomeric excess of at least about 99% and at a rate that is at least about 7000 times or more improved over a reference polypeptide having the amino acid sequence of SEQ ID NO:8. Exemplary polypeptides with such properties include, but are not limited to, polypeptides which comprise an amino acid sequence corresponding to SEQ ID NO: 102, 108, 120, 122, 124, and 126.

In some embodiments, the ketoreductase polypeptides of the disclosure comprise highly stereoselective ketoreductase polypeptides that can reduce the substrate to the product in greater than about 99%, 99.1%, 99.2%, 99.3%, 99.4%, 99.5%, 99.6%, 99.7%, 99.8% or 99.9% stereomeric excess. Exemplary ketoreductase polypeptides with such high stereoselectivity include, but are not limited to, the polypeptides comprising the amino acid sequences corresponding to SEQ ID NO: 42, 44, 46, 50, 52, 54, 56, 58, 60, 62, 64, 66, 68, 70, 72, 74, 76, 78, 80, 82, 84, 86, 88, 90, 92, 96, 98, 100, 102, 104, 106, 108, 110, 112, 114, 116, 118, 120, 122, 124, and 126.

Tables 2, 3 and 4 below provide a list of the SEQ ID NOs disclosed herein with associated activities. The sequences below are based on the wild-type *L. kefir* ketoreductase sequences (SEQ ID NO: 3 and 4) unless otherwise specified. In tables below, each row lists two SEQ ID NOs, where the odd number refers to the nucleotide sequence that codes for the amino acid sequence provided by the even number. The column listing the number of mutations (i.e., residue changes) refers to the number of amino acid substitutions as compared to the *L. kefir* KRED amino acid sequence of SEQ ID NO:4. Each Table is followed by a caption indicating the meaning of the symbols "+" "++" "+++" and "++++" in each context.

TABLE 2

Table 2: Activity of Various KREDs

| SEQ ID NO: | Residue Changes Relative to SEQ ID NO: 4 | Number of Changes Relative to *L Kefir* | Conversion[a] | % DE[b] |
|---|---|---|---|---|
| 5/6 | Y190C; | 1 | + | − |
| 7/8 | G7S; R108H; G117S; E145S; N157T; Y190C; K211R; I223V | 8 | +++ | ++ |
| 9/10 | F147L; Y190P; V196L | 3 | + | + |
| 13/14 | H40R; A94G; S96V; E145F; F147M; Y190P; V196L; L199W; I226V; Y249W | 10 | + | ++ |
| 27/28 | E145A; F147L; Y190C | 3 | +++ | ++ |
| 29/30 | F147L; L153G; Y190P | 3 | +++ | − |
| 31/32 | F147L; Y190P | 2 | ++ | − |
| 33/34 | E145S; F147L; Y190P | 3 | +++ | + |
| 35/36 | E145Q; F147L; Y190A | 3 | ++ | − |
| 37/38 | F147L; Y190P; K211L | 3 | ++ | − |
| 39/40 | F147L; L153Q; Y190P | 3 | +++ | − |

[a]+ indicates <10% conversion of substrate to product; ++ indicates 10-60% conversion; +++ indicates >60% conversion
[b]− indicates R selectivity; + indicates <50% S,S-diastereomeric product; ++ indicates >50% S, S-diastereomeric product The following Table 3 and Table 4 show the activity profiles of various ketoreductases.

TABLE 3

List of Sequences and Corresponding Activity Improvement

| SEQ ID NO | Residue Changes | Number of Changes Relative to the *L. kefir* (SEQ ID NO: 4) | % Conversion[a] | % DE[b] |
|---|---|---|---|---|
| 7/8 | G7S; R108H; G117S; E145S; N157T; Y190C; K211R; I223V | 8 | + | + |
| 11/12 | A94G; S96V; E145L; L153T; Y190P; V196L; I226V; Y249W; | 8 | + | + |
| 15/16 | H40R; A94G; S96V; E145F; F147M; Y190P; V196L; M206F; I226V; Y249W | 10 | + | + |
| 17/18 | A94G; S96V; E145F; F147M; L153T; Y190P; V196L; I226V; Y249W | 9 | + | ++ |
| 19/20 | A94G; S96V; E145F; F147M; L153T; Y190P; L195M; V196L; L199Y; I226V; Y249W | 11 | + | ++ |
| 21/22 | A94G; S96V; E145F; F147M; T152S; L153T; Y190P; V196L; I226V; Y249W | 10 | + | ++ |
| 23/24 | A94G; S96V; E145F; F147M; T152S; Y190P; L195M; V196L; M206F; I226V; Y249W | 11 | + | ++ |
| 25/26 | H40R; A94G; S96V; E145F; F147M; L153T; Y190P; V196L; I226V; Y249W | 10 | + | ++ |
| 41/42 | G7S; A94G; R108H; G117S; E145S; N157T; Y190C; K211R; I223V | 9 | ++ | + |
| 43/44 | G7S; S96Q; R108H; G117S; E145S; N157T; Y190C; K211R; I223V | 9 | ++ | ++ |
| 45/46 | G7S; R108H; G117S; E145S; N157T; Y190C; L199D; K211R; I223V | 9 | ++ | ++ |
| 47/48 | G7S; R108H; G117S; E145S; N157T; Y190C; A202G; K211R; I223V | 9 | ++ | + |
| 49/50 | G7S; R108H; V113A; G117S; E145S; N157T; Y190C; L199D; K211R; I223V | 10 | ++ | ++ |
| 51/52 | G7S; R108H; G117S; E145S; T152K; N157T; Y190C; L199D; K211R; I223V | 10 | +++ | ++ |
| 53/54 | G7S; R108H; G117S; E145S; T152M; N157T; Y190C; L199D; K211R; I223V | 10 | +++ | ++ |
| 55/56 | G7S; A94S; S96Q; R108H; G117S; E145S; N157T; Y190C; L199D; K211R; I223V | 11 | +++ | ++ |
| 57/58 | G7S; R108H; G117S; E145S; N157T; Y190C; P194Q; L199D; K211R; I223V | 10 | +++ | ++ |
| 59/60 | G7S; A94S; S96Q; R108H; G117S; E145S; T152K; N157T; Y190C; L199D; K211R; I223V | 12 | +++ | ++ |
| 61/62 | G7S; A94S; S96Q; R108H; G117S; E145S; T152M; N157T; Y190C; L199D; K211R; I223V; | 12 | +++ | ++ |

TABLE 3-continued

List of Sequences and Corresponding Activity Improvement

| SEQ ID NO | Residue Changes | Number of Changes Relative to the L. kefir (SEQ ID NO: 4) | % Conversion[a] | % DE[b] |
|---|---|---|---|---|
| 63/64 | G7S; R108H; G117S; E145S; F147L; T152M; N157T; Y190C; L199D; K211R; I223V; | 11 | +++ | ++ |
| 65/66 | G7S; S96N; R108H; G117S; E145S; T152M; N157T; Y190C; L199D; K211R; I223V | 11 | +++ | ++ |
| 67/68 | G7S; R108H; G117S; E145S; T152M; N157T; Y190C; P194R; L199D; K211R; I223V | 11 | +++ | ++ |
| 69/70 | G7S; S96Q; R108H; G117S; E145S; T152M; N157T; Y190C; L199D; K211R; I223V; | 11 | +++ | ++ |
| 71/72 | G7S; S96Q; R108H; G117S; E145S; T152M; N157T; Y190C; P194R; L199D; K211R; I223V | 12 | +++ | ++ |
| 73/74 | G7S; S96T; R108H; G117S; E145S; T152M; N157T; Y190C; P194R; L199D; K211R; I223V | 12 | +++ | ++ |
| 75/76 | G7S; D25T; D75N; S96Q; R108H; G117S; E145S; T152M; N157T; Y190C; P194R; L199D; K211R; I223V | 14 | ++++ | ++ |
| 77/78 | G7S; S96Q; R108H; G117S; E145S; T152M; Y190C; L199D; K211R; I223V | 10 | ++++ | ++ |
| 79/80 | G7S; H40R; S96Q; R108H; G117S; E145S; T152M; N157T; Y190C; L199D; K211R; I223V; | 12 | +++ | ++ |
| 81/82 | G7S; D25T; V95L; S96Q; R108H; G117S; E145S; T152M; L176V; Y190C; D198E; L199D; K211R; I223V | 14 | ++++ | ++ |
| 83/84 | G7S; D25T; V95L; S96Q; R108H; G117S; E145S; T152M; L176V; Y190C; D197E; L199D; K211R; I223V | 14 | ++++ | ++ |
| 89/90 | G7S; S96Q; E145S; T152M; Y190C; L199D; K211R | 7 | ++++ | ++ |
| 93/94 | G7S; G53D; S96Q; R108H; G117S; E145S; T152M; V163I; Y190C; L199D; K211R; I223V | 12 | ++++ | ++ |

[a] + indicates <50 mg product/g enzyme; ++ 50-1000 mg product/g enzyme; +++ indicates >1000 mg product/g enzyme
[b] + indicates 90-99% S,S-diastereomeric product; ++ indicates >99% S,S-diastereomeric product

TABLE 4

Table 4: List of Sequences and Corresponding Activity Improvement

| SEQ ID NO: | Residue Changes | Number of Changes Relative to the L. kefir (SEQ ID NO: 4) | % Conversion[a] | % DE[b] |
|---|---|---|---|---|
| 75/76 | G7S; D25T; D75N; S96Q; R108H; G117S; E145S; T152M; N157T; Y190C; P194R; L199D; K211R; I223V | 14 | ++ | |
| 81/82 | G7S; D25T; V95L; S96Q; R108H; G117S; E145S; T152M; L176V; Y190C; D198E; L199D; K211R; I223V | 14 | ++ | ++ |
| 83/84 | G7S; D25T; V95L; S96Q; R108H; G117S; E145S; T152M; L176V; Y190C; D197E; L199D; K211R; I223V; | 14 | ++ | ++ |
| 85/86 | G7S; D25T; V95M; S96Q; R108H; G117S; E145S; T152M; L176V; Y190C; P194R; L199D; K211R; I223V | 14 | ++ | ++ |
| 87/88 | G7S; S96Q; E145S; T152M; Y190C; L199D; K211R; I223V | 8 | ++ | ++ |
| 89/90 | G7S; S96Q; E145S; T152M; Y190C; L199D; K211R; | 7 | ++ | ++ |
| 91/92 | G7S; S96Q; R108H; E145S; T152M; Y190C; L199D; K211R; I223V; | 9 | ++ | ++ |
| 93/94 | G7S; G53D; S96Q; R108H; G117S; E145S; T152M; V163I; Y190C; L199D; K211R; I223V | 12 | ++ | ++ |
| 95/96 | G7S; V95L; S96Q; R108H; G117S; E145S; T152M; Y190C; L199D; K211R; I223V; | 11 | ++ | ++ |
| 97/98 | G7S; S96Q; R108N; G117S; E145S; T152M; Y190C; L199D; K211R; I223V | 10 | ++ | ++ |
| 99/100 | G7S; S96Q; D101G; R108H; G117S; E145S; F147L; T152M; Y190C; L199D; K211R; I223V | 12 | ++ | ++ |
| 101/102 | G7S; S96Q; R108H; L111M; G117S; E145S; T152M; Y190C; L199D; K211R; I223V | 11 | +++ | ++ |
| 103/104 | G7S; S96Q; R108H; G117S; E145S; T152M; Y190C; L199D; K211R; I223V; T250I; | 11 | ++ | ++ |
| 105/106 | G7S; E29G; S96Q; D101N; R108H; G117S; E145S; T152M; Y190C; L199D; E200P; K211R; I223V; | 13 | ++ | ++ |
| 107/108 | G7S; L17Q; S96Q; R108H; G117S; E145S; T152M; Y190C; L199D; K211R; I223V | 11 | +++ | ++ |
| 109/110 | G7S; S96Q; R108H; S112D; G117S; E145S; T152M; Y190C; D198G; L199D; K211R; I223V | 12 | ++ | ++ |

TABLE 4-continued

Table 4: List of Sequences and Corresponding Activity Improvement

| SEQ ID NO: | Residue Changes | Number of Changes Relative to the L. kefir (SEQ ID NO: 4) | % Conversion$^a$ | % DE$^b$ |
|---|---|---|---|---|
| 111/112 | G7S; S96Q; R108S; G117S; E145S; T152M; Y190C; L199D; K211R; I223V | 10 | ++ | ++ |
| 113/114 | D3N; G7S; L17Q; D42G; S96Q; R108H; Q127R; E145S; T152M; L176V; Y190C; P194R; L199D; E200P; K211R; I223V | 16 | ++ | ++ |
| 115/116 | D3N; G7S; L17Q; L21F; S96Q; R108H; E145S; F147L; T152M; L176V; Y190C; L199D; K211R; I223V; | 14 | ++ | ++ |
| 117/118 | D3N; G7S; L17Q; E29A; D42G; S96Q; E105G; R108H; G117S; E145S; T152M; Y190C; D197V; D198K; L199D; E200P; K211R; I223V; | 18 | ++ | ++ |
| 119/120 | G7S; L17Q; D42G; S96Q; R108H; G117S; E145S; T152M; V163I; Y190C; D198K; L199D; K211R; I223V | 14 | +++ | ++ |
| 121/122 | G7S; L17Q; E29A; S96Q; R108H; G117S; E145S; T152M; V163I; Y190C; D198K; L199D; E200P; K211R | 14 | +++ | ++ |
| 123/124 | G7S; L17Q; D42G; S96Q; R108H; G117S; E145S; F147L; T152M; V163I; L176V; Y190C; D198K; L199D; K211R; I223V | 16 | +++ | ++ |
| 125/126 | G7S; L17Q; E29A; S96Q; R108H; G117S; E145S; F147L; T152M; V163I; L176V; Y190C; D198K; L199D; E200P; K211R; I223V | 17 | +++ | ++ |

$^a$+ indicates <1 g product/g enzyme/hr; ++ indicates 1-2.5 g product/g enzyme/hr; and +++ indicates >2.5 g product/g enzyme/hr
$^b$+ indicates 90-99% S,S-diastereomeric product; ++ indicates >99% S,S-diastereomeric product In some embodiments, the ketoreductase polypeptides herein comprises an amino acid sequence that is at least about 85%, 86%, 87%, 88%, 89%, 90%, 91%, 92%, 93%, 94%, 95%, 96%, 97%, 98%, or 99% identical as compared a reference sequence comprising the sequence of SEQ ID NO:128, 130, or 160, with the proviso that the ketoreductase polypeptide comprises an amino acid sequence in which the amino acid residue corresponding to residue position 145 is a polar residue, and the amino acid residue corresponding to residue position 190 is a cysteine. The polypeptides of SEQ ID NO: 128, 130, and 160 are variants of the L. brevis, L. kefir, and L. minor ketoreductases, respectively, each having the sequence substitutions: E145S and Y190C. In some embodiments, the ketoreductase polypeptide comprises an amino acid sequence in which the amino acid residue corresponding to residue position 145 is serine, and the amino acid residue corresponding to position 190 is cysteine. In some embodiments, the ketoreductase polypeptides can have one or more residue differences at other amino acid residues as compared to the reference sequence. The differences can include substitutions, deletions, and insertions as compared to any of the reference sequences of SEQ ID NO:128, 130, or 160. The differences can be non-conservative substitutions, conservative substitutions, or a combination of non-conservative and conservative substitutions. In some embodiments, these ketoreductase polypeptides can have optionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 differences at other amino acid residues. In some embodiments, the number of differences with the reference sequence can be 1, 2, 3, 4, 5, 6, 7, 8, 9, 10, 11, 12, 14, 15, 16, 18, 20, 22, 24, 26, 30, 35 or about 40 differences at other amino acid residues. In some embodiments, the differences comprise conservative mutations as compared to the reference sequence.

In some embodiments, an improved ketoreductase polypeptide comprises an amino acid sequence based on the sequence formulas as laid out in SEQ ID NO:161, 162, or 163, or a region thereof, such as residues 90-211. The sequence formula of SEQ ID NO:161 is based on the amino acid sequence of the *Lactobacillus brevis* ketoreductase, as represented by SEQ ID NO:2. The sequence formula of SEQ ID NO:162 is based on the amino acid sequence of the *Lactobacillus kefir* ketoreductase, as represented by SEQ ID NO:4. The sequence formula of SEQ ID NO:163 is based on the amino acid sequence of the *Lactobacillus minor* ketoreductase, as represented by SEQ ID NO:158. In some embodiments, the ketoreductase polypeptide based on the sequence formulas of SEQ ID NO:161, 162, or 163 can comprise an amino acid sequence that is at least about 85%, 86%, 87%, 88%, 89%, 90%, 91%, 92%, 93%, 94%, 95%, 96%, 97%, 98%, or 99% identical to SEQ ID NO:128, 130, or 160, with the proviso that the ketoreductase polypeptide has an amino acid sequence in which the residue corresponding to X145 is a polar residue, particularly serine, and the amino acid residue corresponding to X190 is a cysteine.

In some embodiments, an improved ketoreductase polypeptide comprises an amino acid sequence based on the sequence formula of SEQ ID NO:161, 162 or 163 in which the amino acid sequence has the specified features for residues X145 and X190 as described herein, and wherein the polypeptide can further include one or more features selected from the following: residue corresponding to X3 is an acidic, a polar, or hydrophilic residue; residue corresponding to X7 is a non-polar or polar residue; residue corresponding to X17 is a non-polar, aliphatic or polar residue; residue corresponding to X21 is a non-polar, aromatic, or hydrophobic residue; residue corresponding to X25 is an acidic, non-polar or polar residue; residue corresponding to X29 is an acidic, aliphatic or non-polar residue; residue corresponding to X40 is a constrained, basic, or hydrophilic residue; residue corresponding to X42 is an acidic or a non-polar residue; residue corresponding to X53 is a non-polar or an acidic residue; residue corresponding to X75 is an acidic or polar residue; residue corresponding to X94 is a non-polar or a polar residue; residue corresponding to X95 is a non-polar or aliphatic residue; residue corresponding to X96 is a polar residue; residue corresponding to X101 is an acidic, non-polar, or a polar residue; residue corresponding to X105 is an acidic or non-polar residue; residue corresponding to X108 is a hydrophilic, polar or constrained residue; residue corresponding to X111 is a non-polar or aliphatic residue; residue corresponding to X112 is an acidic or polar residue; residue corresponding to X113 is a non-polar or aliphatic residue; residue corresponding to X117 is a non-polar or polar residue; residue corresponding to X127 is a basic or polar residue; residue corresponding to X147 is a non-polar, aromatic, or hydrophobic residue; residue corresponding to X152 is a non-polar, basic residue, or hydrophilic residue; residue corresponding to X157 is a polar residue; residue corresponding to X163 is a non-polar or aliphatic residue; residue corresponding to X176 is a non-polar or aliphatic residue; residue corresponding to X194 is a constrained, basic, or polar residue; residue corresponding to X197 is a hydrophilic, acidic, basic, aliphatic or non-polar residue; residue corresponding to X198 is an acidic, basic, hydrophilic, or non-polar residue; residue corresponding to X199 is an acidic, aliphatic, or non-polar residue; residue corresponding to X200 is an acidic or constrained residue; residue corresponding to X202 is a non-polar or aliphatic residue; residue corresponding to X206 is a non-polar, aromatic, or hydrophobic residue; residue corresponding to X211 is a basic residue; residue corresponding to X223 is a non-polar or aliphatic residue; and residue corresponding to X250 is a polar or a non-polar residue. In some embodiments, the polypeptides comprising an amino acid sequence that corresponds to the sequence formulas provided in SEQ ID NO:161, 162 or 163 (or region thereof) can have additionally one or more of the residues not specified by an X to be mutated. In some embodiments, the mutations can be 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues not defined by X above. In some embodiments, the number of mutations can be 1, 2, 3, 4, 5, 6, 7, 8, 9, 10, 11, 12, 14, 15, 16, 18, 20, 22, 24, 26, 30, 35 or about 40 mutations at other amino acid residues. In some embodiments, the mutations comprise conservative mutations.

In some of the embodiments above, the ketoreductase polypeptides comprising an amino acid sequence that corresponds to the sequence formula as laid out in SEQ ID NO:161, 162 or 163 (or region thereof) can have one or more conservatively mutations as compared to the reference sequence of SEQ ID NO:128, 130, or 160. Exemplary conservative mutations include amino acid replacements such as, but not limited to: the replacement of residue corresponding to X95 (valine) with another non-polar amino acid, e.g., alanine, leucine, isoleucine, glycine, or methionine; the replacement of residue corresponding to X96 (serine) with another polar amino acid, e.g., asparagine, glutamine, or threonine; the replacement of residue corresponding to X111 (leucine) with another non-polar amino acid, e.g., alanine, leucine, isoleucine, glycine, or methionine; the replacement of residue corresponding to X113 (valine) with another aliphatic amino acid, e.g., alanine, leucine, or isoleucine; the replacement of residue corresponding to X157 (asparagine) with another polar amino acid, e.g., glutamine, serine, or threonine; the replacement of residue corresponding to X163 (valine) with another aliphatic amino acid, e.g., alanine, leucine, or isoleucine; the replacement of residue corresponding to X176 (leucine) with another aliphatic amino acid, e.g., alanine, valine, and isoleucine; the replacement of residue corresponding to X202 (alanine) with another non-polar amino acid, e.g., alanine, leucine, isoleucine, glycine, or methionine; the replacement of residue corresponding to X211 (lysine) with another basic amino acid, e.g., arginine; the replacement of residue corresponding to X223 (isoleucine) with another aliphatic amino acid, e.g., alanine, leucine, or valine.

In some embodiments, an improved ketoreductase polypeptide comprises an amino acid sequence based on the sequence formula of SEQ ID NO:161, 162 or 163 in which the amino acid sequence has the specified features for residues X145 and X190 as described herein, and wherein the polypeptide can further include one or more features selected from the following: residue corresponding to X3 is aspartic acid, glutamic acid, serine, threonine, asparagine, or glutamine, particularly asparagine; residue corresponding to X7 is glycine, methionine, alanine, valine, leucine, isoleucine, serine, threonine, asparagine, or glutamine, particularly serine; residue corresponding to X17 is glycine, methionine, alanine, valine, leucine, isoleucine, serine, threonine, asparagine, or glutamine, particularly glutamine; residue corresponding to X21 is glycine, methionine, alanine, valine, leucine, isoleucine, tyrosine, phenylalanine, or tryptophan, particularly phenylalanine; residue corresponding to X25 is aspartic acid, glutamic acid, serine, threonine, asparagine, glutamine, glycine, methionine, alanine, valine, leucine, isoleucine, particularly threonine; residue corresponding to X29 is aspartic acid, glutamine acid, glycine, methionine, alanine, valine, leucine, or isoleucine, particularly glycine or alanine; residue corresponding to X40 is histidine, lysine, arginine, serine, threonine, asparagine, or glutamine, particularly arginine; residue corresponding to X42 is aspartic acid, glutamic acid, glycine, methionine, alanine, valine, leucine, or isoleucine, particularly glycine; residue corresponding to X53 is glycine, methionine, alanine, valine, leucine, isoleucine, aspartic acid, glutamic acid, particularly aspartic acid; residue corresponding to X75 is aspartic acid, glutamic acid, serine, threonine, asparagine, or glutamine, particularly arginine; residue corresponding to X94 is glycine, methionine, alanine, valine, leucine, isoleucine, serine, threonine, asparagine, or glutamine, particularly asparagine, glycine, or serine; residue corresponding to X95 is a glycine, methionine, alanine, valine, leucine, or isoleucine, particularly leucine or methionine; residue corresponding to X96 is serine, threonine, asparagine, glutamine, particularly glutamine, asparagine, or threonine; residue; residue corresponding to X101 is aspartic acid, glutamic acid, serine, threonine, asparagine, glutamine, or glycine, methionine, alanine, valine, leucine, or isoleucine, particularly glycine or asparagine; residue corresponding to X105 is glutamic acid, aspartic acid, glycine, methionine, alanine, valine, leucine, isoleucine, particularly glycine; residue corresponding to X108 arginine, lysine, serine, threonine, asparagine, glutamine, histidine, particularly histidine or serine; residue corresponding to X111 is glycine, methionine, alanine, valine, leucine, or isoleucine, particularly methionine; or aliphatic residue; residue corresponding to X112 is aspartic acid, glutamic acid, serine, threonine, asparagine, glutamine, particularly aspartic acid; residue corresponding to X113 is an glycine, methionine, alanine, valine, leucine, isoleucine, particularly alanine; residue corresponding to X117 is glycine, methionine, alanine, valine, leucine, isoleucine, serine, threonine, asparagine, or glutamine, particularly serine; residue corresponding to X127 is lysine, arginine, serine, threonine, asparagine, or glutamine, particularly arginine; residue corresponding to X147 is glycine, methionine, alanine, valine, leucine, isoleucine, tyrosine, phenylalanine, tryptophan, particularly leucine; residue corresponding to X152 is glycine, methionine, valine, leucine, isoleucine, arginine, lysine, serine threonine, asparagine, or glutamine, particularly methionine or lysine; residue corresponding to X157 is a serine, threonine, asparagine, and glutamine, particularly threonine; residue corresponding to X163 is a glycine, methionine, alanine, valine, leucine, or isoleucine, particularly isoleucine; residue corresponding to X176 is glycine, methionine, alanine, valine, leucine, or isoleucine, particularly valine; residue corresponding to X194 is proline, arginine, lysine, serine, threonine, asparagine, glutamine, particularly arginine or glutamine; residue corresponding to X197 is aspartic acid, glutamic acid, arginine, lysine, serine, threonine, asparagine, glutamine, glycine, methionine, alanine, valine, leucine, isoleucine, particularly valine or glutamic acid; residue corresponding to X198 is aspartic acid, glutamic acid, arginine, lysine, serine, threonine, asparagine, glutamine, glycine, methionine, alanine, valine, leucine, or isoleucine, particularly glycine, glutamic acid, or lysine; residue corresponding to X199 is an aspartic acid, glutamic acid, glycine, methionine, alanine, valine, leucine, or isoleucine, particularly aspartic acid; residue corresponding to X200 is an aspartic acid, glutamic acid, or proline, particularly proline; residue corresponding to X202 is glycine, methionine, alanine, valine, leucine, isoleucine, particularly glycine; residue corresponding to X206 is a glycine, methionine, alanine, valine, leucine, isoleucine, tyrosine, phenylalanine, tryptophan, particularly glycine; residue corresponding to X211 is a arginine or lysine; residue corresponding to X223 is glycine, methionine, alanine, valine, leucine, or isoleucine, particularly valine; and residue corresponding to X250 is serine, threonine, asparagine, glutamine, glycine, methionine, alanine, valine, leucine, isoleucine, particularly isoleucine. In some embodiments, the polypeptides comprising an amino acid sequence that corresponds to the sequence formulas of SEQ ID NO:161, 162 or 163 (or region thereof) can have additionally one or more of the residues not specified by an X to be mutated as compared to the reference sequence of SEQ ID NO:128, 130, or 160. In some embodiments, the mutations can be 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues not defined by X above. In some embodiments, the number of mutations can be 1, 2, 3, 4, 5, 6, 7, 8, 9, 10, 11, 12, 14, 15, 16, 18, 20, 22, 24, 26, 30, 35 or about 40 mutations at other amino acid residues. In some embodiments, the mutations comprise conservative mutations.

In some embodiments, an improved ketoreductase polypeptide comprises an amino acid sequence based on the sequence formula of SEQ ID NO:161, 162 or 163 in which the amino acid sequence has the specified features for residues X145 and X190 as described herein, and wherein the polypeptide can further include one or more or at least all of the features selected from the following: the residue corresponding to X7 is a non-polar or polar residue; residue corresponding to X108 is a hydrophilic, polar or constrained residue; residue corresponding to X117 is a non-polar or a polar residue; residue corresponding to X152 is a non-polar, basic, or hydrophilic residue; and residue corresponding to X199 is an acidic, aliphatic, or non-polar residue. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, an improved ketoreductase polypeptide comprises an amino acid sequence based on the sequence formula of SEQ ID NO:161, 162 or 163 in which the amino acid sequence has the specified features for residues X145 and X190 as described herein, and wherein the polypeptide can further include one or more or at least all of the features selected from the following: the residue corresponding to X7 is glycine, methionine, alanine, valine, leucine, isoleucine, serine, threonine, asparagine, or glutamine, particularly serine; residue corresponding to X108 is arginine, lysine, serine, threonine, asparagine, glutamine, histidine, particularly histidine or serine; residue corresponding to X117 is glycine, methionine, alanine, valine, leucine, isoleucine, serine, threonine, asparagine, or glutamine, particularly serine; residue corresponding to X152 is glycine, methionine, valine, leucine, isoleucine, arginine, lysine, serine threonine, asparagine, or glutamine, particularly methionine or lysine; and residue corresponding to X199 is aspartic acid, glutamic acid, glycine, methionine, alanine, valine, leucine, or isoleucine, particularly aspartic acid. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, an improved ketoreductase polypeptide comprises an amino acid sequence based on the sequence formula of SEQ ID NO:161, 162 or 163 in which the amino acid sequence has the specified features for residues X145 and X190 as described herein, and wherein the polypeptide can further include one or more or at least all of the features selected from the following: residue corresponding to X3 is an acidic, polar, or hydrophilic residue; residue corresponding to X17 is a non-polar, aliphatic or polar residue; residue corresponding to X25 is an acidic, non-polar or polar residue; residue corresponding to X42 is an acidic or non-polar residue; residue corresponding to X94 is a non-polar or a polar residue; residue corresponding to X194 is a constrained, basic, or polar residue; residue corresponding to X198 is an acidic, basic, hydrophilic, or non-polar residue; and residue corresponding to X200 is an acidic or a constrained residue. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, an improved ketoreductase polypeptide comprises an amino acid sequence based on the sequence formula of SEQ ID NO:161, 162 or 163 in which the amino acid sequence has the specified features for residues X145 and X190 as described herein, and wherein the polypeptide can further include one or more or at least all of the features selected from the following: residue corresponding to X3 is aspartic acid, glutamic acid, serine, threonine, asparagine, or glutamine, particularly asparagine; residue corresponding to X17 is glycine, methionine, alanine, valine, leucine, isoleucine, serine, threonine, asparagine, or glutamine, particularly glutamine; residue corresponding to X25 is aspartic acid, glutamic acid, serine, threonine, asparagine, glutamine, glycine, methionine, alanine, valine, leucine, isoleucine, particularly threonine; residue corresponding to X42 is aspartic acid, glutamic acid, glycine, methionine, alanine, valine, leucine, or isoleucine, particularly glycine; residue corresponding to X94 is glycine, methionine, alanine, valine, leucine, isoleucine, serine, threonine, asparagine, or glutamine, particularly asparagine, glycine, or serine; residue corresponding to X194 is proline, arginine, lysine, serine, threonine, asparagine, glutamine, particularly arginine or glutamine; residue corresponding to X198 is aspartic acid, glutamic acid, arginine, lysine, serine, threonine, asparagine, glutamine, glycine, methionine, alanine, valine, leucine, or isoleucine, particularly glycine, glutamic acid, or lysine; residue corresponding to X200 is aspartic acid, glutamic acid, or proline, particularly proline. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, an improved ketoreductase polypeptide comprises an amino acid sequence based on the sequence formula of SEQ ID NO:161, 162 or 163 in which the amino acid sequence has the specified features for residues X145 and X190 as described herein, and wherein the polypeptide can further include one or more or at least all of the features selected from the following: residue corresponding to X3 is an acidic, polar, or hydrophilic residue; residue corresponding to X7 is a non-polar or polar residue; residue corresponding to X17 is a non-polar, aliphatic or polar residue; residue corresponding to X25 is an acidic, non-polar or polar residue; residue corresponding to X42 is an acidic or non-polar residue; residue corresponding to X94 is a non-polar or a polar residue; residue corresponding to X108 is a hydrophilic, polar or constrained residue; residue corresponding to X117 is a non-polar or a polar residue; residue corresponding to X152 is a non-polar, basic, or hydrophilic residue; residue corresponding to X194 is a constrained, basic, or polar residue; residue corresponding to X198 is an acidic, basic, hydrophilic, or non-polar residue; residue corresponding to X199 is an acidic, aliphatic, or non-polar residue; residue corresponding to X200 is an acidic or constrained residue. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, an improved ketoreductase polypeptide comprises an amino acid sequence based on the sequence formula of SEQ ID NO:161, 162 or 163 in which the amino acid sequence has the specified features for residues X145 and X190 as described herein, and wherein the polypeptide can further include one or more or at least all of the features selected from the following: residue corresponding to X3 is aspartic acid, glutamic acid, serine, threonine, asparagine, or glutamine, particularly asparagine; residue corresponding to X7 is glycine, methionine, alanine, valine, leucine, isoleucine, serine, threonine, asparagine, or glutamine, particularly serine; residue corresponding to X17 is glycine, methionine, alanine, valine, leucine, isoleucine, serine, threonine, asparagine, or glutamine, particularly glutamine; residue corresponding to X25 is aspartic acid, glutamic acid, serine, threonine, asparagine, glutamine, glycine, methionine, alanine, valine, leucine, isoleucine, particularly threonine; residue corresponding to X42 is aspartic acid, glutamic acid, glycine, methionine, alanine, valine, leucine, or isoleucine, particularly glycine; residue corresponding to X94 is glycine, methionine, alanine, valine, leucine, isoleucine, serine, threonine, asparagine, or glutamine, particularly asparagine, glycine, or serine; residue corresponding to X108 is arginine, lysine, serine, threonine, asparagine, glutamine, histidine, particularly histidine or serine; residue corresponding to X117 is glycine, methionine, alanine, valine, leucine, isoleucine, serine, threonine, asparagine, or glutamine, particularly serine; residue corresponding to X152 is glycine, methionine, valine, leucine, isoleucine, arginine, lysine, serine threonine, asparagine, or glutamine, particularly methionine or lysine; residue corresponding to X194 is proline, arginine, lysine, serine, threonine, asparagine, glutamine, particularly arginine or glutamine; residue corresponding to X198 is aspartic acid, glutamic acid, arginine, lysine, serine, threonine, asparagine, glutamine, glycine, methionine, alanine, valine, leucine, or isoleucine, particularly glycine; residue corresponding to X199 is an aspartic acid, glutamic acid, glycine, methionine, alanine, valine, leucine, or isoleucine, particularly aspartic acid; residue corresponding to X200 is aspartic acid, glutamic acid, or proline, particularly proline. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X3 is an acidic, a polar, or hydrophilic residue, particularly asparagine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X7 is a non-polar or polar residue, particularly serine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X17 is a non-polar, aliphatic or polar residue, particularly glutamine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X21 is a non-polar, aromatic, or hydrophobic residue, particularly phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X25 is an acidic, non-polar or polar residue, particularly threonine or serine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X29 is an acidic, aliphatic or non-polar residue, particularly alanine or glycine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, have at least the following features: amino acid residue corresponding to X145 is a polar residue, particularly serine; amino acid residue corresponding to X190 is a cysteine; and amino acid residue corresponding to X40 is a constrained, basic, or hydrophilic residue, particularly arginine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X42 is an acidic or a non-polar residue, particularly glycine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X53 is a non-polar or an acidic residue, particularly aspartic acid. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X75 is an acidic or polar residue, particularly asparagine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X94 is a non-polar or a polar residue, particularly glycine, serine, or asparagine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162, or 163, or region thereof, such as residues 90-211, in which the amino acid sequence has at least the following features: amino acid residue corresponding to X145 is a polar residue, particularly serine; amino acid residue corresponding to X190 is a cysteine; and the amino acid residue corresponding to X95 is a non-polar or aliphatic residue, particularly leucine or methionine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:128, 130, or 160, or region thereof, such as residues 90-211, in which the amino acid sequence has at least the following features: amino acid residues corresponding to X145 is a polar residue, particularly serine; amino acid residue corresponding to X190 is a cysteine; and the amino acid residue corresponding to X96 is a polar residue, particularly threonine, asparagine or glutamine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X101 is an acidic, non-polar, or a polar residue, particularly asparagine or glycine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X105 is an acidic or non-polar residue, particularly glycine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X108 is a hydrophilic, polar or constrained residue, particularly histidine, serine or asparagine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X111 is a non-polar or aliphatic residue, particularly methionine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X112 is an acidic or polar residue, particularly aspartic acid. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residues corresponding to X145 is a polar residue, particularly serine; amino acid residue corresponding to X190 is a cysteine; and amino acid residue corresponding to X113 is a non-polar or aliphatic residue, particularly alanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X117 is a non-polar or a polar residue, particularly serine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X127 is a basic or polar residue, particularly arginine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X147 is a non-polar, aliphatic, aromatic, or hydrophobic residue, particularly leucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X152 is a non-polar, basic residue, or hydrophilic residue, particularly, methionine or lysine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X157 is a polar residue, particularly threonine or serine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X163 is a non-polar or aliphatic residue, particularly isoleucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X176 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X194 is a basic constrained, basic, or polar residue, particularly arginine or glutamine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X197 is a hydrophilic, acidic, basic, aliphatic or a non-polar residue, particularly glutamic acid or valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X198 is an acidic, basic, hydrophilic, or non-polar residue, particularly glycine, lysine, or glutamic acid. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X199 is an acidic, aliphatic, or non-polar residue, and particularly aspartic acid. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X200 is an acidic or a constrained residue, particularly proline. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X202 is a non-polar residue, and particularly glycine. In some embodiments, the ketoreductase polypeptide can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X206 is a non-polar, aromatic, or hydrophobic residue, and particularly glycine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, have at least the following features: amino acid residue corresponding to X145 is a serine; amino acid residue corresponding to X190 is a cysteine; and amino acid residue corresponding to X211 is a basic residue, particularly arginine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, the improved ketoreductase polypeptides comprising an amino acid sequence based on the sequence formula of SEQ ID NO:161, 162 or 163, or region thereof, such as residues 90-211, in which the amino acid sequence has at least the following features: amino acid residue corresponding to X145 is a polar residue, particularly serine; amino acid residue corresponding to X190 is a cysteine; and amino acid residue corresponding to X250 is a polar or a non-polar residue, particularly isoleucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:128, 130, or 160. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to a reference sequence based on SEQ ID NO:128, 130, or 160 with the preceding features.

In some embodiments, an improved ketoreductase comprises an amino acid sequence that is at least about 85%, 86%, 87%, 88%, 89%, 90%, 91%, 92%, 93%, 94%, 95%, 96%, 97%, 98%, or 99% identical to the amino acid sequence corresponding to SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, or 98 as listed in Tables 3 and 4, wherein the improved ketoreductase polypeptide amino acid sequence includes any one set of the specified amino acid substitution combinations presented in Tables 3 and 4. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved ketoreductase comprises an amino acid sequence corresponding to SEQ ID NO: 8, 42, 44, 46, 48, 50, 52, 54, 56, 58, 60, 62, 64, 66, 68, 70, 72, 74, 76, 78, 80, 82, 84, 86, 88, 90, 92, 96, 98, 100, 102, 104, 106, 108, 110, 112, 114, 116, 118, 120, 122, 124, and 126.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X108 is a hydrophilic, polar or constrained residue, particularly histidine or serine; residue corresponding to X117 is a non-polar or a polar residue, particularly serine; residue corresponding to X145 is a polar residue, particularly serine; residue corresponding to X157 is a polar residue, particularly threonine; residue corresponding to X190 is a cysteine; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:8. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 8.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X94 is a non-polar or a polar residue, particularly serine; residue corresponding to X108 is a hydrophilic, polar or constrained residue, particularly histidine, residue corresponding to X117 is a non-polar or a polar residue, particularly serine; residue corresponding to X145 is a polar residue, particularly serine; residue corresponding to X157 is a polar residue, particularly threonine; residue corresponding to X190 is a cysteine; residue corresponding to X199 is an acidic, aliphatic, or non-polar residue, particularly aspartic acid; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:42. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 42.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X96 is a polar residue, particularly glutamine; residue corresponding to X108 is a hydrophilic, polar or constrained residue, particularly histidine; residue corresponding to X117 is a non-polar or a polar residue, particularly serine; residue corresponding to X145 is a polar residue, particularly serine; residue corresponding to X157 is a polar residue, particularly threonine; residue corresponding to X190 is cysteine; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:44. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 44.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X108 is a hydrophilic, polar or constrained residue, particularly histidine; residue corresponding to X117 is non-polar or a polar residue, particularly serine; residue corresponding to X145 is a polar residue, particularly serine; residue corresponding to X157 is a polar residue, particularly threonine; residue corresponding to X190 is a cysteine; residue corresponding to X199 is an acidic, aliphatic, or non-polar residue, particularly aspartic acid; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:46. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 46.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X108 is hydrophilic, polar or constrained residue, particularly histidine; residue corresponding to X117 is non-polar or a polar residue, particularly serine; residue corresponding to X145 is a polar residue, particularly serine; residue corresponding to X157 is a polar residue, particularly threonine; residue corresponding to X190 is cysteine; residue corresponding to X202 is a is a non-polar residue or aliphatic residue, particularly glycine; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:48. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 48.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X108 is a hydrophilic, polar or constrained residue, particularly histidine; residue corresponding to X117 is a non-polar or a polar residue, particularly serine; residue corresponding to X145 is a polar residue, particularly serine; residue corresponding to X152 is a non-polar or basic residue, particularly methionine or lysine; residue corresponding to X157 is a polar residue, particularly threonine; residue corresponding to X190 is a cysteine; residue corresponding to X199 is an acidic, aliphatic, or non-polar residue, particularly aspartic acid; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:52 or 54. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to 52 or 54.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X94 is a non-polar or a polar residue, particularly serine; residue corresponding to X96 is a polar residue, particularly glutamine; residue corresponding to X108 is a hydrophilic, polar or constrained residue, particularly histidine; residue corresponding to X117 is a non-polar or a polar residue, particularly serine; residue corresponding to X145 is a polar residue, particularly serine; residue corresponding to X157 is a polar residue, particularly threonine; residue corresponding to X190 is a cysteine; residue corresponding to X199 is an acidic, aliphatic, or non-polar residue, particularly aspartic acid; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:56. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:56.

In some embodiments, an improved ketoreductase comprises an amino acid sequence based on the sequence formula of SEQ ID NO:161, 162 or 163, or a region thereof, such as residues 90 to 211, and has at least the following features: corresponding to X7 is a non-polar or polar residue, particularly serine; residue corresponding to X108 is a hydrophilic, polar or constrained residue, particularly histidine; residue corresponding to X117 is a non-polar or a polar residue, particularly serine; residue corresponding to X145 is a polar residue, particularly serine; residue corresponding to X157 is a polar residue, particularly threonine; residue corresponding to X190 is a cysteine; residue corresponding to X194 is a constrained, basic, or polar residue, particularly arginine; residue corresponding to X199 is an acidic, aliphatic, or non-polar residue, particularly aspartic acid; and residue corresponding to X211 is a basic residue. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:58. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 58.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X96 is a polar residue, particularly glutamine or threonine; residue corresponding to X108 is a hydrophilic, polar or constrained residue, particularly, histidine; residue corresponding to X117 is a non-polar or a polar residue, particularly serine; residue corresponding to X145 is a polar residue, particularly serine; residue corresponding to X152 is a non-polar, basic residue, or hydrophilic residue, particularly methionine; residue corresponding to X157 is a polar residue, particularly threonine; residue corresponding to X190 is a cysteine; residue corresponding to X194 is a constrained, basic, or polar residue, particularly arginine; residue corresponding to X199 is an acidic, aliphatic, or non-polar residue, particularly aspartic acid; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:72 or 74. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 72 or 74.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X25 is an acidic, non-polar or polar residue, particularly threonine; residue corresponding to X40 is a constrained, basic, or hydrophilic residue; residue corresponding to X75 is an acidic or polar residue, particularly asparagine; residue corresponding to X96 is a polar residue, particularly glutamine; residue corresponding to X108 is a hydrophilic, polar or constrained residue, particularly histidine; residue corresponding to X117 is a non-polar or a polar residue, particularly serine; residue corresponding to X145 is a polar residue, particularly serine; residue corresponding to X152 is a non-polar, basic residue, or hydrophilic residue, particularly methionine; residue corresponding to X157 is a polar residue, particularly threonine; residue corresponding to X190 is a cysteine; residue corresponding to X199 is an acidic, aliphatic, or non-polar residue, particularly aspartic acid; residue corresponding to X211 is a basic residue, particularly arginine, and residue X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:76. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: SEQ ID NO: 76.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X25 is a acidic, non-polar or polar residue, particularly threonine; residue corresponding to X95 is a non-polar or aliphatic residue, particularly leucine; residue corresponding to X96 is a polar residue, particularly glutamine; residue corresponding to X108 is a hydrophilic, polar or constrained residue, particularly histidine; residue corresponding to X117 is a non-polar or a polar residue, particularly serine; residue corresponding to X145 is a polar residue, particularly serine; residue corresponding to X152 is a non-polar, basic residue, or hydrophilic residue, particularly methionine; residue corresponding to X176 is non-polar or aliphatic residue, particularly valine; residue corresponding to X190 is a cysteine; residue corresponding to X198 is an acidic, basic, hydrophilic, or non-polar residue, particularly glutamic acid; residue corresponding to X199 is an acidic, aliphatic, or non-polar residue, particularly aspartic acid; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:82. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 82.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X25 is an acidic, non-polar or polar residue, particularly threonine; residue corresponding to X95 is a non-polar or aliphatic residue, particularly leucine; residue corresponding to X96 is a polar residue, particularly glutamine; residue corresponding to X108 is a hydrophilic, polar or constrained residue, particularly histidine; residue corresponding to X117 is a non-polar or a polar residue, particularly serine; residue corresponding to X145 is a polar residue, particularly serine; residue corresponding to X152 is a non-polar, basic residue, or hydrophilic residue, particularly methionine; residue corresponding to X176 is a non-polar or aliphatic residue, particularly valine; residue corresponding to X190 is a cysteine; residue corresponding to X197 is a hydrophilic, acidic, basic, aliphatic or a non-polar residue, particularly valine; residue corresponding to X199 is an acidic, aliphatic, or non-polar residue, particularly aspartic acid; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:84. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 84.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X25 is a acidic, non-polar or polar residue, particularly threonine; residue corresponding to X95 is a non-polar or aliphatic residue, particularly methionine; residue corresponding to X96 is a polar residue, particularly glutamine; residue corresponding to X108 is a hydrophilic, polar or constrained residue, particularly histidine; residue corresponding to X117 is a non-polar or a polar residue, particularly serine; residue corresponding to X145 is a polar residue, particularly serine; residue corresponding to X152 is a non-polar, basic residue, or hydrophilic residue, particularly methionine; residue corresponding to X176 is a non-polar or aliphatic residue, particularly valine; residue corresponding to X190 is a cysteine; residue corresponding to X194 is a constrained, basic, or polar residue, particularly arginine; residue corresponding to X199 is an acidic, aliphatic, or non-polar residue, particularly aspartic acid; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: SEQ ID NO: 86.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X96 is a polar residue, particularly glutamine; residue corresponding to X145 is a polar residue, particularly serine; residue corresponding to X152 is a non-polar, basic residue, or hydrophilic residue, particularly methionine; residue corresponding to X190 is a cysteine; residue corresponding to X199 is an acidic, aliphatic, or non-polar residue, particularly aspartic acid; and residue corresponding to X211 is a basic residue, particularly arginine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:90. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 90.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X53 is a non-polar or an acidic residue, particularly aspartic acid; residue corresponding to X96 is a polar residue, particularly glutamine; residue corresponding to X108 is a hydrophilic, polar or constrained residue, particularly histidine; residue corresponding to X117 is a non-polar or a polar residue, particularly serine; residue corresponding to residue X145 is a polar residue, particularly serine; residue corresponding to X152 is a non-polar, basic residue, or hydrophilic residue, particularly methionine; residue corresponding to X163 is a non-polar or aliphatic residue, particularly isoleucine; residue corresponding to X190 is a cysteine; residue corresponding to X199 is an acidic, aliphatic, or non-polar residue, particularly aspartic acid; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:94. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 94.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X96 is a polar residue, particularly glutamine; residue corresponding to X101 is acidic, non-polar, or a polar residue, particularly glycine; residue corresponding to X108 is hydrophilic, polar or constrained residue, particularly histidine; residue corresponding to X117 is non-polar or a polar residue, particularly serine; residue corresponding to X145 is a polar residue, particularly serine; residue corresponding to X147 is non-polar, aliphatic, aromatic, or hydrophobic residue, particularly leucine; residue corresponding to X152 is non-polar, basic residue, particularly methionine; residue corresponding to X190 is cysteine; residue corresponding to X199 is an acidic, aliphatic, or non-polar residue, particularly aspartic acid; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:100. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 100.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X96 is a polar residue, particularly glutamine; residue corresponding to X108 is a hydrophilic, polar or constrained residue, particularly histidine; residue corresponding to X111 is a non-polar or aliphatic residue, particularly methionine; residue corresponding to X117 is a non-polar or a polar residue, particularly serine; residue corresponding to X145 is a polar residue, particularly serine; residue corresponding to X152 is a non-polar, basic residue, or hydrophilic residue, particularly methionine; residue corresponding to X190 is a cysteine; residue corresponding to X199 is an acidic, aliphatic, or non-polar residue, particularly aspartic acid; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:102. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 102.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X96 is a polar residue, particularly glutamine; residue corresponding to X108 is a hydrophilic, polar or constrained residue, particularly histidine; residue corresponding to X117 is a non-polar or a polar residue, particularly serine; residue corresponding to X145 is a polar residue, particularly serine; residue corresponding to X152 is a non-polar, basic residue, or hydrophilic residue, particularly methionine; residue corresponding to X190 is a cysteine; residue corresponding to X199 is an acidic, aliphatic, or non-polar residue, particularly aspartic acid; residue corresponding to X211 is a basic residue, particularly arginine; and residue corresponding to X223 is a non-polar or aliphatic residue, particularly valine; and residue corresponding to X250 is a polar or non-polar residue, particularly isoleucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:104. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:104.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X29 is an acidic, aliphatic or non-polar residue, particularly glycine; residue corresponding to X96 is a polar residue, particularly glutamine; residue corresponding to X101 is an acidic, non-polar, or a polar residue, particularly asparagine; residue corresponding to X108 is a hydrophilic, polar or constrained residue, particularly histidine; residue corresponding to X117 is a non-polar or polar residue, particularly serine; residue corresponding to X145 is a polar residue, particularly serine; residue corresponding to X152 is a non-polar, basic residue, or hydrophilic residue, particularly methionine; residue corresponding to X190 is a cysteine; residue corresponding to X199 is an acidic, aliphatic, or non-polar residue, particularly aspartic acid; residue corresponding to X200 is an acidic or a constrained residue, particularly proline; residue corresponding to X211 is a basic residue, particularly arginine, and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:106. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 106.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X3 is an acidic, polar, or hydrophilic residue, particularly asparagine; residue corresponding to X7 is a non-polar or polar residue, particularly serine; residue corresponding to X17 is a non-polar, aliphatic or polar residue, particularly glutamine; residue corresponding to X42 is an acidic or non-polar residue, particularly glycine; residue corresponding to X96 is a polar residue, particularly glutamine; residue corresponding to X108 is a hydrophilic, polar or constrained residue, particularly histidine; residue corresponding to X127 is a basic or polar residue, particularly arginine; residue corresponding to X145 is a polar residue, particularly serine; residue corresponding to X152 is a non-polar, basic residue, or hydrophilic residue, particularly methionine; residue corresponding to X176 is a non-polar or aliphatic residue, particularly valine; residue corresponding to X190 is a cysteine; residue corresponding to X194 is a constrained, basic, or polar residue, particularly arginine; residue corresponding to X199 is an acidic, aliphatic, or non-polar residue, particularly aspartic acid; residue corresponding to X200 is an acidic or a constrained residue, particularly proline; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:114. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 114.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X3 is an acidic, polar, or hydrophilic residue, particularly asparagine; residue corresponding to X7 is a non-polar or polar residue, particularly serine; residue corresponding to X17 is a non-polar, aliphatic or polar residue, particularly glutamine; residue corresponding to X21 is a non-polar, aromatic, or hydrophobic residue, particularly phenylalanine; residue corresponding to X96 is a polar residue, particularly glutamine; residue corresponding to X108 is a hydrophilic, polar or constrained residue, particularly histidine; residue corresponding to X145 is a polar residue, particularly serine; residue corresponding to X147 is a non-polar, aliphatic, aromatic, or hydrophobic residue, particularly leucine; residue corresponding to X152 is a non-polar, basic, or hydrophilic residue, particularly methionine; residue corresponding to X176 is a non-polar or aliphatic residue, particularly valine; residue corresponding to X190 is a cysteine; residue corresponding to X199 is an acidic, aliphatic, or non-polar residue, particularly aspartic acid; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:116. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:116.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X3 is an acidic, polar, or hydrophilic residue, particularly asparagine; residue corresponding to X7 is a non-polar or polar residue, particularly serine; residue corresponding to X17 is a non-polar, aliphatic or polar residue, particularly glutamine; residue corresponding to X29 is an acidic, aliphatic or non-polar residue, particularly alanine; residue corresponding to X42 is an acidic or non-polar residue, particularly glycine; residue corresponding to X96 is a polar residue, particularly glutamine; residue corresponding to X105 is an acidic or non-polar residue, particularly glycine; residue corresponding to X108 is a hydrophilic, polar or constrained residue, particularly histidine; residue corresponding to X117 is a non-polar or a polar residue, particularly serine; residue corresponding to X145 is a polar residue, particularly serine; residue corresponding to X152 is a non-polar, basic, or hydrophilic residue, particularly methionine; residue corresponding to X190 is a cysteine; residue corresponding to X197 is a hydrophilic, acidic, basic, aliphatic or a non-polar residue, particularly valine; residue corresponding to X198 is an acidic, basic, hydrophilic, or non-polar residue, particularly lysine; residue corresponding to X199 is an acidic, aliphatic, or non-polar residue, particularly aspartic acid; residue corresponding to X200 is an acidic or a constrained residue, particularly proline; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:118. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 118.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X17 is a non-polar, aliphatic or polar residue, particularly glutamine; residue X29 is an acidic, aliphatic or non-polar residue, particularly alanine; residue corresponding to X96 is a polar residue, particularly glutamine; residue corresponding to X108 is a hydrophilic, polar or constrained residue, particularly histidine; residue corresponding to X117 is a non-polar or a polar residue, particularly serine; residue corresponding to X145 is a polar residue, particularly serine; residue corresponding to X152 is a non-polar, basic, or hydrophilic residue, particularly methionine; residue corresponding to X163 is a non-polar or aliphatic residue, particularly isoleucine; residue corresponding to X190 is a cysteine; residue corresponding to X198 is an acidic, basic, hydrophilic, or non-polar residue, particularly lysine; residue corresponding to X199 is an acidic, aliphatic, or non-polar residue, particularly aspartic acid; residue corresponding to X200 is an acidic or a constrained residue, particularly proline; and residue corresponding to X211 is a basic residue, particularly arginine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:122. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO:122.

In some embodiments, an improved ketoreductase comprises an amino acid sequence based on the sequence formula of SEQ ID NO:161, 162 or 163, or a region thereof, such as residues 90 to 211, and has at least the following features: residue corresponding to X7 is a non-polar or polar residue, particularly serine; residue corresponding to X17 is a non-polar, aliphatic or polar residue, particularly glutamine; residue corresponding to X29 is an acidic, aliphatic or non-polar residue, particularly alanine; residue corresponding to X96 is a polar residue, particularly glutamine; residue corresponding to X108 is a hydrophilic, polar or constrained residue, particularly histidine; residue corresponding to X117 is a non-polar or a polar residue, particularly serine; residue corresponding to X145 is polar residue, particularly serine; residue corresponding to X147 is a non-polar, aliphatic, aromatic, or hydrophobic residue, particularly leucine; residue corresponding to X152 is a non-polar, basic, or hydrophilic residue, particularly methionine; residue corresponding to X163 is a non-polar or aliphatic residue, particularly isoleucine; residue corresponding to X176 is a non-polar or aliphatic residue, particularly valine; residue corresponding to X190 is a cysteine; residue corresponding to X198 is an acidic, basic, hydrophilic, or non-polar residue, particularly lysine; residue corresponding to X199 is an acidic, aliphatic, or non-polar residue, particularly aspartic acid; residue corresponding to X200 is an acidic or a constrained residue, particularly proline; residue corresponding to X211 is a basic residue, particularly arginine; and residue corresponding to X223 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:126. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to SEQ ID NO: 126.

In some embodiments, an improved ketoreductase comprises an amino acid sequence that has a region or domain corresponding to residues 90-211 of the sequence formula of SEQ ID NO:161, 162 or 163, in which the amino acid sequence of the domain has at least the following features: the amino acid residue corresponding to X145 is a polar residue, and the amino acid residue corresponding to X190 is a cysteine. In some embodiments, the improved ketoreductase has a region or domain that corresponds to residues 90-211 based on the sequence formula of SEQ ID NO:161, 162 or 163, in which the amino acid sequence of the domain has at least the following features: the amino acid residue corresponding to X145 is a serine, and the amino acid residue corresponding to X190 is a cysteine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the corresponding domain of a reference sequence based on SEQ ID NO:128, 130, or 160. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:128, 130, Or 160 with the preceding features.

In some embodiments, the ketoreductase polypeptides with a domain or region corresponding to residues 90-211 and having the specified features for residues X145 and X190 as described herein, can further include in the region or domain one or more features selected from the following: residue corresponding to X94 is a non-polar or a polar residue; residue corresponding to X95 is a non-polar or aliphatic residue; residue corresponding to X96 is a polar residue; residue corresponding to X101 is an acidic, non-polar, or a polar residue; residue corresponding to X105 is an acidic or non-polar residue; residue corresponding to X108 is a hydrophilic, polar or constrained residue; residue corresponding to X111 is a non-polar or aliphatic residue; residue corresponding to X112 is an acidic or polar residue; residue corresponding to X113 is a non-polar or aliphatic residue; residue corresponding to X117 is a non-polar or a polar residue; residue corresponding to X127 is a basic or polar residue; residue corresponding to X147 is a non-polar, aliphatic, aromatic, or hydrophobic residue; residue corresponding to X152 is a non-polar, basic, or hydrophilic residue; residue corresponding to X157 is a polar residue; residue corresponding to X163 is a non-polar or aliphatic residue; residue corresponding to X176 is a non-polar or aliphatic residue; residue corresponding to X194 is a constrained, basic, or polar residue; residue corresponding to X197 is a hydrophilic, acidic, basic, aliphatic or a non-polar residue; residue corresponding to X198 is an acidic, basic, hydrophilic, or non-polar residue; residue corresponding to X199 is an acidic, aliphatic, or non-polar residue; residue corresponding to X200 is an acidic or constrained residue; residue corresponding to X202 is a non-polar residue; residue corresponding to X206 is a non-polar, aromatic, or hydrophobic residue; residue corresponding to X211 is a basic residue. In some embodiments, the region or domain corresponding to residues 90-211 can have additionally from about 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the corresponding domain of a reference sequence based on SEQ ID NO:128, 130, or 160. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations.

In some embodiments, the ketoreductases polypeptides having a domain with an amino acid sequence corresponding to residues 90-211 of the sequence formula of SEQ ID NO:161, 162 or 163, as described above, can have one or more conservative mutations as compared to the corresponding domain of SEQ ID NO:128, 130, or 160. Examples of such conservative mutations include amino acid replacements such as, but not limited to: the replacement of residue corresponding to X95 (valine) with another non-polar amino acid, e.g., alanine, leucine, isoleucine, glycine, or methionine; the replacement of residue corresponding to X96 (serine) with another polar amino acid, e.g., asparagine, glutamine, or threonine; the replacement of residue corresponding to X111 (leucine) with another non-polar amino acid, e.g., alanine, leucine, isoleucine, glycine, or methionine; the replacement of residue corresponding to X113 (valine) with another aliphatic amino acid, e.g., alanine, leucine, or isoleucine; the replacement of residue corresponding to X157 (asparagine) with another polar amino acid, e.g., glutamine, serine, or threonine; the replacement of residue corresponding to X163 (valine) with another aliphatic amino acid, e.g., alanine, leucine, or isoleucine; the replacement of residue corresponding to X176 (leucine) with another aliphatic amino acid, e.g., alanine, valine, and isoleucine; the replacement of residue corresponding to X202 (alanine) with another non-polar amino acid, e.g., alanine, leucine, isoleucine, glycine, or methionine; and the replacement of residue corresponding to X211 (lysine) with another basic amino acid, e.g., arginine.

In some embodiments, the ketoreductase polypeptides with a domain or region corresponding to residues 90-211 and having the specified features for residues X145 and X190 as described herein, can further include in the region or domain one or more features selected from the following: residue corresponding to X94 is glycine, methionine, alanine, valine, leucine, isoleucine, serine, threonine, asparagine, or glutamine, particularly asparagine, glycine, or serine; residue corresponding to X95 is a glycine, methionine, alanine, valine, leucine, or isoleucine, particularly leucine or methionine; residue corresponding to X96 is serine, threonine, asparagine, glutamine, particularly glutamine, asparagine, or threonine; residue; residue corresponding to X101 is aspartic acid, glutamic acid, serine, threonine, asparagine, glutamine, or glycine, methionine, alanine, valine, leucine, or isoleucine, particularly glycine or asparagine; residue corresponding to X105 is glutamic acid, aspartic acid, glycine, methionine, alanine, valine, leucine, isoleucine, particularly glycine; residue corresponding to X108 is arginine, lysine, serine, threonine, asparagine, glutamine, histidine, particularly histidine or serine; residue corresponding to X112 aspartic acid, glutamic acid, serine, threonine, asparagine, glutamine, particularly aspartic acid; residue corresponding to X113 is an glycine, methionine, alanine, valine, leucine, isoleucine, particularly alanine; residue corresponding to X117 is glycine, methionine, alanine, valine, leucine, isoleucine, serine, threonine, asparagine, or glutamine, particularly serine; residue corresponding to X127 is lysine, arginine, serine, threonine, asparagine, or glutamine, particularly arginine; residue corresponding to X147 is glycine, methionine, alanine, valine, leucine, isoleucine, tyrosine, phenylalanine, tryptophan, particularly leucine; residue corresponding to X152 is glycine, methionine, valine, leucine, isoleucine, arginine, lysine, serine threonine, asparagine, or glutamine, particularly methionine or lysine; residue corresponding to X157 is a serine, threonine, asparagine, and glutamine, particularly threonine; residue corresponding to X163 is a glycine, methionine, alanine, valine, leucine, or isoleucine, particularly isoleucine; residue corresponding to X176 is glycine, methionine, alanine, valine, leucine, or isoleucine, particularly valine; residue corresponding to X194 is proline, arginine, lysine, serine, threonine, asparagine, glutamine, particularly arginine or glutamine; residue corresponding to X197 is aspartic acid, glutamic acid, arginine, lysine, serine, threonine, asparagine, glutamine, glycine, methionine, alanine, valine, leucine, isoleucine, particularly valine or glutamic acid; residue corresponding to X198 is aspartic acid, glutamic acid, arginine, lysine, serine, threonine, asparagine, glutamine, glycine, methionine, alanine, valine, leucine, or isoleucine, particularly glycine, glutamic acid, or lysine; residue corresponding to X199 is an aspartic acid, glutamic acid, glycine, methionine, alanine, valine, leucine, or isoleucine, particularly aspartic acid; residue corresponding to X200 is aspartic acid, glutamic acid, or proline, particularly proline; residue corresponding to X202 is glycine, methionine, alanine, valine, leucine, isoleucine, particularly glycine; residue corresponding to X206 is a glycine, methionine, alanine, valine, leucine, isoleucine, tyrosine, phenylalanine, tryptophan, particularly glycine; residue corresponding to X211 is a arginine or lysine. In some embodiments, the region or domain corresponding to residues 90-211 can have additionally from about 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the corresponding domain of a reference sequence based on SEQ ID NO:128, 130, or 160. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations.

In some embodiments, the ketoreductase polypeptides with a domain or region corresponding to residues 90-211 and having the specified features for residues X145 and X190 as described herein, can further include in the region or domain one or more features selected from the following: residue corresponding to X108 is a hydrophilic, polar or constrained residue; residue corresponding to X117 is a non-polar or a polar residue; residue corresponding to X152 is a non-polar, basic, or hydrophilic residue; and residue corresponding to X199 is an acidic, aliphatic, or non-polar residue. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:128, 130, or 160. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:128, 130, or 160 with the preceding features.

In some embodiments, the ketoreductase polypeptides with a domain or region corresponding to residues 90-211 and having the specified features for residues X145 and X190 as described herein, can further include in the region or domain one or more features selected from the following: residue corresponding to X108 is arginine, lysine, serine, threonine, asparagine, glutamine, histidine, particularly histidine or serine; residue corresponding to X117 is glycine, methionine, alanine, valine, leucine, isoleucine, serine, threonine, asparagine, or glutamine, particularly serine; residue corresponding to X152 is glycine, methionine, valine, leucine, isoleucine, arginine, lysine, serine threonine, asparagine, or glutamine, particularly methionine or lysine; and residue corresponding to X199 is an aspartic acid, glutamic acid, glycine, methionine, alanine, valine, leucine, or isoleucine, particularly aspartic acid. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:128, 130, or 160. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:128, 130, or 160 with the preceding features.

In some embodiments, the ketoreductase polypeptides with a domain or region corresponding to residues 90-211 and having the specified features for residues X145 and X190 as described herein, can further include in the region or domain one or more features selected from the following: residue corresponding to X94 is a non-polar or a polar residue; residue corresponding to X194 is a constrained, basic, or polar residue; residue corresponding to X198 is an acidic, basic, hydrophilic, or non-polar residue; and residue corresponding to X200 is an acidic or a constrained residue. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:128, 130, or 160. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:128, 130, or 160 with the preceding features. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:128, 130, or 160. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:128, 130, or 160 with the preceding features.

In some embodiments, the ketoreductase polypeptides with a domain or region corresponding to residues 90-211 and having the specified features for residues X145 and X190 as described herein, can further include in the region or domain one or more features selected from the following: residue corresponding to X94 is glycine, methionine, alanine, valine, leucine, isoleucine, serine, threonine, asparagine, or glutamine, particularly asparagine, glycine, or serine; residue corresponding to X194 is proline, arginine, lysine, serine, threonine, asparagine, glutamine, particularly arginine or glutamine; residue corresponding to X198 is aspartic acid, glutamic acid, arginine, lysine, serine, threonine, asparagine, glutamine, glycine, methionine, alanine, valine, leucine, or isoleucine, particularly glycine, glutamic acid, or lysine; residue corresponding to X200 is an aspartic acid, glutamic acid, or proline, particularly proline. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:128, 130, or 160. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:128, 130, or 160 with the preceding features.

In some embodiments, the ketoreductase polypeptides with a domain or region corresponding to residues 90-211 and having the specified features for residues X145 and X190 as described herein, can further include in the region or domain one or more features selected from the following: residue corresponding to X94 is a non-polar or a polar residue; residue corresponding to X108 is a hydrophilic, polar or constrained residue; residue corresponding to X117 is a non-polar or a polar residue; residue corresponding to X152 is a non-polar, basic, or hydrophilic residue; residue corresponding to X194 is a constrained, basic, or polar residue; residue corresponding to X198 is an acidic, basic, hydrophilic, or non-polar residue; residue corresponding to X199 is an acidic, aliphatic, or non-polar residue; residue corresponding to X200 is an acidic or constrained residue. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:128, 130, or 160. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:128, 130, or 160 with the preceding features.

In some embodiments, the ketoreductase polypeptides with a domain or region corresponding to residues 90-211 and having the specified features for residues X145 and X190 as described herein, can further include in the region or domain one or more features selected from the following: residue corresponding to X94 is glycine, methionine, alanine, valine, leucine, isoleucine, serine, threonine, asparagine, or glutamine, particularly asparagine, glycine, or serine; residue corresponding to X108 is arginine, lysine, serine, threonine, asparagine, glutamine, histidine, particularly histidine or serine; residue corresponding to X117 is glycine, methionine, alanine, valine, leucine, isoleucine, serine, threonine, asparagine, or glutamine, particularly serine; residue corresponding to X152 is glycine, methionine, valine, leucine, isoleucine, arginine, lysine, serine threonine, asparagine, or glutamine, particularly methionine or lysine; residue corresponding to X194 is proline, arginine, lysine, serine, threonine, asparagine, glutamine, particularly arginine or glutamine; residue corresponding to X198 is aspartic acid, glutamic acid, arginine, lysine, serine, threonine, asparagine, glutamine, glycine, methionine, alanine, valine, leucine, or isoleucine, particularly glycine; residue corresponding to X199 is an aspartic acid, glutamic acid, glycine, methionine, alanine, valine, leucine, or isoleucine, particularly aspartic acid; residue corresponding to X200 is aspartic acid, glutamic acid, or proline, particularly proline. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:128, 130, or 160. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:128, 130, or 160 with the preceding features.

In some embodiments, the ketoreductase polypeptide has a region that corresponds to residues 1-89 of the sequence formula of SEQ ID NO:161, 162 or 163, in which the amino acid sequence has one or more of the following features: residue corresponding to X3 is an acidic, polar, or hydrophilic residue; residue corresponding to X7 is a non-polar or polar residue; residue corresponding to X17 is a non-polar, aliphatic or polar residue; residue corresponding to X21 is a non-polar, aromatic, or hydrophobic residue; residue corresponding to X25 is an acidic, non-polar or polar residue; residue corresponding to X29 is an acidic, aliphatic or non-polar residue; residue corresponding to X40 is a constrained, basic, or hydrophilic residue; residue corresponding to X42 is an acidic or non-polar residue; residue corresponding to X53 is a non-polar or an acidic residue; residue corresponding to X75 is an acidic or polar residue.

In some embodiments, the ketoreductase polypeptide has a region that corresponds to residues 1-89 of the sequence formula of SEQ ID NO:161, 162 or 163, in which the amino sequence of the domain or region has one or more of the following features: residue corresponding to X3 is aspartic acid, glutamic acid, serine, threonine, asparagine, or glutamine, particularly asparagine; residue corresponding to X7 is glycine, methionine, alanine, valine, leucine, isoleucine, serine, threonine, asparagine, or glutamine, particularly serine; residue corresponding to X17 is glycine, methionine, alanine, valine, leucine, isoleucine, serine, threonine, asparagine, or glutamine, particularly glutamine; residue corresponding to X21 is glycine, methionine, alanine, valine, leucine, isoleucine, tyrosine, phenylalanine, or tryptophan, particularly phenylalanine; residue corresponding to X25 is aspartic acid, glutamic acid, serine, threonine, asparagine, glutamine, glycine, methionine, alanine, valine, leucine, isoleucine, particularly threonine; residue corresponding to X29 is aspartic acid, glutamine acid, glycine, methionine, alanine, valine, leucine, or isoleucine, particularly glycine or alanine; residue corresponding to X40 is histidine, lysine, arginine, serine, threonine, asparagine, or glutamine, particularly arginine; residue corresponding to X42 is aspartic acid, glutamic acid, glycine, methionine, alanine, valine, leucine, or isoleucine, particularly glycine; residue corresponding to X53 is glycine, methionine, alanine, valine, leucine, isoleucine, aspartic acid, glutamic acid, particularly aspartic acid; residue corresponding to X75 is aspartic acid, glutamic acid, serine, threonine, asparagine, or glutamine, particularly arginine.

In some embodiments, the ketoreductase polypeptide has a region that corresponds to residues 212-252 of the sequence formula of SEQ ID NO:161, 162 or 163, in which the amino acid sequence has one or more of the following features: residue corresponding to X223 is a non-polar or aliphatic residue; and residue corresponding to X250 is a polar or non-polar residue.

In some embodiments, the ketoreductase polypeptide has a region that corresponds to residues 212-252 of the sequence formula of SEQ ID NO:161, 162 or 163, in which the amino acid sequence has one or more of the following features: residue corresponding to X223 is glycine, methionine, alanine, valine, leucine, or isoleucine, particularly valine; and residue corresponding to X250 is serine, threonine, asparagine, glutamine, glycine, methionine, alanine, valine, leucine, isoleucine, particularly isoleucine.

In some embodiments, the ketoreductase polypeptides of the disclosure can comprise a having an amino acid sequence that is at least about 85%, 86%, 87%, 88%, 89%, 90%, 91%, 92%, 93%, 94%, 95%, 96%, 97%, 98%, or 99% identical to a region or domain of SEQ ID NO:128, 130, or 160, such as residues 90-211, with the proviso that the residue corresponding to X145 is serine and the residue corresponding to X190 is cysteine, and wherein the amino acid sequence can have additionally one or more of the following substitutions such that the polypeptide is further improved (e.g., with respect to stereoselectivity, enzymatic activity, and/or thermostability) over the wild-type $L.$ $kefir$ ketoreductase or another engineered ketoreductase (such as SEQ ID NO:8): 3→N, 7→S, 17→Q, 21→F, 25→T, 29→A or G, 42→G, 53→D, 75→N, 95→L or M, 96→Q, 101→Q or G, 105→G, 108→H or S, 112→D, 117→S, 127→R, 147→L, 152→M, 157→T, 163→L or I, 167→V, 176→V, 194→R, 197→V or E, 198→K or E, 199→D, 200→P, 211→R, 223→V, and 250→I.

In some embodiments, the ketoreductase polypeptides of the disclosure can comprise a region having an amino acid sequence that is at least about 85%, 86%, 87%, 88%, 89%, 90%, 91%, 92%, 93%, 94%, 95%, 96%, 97%, 98%, or 99% identical to a region or domain of SEQ ID NO:128, 130, or 160, such as residues 90-211, wherein the amino acid sequence can have additionally one or more of the following substitutions such that the polypeptide is further improved (e.g., with respect to stereoselectivity, enzymatic activity, and/or thermostability) over the wild-type $L.$ $kefir$ ketoreductase or another engineered ketoreductase (such as SEQ ID NO:8): 7→5, 17→Q, 96→Q, 108→H, 117→S, 152→M, 163→I, 176→V, 198→K, 199→D, 211→R, and 223→V.

In some embodiments, the ketoreductases of the disclosure are subject to one or more of the following provisos: (1) specifically excluded are polypeptides with the specific sequences selected from SEQ ID NO: 8, 44, 46, 48, 164 and 165; (2) the amino acid sequence requires at residue corresponding to X152 a basic or non-polar residue, particularly methionine or lysine; (3) the amino acid sequence requires at residue corresponding to X199 an acidic residue, particularly aspartic acid; and (4) the amino acid sequence requires at residue corresponding to X96 a glutamine.

In some embodiments, each of the improved engineered ketoreductase enzymes described herein can comprise deletions of the polypeptides described herein. Thus, for each and every embodiment of the ketoreductase polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the ketoreductase polypeptides, as long as the functional activity of the ketoreductase activity is maintained. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acids. In some embodiments, the deletions can comprise deletions of 1-2, 1-3, 1-4, 1-5, 1-6, 1-7, 1-8, 1-9, 1-10, or 1-20 amino acid residues. In some embodiments, the number of deletions can be 1, 2, 3, 4, 5, 6, 7, 8, 9, 10, 11, 12, 14, 15, 16, 18, 20, 22, 24, 26, 30, 35 or about 40 amino acids. In some embodiments, the deletions can comprise deletions of 1, 2, 3, 4, 5, 6, 7, 8, 9, 10, 11, 12, 13, 14, 15, 16, 18, or 20 amino acid residues.

As will be appreciated by the skilled art, the polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane- 3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

As described above the various modifications introduced into the naturally occurring polypeptide to generate an engineered ketoreductase enzyme can be targeted to a specific property of the enzyme.

6.3 Polynucleotides Encoding Engineered Ketoreductases

In another aspect, the present disclosure provides polynucleotides encoding the engineered ketoreductase enzymes disclosed herein. The polynucleotides may be operatively linked to one or more heterologous regulatory sequences that control gene expression to create a recombinant polynucleotide capable of expressing the polypeptide. Expression constructs containing a heterologous polynucleotide encoding the engineered ketoreductase can be introduced into appropriate host cells to express the corresponding ketoreductase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved ketoreductase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Tables 3 and 4.

In some embodiments, the polynucleotides encode a ketoreductase polypeptides having at least the following features as compared to the amino acid sequence of SEQ ID NO:2, SEQ ID NO:4, or SEQ ID NO:158: (1) the amino acid residue corresponding to residue X145 is a serine residue, and (2) the amino acid residue corresponding to residue X190 is a cysteine residue. In some embodiments, the polynucleotide comprises a nucleotide sequence encoding a ketoreductase polypeptide with an amino acid sequence that has at least about 85%, 86%, 87%, 88%, 89%, 90%, 91%, 92%, 93%, 94%, 95%, 96%, 97%, 98%, or 99% or more sequence identity to any of the reference engineered ketoreductase polypeptides described herein, where the ketoreductase polypeptide comprises an amino acid sequence that has at least the following features: an amino acid residue corresponding to residue position of 145 of SEQ ID NO:2, 4, or 158 is serine and the amino acid residue corresponding to residue residue position 190 of SEQ ID NO:2, 4 or 158 is cysteine.

In some embodiments, the polynucleotides encode the polypeptides described herein but have at least about 85%, 86%, 87%, 88%, 89%, 90%, 91%, 92%, 93%, 94%, 95%, 96%, 97%, 98%, or 99% or more sequence identity at the nucleotide level to a reference polynucleotide encoding an engineered ketoreductase. In some embodiments, the reference polynucleotide is selected from polynucleotide sequences represented by SEQ ID NO: 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, and 125.

In some embodiments, the polynucleotide can encode an improved ketoreductase comprising an amino acid sequence that is at least about 85%, 86%, 87%, 88%, 89%, 90%, 91%, 92%, 93%, 94%, 95%, 96%, 97%, 98%, or 99% identical to the amino acid sequence corresponding to SEQ ID NO: 42, 44, 46, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, and 126 as listed in Tables 3 and 4, wherein the improved ketoreductase polypeptide amino acid sequence includes any one set of the specified amino acid substitution combinations presented in Tables 3 and 4. In some embodiments, the polynucleotides encode an engineered ketoreductase polypeptide comprising an amino acid sequence selected from SEQ ID NO: 42, 44, 46, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, and 126.

In some embodiments, the polynucleotides are capable of hybridizing under highly stringent conditions to a polynucleotide comprising SEQ ID NO: 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, and 125, where the polynucleotides encode a functional ketoreductase carrying out the conversion of substrate to product as described herein.

In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. By way of example, the polynucleotide of SEQ ID NO: 3 has been codon optimized for expression in *E. coli*, but otherwise encodes the naturally occurring ketoreductase of *Lactobacillus kefir*.

In certain embodiments, all codons need not be replaced to optimize the codon usage of the ketoreductases since the natural sequence will comprise preferred codons and because use of preferred codons may not be required for all amino acid residues. Consequently, codon optimized polynucleotides encoding the ketoreductase enzymes may contain preferred codons at about 40%, 50%, 60%, 70%, 80%, or greater than 90% of codon positions of the full length coding region.

In various embodiments, an isolated polynucleotide encoding an improved ketoreductase polypeptide may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, $3^{rd}$ Ed., Cold Spring Harbor Laboratory Press; and Current Protocols in Molecular Biology, Ausubel. F. ed., Greene Pub. Associates, 1998, updates to 2006.

For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proc. Natl Acad. Sci. USA 75: 3727-3731), as well as the tac promoter (DeBoer et al., 1983, Proc. Natl Acad. Sci. USA 80: 21-25).

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, Mol Cell Bio 15:5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus lichenifor-*

*mis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57: 109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* gluco amylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the KRED polypeptide of the present invention would be operably linked with the regulatory sequence.

Thus, in another embodiment, the present disclosure is also directed to a recombinant expression vector comprising a polynucleotide encoding an engineered ketoreductase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

The expression vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori (as shown in the plasmid of FIG. 5) or the origins of replication of plasmids pBR322, pUC19, pACYC177 (which plasmid has the P15A ori), or pACYC184 permitting replication in *E. coli*, and pUB110, pE194, pTA1060, or pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it's functioning temperature-sensitive in the host cell (see, e.g., Ehrlich, 1978, Proc Natl Acad Sci. USA 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available. Suitable commercial expression vectors include p3×FLAGTM™ expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptll SK(-) and pBK-CMV, which are commercially available from Stratagene, LaJolla Calif., and plasmids which are derived from pBR322 (Gibco BRL), pUC (Gibco BRL), pREP4, pCEP4 (Invitrogen) or pPoly (Lathe et al., 1987, Gene 57:193-201).

6.4 Host Cells for Expression of Ketoreductase Polypeptides

In another aspect, the present disclosure provides a host cell comprising a polynucleotide encoding an improved ketoreductase polypeptide of the present disclosure, the polynucleotide being operatively linked to one or more control sequences for expression of the ketoreductase enzyme in the host cell. Host cells for use in expressing the KRED polypeptides encoded by the expression vectors of the present invention are well known in the art and include but are not limited to, bacterial cells, such as *E. coli, Lactobacillus kefir, Lactobacillus brevis, Lactobacillus minor, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the ketoreductase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

An exemplary host cell is *Escherichia coli* W3110. The expression vector was created by operatively linking a polynucleotide encoding an improved ketoreductase into the plasmid pCK110900 operatively linked to the lac promoter under control of the lad repressor. The expression vector also contained the P15a origin of replication and the chloramphenicol resistance gene. Cells containing the subject polynucleotide in *Escherichia coli* W3110 were isolated by subjecting the cells to chloramphenicol selection.

6.5 Methods of Generating Engineered Ketoreductase Polypeptides

In some embodiments, to make the improved KRED polynucleotides and polypeptides of the present disclosure, the naturally-occurring ketoreductase enzyme that catalyzes the reduction reaction is obtained (or derived) from *Lactobacillus kefir* or *Lactobacillus brevis*. In some embodiments, the parent polynucleotide sequence is codon optimized to enhance expression of the ketoreductase in a specified host cell. As an illustration, the parental polynucleotide sequence encoding the wild-type KRED polypeptide of *Lactobacillus kefir* was constructed from oligonucleotides prepared based upon the known polypeptide sequence of *Lactobacillus kefir* KRED sequence available in Genbank database (Genbank accession no. AAP94029 GI:33112056). The parental polynucleotide sequence, designated as SEQ ID NO: 3, was codon optimized for expression in *E. coli* and the codon-optimized polynucleotide cloned into an expression vector, placing the expression of the ketoreductase gene under the control of the lac promoter and lad repressor gene. Clones expressing the active ketoreductase in *E. coli* were identified and the genes sequenced to confirm their identity. The sequence designated (SEQ ID NO: 3) was the parent sequence utilized as the starting point for most experiments and library construction of engineered ketoreductases evolved from the *Lactobacillus kefir* ketoreductase.

The engineered ketoreductases can be obtained by subjecting the polynucleoticde encoding the naturally occurring ketoreductase to mutagenesis and/or directed evolution methods, as discussed above. An exemplary directed evolution technique is mutagenesis and/or DNA shuffling as described in Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529).

The clones obtained following mutagenesis treatment are screened for engineered ketoreductases having a desired improved enzyme property. Measuring enzyme activity from the expression libraries can be performed using the standard biochemistry technique of monitoring the rate of decrease (via a decrease in absorbance or fluorescence) of NADH or NADPH concentration, as it is converted into NAD+ or NADP+. In this reaction, the NADH or NADPH is consumed (oxidized) by the ketoreductase as the ketoreductase reduces a ketone substrate to the corresponding hydroxyl group. The rate of decrease of NADH or NADPH concentration, as measured by the decrease in absorbance or fluorescence, per unit time indicates the relative (enzymatic) activity of the KRED polypeptide in a fixed amount of the lysate (or a lyophilized powder made therefrom). Where the improved enzyme property desired is thermal stability, enzyme activity may be measured after subjecting the enzyme preparations to a defined temperature and measuring the amount of enzyme activity remaining after heat treatments. Clones containing a polynucleotide encoding a ketoreductase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the invention can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Midland Certified Reagent Company, Midland, Tex., The Great American Gene Company, Ramona, Calif., ExpressGen Inc. Chicago, Ill., Operon Technologies Inc., Alameda, Calif., and many others.

Engineered ketoreductase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as E. coli, are commercially available under the trade name CelLytic B™ from Sigma-Aldrich of St. Louis Mo.

Chromatographic techniques for isolation of the ketoreductase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved ketoreductase enzymes. For affinity chromatography purification, any antibody which specifically binds the ketoreductase polypeptide may be used. For the production of antibodies, various host animals, including but not limited to rabbits, mice, rats, etc., may be immunized by injection with a compound. The compound may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

6.6 Methods of Using the Engineered Ketoreductase Enzymes and Compounds Prepared Therewith The ketoreductase enzymes described herein can catalyze the reduction of the substrate compound of structural formula (I) (5-((4S)-2-oxo-4-phenyl (1,3-oxazolidin-3-yl))-1-(4-fluorophenyl) pentane-1,5-dione:

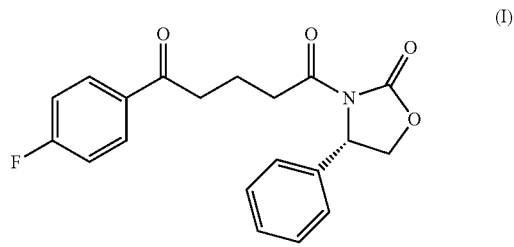 [SMILES: O=C(CCCC(=O)N1C(=O)OC[C@@H]1c1ccccc1)c1ccc(F)cc1]

to the corresponding stereosiomeric product of structural formula (II) ((4S)-3-[(5S)-5-(4-fluorophenyl)-5-hydroxy-pentanoyl]-4-phenyl-1,3-oxazolidin-2-one):

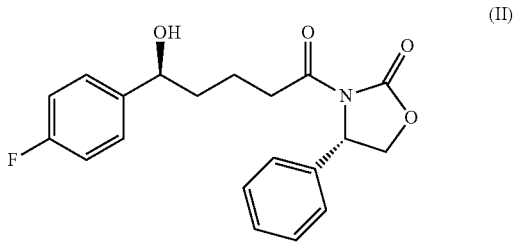 [SMILES: O=C(CCC[C@H](O)c1ccc(F)cc1)N1C(=O)OC[C@@H]1c1ccccc1]

In some embodiments, the method for reducing the substrate having the chemical formula (I) to the corresponding product of formula (II) comprises contacting or incubating the substrate with a ketoreductase polypeptides disclosed herein under reaction conditions suitable for reducing or converting the substrate to the product compound. The product in an intermediate for the synthesis of Ezetimibe, an anti-hyperlipidemic drug for lowering cholesterol levels (U.S. Pat. No. 5,767,115). Thus, in a method for synthesizing Ezetimibe, the method can comprises a step in which the compound of formula (I) is converted to the compound of formula (II) using a ketoreductase polypeptide disclosed herein. In some embodiments, the product in greater than about 99%, 99.1%, 99.2%, 99.3%, 99.4%, 99.5%, 99.6%, 99.7%, 99.8% or 99.9% stereomeric excess over the corresponding (R) alcohol product.

In some embodiments, the ketoreductase enzymes described herein are also capable of catalyzing the reduction reaction of the keto group in the compound of structural formula (III), 1-(4-fluorophenyl)-3(R)-[3-oxo-3-(4-fluorophenyl)propyl)]-4(S)-(4-hydroxyphenyl)-2-azetidinone,

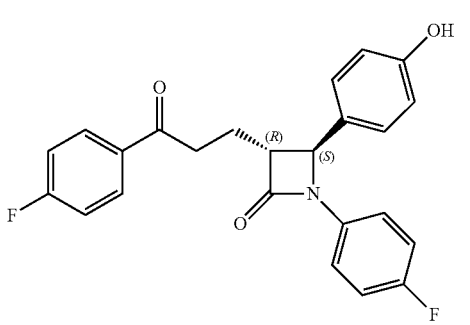

to the corresponding stereoisomeric alcohol product of structural formula (IV), 1-(4-fluorophenyl)-3(R)-[3(S)-hydroxy-3(4-fluorophenyl)-propyl)]-4(S)-(4-hydroxyphenyl)-2-azetidinone (i.e., Ezetimibe):

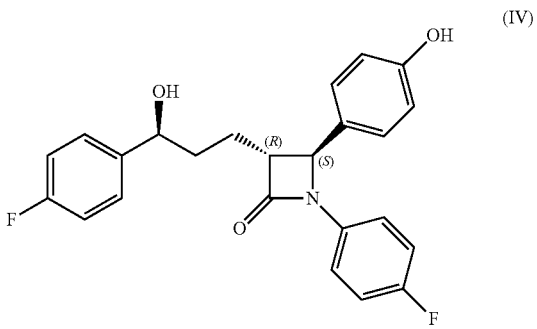

Thus, the present disclosure provides a method of synthesizing Ezetimibe, the method comprising contacting or incubating the compound of formula (III) with a ketoreductase polypeptide disclosed herein under reaction conditions suitable for reducing or converting the substrate compound of formula (III) to the production compound of formula (IV). Other compounds similar to the compounds of formula (I) and compounds of formula (III) are described in U.S. Pat. No. 5,767,115 (incorporated herein by reference).

In the method for reducing the compound of formula (I) to the compound of formula (II), or for reducing the compound of formula (III) to the compound of formula (IV), the ketoreductase polypeptides have, as compared to the wild-type L. kefir, L. brevis, L. minor KRED sequences of SEQ ID NO:4, 2, and 158, respectively, at least the following amino acid substitutions: (1) residue 145 is serine and (2) residue 190 is cysteine. Various embodiments of the ketoreductase polypeptides are described above. In some embodiments, as compared to the wild-type L. kefi, L. brevis, L. minor KRED sequences of SEQ ID NO:4, 2, and 158, the ketoreductase polypeptides have at least the following amino acid substitutions: (1) residue 145 is a serine residue, (2) residue 190 is a cysteine residue, and (3) residue 96 is a glutamine residue. In some embodiments, as compared to the wild-type L. kefi, L. brevis, L. minor KRED sequences of SEQ ID NO:4, 2, and 158, the ketoreductase polypeptides of the invention have at least the following amino acid substitutions: (1) residue X145 is a serine residue, (2) residue X190 is a cysteine residue, and (3) residue X211 is an arginine residue.

As noted herein, in some embodiments, the ketoreductase polypeptides can comprise an amino acid sequence that is at least about 85%, 86%, 87%, 88%, 89%, 90%, 91%, 92%, 93%, 94%, 95%, 96%, 97%, 98%, or 99% identical as compared a reference sequence comprising the sequence of SEQ ID NO:128, 130, or 160, with the proviso that the polypeptide comprises an amino acid sequence in which the amino acid residue corresponding to residue X145 is a serine, and the amino acid residue corresponding to residue X190 is a cysteine. In some embodiments, these ketoreductase polypeptides can have one or more modifications to the amino acid sequence of SEQ ID NO:128, 130 or 160. The modifications can include substitutions, deletions, and insertions. The substitutions can be non-conservative substitutions, conservative substitutions, or a combination of non-conservative and conservative substitutions.

In some embodiments of the method for reducing the substrate to the product, the substrate is reduced to the product in greater than about 99% stereomeric excess, wherein the ketoreductase polypeptide comprises a sequence that corresponds to SEQ ID NO: SEQ ID NO: 42, 44, 46, 48, 50, 52, 54, 56, 58, 60, 62, 64, 66, 68, 70, 72, 74, 76, 78, 80, 82, 84, 86, 88, 90, 92, 96, 98, 100, 102, 104, 106, 108, 110, 112, 114, 116, 118, 120, 122, 124, and 126.

In another embodiment of this method for reducing the substrate to the product, at least about 95% of the substrate is converted to the product in less than about 24 hours when carried out with greater than about 100 g/L of substrate and less than about 5 g/L of the polypeptide, wherein the polypeptide comprises an amino acid sequence corresponding to SEQ ID NO:102, 108, 120, 122, 124, 126.

As is known by those of skill in the art, ketoreductase-catalyzed reduction reactions typically require a cofactor. Reduction reactions catalyzed by the engineered ketoreductase enzymes described herein also typically require a cofactor, although many embodiments of the engineered ketoreductases require far less cofactor than reactions catalyzed with wild-type ketoreductase enzymes. As used herein, the term "cofactor" refers to a non-protein compound that operates in combination with a ketoreductase enzyme. Cofactors suitable for use with the engineered ketoreductase enzymes described herein include, but are not limited to, $NADP^+$ (nicotinamide adenine dinucleotide phosphate), NADPH (the reduced form of $NADP^+$), $NAD^+$ (nicotinamide adenine dinucleotide) and NADH (the reduced form of $NAD^+$). Generally, the reduced form of the cofactor is added to the reaction mixture. The reduced NAD(P)H form can be optionally regenerated from the oxidized $NAD(P)^+$ form using a cofactor regeneration system.

The term "cofactor regeneration system" refers to a set of reactants that participate in a reaction that reduces the oxidized form of the cofactor (e.g., $NADP^+$ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst that catalyzes the reduction of the oxidized form of the cofactor by the reductant. Cofactor regeneration systems to regenerate NADH or NADPH from $NAD^+$ or $NADP^+$, respectively, are known in the art and may be used in the methods described herein.

Suitable exemplary cofactor regeneration systems that may be employed include, but are not limited to, glucose and glucose dehydrogenase, formate and formate dehydrogenase, glucose-6-phosphate and glucose-6-phosphate dehydrogenase, a secondary (e.g., isopropanol) alcohol and secondary alcohol dehydrogenase, phosphite and phosphite dehydrogenase, molecular hydrogen and hydrogenase, and the like. These systems may be used in combination with either NADP+/NADPH or NAD+/NADH as the cofactor. Electrochemical regeneration using hydrogenase may also be used as a cofactor regeneration system. See, e.g., U.S. Pat. Nos. 5,538,867 and 6,495,023, both of which are incorporated herein by reference. Chemical cofactor regeneration systems comprising a metal catalyst and a reducing agent (for example, molecular hydrogen or formate) are also suitable. See, e.g., PCT publication WO 2000/053731, which is incorporated herein by reference.

The terms "glucose dehydrogenase" and "GDH" are used interchangeably herein to refer to an NAD+ or NADP+-dependent enzyme that catalyzes the conversion of D-glucose and NAD+ or NADP+ to gluconic acid and NADH or NADPH, respectively. Equation (1), below, describes the glucose dehydrogenase-catalyzed reduction of NAD+ or NADP+ by glucose.

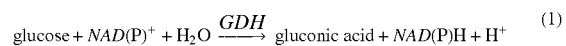
(1)

$$\text{glucose} + NAD(P)^+ + H_2O \xrightarrow{GDH} \text{gluconic acid} + NAD(P)H + H^+$$

Glucose dehydrogenases that are suitable for use in the practice of the methods described herein include both naturally occurring glucose dehydrogenases, as well as non-naturally occurring glucose dehydrogenases. Naturally occurring glucose dehydrogenase encoding genes have been reported in the literature. For example, the *Bacillus subtilis* 61297 GDH gene was expressed in *E. coli* and was reported to exhibit the same physicochemical properties as the enzyme produced in its native host (Vasantha et al., 1983, Proc. Natl. Acad. Sci. USA 80:785). The gene sequence of the *B. subtilis* GDH gene, which corresponds to Genbank Acc. No. M12276, was reported by Lampel et al., 1986, J. Bacteriol. 166:238-243, and in corrected form by Yamane et al., 1996, Microbiology 142:3047-3056 as Genbank Acc. No. D50453. Naturally occurring GDH genes also include those that encode the GDH from *B. cereus* ATCC 14579 (Nature, 2003, 423:87-91; Genbank Acc. No. AE017013) and *B. megaterium* (Eur. J. Biochem., 1988, 174:485-490, Genbank Acc. No. X12370; J. Ferment. Bioeng., 1990, 70:363-369, Genbank Acc. No. GI216270). Glucose dehydrogenases from *Bacillus* sp. are provided in PCT publication WO 2005/018579 as SEQ ID NOS: 10 and 12 (encoded by polynucleotide sequences corresponding to SEQ ID NOS: 9 and 11, respectively, of the PCT publication), the disclosure of which is incorporated herein by reference.

Non-naturally occurring glucose dehydrogenases may be generated using known methods, such as, for example, mutagenesis, directed evolution, and the like. GDH enzymes having suitable activity, whether naturally occurring or non-naturally occurring, may be readily identified using the assay described in Example 4 of PCT publication WO 2005/018579, the disclosure of which is incorporated herein by reference. Exemplary non-naturally occurring glucose dehydrogenases are provided in PCT publication WO 2005/018579 as SEQ ID NOS: 62, 64, 66, 68, 122, 124, and 126. The polynucleotide sequences that encode them are provided in PCT publication WO 2005/018579 as SEQ ID NOS: 61, 63, 65, 67, 121, 123, and 125, respectively. All of these sequences are incorporated herein by reference. Additional non-naturally occurring glucose dehydrogenases that are suitable for use in the ketoreductase-catalyzed reduction reactions disclosed herein are provided in U.S. application publication Nos. 2005/0095619 and 2005/0153417, the disclosures of which are incorporated herein by reference.

Glucose dehydrogenases employed in the ketoreductase-catalyzed reduction reactions described herein may exhibit an activity of at least about 10 μmol/min/mg and sometimes at least about $10^2$ μmol/min/mg or about $10^3$ μmol/min/mg, up to about $10^4$ μmol/min/mg or higher in the assay described in Example 4 of PCT publication WO 2005/018579.

The ketoreductase-catalyzed reduction reactions described herein are generally carried out in a solvent. Suitable solvents include water, organic solvents (e.g., ethyl acetate, butyl acetate, 1-octanol, heptane, octane, methyl t-butyl ether (MTBE), toluene, and the like), and ionic liquids (e.g., 1-ethyl 4-methylimidazolium tetrafluoroborate, 1-butyl-3-methylimidazolium tetrafluoroborate, 1-butyl-3-methylimidazolium hexafluorophosphate, and the like). In some embodiments, aqueous solvents, including water and aqueous co-solvent systems, are used.

Exemplary aqueous co-solvent systems have water and one or more organic solvents. In general, an organic solvent component of an aqueous co-solvent system is selected such that it does not completely inactivate the ketoreductase enzyme. Appropriate co-solvent systems can be readily identified by measuring the enzymatic activity of the specified engineered ketoreductase enzyme with a defined substrate of interest in the candidate solvent system, utilizing an enzyme activity assay, such as those described herein.

The organic solvent component of an aqueous co-solvent system may be miscible with the aqueous component, providing a single liquid phase, or may be partly miscible or immiscible with the aqueous component, providing two liquid phases. Generally, when an aqueous co-solvent system is employed, it is selected to be biphasic, with water dispersed in an organic solvent, or vice-versa. Generally, when an aqueous co-solvent system is utilized, it is desirable to select an organic solvent that can be readily separated from the aqueous phase. In general, the ratio of water to organic solvent in the co-solvent system is typically in the range of from about 90:10 to about 10:90 (v/v) organic solvent to water, and between 80:20 and 20:80 (v/v) organic solvent to water. The co-solvent system may be pre-formed prior to addition to the reaction mixture, or it may be formed in situ in the reaction vessel.

The aqueous solvent (water or aqueous co-solvent system) may be pH-buffered or unbuffered. Generally, the reduction can be carried out at a pH of about 10 or below, usually in the range of from about 5 to about 10. In some embodiments, the reduction is carried out at a pH of about 9 or below, usually in the range of from about 5 to about 9. In some embodiments, the reduction is carried out at a pH of about 8 or below, often in the range of from about 5 to about 8, and usually in the range of from about 6 to about 8. The reduction may also be carried out at a pH of about 7.8 or below, or 7.5 or below. Alternatively, the reduction may be carried out a neutral pH, i.e., about 7.

During the course of the reduction reactions, the pH of the reaction mixture may change. The pH of the reaction mixture may be maintained at a desired pH or within a desired pH range by the addition of an acid or a base during the course of the reaction. Alternatively, the pH may be controlled by using an aqueous solvent that comprises a buffer. Suitable buffers to maintain desired pH ranges are known in the art and include, for example, phosphate buffer, triethanolamine buffer, and the like. Combinations of buffering and acid or base addition may also be used.

When the glucose/glucose dehydrogenase cofactor regeneration system is employed, the co-production of gluconic acid (pKa=3.6), as represented in equation (1) causes the pH of the reaction mixture to drop if the resulting aqueous gluconic acid is not otherwise neutralized. The pH of the reaction mixture may be maintained at the desired level by standard buffering techniques, wherein the buffer neutralizes the gluconic acid up to the buffering capacity provided, or by the addition of a base concurrent with the course of the conversion. Combinations of buffering and base addition may also be used. Suitable buffers to maintain desired pH ranges are described above. Suitable bases for neutralization of gluconic acid are organic bases, for example amines, alkoxides and the like, and inorganic bases, for example, hydroxide salts (e.g., NaOH), carbonate salts (e.g., NaHCO$_3$), bicarbonate salts (e.g., K$_2$CO$_3$), basic phosphate salts (e.g., K$_2$HPO$_4$, Na$_3$PO$_4$), and the like. The addition of a base concurrent with the course of the conversion may be done manually while monitoring the reaction mixture pH or, more conveniently, by using an automatic titrator as a pH stat. A combination of partial buffering capacity and base addition can also be used for process control.

When base addition is employed to neutralize gluconic acid released during a ketoreductase-catalyzed reduction reaction, the progress of the conversion may be monitored by the amount of base added to maintain the pH. Typically, bases added to unbuffered or partially buffered reaction mixtures over the course of the reduction are added in aqueous solutions.

In some embodiments, the co-factor regenerating system can comprises a formate dehydrogenase. The terms "formate dehydrogenase" and "FDH" are used interchangeably herein to refer to an NAD$^+$ or NADP$^+$-dependent enzyme that catalyzes the conversion of formate and NAD$^+$ or NADP$^+$ to carbon dioxide and NADH or NADPH, respectively. Formate dehydrogenases that are suitable for use as cofactor regenerating systems in the ketoreductase-catalyzed reduction reactions described herein include both naturally occurring formate dehydrogenases, as well as non-naturally occurring formate dehydrogenases. Formate dehydrogenases include those corresponding to SEQ ID NOS: 70 (*Pseudomonas* sp.) and 72 (*Candida boidinii*) of PCT publication WO 2005/018579, which are encoded by polynucleotide sequences corresponding to SEQ ID NOS: 69 and 71, respectively, of PCT publication 2005/018579, the disclosures of which are incorporated herein by reference. Formate dehydrogenases employed in the methods described herein, whether naturally occurring or non-naturally occurring, may exhibit an activity of at least about 1 µmol/min/mg, sometimes at least about 10 µmol/min/mg, or at least about 10$^2$ µmol/min/mg, up to about 10$^3$ µmol/min/mg or higher, and can be readily screened for activity in the assay described in Example 4 of PCT publication WO 2005/018579.

As used herein, the term "formate" refers to formate anion (HCO$_2^-$), formic acid (HCO$_2$H), and mixtures thereof. Formate may be provided in the form of a salt, typically an alkali or ammonium salt (for example, HCO$_2$Na, KHCO$_2$NH$_4$, and the like), in the form of formic acid, typically aqueous formic acid, or mixtures thereof. Formic acid is a moderate acid. In aqueous solutions within several pH units of its pKa (pKa=3.7 in water) formate is present as both HCO$_2^-$ and HCO$_2$H in equilibrium concentrations. At pH values above about pH 4, formate is predominantly present as HCO$_2^-$. When formate is provided as formic acid, the reaction mixture is typically buffered or made less acidic by adding a base to provide the desired pH, typically of about pH 5 or above. Suitable bases for neutralization of formic acid include, but are not limited to, organic bases, for example amines, alkoxides and the like, and inorganic bases, for example, hydroxide salts (e.g., NaOH), carbonate salts (e.g., NaHCO$_3$), bicarbonate salts (e.g., K$_2$CO$_3$), basic phosphate salts (e.g., K$_2$HPO$_4$, Na$_3$PO$_4$), and the like.

For pH values above about pH 5, at which formate is predominantly present as HCO$_2^-$, Equation (2) below, describes the formate dehydrogenase-catalyzed reduction of NAD$^+$ or NADP$^+$ by formate.

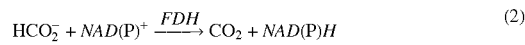

(2)

When formate and formate dehydrogenase are employed as the cofactor regeneration system, the pH of the reaction mixture may be maintained at the desired level by standard buffering techniques, wherein the buffer releases protons up to the buffering capacity provided, or by the addition of an acid concurrent with the course of the conversion. Suitable acids to add during the course of the reaction to maintain the pH include organic acids, for example carboxylic acids, sulfonic acids, phosphonic acids, and the like, mineral acids, for example hydrohalic acids (such as hydrochloric acid), sulfuric acid, phosphoric acid, and the like, acidic salts, for example dihydrogenphosphate salts (e.g., KH$_2$PO$_4$), bisulfate salts (e.g., NaHSO$_4$) and the like. Some embodiments utilize formic acid, whereby both the formate concentration and the pH of the solution are maintained.

When acid addition is employed to maintain the pH during a reduction reaction using the formate/formate dehydrogenase cofactor regeneration system, the progress of the conversion may be monitored by the amount of acid added to maintain the pH. Typically, acids added to unbuffered or partially buffered reaction mixtures over the course of conversion are added in aqueous solutions.

The terms "secondary alcohol dehydrogenase" and "sADH" are used interchangeably herein to refer to an NAD$^+$ or NADP$^+$-dependent enzyme that catalyzes the conversion of a secondary alcohol and NAD$^+$ or NADP$^+$ to a ketone and NADH or NADPH, respectively. Equation (3), below, describes the reduction of NAD$^+$ or NADP$^+$ by a secondary alcohol, illustrated by isopropanol.

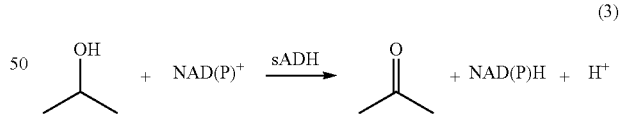

(3)

Secondary alcohol dehydrogenases that are suitable for use as cofactor regenerating systems in the ketoreductase-catalyzed reduction reactions described herein include both naturally occurring secondary alcohol dehydrogenases, as well as non-naturally occurring secondary alcohol dehydrogenases. Naturally occurring secondary alcohol dehydrogenases include known alcohol dehydrogenases from, *Thermoanerobium brockii*, *Rhodococcus etythropolis*, *Lactobacillus kefir*, *Lactobacillus minor* and *Lactobacillus brevis*, and non-naturally occurring secondary alcohol dehydrogenases include engineered alcohol dehydrogenases derived therefrom. Secondary alcohol dehydrogenases employed in the methods described herein, whether naturally occurring or non-naturally occurring, may exhibit an activity of at least about 1 µmol/min/mg, sometimes at least about 10 µmol/min/mg, or at least about $10^2$ µmol/min/mg, up to about $10^3$ µmol/min/mg or higher.

Suitable secondary alcohols include lower secondary alkanols and aryl-alkyl carbinols. Examples of lower secondary alcohols include isopropanol, 2-butanol, 3-methyl-2-butanol, 2-pentanol, 3-pentanol, 3,3-dimethyl-2-butanol, and the like. In one embodiment the secondary alcohol is isopropanol. Suitable aryl-akyl carbinols include unsubstituted and substituted 1-arylethanols.

In one embodiment, where oxidation of isopropanol to acetone is used for regeneration of NADH/NADPH, the reaction may be run at reduced pressure in such a manner that the acetone is removed from the reaction mixture.

When a secondary alcohol and secondary alcohol dehydrogenase are employed as the cofactor regeneration system, the resulting $NAD^+$ or $NADP^+$ is reduced by the coupled oxidation of the secondary alcohol to the ketone by the secondary alcohol dehydrogenase. Some engineered ketoreductases also have activity to dehydrogenate a secondary alcohol reductant. In some embodiments using secondary alcohol as reductant, the engineered ketoreductase and the secondary alcohol dehydrogenase are the same enzyme.

In carrying out embodiments of the ketoreductase-catalyzed reduction reactions described herein employing a cofactor regeneration system, either the oxidized or reduced form of the cofactor may be provided initially. As described above, the cofactor regeneration system converts oxidized cofactor to its reduced form, which is then utilized in the reduction of the ketoreductase substrate.

In some embodiments, cofactor regeneration systems are not used. For reduction reactions carried out without the use of a cofactor regenerating systems, the cofactor is added to the reaction mixture in reduced form.

In some embodiments, when the process is carried out using whole cells of the host organism, the whole cell may natively provide the cofactor. Alternatively or in combination, the cell may natively or recombinantly provide the glucose dehydrogenase.

In carrying out the stereoselective reduction reactions described herein, the engineered ketoreductase enzyme, and any enzymes comprising the optional cofactor regeneration system, may be added to the reaction mixture in the form of the purified enzymes, whole cells transformed with gene(s) encoding the enzymes, and/or cell extracts and/or lysates of such cells. The gene(s) encoding the engineered ketoreductase enzyme and the optional cofactor regeneration enzymes can be transformed into host cells separately or together into the same host cell. For example, in some embodiments one set of host cells can be transformed with gene(s) encoding the engineered ketoreductase enzyme and another set can be transformed with gene(s) encoding the cofactor regeneration enzymes. Both sets of transformed cells can be utilized together in the reaction mixture in the form of whole cells, or in the form of lysates or extracts derived therefrom. In other embodiments, a host cell can be transformed with gene(s) encoding both the engineered ketoreductase enzyme and the cofactor regeneration enzymes.

Whole cells transformed with gene(s) encoding the engineered ketoreductase enzyme and/or the optional cofactor regeneration enzymes, or cell extracts and/or lysates thereof, may be employed in a variety of different forms, including solid (e.g., lyophilized, spray-dried, and the like) or semi-solid (e.g., a crude paste).

The cell extracts or cell lysates may be partially purified by precipitation (ammonium sulfate, polyethyleneimine, heat treatment or the like, followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like).

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a prechilled lyophilization chamber, followed by the application of a vacuum. After the removal of water from the samples, the temperature is typically raised to 4° C. for two hours before release of the vacuum and retrieval of the lyophilized samples.

The quantities of reactants used in the reduction reaction will generally vary depending on the quantities of product desired, and concomitantly the amount of ketoreductase substrate employed. The following guidelines can be used to determine the amounts of ketoreductase, cofactor, and optional cofactor regeneration system to use. Generally, keto substrates can be employed at a concentration of about 20 to 300 grams/liter using from about 50 mg to about 5 g of ketoreductase and about 10 mg to about 150 mg of cofactor. Those having ordinary skill in the art will readily understand how to vary these quantities to tailor them to the desired level of productivity and scale of production. Appropriate quantities of optional cofactor regeneration system may be readily determined by routine experimentation based on the amount of cofactor and/or ketoreductase utilized. In general, the reductant (e.g., glucose, formate, and isopropanol) is utilized at levels above the equimolar level of ketoreductase substrate to achieve essentially complete or near complete conversion of the ketoreductase substrate.

The order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor regeneration system, cofactor, ketoreductase, and ketoreductase substrate may be added first to the solvent.

For improved mixing efficiency when an aqueous co-solvent system is used, the cofactor regeneration system, ketoreductase, and cofactor may be added and mixed into the aqueous phase first. The organic phase may then be added and mixed in, followed by addition of the ketoreductase substrate. Alternatively, the ketoreductase substrate may be premixed in the organic phase, prior to addition to the aqueous phase Suitable conditions for carrying out the ketoreductase-catalyzed reduction reactions described herein include a wide variety of conditions which can be readily optimized by routine experimentation that includes, but is not limited to, contacting the engineered ketoreductase enzyme and substrate at an experimental pH and temperature and detecting product, for example, using the methods described in the Examples provided herein.

The ketoreductase catalyzed reduction is typically carried out at a temperature in the range of from about 15° C. to about 75° C. For some embodiments, the reaction is carried out at a temperature in the range of from about 20° C. to about 55° C. In still other embodiments, it is carried out at a temperature in the range of from about 20° C. to about 45° C. The reaction may also be carried out under ambient conditions.

The reduction reaction is generally allowed to proceed until essentially complete, or near complete, reduction of substrate is obtained. Reduction of substrate to product can be monitored using known methods by detecting substrate and/or product. Suitable methods include gas chromatography, HPLC, and the like. Conversion yields of the alcohol reduction product generated in the reaction mixture are generally greater than about 50%, may also be greater than about 60%, may also be greater than about 70%, may also be greater than about 80%, may also be greater than about 90%, and are often greater than about 97%.

7. EXAMPLES

Various features and embodiments of the disclosure are illustrated in the following representative examples, which are intended to be illustrative, and not limiting.

In the following descriptions, wherever glucose dehydrogenase (GDH) is used, it is GDH CDX901, obtainable from Julich Chiral Solutions, Jülich, Germany.

7.1 Example 1: Wild-Type Ketoreductase Gene Acquisition and Construction of Expression Vectors Ketoreductase (KRED) encoding genes are designed for expression in *E. coli* based on the reported amino acid sequence of the ketoreductase and a codon optimization algorithm as described in Example 1 of U.S. provisional application Ser. No. 60/848,950, incorporated herein by reference. (Standard codon-optimization software also is reviewed in e.g., "OPTIMIZER: a web server for optimizing the codon usage of DNA sequences," Puigbò et al., Nucleic Acids Res. 2007 July; 35 (Web Server issue): W126-31. Epub 2007 Apr. 16.) Genes are synthesized using oligonucleotides composed, e.g., of 42 nucleotides and cloned into expression vector pCK110900 (depicted as FIG. 3 in United States Patent Application Publication 20060195947) under the control of a lac promoter. The expression vector also contains the P15a origin of replication and the chloramphenicol resistance gene. Resulting plasmids are transformed into *E. coli* W3110 using standard methods. Examples of codon-optimized genes and the encoding polypeptides as well are listed in Table 5. The activity of the wild-type ketoreductases is confirmed as described in U.S. provisional application Ser. No. 60/848,950.

TABLE 5

Abbreviations, Source and Citations for Representative Ketoreductases

| Ketoreductase | Microorganism from which enzyme was originally identified | Genbank Acc. No. | GI Number | Polynucleotide SEQ ID No | Polypeptide SEQ ID No or Source |
|---|---|---|---|---|---|
| ADH-CM | *Candida magnoliae* | AB036927.1 | 12657576 | SEQ ID NO: 131 | SEQ ID NO: 132 |
| YDL | *Saccharomyces cerevisiae* | NP_010159.1 | 6320079 | SEQ ID NO: 137 | SEQ ID NO: 138 |
| ADH-LB | *Lactobacillus brevis* | 1NXQ_A | 30749782 | SEQ ID NO: 1 | SEQ ID NO: 2 |
| ADH-RE | *Rhodococcus erythropolis* | AAN73270.1 | 34776951 | SEQ ID NO: 133 | SEQ ID NO: 134 |
| YGL | *Saccharomyces cerevisiae* | NP_011476 | 6321399 | SEQ ID NO: 135 | SEQ ID NO: 136 |
| YPR | *Saccharomyces cerevisiae* | NP_010656.1 | 6320576 | SEQ ID NO: 139 | SEQ ID NO: 140 |
| GRE | *Saccharomyces cerevisiae* | NP_014490.1 | 6324421 | SEQ ID NO: 141 | SEQ ID NO: 142 |
| ADH-LK | *Lactobacillus kefir* | AAP94029.1 | 33112056 | SEQ ID NO: 3 | SEQ ID NO: 4 |
| ADH-SB | *Sporobolomyces salmonicolor* | Q9UUN9 | 30315955 | SEQ ID NO: 145 | SEQ ID NO: 146 |
| ADH-SC | *Streptomyces coelicolor* | NP_631415.1 | 21225636 | SEQ ID NO: 143 | SEQ ID NO: 144 |
| ADH-TB | *Thermoanaerobium brockii* | X64841.1 | 1771790 | SEQ ID NO: 153 | SEQ ID NO: 154 |
| ADH-CP | *Candida parapsilosis* | BAA24528 | 2815409 | | Julich Chiral Solutions Cat. No. 03.11 |
| DR-LB | *Lactobacillus brevis* diacetyl reductase | ABJ63353.1 | 116098204 | | Julich Chiral Solutions Cat. No. 8.1 |
| ADH-HE | Horse liver | DEHOAL | 625197 | SEQ ID NO: 155 | SEQ ID NO: 156 |
| ADH-CB | *Candida boidinii* | CAD66648 | 28400789 | | Julich Chiral Solutions Cat. No. 02.10 |
| LDH-LL | *Lactobacillus leichmannii* | | | | Fluka Cat. No. 61306 |
| ADH-AF | *Aspergillus flavus* | P41747 | 1168346 | SEQ ID NO: 147 | SEQ ID NO: 148 |
| ADH-001 | *Oenococcus oeni* | ZP_00318704.1 | 48864831 | SEQ ID NO: 149 | SEQ ID NO: 150 |

TABLE 5-continued

Abbreviations, Source and Citations for Representative Ketoreductases

| Ketoreductase | Microorganism from which enzyme was originally identified | Genbank Acc. No. | GI Number | Polynucleotide SEQ ID No | Polypeptide SEQ ID No or Source |
|---|---|---|---|---|---|
| ADH-RU | Ralstonia eutropha Lactobacillus minor | ZP_00202558.1 | 46131317 | SEQ ID NO: 151 SEQ ID NO: 157 | SEQ ID NO: 152 SEQ ID NO: 158 |

Polynucleotides encoding engineered ketoreductases of the present invention are likewise cloned into vector pCK110900 for expression in E. coli W3110.

7.2 Example 2: Production of Ketoreductase Powders; Shake Flask Procedure

A single microbial colony of E. coli containing a plasmid with the ketoreductase gene of interest is inoculated into 50 ml Luria Bertani broth containing 30 µg/ml chloramphenicol and 1% glucose. Cells are grown overnight (at least 16 hrs) in an incubator at 30° C. with shaking at 250 rpm. The culture is diluted into 250 ml Terrific Broth (12 g/L bacto-tryptone, 24 g/L yeast extract, 4 ml/L glycerol, 65 mM potassium phosphate, pH 7.0, 1 mM MgSO4, 30 µg/ml chloramphenicol) in 1 liter flask to an optical density at 600 nm (OD600) of 0.2 and allowed to grow at 30° C. Expression of the ketoreductase gene is induced with 1 mM IPTG when the OD600 of the culture is 0.6 to 0.8 and incubated overnight (at least 16 hrs). Cells are harvested by centrifugation (5000 rpm, 15 min, and 4° C.) and the supernatant discarded. The cell pellet is resuspended with an equal volume of cold (4° C.) 100 mM triethanolamine (chloride) buffer, pH 7.0 (including 2 mM MgSO4 in the case of ADH-LK and ADH-LB and engineered ketoreductases derived therefrom), and harvested by centrifugation as above. The washed cells are resuspended in two volumes of the cold triethanolamine (chloride) buffer and passed through a French Press twice at 12000 psi while maintaining the temperature at 4° C. Cell debris is removed by centrifugation (9000 rpm, 45 min, and 4° C.). The clear lysate supernatant is collected and stored at −20° C. Lyophilization of frozen clear lysate provides a dry powder of crude ketoreductase enzyme.

7.3 Example 3: Production of Ketoreductases; Fermentation Procedure

In an aerated agitated 15 L fermenter, 6.0 L of growth medium containing 0.88 g/L ammonium sulfate, 0.98 g/L of sodium citrate; 12.5 g/L of dipotassium hydrogen phosphate trihydrate, 6.25 g/L of potassium dihydrogen phosphate, 6.2 g/L of Tastone-154 yeast extract, 0.083 g/L ferric ammonium citrate, and 8.3 ml/L of a trace element solution containing 2 g/L of calcium chloride dihydrate, 2.2 g/L of zinc sulfate septahydrate, 0.5 g/L manganese sulfate monohydrate, 1 g/L cuprous sulfate heptahydrate, 0.1 g/L ammonium molybdate tetrahydrate and 0.02 g/L sodium tetraborate decahydrate are brought to a temperature of 30° C. The fermenter is inoculated with a late exponential culture of E. coli W3110, containing a plasmid with the ketoreductase gene of interest, grown in a shake flask as described in Example 3 to a starting OD600 of 0.5 to 2.0. The fermenter is agitated at 500-1500 rpm and air is supplied to the fermentation vessel at 1.0-15.0 L/min to maintain dissolved oxygen level of 30% saturation or greater. The pH of the culture is controlled at 7.0 by addition of 20% v/v ammonium hydroxide. Growth of the culture is maintained by the addition of a feed solution containing 500 g/L cerelose, 12 g/L ammonium chloride and 10.4 g/L magnesium sulfate heptahydrate. After the culture reached an OD600 of 50, expression of ketoreductase is induced by the addition of isopropyl-b-D-thiogalactoside (IPTG) to a final concentration of 1 mM. The culture is grown for another 14 hours. The culture is then chilled to 4° C. and maintained at 4° C. until harvested. Cells are harvested by centrifugation at 5000 G for 40 minutes in a Sorval RC12BP centrifuge at 4° C. Harvested cells are used directly in the following downstream recovery process or are stored at 4° C. until such use.

The cell pellet is resuspended in 2 volumes of 100 mM triethanolamine (chloride) buffer, pH 6.8, at 4° C. to each volume of wet cell paste. The intracellular ketoreductase is released from the cells by passing the suspension through a homogenizer fitted with a two-stage homogenizing valve assembly using a pressure of 12000 psig. The cell homogenate is cooled to 4° C. immediately after disruption. A solution of 10% w/v polyethyleneimine, pH 7.2, is added to the lysate to a final concentration of 0.5% w/v and stirred for 30 minutes. The resulting suspension is clarified by centrifugation at 5000 G in a standard laboratory centrifuge for 30 minutes. The clear supernatant is decanted and concentrated ten times using a cellulose ultrafiltration membrane with a molecular weight cut off of 30 KD. The final concentrate is dispensed into shallow containers, frozen at −20° C. and lyophilized to powder. The ketoreductase powder is stored at −20° C.

7.4 Example 4: Analytical Methods for the Conversion of 5-((4S)-2-oxo-4-phenyl (1,3-oxazolidin-3-yl))-1-(4-fluorophenyl) pentane-1,5-dione to (4S)-3-[(5 S)-5-(4-fluorophenyl)-5-hydroxypentanoyl]-4-phenyl-1,3-oxazolidin-2-one Analytical methods to determine conversion of (S)-1-(4-Fluoro-phenyl)-5-(2-oxo-4-phenyl-oxazolidin-3-yl)-pentane-1,5-dione and enantiomeric excess of (4S)-3-[(5S)-5-(4-Fluoro-phenyl)-5-hydroxy-pentanoyl]-4-phenyl-oxazolidin-2-one.

Achiral HPLC method to determine conversion. Reduction (S)-1-(4-Fluoro-phenyl)-5-(2-oxo-4-phenyl-oxazolidin-3-yl)-pentane-1,5-dione to (4S)-3-[(5 S)-5-(4-Fluoro-phenyl)-5-hydroxy-pentanoyl]-4-phenyl-oxazolidin-2-one was determined using an Agilent 1100 HPLC equipped with an Agilent Zorbax Eclipse XDB column (7.5 cm length, 2.1 mm diameter), eluent: water/acetonitrile 50:50, flow 0.7 ml/min; column temperature 40° C.). Retention times: (4S)-

3-[(5S)-5-(4-Fluoro-phenyl)-5-hydroxy-pentanoyl]-4-phenyl-oxazolidin-2-one: 1.3 min, (S)-1-(4-Fluoro-phenyl)-5-(2-oxo-4-phenyl-oxazolidin-3-yl)-pentane-1,5-dione: 2.2 min.

Chiral HPLC method to determine stereopurity of (4S)-3-[5-(4-Fluoro-phenyl)-5-hydroxy-pentanoyl]-4-phenyl-oxazolidin-2-one. The stereomeric purity of (4S)-3-[5-(4-Fluoro-phenyl)-5-hydroxy-pentanoyl]-4-phenyl-oxazolidin-2-one was determined using an Agilent 1100 HPLC equipped with a Chiralcel OD-H column (15 cm length, 2.1 mm diameter, eluent: hexane/ethanol 80:20, flow 1 ml/min) Retention times: (4R)-3-[(5S)-5-(4-Fluoro-phenyl)-5-hydroxy-pentanoyl]-4-phenyl-oxazolidin-2-one: 6.64 min, (4S)-3-[(5S)-5-(4-Fluoro-phenyl)-5-hydroxy-pentanoyl]-4-phenyl-oxazolidin-2-one: 7.93 min, (S)-1-(4-Fluoro-phenyl)-5-(2-oxo-4-phenyl-oxazolidin-3-yl)-pentane-1,5-dione: 10.44 min.

7.5 Example 5: Evaluation of Wild-Type Ketoreductases for Reduction of 5-((4S)-2-oxo-4-phenyl (1,3-oxazolidin-3-yl))-1-(4-fluorophenyl) pentane-1,5-dione KREDs described in Table 5 of Example 1 are screened using NADH and NADPH as cofactors and glucose dehydrogenase/glucose or isopropylalcohol ("IPA") as co-factor regeneration system. 100 µl of cell lysate was added to a deep well plate (Costar #3960) containing 25 µl 5 mg/ml Na-NADP (Oriental Yeast) and 2 mM $MgSO_4$ in 100 mM triethanolamine(chloride) (pH7.0), and 125 µl isopropyl alcohol containing 2 g/L (S)-1-(4-Fluoro-phenyl)-5-(2-oxo-4-phenyl-oxazolidin-3-yl)-pentane-1,5-dione. After sealing the plates with aluminum/polypropylene laminate heat seal tape (Velocity 11 (Menlo Park, Calif.), Cat#06643-001), reactions were run for at least 16 hrs at ambient temperature. At the end of the reaction 1 ml acetonitrile (for reversed phase HPLC) or MTBE (for normal phase HPLC) was added per well. Plates were resealed, shaken for 20 minutes, and centrifuged (4000 rpm, 10 min, 4° C.). 200 ul of the organic layer was transferred into a new shallow-well microtiter plate for analysis.

This example will demonstrate that wild-type ketoreductases have very little if any activity on 5-((4S)-2-oxo-4-phenyl (1,3-oxazolidin-3-yl))-1-(4-fluorophenyl) pentane-1,5-dione.

7.6 Example 6: Evaluation of ADH-LK Variants for Reduction of 5-((4S)-2-oxo-4-phenyl (1,3-oxazolidin-3-yl))-1-(4-fluorophenyl) pentane-1,5-dione Several ADH-LK variants that had been generated are evaluated and found that an ADH-LK variant with SEQ ID NO:8 converted the substrate to the chiral (4S)-3-[(5S)-5-(4-fluorophenyl)-5-hydroxypentanoyl]-4-phenyl-1,3-oxazolidin-2-one product when evaluated under the conditions described in Example 5 and as listed in Table 6.

TABLE 6

Activity of an ADH-LK variant

| SEQ ID NO | Number of mutations relative to ADH-LK | Activity |
|---|---|---|
| ADH-LK | 0 | 0 |
| 8 | 8 | ~0.008 g/L · $g_{enzyme}$ · day |

This example shows that an ADH-LK variant containing G7S, R108H, G117S, E145S, N157T, Y190C, K112R, and I223V mutations converts 5-((4S)-2-oxo-4-phenyl (1,3-oxazolidin-3-yl))-1-(4-fluorophenyl) pentane-1,5-dione to (4S)-3-[(5S)-5-(4-fluorophenyl)-5-hydroxypentanoyl]-4-phenyl-1,3-oxazolidin-2-one with high stereoselectivity (94% stereomeric excess).

7.7 Example 7: High Throughput HPLC Assay for Ketoreductase Activity on 5-((4S)-2-oxo-4-phenyl (1,3-oxazolidin-3-yl))-1-(4-fluorophenyl) pentane-1, 5-dione Using Isopropylalcohol for Co-Factor Recycling Plasmid libraries obtained by directed evolution and containing evolved ketoreductase genes are transformed into *E. coli* and plated on Luria-Bertani (LB) broth containing 1% glucose and 30 µg/mL chloramphenicol (CAM). After incubation for at least 16 hrs at 30° C., colonies are picked using a Q-bot® robotic colony picker (Genetix USA, Inc., Beaverton, Oreg.) into 96-well shallow well microtiter plates containing 180 µL Terrific broth (TB), 1% glucose, 30 µg/mL chloramphenicol (CAM), and 2 mM $MgSO_4$. Cells are grown overnight at 30° C. with shaking at 200 rpm. 20 µL of this culture was then transferred into 96-deep well plates containing 350 µL Terrific broth (TB), 2 mM $MgSO_4$ and 30 µg/mL CAM. After incubation of deep-well plates at 30° C. with shaking at 250 rpm for 2.5 to 3 hours ($OD_{600}$ 0.6-0.8), recombinant gene expression by the cell cultures is induced by addition of isopropyl thiogalactoside (IPTG) to a final concentration of 1 mM. The plates are then incubated at 30° C. with shaking at 250 rpm for 15-23 hrs.

100 µl of cell lysate was added to a deep well plate (Costar #3960) containing 25 µl 5 mg/ml Na-NADP (Oriental Yeast) and 2 mM $MgSO_4$ in 100 mM triethanolamine(chloride) (pH7.0), and 125 µl isopropyl alcohol containing 2 g/L (S)-1-(4-Fluoro-phenyl)-5-(2-oxo-4-phenyl-oxazolidin-3-yl)-pentane-1,5-dione. After sealing the plates with aluminum/polypropylene laminate heat seal tape (Velocity 11 (Menlo Park, Calif.), Cat#06643-001), reactions were run for at least 16 hrs at ambient temperature. At the end of the reaction 1 ml acetonitrile (for reversed phase HPLC) or MTBE (for normal phase HPLC) was added per well. Plates were resealed, shaken for 20 minutes, and centrifuged (4000 rpm, 10 min, 4° C.). 200 ul of the organic layer was transferred into a new shallow-well microtiter plate for analysis as described in Example 4.

This example describes the method that was used to identify KRED variants improved for 5-((4S)-2-oxo-4-phenyl (1,3-oxazolidin-3-yl))-1-(4-fluorophenyl) pentane-1,5-dione reduction.

7.8 Example 8: Reduction of 5-((4S)-2-oxo-4-phenyl (1,3-oxazolidin-3-yl))-1-(4-fluorophenyl) pentane-1,5-dione by Engineered Ketoreductases Derived from ADH-LK Improved ADH-LK variants for the reduction of (S)-1-(4-Fluoro-phenyl)-5-(2-oxo-4-phenyl-oxazolidin-3-yl)-pentane-1,5-dione to (4S)-3-[(5S)-5-(4-Fluoro-phenyl)-5-hydroxy-pentanoyl]-4-phenyl-oxazolidin-2-one were analyzed in small scale chemical reactions. In a glass vial with a teflon stirring bar, 500 mg (S)-1-(4-Fluoro-phenyl)-5-(2-oxo-4-phenyl-oxazolidin-3-yl)-pentane-1,5-dione, 100 mg KRED variant, 0.5 mg Na-NADP (Oriental Yeast), 2.5 ml isopropyl alcohol, and 2.5 ml 100 mM triethanolamine(chloride) buffer, pH 7.0, 2 mM MgSO$_4$ was mixed and stirred overnight at 25° C. Reaction samples were analyzed by the method of Example 4.

7.9 Example 9: Preparative Scale Production of (4S)-3-[(5S)-5-(4-fluorophenyl)-5-hydroxypentanoyl]-4-phenyl-1,3-oxazolidin-2-one Preparative scale production of (4S)-3-[(5S)-5-(4-Fluorophenyl)-5-hydroxy-pentanoyl]-4-phenyl-oxazolidin-2-one using iPA for cofactor recycle. In a 1 liter round bottom flask thermostatted at 25° C. with Teflon stirring bar, 2.5 grams lyophilized KRED catalyst was dissolved in 200 ml 100 mM triethanolamine(chloride), pH 7.0, 2 mM MgSO$_4$. After the enzyme was dissolved, 175 mg □-NADP$^+$ was added, followed by 5 grams of (S)-1-(4-Fluoro-phenyl)-5-(2-oxo-4-phenyl-oxazolidin-3-yl)-pentane-1,5-dione. 200 ml 2-propanol was added, resulting in the formation of a white precipitate. After stirring for 5 hours at 25° C. by which time the reaction was complete, the mixture was filtered through Celite to remove the insoluble protein fraction. Isopropanol was distilled off until about 200 ml solution remained. The aqueous layer was extracted twice with 200 ml ethyl acetate and the combined ethyl acetate layers were washed with saturated NaCl. The ethyl acetate layer was dried over Na$_2$SO$_4$ and after filtration, ethyl acetate was distilled off yielding ~5 g of the chiral alcohol 2 as slightly yellow colored oil. The stereomeric purity (determined as described in Example 4) of (4S)-3-[(5S)-5-(4-Fluoro-phenyl)-5-hydroxy-pentanoyl]-4-phenyl-oxazolidin-2-one was >99% (S,S).

Preparative scale production of (4S)-3-[(5S)-5-(4-Fluorophenyl)-5-hydroxy-pentanoyl]-4-phenyl-oxazolidin-2-one using GDH and external pH control. A 2 L resin kettle is equipped with a mechanical overhead stirrer, pH probe and a port for titrating aqueous 4N NaOH. The external titrator (Schott Titronic) is programmed to maintain the pH at 7.00+/−0.10

To the resin kettle is charged 5-((4S)-2-oxo-4-phenyl (1,3-oxazolidin-3-yl))-1-(4-fluorophenyl) pentane-1,5-dione (120 g) as a powder, followed by dextrose powder (91 g), toluene (200 ml), and buffer (750 ml of 0.02M potassium phosphate and 0.002 M Magnesium sulfate). The head plate is fitted and dogged down. All appropriate ports are closed except for the pH probe port which is fitted with the pH probe. The motor is then fitted to the coupling and stirring is initiated to a rate of 1200 rpm. The pH of the reaction mixture is measured and adjusted to 7.0+0.1. The temperature of the reaction mixture is brought to 30+1° C. While the reaction is brought to temperature, 0.4 g Na-NADP, 0.8 g GDH, and 2.00 g of lyophilized KRED were dissolved in 40 ml of de-ionized water. When the reactor temperature is in the appropriate range, the enzyme suspension is added in one portion while stirring. The titration program is started and the pH is maintained at 7.0+/−0.1 for the duration of the reaction by addition of 4N NaOH. The reaction is stirred at 30° C. for 16 hr. The reactor is sampled periodically and checked for substrate conversion by HPLC as described in Example 4. Periodic sampling and analysis is continued until the conversion reaches 99% or better.

When the reaction is deemed to be over, stirring is stopped and the bi-phasic mixture is allowed to separate. Clear aqueous layer (240 ml) is removed from the bottom of the vessel as best as possible by syringe. 90 ml of this aqueous layer is added to 22 g Celite and set aside, the rest is discarded. Toluene (240 ml) is added to the reaction mixture, which is then stirred for 10 minutes and allowed to settle again for 30 minutes. Another portion of 180 ml of clear aqueous phase is removed by syringe and discarded. The stirring is restarted, followed by addition of the Celite and aqueous mixture that had been set aside. Stirring is continued for 10 minutes. The reaction mixture is filtered through an "M" sintered glass funnel to remove insoluble material (primarily denatured enzymes and Celite). The cake is filtered until almost dry. The reactor is rinsed with toluene (100 mL). The reactor rinse is added to the filter cake. The filter cake is tamped down, then washed with 100 ml more toluene and allowed to run dry. The biphasic filtrate is transferred to a separatory funnel and separated. Saturated aqueous ammonium sulfate (100 ml) is added to the organic layer and mixed lightly and allowed to separate. The lower (aqueous) layer is removed. The toluene is then washed twice with de-ionized water. After the final separation, the resulting wet toluene solution containing the product is charged to a 1 liter flask and stripped down under vacuum on a rotary evaporator. While doing this, the heating bath is warmed to no more than 50° C. and the vacuum is brought down from 110 mm (initially) to 2 mm. The resulting crude product is an oil that solidifies on standing within two days. Yield: 125 g.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An engineered polypeptide having ketoreductase activity, wherein said engineered polypeptide comprises a region with an amino acid sequence having at least 90% identity to residues 90 to 211 of SEQ ID NO: 130, and further comprising one or more of the following features selected from:
   residue corresponding to X94 is a non-polar or a polar residue;
   residue corresponding to X95 is a non-polar or aliphatic residue;
   residue corresponding to X96 is a polar residue;
   residue corresponding to X101 is an acidic, non-polar, or a polar residue;
   residue corresponding to X105 is an acidic or non-polar residue;
   residue corresponding to X108 is a hydrophilic, polar or constrained residue;
   residue corresponding to X111 is a non-polar or aliphatic residue;
   residue corresponding to X112 is an acidic or polar residue;
   residue corresponding to X113 is a non-polar or aliphatic residue;
   residue corresponding to X117 is a non-polar or a polar residue;
   residue corresponding to X127 is a basic or polar residue;
   residue corresponding to X147 is a non-polar, aliphatic, aromatic, or hydrophobic residue;
   residue corresponding to X152 is a non-polar, basic, or hydrophilic residue;
   residue corresponding to X157 is a polar residue;
   residue corresponding to X163 is a non-polar or aliphatic residue;
   residue corresponding to X176 is a non-polar or aliphatic residue;
   residue corresponding to X194 is a constrained, basic, or polar residue;
   residue corresponding to X197 is a hydrophilic, acidic, basic, aliphatic or a non-polar residue;
   residue corresponding to X198 is an acidic, basic, hydrophilic, or non-polar residue;
   residue corresponding to X199 is an acidic, aliphatic, or non-polar residue;
   residue corresponding to X200 is an acidic or constrained residue;
   residue corresponding to X202 is a non-polar residue;
   residue corresponding to X206 is a non-polar, aromatic, or hydrophobic residue;
   residue corresponding to X211 is a basic residue, and
   wherein the amino acid sequence can optionally have one or more differences at other amino acid residues in the domain as compared to the reference sequence.

2. An engineered polypeptide having ketoreductase activity, wherein said engineered polypeptide comprises a region with an amino acid sequence having at least 90% identity residues 90 to 211 of SEQ ID NO: 130, and further comprising one or more of the following features selected from:
   residue corresponding to X94 is asparagine, glycine, or serine;
   residue corresponding to X95 is leucine or methionine;

residue corresponding to X96 is glutamine, asparagine, or threonine;
residue corresponding to X101 is glycine or asparagine;
residue corresponding to X105 is glycine;
residue corresponding to X108 is histidine or serine;
residue corresponding to X112 is aspartic acid;
residue corresponding to X113 is alanine;
residue corresponding to X117 is serine;
residue corresponding to X127 is arginine;
residue corresponding to X147 is leucine;
residue corresponding to X152 is methionine or lysine;
residue corresponding to X157 is threonine;
residue corresponding to X163 is isoleucine;
residue corresponding to X176 is valine;
residue corresponding to X194 is arginine or glutamine;
residue corresponding to X197 is valine or glutamic acid;
residue corresponding to X198 is glycine, glutamic acid, or lysine;
residue corresponding to X199 is aspartic acid;
residue corresponding to X200 is proline;
residue corresponding to X202 is glycine;
residue corresponding to X206 is a glycine;
residue corresponding to X211 is a arginine or lysine; and
wherein the amino acid sequence can optionally have one or more differences at other amino acid residues in the domain as compared to the reference sequence.

* * * * *

SEQUENCE LISTING

```
<160> NUMBER OF SEQ ID NOS: 165

<210> SEQ ID NO 1
<211> LENGTH: 762
<212> TYPE: DNA
<213> ORGANISM: Artificial Sequence
<220> FEATURE:
<223> OTHER INFORMATION: Synthetic Codon Optimized L. Brevis Sequence

<400> SEQUENCE: 1
atgtctaacc gtctggatgg caaagtagcc atcattaccg gcgggactct gggtatcggt      60
ttggcaatcg ccacgaaatt tgtagaggag ggtgcgaaag taatgattac tggtcgtcac     120
```

```
tccgatgtag gtgaaaaggc cgccaaatca gtaggcactc cggatcagat tcagtttttt      180
cagcacgatt catccgatga agatggctgg acgaaactgt tcgacgccac cgagaaagca      240
ttcggcccgg ttagcacctt agtgaacaat gcagggattg cagttaacaa aagcgttgaa      300
gaaactacca cggccgaatg gcgtaaactg ctggccgtta atctggatgg tgttttttc      360 ggcacccgtc tgggcattca gcgcatgaaa aataaaggct tgggcgctag catcatcaat      420
atgagcagta ttgaggggtt cgtaggcgat ccgagcctgg gggcatacaa cgcttccaag      480
ggggcggtac gtatcatgtc gaaaagcgca gcgctggatt gcgcactgaa ggactacgat      540
gtgcgtgtca acacagtaca tccgggctat atcaagaccc cgctggtcga tgatctgccg      600
ggtgctgagg aagcgatgtc acagcgtacg aaaacccta tgggccacat tggcgaaccg      660
aatgacatcg catatatctg tgtgtacctg gcatctaatg aatcgaaatt tgcgacgggt      720
tccgaatttg tggtcgacgg cgggtatacc gcacagtaat ga                        762

<210> SEQ ID NO 2
<211> LENGTH: 252
<212> TYPE: PRT
<213> ORGANISM: Artificial Sequence
<220> FEATURE:
<223> OTHER INFORMATION: Translation of Synthetic Codon Optimized L.
      Brevis Sequence

<400> SEQUENCE: 2

Met Ser Asn Arg Leu Asp Gly Lys Val Ala Ile Ile Thr Gly Gly Thr
1               5                   10                  15

Leu Gly Ile Gly Leu Ala Ile Ala Thr Lys Phe Val Glu Glu Gly Ala
            20                  25                  30

Lys Val Met Ile Thr Gly Arg His Ser Asp Val Gly Glu Lys Ala Ala
        35                  40                  45

Lys Ser Val Gly Thr Pro Asp Gln Ile Gln Phe Phe Gln His Asp Ser
    50                  55                  60

Ser Asp Glu Asp Gly Trp Thr Lys Leu Phe Asp Ala Thr Glu Lys Ala
65                  70                  75                  80

Phe Gly Pro Val Ser Thr Leu Val Asn Asn Ala Gly Ile Ala Val Asn
                85                  90                  95

Lys Ser Val Glu Glu Thr Thr Thr Ala Glu Trp Arg Lys Leu Leu Ala
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Ser Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Pro Gly Ala Glu Glu Ala Met Ser Gln
        195                 200                 205

Arg Thr Lys Thr Pro Met Gly His Ile Gly Glu Pro Asn Asp Ile Ala
    210                 215                 220

Tyr Ile Cys Val Tyr Leu Ala Ser Asn Glu Ser Lys Phe Ala Thr Gly
225                 230                 235                 240

Ser Glu Phe Val Val Asp Gly Gly Tyr Thr Ala Gln
```

<210> SEQ ID NO 3
<211> LENGTH: 759
<212> TYPE: DNA
<213> ORGANISM: Artificial Sequence
<220> FEATURE:
<223> OTHER INFORMATION: Synthetic Codon Optimized L. Kefir Sequence

<400> SEQUENCE: 3

```
atgaccgatc gtctgaaggg caaagtagcc atcgtaaccg gcgggactct gggtatcggt     60
ttggcaatcg ccgataaatt tgtagaggag ggtgcgaaag tagttattac tggtcgtcac    120
gcggatgtag gtgaaaaggc cgccaaatca atcggcggca ctgatgttat tcgctttgtc    180
cagcacgatg catccgatga agcaggctgg acgaaactgt tcgacaccac cgaggaggca    240
ttcggcccgg ttacgaccgt cgtgaacaat gcagggattg cagtttccaa aagcgttgaa    300
gacactacca cggaggaatg gcgtaaactg ctgtccgtta atctggatgg tgttttttc     360
ggcacccgtc tgggcattca gcgcatgaaa aataaaggct gggcgctag catcatcaat    420
atgagcagta ttgaggggtt cgtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgctgagg aaatgatgtc acagcgtacg aaaaccccta tgggccacat ggcgaaccg    660
aatgacatcg catggatctg tgtgtacctg gcatctgacg aatcgaaatt tgcgacgggt    720
gcagaatttg tggtcgacgg cgggtatacc gcacagtga                          759
```

<210> SEQ ID NO 4
<211> LENGTH: 252
<212> TYPE: PRT
<213> ORGANISM: Artificial Sequence
<220> FEATURE:
<223> OTHER INFORMATION: Translation of Synthetic Codon Optimized L. kefir Sequence

<400> SEQUENCE: 4

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

```
Gly Ala Val Arg Ile Met Ser Lys Ser Ala Leu Asp Cys Ala Leu
            165                 170                 175

Lys Asp Tyr Asp Val Arg Val Asn Thr Val His Pro Gly Tyr Ile Lys
        180                 185                 190

Thr Pro Leu Val Asp Asp Leu Glu Gly Ala Glu Glu Met Met Ser Gln
            195                 200                 205

Arg Thr Lys Thr Pro Met Gly His Ile Gly Glu Pro Asn Asp Ile Ala
        210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
            245                 250
```

<210> SEQ ID NO 5
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 5

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat cgctttgtc      180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcgtaaactg ctgtccgtta atctggatgg tgtttttttc     360
ggcacccgtc tgggcattca gcgcatgaaa aataaaggct gggcgctag catcatcaat      420
atgagcagta ttgaggggtt cgtaggcgat ccgacgctgg gggcatacaa cgcttccaag     480
ggggcggtac gtatcatgtc gaaaagcgca gcgctggatt gcgcactgaa ggactacgat     540
gtgcgtgtca acacagtaca tccgggctgc atcaagaccc cgctggtcga tgatctggaa     600
ggtgctgagg aaatgatgtc acagcgtacg aaaaccccta tgggccacat tggcgagccg     660
aatgacatcg catggatctg tgtgtacctg gcatctgacg aatcgaaatt tgcgacgggt     720
gcagaatttg tggtcgacgg cgggtacacc gcacagtga                            759
```

<210> SEQ ID NO 6
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 6

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80
```

```
Phe Gly Pro Val Thr Thr Val Asn Asn Ala Gly Ile Ala Val Ser
                 85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Leu Glu Gly Ala Glu Met Met Ser Gln
        195                 200                 205

Arg Thr Lys Thr Pro Met Gly His Ile Gly Glu Pro Asn Asp Ile Ala
        210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 7
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 7
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa agcgttgaa      300 gacactacca cggaggaatg cacaaactg ctgtccgtta tctggatag tgtttttttc       360 ggcaccgtc tgggcattca gcgcatgaag aataaaggct gggcgctag catcatcaat      420 atgagcagta tcagtgggtt cgtaggcgat ccgacgctgg gggcatacac tgcttccaag     480
ggggcggtac gtatcatgtc gaaaagcgca gcgctggatt gcgcactgaa ggactacgat     540
gtgcgtgtca acacagtaca tccgggctgt atcaagaccc cgctggtcga tgatctggaa     600
ggtgctgagg aaatgatgtc acagcgtacg agaaccccta tgggccacat tggcgaaccg     660
aatgacgtgg catggatctg tgtgtacctg gcatctgacg aatcgaaatt tgcgacgggt     720
gcagaatttg tggtcgacgg cgggtatacc gcacagtga                             759

<210> SEQ ID NO 8
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 8
```

Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Thr Leu Gly Ala Tyr Thr Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Leu Glu Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 9
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 9
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa agcgttgaa      300 gacactacca cggaggaatg gcgtaaactg ctgtccgtta atctggatgg tgttttttc      360 ggcacccgtc tgggcattca gcgcatgaaa aataaaggct gggcgctag catcatcaat     420 atgagcagta ttgagggggct ggtaggcgat ccgacgctgg gggcatacaa cgcttccaag    480
ggggcggtac gtatcatgtc gaaaagcgca gcgctggatt gcgcactgaa ggactacgat     540
gtgcgtgtca acacagtaca tccgggcccc atcaagaccc cgctgctcga tgatctggaa     600
ggtgctgagg aaatgatgtc acagcgtacg aaaaccccta tgggccacat tggcgaaccg     660

```
aatgacatcg catggatctg tgtgtacctg gcatctgacg aatcgaaatt tgcgacgggt    720
gcagaatttg tggtcgacgg cgggtatacc gcacagtga                          759
```

<210> SEQ ID NO 10
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 10

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 11
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 11

```
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
```

```
cagcacgatg cgtccgatga agcaggctgg acgaaactgt tcgacaccac cgaggaggca    240
ttcggcccgg ttacgaccgt cgtgaacaat gcagggattg gggttgttaa aagcgttgaa    300
gacactacca cggaggaatg gcgtaaactg ctgtccgtta atctggatgg tgttttttc     360
ggcacccgtc tgggcattca gcgcatgaaa aataaaggct tgggcgctag catcatcaat    420
atgagcagta ttctggggtt cgtaggcgat ccgacgacgg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgctgctcga tgatctggaa    600
ggtgctgagg aaatgatgtc acagcgtacg aaaaccccta tgggccacat ggcgaaccg     660
aatgacatcg catgggtctg tgtgtacctg gcatctgacg aatcgaaatt tgcgacgggt    720
gcagaatttg tggtcgacgg cgggtggacc gcacagtga                            759
```

```
<210> SEQ ID NO 12
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 12

Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Gly Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Leu Gly Phe Val Gly Asp Pro Thr Thr Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Leu Leu Asp Asp Leu Glu Gly Ala Glu Glu Met Met Ser Gln
        195                 200                 205
Arg Thr Lys Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Trp Thr Ala Gln
                245                 250
```

-continued

```
<210> SEQ ID NO 13
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 13
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat cgctttgtc     180 cagcacgatg cgtccgatga agcaggctgg acgaaactgt tcgacaccac cgaggaggca    240
ttcggcccgg ttacgaccgt cgtgaacaat gcagggattg gggttgttaa aagcgttgaa    300
gacactacca cggaggaatg gcgtaaactg ctgtccgtta atctggatgg tgttttttc     360 ggcacccgtc tgggcattca gcgcatgaaa aataaaggct gggcgctag catcatcaat     420 atgagcagta ttttcgggat ggtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgctgctcga tgattgggaa    600
ggtgctgagg aaatgatgtc acagcgtacg aaaaccccta tgggccacat tggcgaaccg    660
aatgacatcg catgggtctg tgtgtacctg gcatctgatg aatcgaaatt tgcgacgggt    720
gcagaatttg tggtcgacgg cgggtggacc gcacagtga                           759

<210> SEQ ID NO 14
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 14

Met Thr Asp Arg Leu Lys Gly Lys Val Ala Ile Val Thr Gly Gly Thr
  1               5                  10                  15

Leu Gly Ile Gly Leu Ala Ile Ala Asp Lys Phe Val Glu Glu Gly Ala
             20                  25                  30

Lys Val Val Ile Thr Gly Arg Arg Ala Asp Val Gly Glu Lys Ala Ala
         35                  40                  45

Lys Ser Ile Gly Gly Thr Asp Val Ile Arg Phe Val Gln His Asp Ala
     50                  55                  60

Ser Asp Glu Ala Gly Trp Thr Lys Leu Phe Asp Thr Thr Glu Glu Ala
 65                  70                  75                  80

Phe Gly Pro Val Thr Thr Val Val Asn Asn Ala Gly Ile Gly Val Val
                 85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
```

```
                180              185              190
Thr Pro Leu Leu Asp Asp Trp Glu Gly Ala Glu Glu Met Met Ser Gln
            195              200              205

Arg Thr Lys Thr Pro Met Gly His Ile Gly Glu Pro Asn Asp Ile Ala
        210              215              220

Trp Val Cys Val Tyr Leu Ala Ser Asp Glu Ser Lys Phe Ala Thr Gly
225              230              235              240

Ala Glu Phe Val Val Asp Gly Gly Trp Thr Ala Gln
            245              250

<210> SEQ ID NO 15
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 15
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgc     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattg ggttgttaa aagcgttgaa      300 gacactacca cggaggaatg gcgtaaactg ctgtccgtta atctggatgg tgttttttc      360 ggcacccgtc tgggcattca cgcatgaaa aataaaggct gggcgctag catcatcaat      420 atgagcagta ttttcgggat ggtaggcgat ccgacgctgg gggcatacaa cgcttccaag     480
ggggcggtac gtatcatgtc gaaaagcgca cgcgctggat tgcgcactga aggactacgat    540 gtgcgtgtca acacagtaca tccgggcccc atcaagaccc cgctgctcga tgatctggaa     600
ggtgctgagg aaatgttttc acagcgtacg aaaaccccta tgggccacat tggcgaaccg     660
aatgacatcg catgggtctg tgtgtacctg gcatctgacg aatcgaaatt tgcgacgggt     720
gcagaatttg tggtcgacgg cgggtggacc gcacagtga                            759

<210> SEQ ID NO 16
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 16

Met Thr Asp Arg Leu Lys Gly Lys Val Ala Ile Val Thr Gly Gly Thr
1               5                  10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
```

100                 105                 110
Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
        130                 135                 140

Phe Gly Met Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Met Phe Ser Gln
            195                 200                 205

Arg Thr Lys Thr Pro Met Gly His Ile Gly Glu Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 17
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 17
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcaggattg gggttgttaa aagcgttgaa      300
gacactacca cggaggaatg gcgtaaactg ctgtccgtta atctggatgg tgtttttttc     360
ggcacccgtc tgggcattca gcgcatgaaa aataaaggct ggggcgctag catcatcaat     420
atgagcagta ttttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgctgctcga tgatctggaa     600
ggtgctgagg aaatgatgtc acagcgtacg aaaaccccta tgggccacat tggcgaaccg     660
aatgacatcg catgggtctg tgtgtacctg gcatctgacg aatcgaaatt tgcgacgggt     720
gcagaatttg tggtcgacgg cgggtggacc gcacagtga                            759

<210> SEQ ID NO 18
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 18

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala

```
            20                  25                  30
Lys Val Val Ile Thr Gly Arg His Ala Asp Val Gly Glu Lys Ala Ala
             35                  40                  45
Lys Ser Ile Gly Gly Thr Asp Val Ile Arg Phe Val Gln His Asp Ala
         50                  55                  60
Ser Asp Glu Ala Gly Trp Thr Lys Leu Phe Asp Thr Thr Glu Glu Ala
 65                  70                  75                  80
Phe Gly Pro Val Thr Thr Val Val Asn Asn Ala Gly Ile Gly Val Val
                 85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Phe Gly Met Val Gly Asp Pro Thr Thr Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Leu Leu Asp Asp Leu Glu Gly Ala Glu Glu Met Met Ser Gln
        195                 200                 205
Arg Thr Lys Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Trp Thr Ala Gln
                245                 250

<210> SEQ ID NO 19
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 19
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattg gggttgttaa aagcgttgaa     300
gacactacca cggaggaatg gcgtaaactg ctgtccgtta atctggatgg tgttttttc      360 ggcacccgtc tgggcattca gcgcatgaaa aataaaggct gggcgctag  catcatcaat     420 atgagcagta ttttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgatgctcga tgattatgaa     600
ggtgctgagg aaatgatgtc acagcgtacg aaaaccccta tgggccacat tggcgaaccg     660
aatgacatcg catgggtctg tgtgtacctg gcatctgacg aatcgaaatt tgcgacgggt     720
gcagaatttg tggtcgacgg cgggtggacc gcacagtga                           759
```

<210> SEQ ID NO 20
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 20

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Tyr Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 21
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 21
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattg ggttgttaa aagcgttgaa      300

```
gacactacca cggaggaatg gcgtaaactg ctgtccgtta atctggatgg tgttttttc     360
ggcacccgtc tgggcattca gcgcatgaaa aataaaggct tgggcgctag catcatcaat   420
atgagcagta ttttcgggat ggtaggcgat ccgtctaccg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgctgctcga tgatctggaa   600
ggtgctgagg aaatgatgtc acagcgtacg aaaaccccta tgggccacat tggcgaaccg   660
aatgacatcg catgggtctg tgtgtacctg gcatctgacg aatcgaaatt tgcgacgggt   720
gcagaatttg tggtcgacgg cgggtggacc gcacagtga                          759
```

<210> SEQ ID NO 22
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 22

```
Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Gly Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Phe Gly Met Val Gly Asp Pro Ser Thr Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Leu Leu Asp Asp Leu Glu Gly Ala Glu Glu Met Met Ser Gln
        195                 200                 205
Arg Thr Lys Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Trp Thr Ala Gln
                245                 250
```

<210> SEQ ID NO 23
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 23

| | | |
|---|---|---|
| atgaccgatc gtctgaaggg caaagtagcc atcgtaaccg gcgggacact gggtatcggt | 60 |
| ttggcaatcg ccgataaatt tgtagaggag ggtgcgaaag tagttattac tggtcgtcac | 120 |
| gcggatgtag gtgaaaaggc cgccaaatca atcggcggca ctgatgttat tcgctttgtc | 180 |
| cagcacgatg cgtccgatga agcaggctgg acgaaactgt tcgacaccac cgaggaggca | 240 |
| ttcggcccgg ttacgaccgt cgtgaacaat gcagggattg gggttgttaa agcgttgaa | 300 |
| gacactacca cggaggaatg gcgtaaactg ctgtccgtta atctggatgg tgttttttc | 360 |
| ggcacccgtc tgggcattca gcgcatgaaa aataaaggct gggcgctag catcatcaat | 420 |
| atgagcagta ttttcgggat ggtaggcgat ccgtctctgg gggcatacaa cgcttccaag | 480 |
| ggggcggtac gtatcatgtc gaaaagcgca gcgctggatt gcgcactgaa ggactacgat | 540 |
| gtgcgtgtca acacagtaca tccgggcccc atcaagaccc cgatgctcga tgatctggaa | 600 |
| ggtgctgagg aaatgttttc acagcgtacg aaaaccccta tgggccacat tggcgaaccg | 660 |
| aatgacatcg catgggtctg tgtgtacctg gcatctgacg aatcgaaatt tgcgacgggt | 720 |
| gcagaatttg tggtcgacgg cgggtggacc gcacagtga | 759 |

<210> SEQ ID NO 24
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 24

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Phe Gly Met Val Gly Asp Pro Ser Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Met Leu Asp Asp Leu Glu Gly Ala Glu Glu Met Phe Ser Gln
        195                 200                 205
```

```
Arg Thr Lys Thr Pro Met Gly His Ile Gly Glu Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 25
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 25
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgc     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattg ggttgttaa aagcgttgaa      300 gacactacca cggaggaatg gcgtaaactg ctgtccgtta atctggatgg tgttttttc     360 ggcacccgtc tgggcattca gcgcatgaaa ataaaggct tgggcgctag catcatcaat      420
atgagcagta ttttcgggat ggtaggcgat ccgactaccg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgctgctcga tgatctggaa     600
ggtgctgagg aaatgatgtc acagcgtacg aaaaccccta tgggccacat tggcgaaccg     660
aatgacatcg catgggtctg tgtgtacctg gcatctgacg aatcgaaatt tgcgacgggt     720
gcagaatttg tggtcgacgg cgggtggacc gcacagtga                           759

<210> SEQ ID NO 26
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 26
```

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

```
Met Lys Asn Lys Gly Leu Gly Ala Ser Ile Ile Asn Met Ser Ser Ile
        130                 135                 140

Phe Gly Met Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 27
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 27
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa agcgttgaa      300 gacactacca cggaggaatg gcgtaaactg ctgtccgtta atctggatgg tgtttttttc     360
ggcacccgtc tgggcattca gcgcatgaaa aataaaggct gggcgctag catcatcaat     420 atgagcagta ttgcggggct ggtaggcgat ccgacgctgg gggcatacaa cgcttccaag     480
ggggcggtac gtatcatgtc gaaaagcgca gcgctggatt gcgcactgaa ggactacgat     540
gtgcgtgtca acacagtaca tccgggctgc atcaagaccc cgctggtcga tgatctggaa     600
ggtgctgagg aaatgatgtc acagcgtacg aaaaccccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacagtga                           759

<210> SEQ ID NO 28
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 28

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45
```

```
Lys Ser Ile Gly Gly Thr Asp Val Ile Arg Phe Val Gln His Asp Ala
 50                  55                  60
Ser Asp Glu Ala Gly Trp Thr Lys Leu Phe Asp Thr Thr Glu Glu Ala
 65                  70                  75                  80
Phe Gly Pro Val Thr Thr Val Val Asn Asn Ala Gly Ile Ala Val Ser
                 85                  90                  95
Lys Ser Val Glu Asp Thr Thr Thr Glu Glu Trp Arg Lys Leu Leu Ser
                100                 105                 110
Val Asn Leu Asp Gly Val Phe Phe Gly Thr Arg Leu Gly Ile Gln Arg
                115                 120                 125
Met Lys Asn Lys Gly Leu Gly Ala Ser Ile Ile Asn Met Ser Ser Ile
130                 135                 140
Ala Gly Leu Val Gly Asp Pro Thr Leu Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Cys Ile Lys
                180                 185                 190
Thr Pro Leu Val Asp Asp Leu Glu Gly Ala Glu Met Met Ser Gln
                195                 200                 205
Arg Thr Lys Thr Pro Met Gly His Ile Gly Glu Pro Asn Asp Ile Ala
210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250

<210> SEQ ID NO 29
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 29
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcgtaaactg ctgtccgtta atctggatgg tgttttttc     360
ggcacccgtc tgggcattca gcgcatgaaa aataaaggct gggcgctag catcatcaat     420
atgagcagta ttgaggggct cgtaggcgat ccgacgggcg gggcatacaa cgcttccaag     480
ggggcggtac gtatcatgtc gaaaagcgca gcgctggatt gcgcactgaa ggactacgat     540
gtgcgtgtca acacagtaca tccgggccct atcaagaccc cgctggtcga tgatctggaa     600
ggtgctgagg aaatgatgtc acagcgtacg aaaacccta tggccacat ggcgaaccg       660
aatgacatcg catggatctg tgtgtacctg gcatctgacg aatcgaaatt tgcgacgggt     720
gcagaatttg tggtcgacgg cgggtatacc gcacagtga                           759

<210> SEQ ID NO 30
<211> LENGTH: 252
```

<212> TYPE: PRT
<213> ORGANISM: Artificial Sequence
<220> FEATURE:
<223> OTHER INFORMATION: Synthetic Variant of L. kefir

<400> SEQUENCE: 30

Met Thr Asp Arg Leu Lys Gly Lys Val Ala Ile Val Thr Gly Thr
1               5                   10                  15

Leu Gly Ile Gly Leu Ala Ile Ala Asp Lys Phe Val Glu Glu Gly Ala
            20                  25                  30

Lys Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Ala Val Ser
                85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
130                 135                 140

Glu Gly Leu Val Gly Asp Pro Thr Gly Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 31
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 31
atgaccgatc gtctgaaggg caaagtagcc atcgtaaccg gcgggactct gggtatcggt     60
ttggcaatcg ccgataaatt tgtagaggag ggtgcgaaag tagttattac tggtcgtcac    120
gcggatgtag tgaaaaggc cgccaaatca atcggcggca ctgatgttat tcgctttgtc    180
cagcacgatg catccgatga agcaggctgg acgaaactgt tcgacaccac cgaggaggca    240
ttcggcccgg ttacgaccgt cgtgaacaat gcagggattg cagtttccaa aagcgttgaa    300
gacactacca cggaggaatg gcgtaaactg ctgtccgtta atctggatgg tgttttttc     360 ggcacccgtc tgggcattca gcgcatgaaa aataaaggct gggcgctag catcatcaat    420

```
atgagcagta ttgaggggct cgtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggccct atcaagaccc cgctggtcga tgatctggaa    600
ggtgctgagg aaatgatgtc acagcgtacg aaaaccccta tgggccacat tggcgaaccg    660
aatgacatcg catggatctg tgtgtacctg gcatctgacg aatcgaaatt tgcgacgggt    720
gcagaatttg tggtcgacgg cgggtatacc gcacagtga                          759
```

<210> SEQ ID NO 32
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 32

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 33
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 33

```
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcgtaaactg ctgtccgtta atctggatgg tgttttttc   360 ggcacccgtc tgggcattca gcgcatgaaa aataaaggct ggggcgctag catcatcaat   420
atgagcagta ttagtgggct cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggcccct atcaagaccc cgctggtcga tgatctggaa   600
ggtgctgagg aaatgatgtc acagcgtacg aaaaccccta tgggccacat tggcgaaccg   660
aatgacatcg catggatctg tgtgtacctg gcatctgacg aatcgaaatt tgcgacgggt   720
gcagaatttg tggtcgacgg cgggtatacc gcacagtga                          759

<210> SEQ ID NO 34
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 34

Met Thr Asp Arg Leu Lys Gly Lys Val Ala Ile Val Thr Gly Gly Thr
 1               5                  10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220
```

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 35
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 35

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcgtaaactg ctgtccgtta atctggatgg tgtttttttc     360
ggcacccgtc tgggcattca gcgcatgaaa aataaaggct gggcgctag catcatcaat      420 atgagcagta ttcaggggct cgtaggcgat ccgacgctgg gggcatacaa cgcttccaag     480
ggggcggtac gtatcatgtc gaaaagcgca gcgctggatt gcgcactgaa ggactacgat     540
gtgcgtgtca acacagtaca tccgggcgca atcaagaccc cgctggtcga tgatctggaa     600
ggtgctgagg aaatgatgtc acagcgtacg aaaacccctta tgggccacat ggcgaaccg      660 aatgacatcg catggatctg tgtgtacctg gcatctgacg aatcgaaatt tgcgacgggt     720
gcagaatttg tggtcgacgg cgggtatacc gcacagtga                           759
```

<210> SEQ ID NO 36
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 36

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
                20                  25                  30

Lys Val Val Ile Thr Gly Arg His Ala Asp Val Gly Glu Lys Ala Ala
            35                  40                  45

Lys Ser Ile Gly Gly Thr Asp Val Ile Arg Phe Val Gln His Asp Ala
        50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

```
Gln Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
            165                 170                 175

Lys Asp Tyr Asp Val Arg Val Asn Thr Val His Pro Gly Ala Ile Lys
            180                 185                 190

Thr Pro Leu Val Asp Asp Leu Glu Gly Ala Glu Glu Met Met Ser Gln
            195                 200                 205

Arg Thr Lys Thr Pro Met Gly His Ile Gly Glu Pro Asn Asp Ile Ala
            210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
            245                 250

<210> SEQ ID NO 37
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 37
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcgtaaactg ctgtccgtta atctggatgg tgttttttc      360 ggcacccgtc tgggcattca gcgcatgaaa aataaaggct gggcgctag catcatcaat     420 atgagcagta ttgagggct cgtaggcgat ccgacgctgg gggcatacaa cgcttccaag     480
ggggcggtac gtatcatgtc gaaaagcgca gcgctggatt gcgcactgaa ggactacgat     540
gtgcgtgtca acacagtaca tccgggccct atcaagaccc cgctggtcga tgatctggaa     600
ggtgctgagg aaatgatgtc acagcgtacg ctgacccccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacagtga                            759

<210> SEQ ID NO 38
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 38

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60
```

```
Ser Asp Glu Ala Gly Trp Thr Lys Leu Phe Asp Thr Thr Glu Glu Ala
 65                  70                  75                  80

Phe Gly Pro Val Thr Val Val Asn Asn Ala Gly Ile Ala Val Ser
                 85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Val Asp Asp Leu Glu Gly Ala Glu Met Met Ser Gln
        195                 200                 205

Arg Thr Leu Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 39
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 39

```
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttgaggggct cgtaggcgat ccgacgcagg gggcatacaa cgcttccaag   480
ggggcggtac gtatcatgtc gaaaagcgca gcgctggatt gcgcactgaa ggactacgat   540
gtgcgtgtca acacagtaca tccgggccct atcaagaccc cgctggtcga tgatctggaa   600
ggtgctgagg aaatgatgtc acagcgtacg aaaacccta tgggccacat tggcgaaccg    660
aatgacatcg catggatctg tgtgtacctg gcatctgacg aatcgaaatt tgcgacgggt   720
gcagaatttg tggtcgacgg cgggtatacc gcacagtga                          759
```

<210> SEQ ID NO 40
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 40

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Gln Gly Ala Tyr Asn Ala Ser Lys
145                 150                 155                 160

Gly Ala Val Arg Ile Met Ser Lys Ser Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 41
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 41
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg gtgtttccaa aagcgttgaa     300
gacactacca cggaggaatg gcacaaactg ctgtccgtta atctggatag tgttttttc      360 ggcacccgtc tgggcattca gcgcatgaag aataaaggct gggcgctag catcatcaat      420 atgagcagta tcagtgggtt cgtaggcgat ccgacgctgg gggcatacac tgcttccaag     480
ggggcggtac gtatcatgtc gaaaagcgca gcgctggatt gcgcactgaa ggactacgat     540

```
gtgcgtgtca acacagtaca tccgggctgt atcaagaccc cgctggtcga tgatctggaa    600
ggtgctgagg aaatgatgtc acagcgtacg agaaccccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                           759
```

<210> SEQ ID NO 42
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 42

```
Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Gly Val Ser
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Thr Leu Gly Ala Tyr Thr Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Leu Glu Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 43
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 43

```
atgaccgatc gtctgaagag caaagtagcc atcgtaaccg gcgggaccct gggtatcggt     60
ttggcaatcg ccgataaatt tgtagaggag ggtgcgaaag tagttattac tggtcgccac    120
```

```
gcggatgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcagggattg cagttcagaa aagcgttgaa    300
gacactacca cggaggaatg gcacaaactg ctgtccgtta atctggatag tgttttttc    360 ggcacccgtc tgggcattca gcgcatgaag aataaaggct tgggcgctag catcatcaac    420
atgagcagta tcagtgggtt cgtaggcgat ccgacgctgg gggcatacac tgcttccaag    480
ggggcggtac gtatcatgtc gaaaagcgca gcgctggatt gcgcactgaa ggactacgat    540
gtgcgtgtca acacagtaca tccgggctgt atcaagaccc cgctggtcga tgatctggaa    600
ggtgctgagg aaatgatgtc acagcgtacg agaaccccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                           759
```

<210> SEQ ID NO 44  
<211> LENGTH: 252  
<212> TYPE: PRT  
<213> ORGANISM: Artificial Sequence  
<220> FEATURE:  
<223> OTHER INFORMATION: Synthetic Variant of L. kefir

<400> SEQUENCE: 44

```
Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Gln
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Thr Leu Gly Ala Tyr Thr Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Leu Glu Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
```

<210> SEQ ID NO 45
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 45

```
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcacaaactg ctgtccgtta atctggatag tgttttttc     360
ggcacccgtc tgggcattca gcgcatgaag aataaaggct gggcgctag catcatcaat     420
atgagcagta tcagtgggtt cgtaggcgat ccgacgctgg gggcatacac tgcttccaag     480
ggggcggtac gtatcatgtc gaaaagcgca gcgctggatt gcgcactgaa ggactacgat     540
gtgcgtgtca acacagtaca tccgggctgt atcaagaccc cgctggtcga tgatgatgaa     600
ggtgctgagg aaatgatgtc acagcgtacg agaaccccta tgggccacat tggcgaaccg     660
aatgacgtgg catggatctg tgtgtacctg gcatctgacg aatcgaaatt tgcgacgggt     720
gcagaatttg tggtcgacgg cgggtatacc gcacagtga                            759
```

<210> SEQ ID NO 46
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 46

```
Met Thr Asp Arg Leu Lys Ser Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Ala Val Ser
                85                  90                  95
Lys Ser Val Glu Asp Thr Thr Thr Glu Glu Trp His Lys Leu Leu Ser
            100                 105                 110
Val Asn Leu Asp Ser Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Ser Gly Phe Val Gly Asp Pro Thr Leu Gly Ala Tyr Thr Ala Ser Lys
145                 150                 155                 160
Gly Ala Val Arg Ile Met Ser Lys Ser Ala Ala Leu Asp Cys Ala Leu
```

```
                165                 170                 175
Lys Asp Tyr Asp Val Arg Val Asn Thr Val His Pro Gly Cys Ile Lys
            180                 185                 190

Thr Pro Leu Val Asp Asp Glu Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 47
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 47

```
atgaccgatc gtctgaagag caaagtagcc atcgtaaccg gcgggaccct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg cacaaactg ctgtccgtta atctggatag tgttttttc    360
ggcacccgtc tgggcattca gcgcatgaag aataaaggct tgggcgctag catcatcaat   420
atgagcagta tcagtgggtt cgtaggcgat ccgacgctgg gggcatacac tgcttccaag   480
ggggcggtac gtatcatgtc gaaaagcgca gcgctggatt gcgcactgaa ggactacgat   540
gtgcgtgtca acacagtaca tccgggctgt atcaagaccc cgctggtcga tgatctggaa   600
ggtggggagg aaatgatgtc acagcgtacg agaacccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                          759
```

<210> SEQ ID NO 48
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 48

```
Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
```

```
                85                  90                  95
Lys Ser Val Glu Asp Thr Thr Thr Glu Glu Trp His Lys Leu Leu Ser
                100                 105                 110

Val Asn Leu Asp Ser Val Phe Phe Gly Thr Arg Leu Gly Ile Gln Arg
                115                 120                 125

Met Lys Asn Lys Gly Leu Gly Ala Ser Ile Ile Asn Met Ser Ser Ile
                130                 135                 140

Ser Gly Phe Val Gly Asp Pro Thr Leu Gly Ala Tyr Thr Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
                180                 185                 190

Thr Pro Leu Val Asp Asp Leu Glu Gly Gly Glu Met Met Ser Gln
                195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 49
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 49
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg cacaaactg ctgtccgcta atctggatag tgttttttc      360 ggcacccgtc tgggcattca gcgcatgaag aataaaggct gggcgctag catcatcaat     420 atgagcagta tcagtgggtt cgtaggcgat ccgacgctgg gggcatacac tgcttccaag     480
ggggcggtac gtatcatgtc gaaaagcgca gcgctggatt gcgcactgaa ggactacgat     540
gtgcgtgtca acacagtaca tccgggctgt atcaagaccc cgctggtcga tgatgatgaa     600
ggtgctgagg aaatgatgtc acagcgtacg agaaccccta tgggccacat tggcgaaccg     660
aatgacgtgg catggatctg tgtgtacctg gcatctgacg aatcgaaatt tgcgacgggt     720
gcagaatttg tggtcgacgg cgggtatacc gcacagtga                            759

<210> SEQ ID NO 50
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 50

Met Thr Asp Arg Leu Lys Ser Lys Val Ala Ile Val Thr Gly Gly Thr
```

```
  1               5                   10                  15
Leu Gly Ile Gly Leu Ala Ile Ala Asp Lys Phe Val Glu Glu Gly Ala
                20                  25                  30
Lys Val Val Ile Thr Gly Arg His Ala Asp Val Gly Glu Lys Ala Ala
                35                  40                  45
Lys Ser Ile Gly Gly Thr Asp Val Ile Arg Phe Val Gln His Asp Ala
                50                  55                  60
Ser Asp Glu Ala Gly Trp Thr Lys Leu Phe Asp Thr Thr Glu Glu Ala
 65                 70                  75                  80
Phe Gly Pro Val Thr Thr Val Asn Asn Ala Gly Ile Ala Val Ser
                    85                  90                  95
Lys Ser Val Glu Asp Thr Thr Thr Glu Glu Trp His Lys Leu Leu Ser
                100                 105                 110
Ala Asn Leu Asp Ser Val Phe Phe Gly Thr Arg Leu Gly Ile Gln Arg
                115                 120                 125
Met Lys Asn Lys Gly Leu Gly Ala Ser Ile Ile Asn Met Ser Ser Ile
                130                 135                 140
Ser Gly Phe Val Gly Asp Pro Thr Leu Gly Ala Tyr Thr Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Cys Ile Lys
                180                 185                 190
Thr Pro Leu Val Asp Asp Asp Glu Gly Ala Glu Glu Met Met Ser Gln
                195                 200                 205
Arg Thr Arg Thr Pro Met Gly His Ile Gly Glu Pro Asn Asp Val Ala
                210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```

<210> SEQ ID NO 51
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 51

```
atgaccgatc gtctgaagag caaagtagcc atcgtaaccg gcgggaccct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa agcgttgaa    300
gacactacca cggaggaatg gcacaaactg ctgtccgtta atctggatag tgtttttttc   360
ggcacccgtc tgggcattca gcgcatgaag aataaaggct gggcgctag catcatcaat    420
atgagcagta tcagtgggtt cgtaggcgat ccgaagctgg ggcatacac tgcttccaag    480
ggggcggtac gtatcatgtc gaaaagcgca gcgctggatt gcgcactgaa ggactacgat    540
gtgcgtgtca acacagtaca tccgggctgt atcaagaccc cgctggtcga tgatgatgaa   600
ggtgctgagg aaatgatgtc acagcgtacg agaacccta tgggccacat tggcgaaccg    660
```

```
aatgacgtgg catggatctg tgtgtacctg gcatctgacg aatcgaaatt tgcgacgggt    720
gcagaatttg tggtcgacgg cgggtatacc gcacagtga                          759
```

<210> SEQ ID NO 52
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 52

```
Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Ala Val Ser
                85                  90                  95

Lys Ser Val Glu Asp Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Lys Leu Gly Ala Tyr Thr Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Asp Glu Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 53
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 53

```
atgaccgatc gtctgaagag caaagtagcc atcgtaaccg gcgggaccct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
```

```
ttcggcccgg ttacgaccgt cgtgaacaat gcagggattg cagtttccaa aagcgttgaa      300
gacactacca cggaggaatg cacaaactg ctgtccgtta atctggatag tgtttttttc       360
ggcacccgtc tgggcattca gcgcatgaag aataaaggct tgggcgctag catcatcaat      420
atgagcagta tcagtgggtt cgtaggcgat ccgatgctgg gggcatacac tgcttccaag      480
ggggcggtac gtatcatgtc gaaaagcgca gcgctggatt gcgcactgaa ggactacgat      540
gtgcgtgtca acacagtaca tccgggctgt atcaagaccc cgctggtcga tgatgatgaa      600
ggtgctgagg aaatgatgtc acagcgtacg agaaccccta tgggccacat tggcgaaccg      660
aatgacgtgg catggatctg tgtgtacctg gcatctgacg aatcgaaatt tgcgacgggt      720
gcagaatttg tggtcgacgg cgggtatacc gcacagtga                            759
```

<210> SEQ ID NO 54
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 54

```
Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Ala Val Ser
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Met Leu Gly Ala Tyr Thr Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Glu Gly Ala Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 55

<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 55

```
atgaccgatc gtctgaagag caaagtagcc atcgtaaccg gcgggaccct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcaggggatta gtgttcaaaa aagcgttgaa   300
gacactacca cggaggaatg cacaaactg ctgtccgtta atctggatag tgttttttc   360
ggcacccgtc tgggcattca gcgcatgaag aataaaggct gggcgctag catcatcaat   420
atgagcagta tcagtgggtt cgtaggcgat ccgacgctgg gggcatacac tgcttccaag   480
ggggcggtac gtatcatgtc gaaaagcgca gcgctggatt gcgcactgaa ggactacgat   540
gtgcgtgtca acacagtaca tccgggctgt atcaagaccc cgctggtcga tgatgatgaa   600
ggtgctgagg aaatgatgtc acagcgtacg agaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                          759
```

<210> SEQ ID NO 56
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 56

```
Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ser Val Gln
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Thr Leu Gly Ala Tyr Thr Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190
```

Thr Pro Leu Val Asp Asp Glu Gly Ala Glu Met Met Ser Gln
       195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 57
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 57

```
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac    120
gcggatgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcagggattg cagtttccaa aagcgttgaa    300
gacactacca cggaggaatg gcacaaactg ctgtccgtta atctggatag tgtttttttc    360
ggcacccgtc tgggcattca gcgcatgaag aataaaggct gggcgctag catcatcaat    420
atgagcagta tcagtgggtt cgtaggcgat ccgacgctgg gggcatacac tgcttccaag    480
ggggcggtac gtatcatgtc gaaaagcgca gcgctggatt gcgcactgaa ggactacgat    540
gtgcgtgtca acacagtaca tccgggctgt atcaagaccc agctggtcga tgatgatgaa    600
ggtgctgagg aaatgatgtc acagcgtacg agaaccccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                          759
```

<210> SEQ ID NO 58
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 58

Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp His Lys Leu Leu Ser
            100                 105                 110

-continued

```
Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Thr Leu Gly Ala Tyr Thr Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Gln Leu Val Asp Asp Glu Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 59
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 59

```
atgaccgatc gtctgaagag caaagtagcc atcgtaaccg gcgggaccct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta gtgttcagaa aagcgttgaa   300
gacactacca cggaggaatg cacaaactg ctgtccgtta atctggatag tgttttttc    360
ggcacccgtc tgggcattca gcgcatgaag aataaaggct gggcgctag catcatcaat    420
atgagcagta tcagtgggtt cgtaggcgat ccgaagctgg ggcatacac tgcttccaag    480
ggggcggtac gtatcatgtc gaaaagcgca gcgctggatt gcgcactgaa ggactacgat   540
gtgcgtgtca acacagtaca tccgggctgt atcaagaccc agctggtcga tgatgatgaa   600
ggtgctgagg aaatgatgtc acagcgtacg agaaccccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                           759
```

<210> SEQ ID NO 60
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 60

```
Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30
```

Lys Val Val Ile Thr Gly Arg His Ala Asp Val Gly Glu Lys Ala Ala
                35                  40                  45

Lys Ser Ile Gly Gly Thr Asp Val Ile Arg Phe Val Gln His Asp Ala
        50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Ser Val Gln
                85                  90                  95

Lys Ser Val Glu Asp Thr Thr Glu Glu Trp His Lys Leu Leu Ser
                100                 105                 110

Val Asn Leu Asp Ser Val Phe Phe Gly Thr Arg Leu Gly Ile Gln Arg
                115                 120                 125

Met Lys Asn Lys Gly Leu Gly Ala Ser Ile Ile Asn Met Ser Ser Ile
        130                 135                 140

Ser Gly Phe Val Gly Asp Pro Lys Leu Gly Ala Tyr Thr Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
                180                 185                 190

Thr Pro Leu Val Asp Asp Glu Gly Ala Glu Met Met Ser Gln
                195                 200                 205

Arg Thr Arg Thr Pro Met Gly His Ile Gly Glu Pro Asn Asp Val Ala
        210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 61
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 61
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag tgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcaggattaa gtgttcagaa aagcgttgaa     300
gacactacca cggaggaatg gcacaaactg ctgtccgtta atctggatag tgttttttc      360 ggcacccgtc tgggcattca gcgcatgaag aataaaggct gggcgctag catcatcaat     420 atgagcagta tcagtgggtt cgtaggcgat ccgatgctgg gggcatacac tgcttccaag     480
ggggcggtac gtatcatgtc gaaaagcgca gcgctggatt gcgcactgaa ggactacgat     540
gtgcgtgtca acacagtaca tccgggctgt atcaagaccc cgctggtcga tgatgatgaa     600
ggtgctgagg aaatgatgtc acagcgtacg agaaccccta tgggccacat tggcgaaccg     660
aatgacgtgg catggatctg tgtgtacctg gcatctgacg aatcgaaatt tgcgacgggt     720
gcagaatttg tggtcgacgg cgggtatacc gcacagtga                           759

<210> SEQ ID NO 62
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 62

```
Met Thr Asp Arg Leu Lys Ser Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Ser Val Gln
                85                  90                  95
Lys Ser Val Glu Asp Thr Thr Glu Glu Trp His Lys Leu Leu Ser
            100                 105                 110
Val Asn Leu Asp Ser Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Ser Gly Phe Val Gly Asp Pro Met Leu Gly Ala Tyr Thr Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Cys Ile Lys
            180                 185                 190
Thr Pro Leu Val Asp Asp Asp Glu Gly Ala Glu Glu Met Met Ser Gln
        195                 200                 205
Arg Thr Arg Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```

<210> SEQ ID NO 63
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 63

```
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagttccaa aagcgttgaa      300 gacactacca cggaggaatg gcacaaactg ctgtccgtta atctggatag tgtttttttc     360
```

```
ggcacccgtc tgggcattca gcgcatgaag aataaaggct tgggcgctag catcatcaat    420
atgagcagta tcagtgggct ggtaggcgat ccgatgctgg gggcatacac tgcttccaag    480
ggggcggtac gtatcatgtc gaaaagcgca gcgctggatt gcgcactgaa ggactacgat    540
gtgcgtgtca acacagtaca tccgggctgt atcaagaccc cgctggtcga tgatgatgaa    600
ggtgctgagg aaatgatgtc acagcgtacg agaaccccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                           759
```

<210> SEQ ID NO 64
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 64

```
Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Thr Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Asp Glu Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 65
<211> LENGTH: 759
<212> TYPE: DNA
<213> ORGANISM: Artificial Sequence
<220> FEATURE:

<223> OTHER INFORMATION: Synthetic Variant of L. kefir

<400> SEQUENCE: 65

```
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagttaataa aagcgttgaa     300
gacactacca cggaggaatg gcacaaactg ctgtccgtta atctggatag tgttttttc      360
ggcacccgtc tgggcattca gcgcatgaag aataaaggct gggcgctag catcatcaat      420
atgagcagta tcagtgggtt cgtaggcgat ccgatgctgg gggcatacac tgcttccaag     480
ggggcggtac gtatcatgtc gaaaagcgca gcgctggatt gcgcactgaa ggactacgat     540
gtgcgtgtca acacagtaca tccgggctgt atcaagaccc cgctggtcga tgatgatgaa     600
ggtgctgagg aaatgatgtc acagcgtacg agaaccccta tgggccacat ggcgaaccg      660
aatgacgtgg catggatctg tgtgtacctg gcatctgacg aatcgaaatt tgcgacgggt     720
gcagaatttg tggtcgacgg cgggtatacc gcacagtga                            759
```

<210> SEQ ID NO 66
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 66

```
Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Ala Val Asn
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Met Leu Gly Ala Tyr Thr Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Asp Glu Gly Ala Glu Glu Met Met Ser Gln
        195                 200                 205
```

```
Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 67
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 67

```
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcacaaactg ctgtccgtta atctggatag tgttttttc     360
ggcacccgtc tgggcattca gcgcatgaag aataaaggct gggcgctag catcatcaat     420
atgagcagta tcagtgggtt cgtaggcgat ccgatgctgg gggcatacac tgcttccaag     480
ggggcggtac gtatcatgtc gaaaagcgca gcgctggatt gcgcactgaa ggactacgat     540
gtgcgtgtca acacagtaca tccgggctgt atcaagaccc ggctggtcga tgatgatgaa     600
ggtgctgagg aaatgatgtc acagcgtacg agaaccccta tgggccacat ggcgaaccg     660
aatgacgtgg catggatctg tgtgtacctg gcatctgacg aatcgaaatt tgcgacgggt     720
gcagaatttg tggtcgacgg cgggtatacc gcacagtga                            759
```

<210> SEQ ID NO 68
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 68

```
Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125
```

```
Met Lys Asn Lys Gly Leu Gly Ala Ser Ile Ile Asn Met Ser Ser Ile
    130                 135                 140
Ser Gly Phe Val Gly Asp Pro Met Leu Gly Ala Tyr Thr Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Cys Ile Lys
            180                 185                 190
Thr Arg Leu Val Asp Asp Glu Gly Ala Glu Met Met Ser Gln
        195                 200                 205
Arg Thr Arg Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```

```
<210> SEQ ID NO 69
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 69
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag gtgaaaaggc cgccaaatca atcgcggta ctgatgttat cgctttgtc      180
cagcacgatg catccgatga agcaggctgg acgaaactgt tcgacaccac cgaggaggca     240
ttcggcccgg ttacgaccgt cgtgaacaat gcagggattg cagttcagaa aagcgttgaa     300
gacactacca cggaggaatg cacaaactg ctgtccgtta atctggatag tgttttttc      360
ggcacccgtc tgggcattca gcgcatgaag aataaaggct gggcgctag catcatcaat     420
atgagcagta tcagtgggtt cgtaggcgat ccgatgctgg gggcatacac tgcttccaag     480
ggggcggtac gtatcatgtc gaaaagcgca gcgctggatt gcgcactgaa ggactacgat     540
gtgcgtgtca acacagtaca tccgggctgt atcaagaccc gctggtcga tgatgatgaa     600
ggtgctgagg aaatgatgtc acagcgtacg agaaccccta tgggccacat tggcgaaccg     660
aatgacgtgg catggatctg tgtgtacctg gcatctgacg aatcgaaatt tgcgacgggt     720
gcagaatttg tggtcgacgg cgggtatacc gcacagtga                            759
```

```
<210> SEQ ID NO 70
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 70

Met Thr Asp Arg Leu Lys Ser Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
```

```
                Lys Ser Ile Gly Gly Thr Asp Val Ile Arg Phe Val Gln His Asp Ala
                    50                  55                  60

Ser Asp Glu Ala Gly Trp Thr Lys Leu Phe Asp Thr Thr Glu Glu Ala
                65                  70                  75                  80

Phe Gly Pro Val Thr Thr Val Val Asn Asn Ala Gly Ile Ala Val Gln
                                    85                  90                  95

Lys Ser Val Glu Asp Thr Thr Glu Glu Trp His Lys Leu Leu Ser
                                100                 105                 110

Val Asn Leu Asp Ser Val Phe Phe Gly Thr Arg Leu Gly Ile Gln Arg
                            115                 120                 125

Met Lys Asn Lys Gly Leu Gly Ala Ser Ile Ile Asn Met Ser Ser Ile
                    130                 135                 140

Ser Gly Phe Val Gly Asp Pro Met Leu Gly Ala Tyr Thr Ala Ser Lys
                145                 150                 155                 160

Gly Ala Val Arg Ile Met Ser Lys Ser Ala Ala Leu Asp Cys Ala Leu
                                165                 170                 175

Lys Asp Tyr Asp Val Arg Val Asn Thr Val His Pro Gly Cys Ile Lys
                            180                 185                 190

Thr Pro Leu Val Asp Asp Glu Gly Ala Glu Glu Met Met Ser Gln
                        195                 200                 205

Arg Thr Arg Thr Pro Met Gly His Ile Gly Glu Pro Asn Asp Val Ala
                    210                 215                 220

Trp Ile Cys Val Tyr Leu Ala Ser Asp Glu Ser Lys Phe Ala Thr Gly
                225                 230                 235                 240

Ala Glu Phe Val Val Asp Gly Gly Tyr Thr Ala Gln
                                245                 250

<210> SEQ ID NO 71
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 71
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag tgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagttcagaa aagcgttgaa     300
gacactacca cggaggaatg gcacaaactg ctgtccgtta atctggatag tgtttttttc     360
ggcacccgtc tgggcattca gcgcatgaag aataaaggct gggcgctag catcatcaat     420 atgagcagta tcagtgggtt cgtaggcgat ccgatgctgg gggcatacac tgcttccaag     480
ggggcggtac gtatcatgtc gaaaagcgca gcgctggatt gcgcactgaa ggactacgat     540
gtgcgtgtca acacagtaca tccgggctgt atcaagaccc ggctggtcga tgatgatgaa     600
ggtgctgagg aaatgatgtc acagcgtacg agaaccccta tgggccacat tggcgaaccg     660
aatgacgtgg catggatctg tgtgtacctg gcatctgacg aatcgaaatt tgcgacgggt     720
gcagaatttg tggtcgacgg cgggtatacc gcacagtga                           759

<210> SEQ ID NO 72
<211> LENGTH: 252
<212> TYPE: PRT
```

<213> ORGANISM: Artificial Sequence
<220> FEATURE:
<223> OTHER INFORMATION: Synthetic Variant of L. kefir

<400> SEQUENCE: 72

```
Met Thr Asp Arg Leu Lys Ser Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Ala Val Gln
                85                  90                  95
Lys Ser Val Glu Asp Thr Thr Thr Glu Glu Trp His Lys Leu Leu Ser
            100                 105                 110
Val Asn Leu Asp Ser Val Phe Phe Gly Thr Arg Leu Gly Ile Gln Arg
        115                 120                 125
Met Lys Asn Lys Gly Leu Gly Ala Ser Ile Ile Asn Met Ser Ser Ile
130                 135                 140
Ser Gly Phe Val Gly Asp Pro Met Leu Gly Ala Tyr Thr Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Cys Ile Lys
            180                 185                 190
Thr Arg Leu Val Asp Asp Asp Glu Gly Ala Glu Glu Met Met Ser Gln
        195                 200                 205
Arg Thr Arg Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```

<210> SEQ ID NO 73
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 73

```
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagttactaa aagcgttgaa     300
gacactacca cggaggaatg gcacaaactg ctgtccgtta atctggatag tgttttttc      360
ggcacccgtc tgggcattca gcgcatgaag aataaaggct gggcgctag catcatcaat      420
atgagcagta tcagtgggtt cgtaggcgat ccgatgctgg gggcatacac tgcttccaag     480
```

```
gggcggtac gtatcatgtc gaaaagcgca gcgctggatt gcgcactgaa ggactacgat        540
gtgcgtgtca acacagtaca tccgggctgt atcaagaccc ggctggtcga tgatgatgaa        600
ggtgctgagg aaatgatgtc acagcgtacg agaaccccta tgggccacat tggcgaaccg        660
aatgacgtgg catggatctg tgtgtacctg gcatctgacg aatcgaaatt tgcgacgggt        720
gcagaatttg tggtcgacgg cgggtatacc gcacagtga                              759
```

```
<210> SEQ ID NO 74
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 74
```

```
Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Thr
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Met Leu Gly Ala Tyr Thr Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Arg Leu Val Asp Asp Glu Gly Ala Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

```
<210> SEQ ID NO 75
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 75
```

```
atgaccgatc gtctgaagag caaagtagcc atcgtaaccg gcgggaccct gggtatcggt    60
ttggcaatcg ccactaaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcaacaccac cgaggaggca   240
ttcggcccgg ttacgaccgt cgtgaacaat gcagggattg cagttcagaa aagcgttgaa   300
gacactacca cggaggaatg gcacaaactg ctgtccgtta atctggatag tgttttttc   360
ggcacccgtc tgggcattca gcgcatgaag aataaaggct gggcgctag catcatcaat   420
atgagcagta tcagtgggtt cgtaggcgat ccgatgctgg gggcatacac tgcttccaag   480
ggggcggtac gtatcatgtc gaaaagcgca gcgctggatt gcgcactgaa ggactacgat   540
gtgcgtgtca acacagtaca tccgggctgt atcaagaccc gcctggtcga tgatgatgaa   600
ggtgctgagg aaatgatgtc acagcgtacg agaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                          759
```

<210> SEQ ID NO 76
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 76

```
Met Thr Asp Arg Leu Lys Ser Lys Val Ala Ile Val Thr Gly Gly Thr
1               5                   10                  15
Leu Gly Ile Gly Leu Ala Ile Ala Thr Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asn Thr Thr Glu Glu Ala
65                  70                  75                  80
Phe Gly Pro Val Thr Thr Val Asn Asn Ala Gly Ile Ala Val Gln
                85                  90                  95
Lys Ser Val Glu Asp Thr Thr Glu Glu Trp His Lys Leu Leu Ser
            100                 105                 110
Val Asn Leu Asp Ser Val Phe Phe Gly Thr Arg Leu Gly Ile Gln Arg
            115                 120                 125
Met Lys Asn Lys Gly Leu Gly Ala Ser Ile Ile Asn Met Ser Ser Ile
    130                 135                 140
Ser Gly Phe Val Gly Asp Pro Met Leu Gly Ala Tyr Thr Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Cys Ile Lys
            180                 185                 190
Thr Arg Leu Val Asp Asp Glu Gly Ala Glu Met Met Ser Gln
            195                 200                 205
Arg Thr Arg Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
```

```
                    225                 230                 235                 240

Ala Glu Phe Val Val Asp Gly Gly Tyr Thr Ala Gln
                245                 250

<210> SEQ ID NO 77
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 77
atgaccgatc gtctgaagag caaagtagcc atcgtaaccg gcgggaccct gggtatcggt     60
ttggcaatcg ccgataaatt tgtagaggag ggtgcgaaag tagttattac tggtcgccac    120
gcggatgtag gtgaaaaggc cgccaaatca atcggcggta ctgatgttat cgctttgtc     180 cagcacgatg catccgatga agcaggctgg acgaaactgt tcgacaccac cgaggaggca    240
ttcggcccgg ttacgaccgt cgtgaacaat gcaggattg cagttcagaa aagcgttgaa     300
gacactacca cggaggaatg cacaaactg ctgtccgtta atctggatag tgtttttttc     360
ggcacccgtc tgggcattca gcgcatgaag aataaaggct gggcgctag catcatcaat     420 atgagcagta tcagtgggtt cgtaggcgat ccgatgctgg gggcatacaa tgcttccaag    480
ggggcggtac gtatcatgtc gaaaagcgca gcgctggatt gcgcactgaa ggactacgat    540
gtgcgtgtca acacagtaca tccgggctgt atcaagaccc cgctggtcga tgatgatgaa    600
ggtgctgagg aaatgatgtc acagcgtacg agaaccccta tgggccacat ggcgaaccg     660 aatgacgtgg catggatctg tgtgtacctg gcatctgacg aatcgaaatt tgcgacgggt    720
gcagaatttg tggtcgacgg cgggtatacc gcacagtga                          759

<210> SEQ ID NO 78
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 78

Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Gln
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Met Leu Gly Ala Tyr Asn Ala Ser Lys
```

Gly Ala Val Arg Ile Met Ser Lys Ser Ala Ala Leu Asp Cys Ala Leu
              145                 150                 155                 160

Lys Asp Tyr Asp Val Arg Val Asn Thr Val His Pro Gly Cys Ile Lys
              165                 170                 175

Thr Pro Leu Val Asp Asp Glu Gly Ala Glu Met Met Ser Gln
              180                 185                 190

Arg Thr Arg Thr Pro Met Gly His Ile Gly Pro Asn Asp Val Ala
              195                 200                 205

Trp Ile Cys Val Tyr Leu Ala Ser Asp Glu Ser Lys Phe Ala Thr Gly
          210                 215                 220

Ala Glu Phe Val Val Asp Gly Gly Tyr Thr Ala Gln
225                 230                 235                 240

245                 250

<210> SEQ ID NO 79
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 79

```
atgaccgatc gtctgaagag caaagtagcc atcgtaaccg gcgggaccct gggtatcggt      60
ttggcaatcg ccgataaatt tgtagaggag ggtgcgaaag tagttattac tggtcgccgt     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagttcagaa aagcgttgaa     300
gacactacca cggaggaatg cacaaaactg ctgtccgtta atctggatag tgttttttc    360
ggcacccgtc tgggcattca gcgcatgaag aataaaggct gggcgctag catcatcaat     420
atgagcagta tcagtgggtt cgtaggcgat ccgatgctgg gggcatacac tgcttccaag     480
ggggcggtac gtatcatgtc gaaaagcgca gcgctggatt gcgcactgaa ggactacgat     540
gtgcgtgtca acacagtaca tccgggctgt atcaagaccc cgctggtcga tgatgatgaa     600
ggtgctgagg aaatgatgtc acagcgtacg agaaccccta tgggccacat tggcgaaccg     660
aatgacgtgg catggatctg tgtgtacctg gcatctgacg aatcgaaatt tgcgacgggt     720
gcagaatttg tggtcgacgg cgggtatacc gcacagtga                            759
```

<210> SEQ ID NO 80
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 80

Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg Arg Ala Asp Val Gly Lys Ala Ala
            35                  40                  45

Lys Ser Ile Gly Gly Thr Asp Val Ile Arg Phe Val Gln His Asp Ala
        50                  55                  60

Ser Asp Glu Ala Gly Trp Thr Lys Leu Phe Asp Thr Thr Glu Glu Ala

```
              65                  70                  75                  80
          Phe Gly Pro Val Thr Thr Val Asn Asn Ala Gly Ile Ala Val Gln
                              85                  90                  95

Lys Ser Val Glu Asp Thr Thr Glu Glu Trp His Lys Leu Leu Ser
                         100                 105                 110

Val Asn Leu Asp Ser Val Phe Phe Gly Thr Arg Leu Gly Ile Gln Arg
                         115                 120                 125

Met Lys Asn Lys Gly Leu Gly Ala Ser Ile Ile Asn Met Ser Ser Ile
          130                 135                 140

Ser Gly Phe Val Gly Asp Pro Met Leu Gly Ala Tyr Thr Ala Ser Lys
          145                 150                 155                 160

Gly Ala Val Arg Ile Met Ser Lys Ser Ala Ala Leu Asp Cys Ala Leu
                              165                 170                 175

Lys Asp Tyr Asp Val Arg Val Asn Thr Val His Pro Gly Cys Ile Lys
                         180                 185                 190

Thr Pro Leu Val Asp Asp Glu Gly Ala Glu Glu Met Met Ser Gln
                         195                 200                 205

Arg Thr Arg Thr Pro Met Gly His Ile Gly Glu Pro Asn Asp Val Ala
                    210                 215                 220

Trp Ile Cys Val Tyr Leu Ala Ser Asp Glu Ser Lys Phe Ala Thr Gly
          225                 230                 235                 240

Ala Glu Phe Val Val Asp Gly Gly Tyr Thr Ala Gln
                              245                 250

<210> SEQ ID NO 81
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 81
atgaccgatc gtctgaagag caaagtagcc atcgtaaccg gcgggaccct gggtatcggt      60
ttggcaatcg ccactaaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cattgcagaa agcgttgaa      300 gacactacca cggaggaatg gcacaaactg ctgtccgtta atctggatag tgttttttc      360 ggcacccgtc tgggcattca gcgcatgaag aataaaggct gggcgctag catcatcaat     420 atgagcagta tcagtgggtt cgtaggcgat ccgatgctgg ggcatacaa tgcttccaag      480 ggggcggtac gtatcatgtc gaaaagcgca gcgctggatt gcgcagtgaa ggactacgat     540
gtgcgtgtca acacagtaca tccgggctgt atcaagaccc cgctggtcga tgaagatgaa     600
ggtgctgagg aaatgatgtc acagcgtacg agaaccccta tggccacat tggcgaaccg      660 aatgacgtgg catggatctg tgtgtacctg gcatctgacg aatcgaaatt tgcgacgggt     720
gcagaatttg tggtcgacgg cgggtatacc gcacagtga                            759

<210> SEQ ID NO 82
<211> LENGTH: 252
<212> TYPE: PRT
<213> ORGANISM: Artificial Sequence
<220> FEATURE:
<223> OTHER INFORMATION: Synthetic Variant of L. kefir
```

```
<400> SEQUENCE: 82

Met Thr Asp Arg Leu Lys Ser Lys Val Ala Ile Val Thr Gly Gly Thr
 1               5                  10                  15
Leu Gly Ile Gly Leu Ala Ile Ala Thr Lys Phe Val Glu Glu Gly Ala
            20                  25                  30
Lys Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Asn Asn Ala Gly Ile Ala Leu Gln
                85                  90                  95
Lys Ser Val Glu Asp Thr Thr Glu Glu Trp His Lys Leu Leu Ser
            100                 105                 110
Val Asn Leu Asp Ser Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Ser Gly Phe Val Gly Asp Pro Met Leu Gly Ala Tyr Asn Ala Ser Lys
145                 150                 155                 160
Gly Ala Val Arg Ile Met Ser Lys Ser Ala Ala Leu Asp Cys Ala Val
                165                 170                 175
Lys Asp Tyr Asp Val Arg Val Asn Thr Val His Pro Gly Cys Ile Lys
            180                 185                 190
Thr Pro Leu Val Asp Glu Asp Gly Ala Glu Glu Met Met Ser Gln
        195                 200                 205
Arg Thr Arg Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250

<210> SEQ ID NO 83
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 83
atgaccgatc gtctgaagag caaagtagcc atcgtaaccg gcgggaccct gggtatcggt      60
ttggcaatcg ccactaaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cattgcagaa aagcgttgaa     300
gacactacca cggaggaatg gcacaaactg ctgtccgtta atctggatag tgttttttc     360 ggcacccgtc tgggcattca gcgcatgaag aataaaggct gggcgctag catcatcaat     420 atgagcagta tcagtgggtt cgtaggcgat ccgatgctgg gggcatacaa tgcttccaag     480
ggggcggtac gtatcatgtc gaaaagcgca gcgctggatt gcgcagtgaa ggactacgat     540
gtgcgtgtca acacagtaca tccgggctgt atcaagaccc ctctggtcga ggatgatgaa     600
```

```
ggtgctgagg aaatgatgtc acagcgtacg agaacccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                          759
```

```
<210> SEQ ID NO 84
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 84
```

Met Thr Asp Arg Leu Lys Ser Lys Val Ala Ile Val Thr Gly Gly Thr
1               5                   10                  15

Leu Gly Ile Gly Leu Ala Ile Ala Thr Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Gln
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Cys Ile Lys
            180                 185                 190

Thr Pro Leu Val Glu Asp Asp Glu Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

```
<210> SEQ ID NO 85
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 85
atgaccgatc gtctgaagag caaagtagcc atcgtaaccg gcgggaccct gggtatcggt    60
ttggcaatcg ccactaaatt tgtagaggag ggtgcgaaag tagttattac tggtcgccac   120
```

```
gcggatgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcagggattg caatgcagaa aagcgttgaa    300
gacactacca cggaggaatg gcacaaactg ctgtccgtta atctggatag tgttttttc    360 ggcacccgtc tgggcattca gcgcatgaag aataaaggct gggcgctag catcatcaat    420 atgagcagta tcagtgggtt cgtaggcgat ccgatgctgg gggcatacaa tgcttccaag    480
ggggcggtac gtatcatgtc gaaaagcgca gcgctggatt gcgcagtgaa ggactacgat    540
gtgcgtgtca acacagtaca tccgggctgt atcaagaccc gtctggtcga tgatgatgaa    600
ggtgctgagg aaatgatgtc acagcgtacg agaaccccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                          759
```

<210> SEQ ID NO 86  
<211> LENGTH: 252  
<212> TYPE: PRT  
<213> ORGANISM: Artificial Sequence  
<220> FEATURE:  
<223> OTHER INFORMATION: Synthetic Variant of L. kefir

<400> SEQUENCE: 86

```
Met Thr Asp Arg Leu Lys Ser Lys Val Ala Ile Val Thr Gly Gly Thr
1               5                   10                  15

Leu Gly Ile Gly Leu Ala Ile Ala Thr Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Met Gln
                85                  90                  95

Lys Ser Val Glu Asp Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Cys Ile Lys
            180                 185                 190

Thr Arg Leu Val Asp Asp Asp Glu Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 87
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 87

```
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagttcagaa aagcgttgaa     300
gacactacca cggaggaatg gcgtaaactg ctgtccgtta atctggatgg tgttttttc      360
ggcacccgtc tgggcattca gcgcatgaag aataaaggct gggcgctag catcatcaat     420
atgagcagta tcagtgggtt cgtaggcgat ccgatgctgg gggcatacaa tgcttccaag     480
ggggcggtac gtatcatgtc gaaaagcgca gcgctggatt gcgcactgaa ggactacgat     540
gtgcgtgtca acacagtaca tccgggctgt atcaagaccc cgctggtcga tgatgatgaa     600
ggtgctgagg aaatgatgtc acagcgtacg agaacccctg tggccacat tggcgaaccg      660
aatgacgtgg catggatctg tgtgtacctg gcatctgacg aatcgaaatt tgcgacgggt     720
gcagaatttg tggtcgacgg cgggtatacc gcacagtga                            759
```

<210> SEQ ID NO 88
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 88

```
Met Thr Asp Arg Leu Lys Ser Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Ala Val Gln
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Ser Gly Phe Val Gly Asp Pro Met Leu Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
```

Lys Asp Tyr Asp Val Arg Val Asn Thr Val His Pro Gly Cys Ile Lys
            180                 185                 190

Thr Pro Leu Val Asp Asp Asp Glu Gly Ala Glu Met Met Ser Gln
        195                 200                 205

Arg Thr Arg Thr Pro Met Gly His Ile Gly Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 89
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 89

```
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagttcagaa aagcgttgaa     300
gacactacca cggaggaatg gcgtaaactg ctgtccgtta atctggatgg tgttttttc     360
ggcacccgtc tgggcattca gcgcatgaag aataaaggct gggcgctag catcatcaat     420
atgagcagta tcagcgggtt cgtaggcgat ccgatgctgg gggcatacaa tgcttccaag     480
ggggcggtac gtatcatgtc gaaaagcgca gcgctggatt gcgcactgaa ggactacgat     540
gtgcgtgtca acacagtaca tccgggctgt atcaagaccc cgctggtcga tgatgatgaa     600
ggtgctgagg aaatgatgtc acagcgtacg agaacccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacagtga                           759
```

<210> SEQ ID NO 90
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 90

Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Gln
                85                  90                  95

```
Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
        130                 135                 140

Ser Gly Phe Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Glu Gly Ala Glu Glu Met Met Ser Gln
        195                 200                 205

Arg Thr Arg Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 91
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 91
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagttcagaa aagcgttgaa     300
gacactacca cggaggaatg gcgcaaactg ctgtccgtta atctggatgg tgttttttc     360 ggcacccgtc tgggcattca gcgcatgaag aataaaggct gggcgctag catcatcaat     420 atgagcagta tcagtgggtt cgtaggcgat ccgatgctgg gggcatacaa tgcttccaag     480
ggggcggtac gtatcatgtc gaaaagcgca gcgctggatt gcgcactgaa ggactacgat     540
gtgcgtgtca acacagtaca tccgggctgt atcaagaccc cgctggtcga tgatgatgaa     600
ggtgctgagg aaatgatgtc acagcgtacg agaaccccta tgggccacat tggcgaaccg     660
aatgacgtgg catggatctg tgtgtacctg gcatctgacg aatcgaaatt tgcgacgggt     720
gcagaatttg tggtcgacgg cgggtatacc gcacagtga                            759

<210> SEQ ID NO 92
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 92

Met Thr Asp Arg Leu Lys Ser Lys Val Ala Ile Val Thr Gly Gly Thr
1               5                   10                  15
```

```
Leu Gly Ile Gly Leu Ala Ile Ala Asp Lys Phe Val Glu Glu Gly Ala
             20                  25                  30
Lys Val Val Ile Thr Gly Arg His Ala Asp Val Gly Glu Lys Ala Ala
         35                  40                  45
Lys Ser Ile Gly Gly Thr Asp Val Ile Arg Phe Val Gln His Asp Ala
     50                  55                  60
Ser Asp Glu Ala Gly Trp Thr Lys Leu Phe Asp Thr Thr Glu Glu Ala
 65                  70                  75                  80
Phe Gly Pro Val Thr Thr Val Asn Asn Ala Gly Ile Ala Val Gln
                 85                  90                  95
Lys Ser Val Glu Asp Thr Thr Thr Glu Glu Trp His Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Ser Gly Phe Val Gly Asp Pro Met Leu Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Cys Ile Lys
            180                 185                 190
Thr Pro Leu Val Asp Asp Glu Gly Ala Glu Glu Met Met Ser Gln
        195                 200                 205
Arg Thr Arg Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```

<210> SEQ ID NO 93
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 93

| | | |
|---|---|---|
| atgaccgatc gtctgaagag caaagtagcc atcgtaaccg cgggacccct gggtatcggt | 60 |
| ttggcaatcg ccgataaatt tgtagaggag ggtgcgaaag tagttattac tggtcgccac | 120 |
| gcggatgtag gtgaaaaggc cgccaaatca atcggcgata ctgatgttat tcgctttgtc | 180 |
| cagcacgatg catccgatga agcaggctgg acgaaactgt tcgacaccac cgaggaggca | 240 |
| ttcggcccgg ttacgaccgt cgtgaacaat gcaggattg cagttcagaa aagcgttgaa | 300 |
| gacactacca cggaggaatg gcacaaactg ctgtccgtta atctggatag tgttttttc | 360 |
| ggcacccgtc tgggcattca gcgcatgaag aataaaggct gggcgctag catcatcaat | 420 |
| atgagcagta tcagtgggtt cgtaggcgat ccgatgctgg gggcatacaa tgcttccaag | 480 |
| ggggcgatac gtatcatgtc gaaaagcgca gcgctggatt gcgcactgaa ggactacgat | 540 |
| gtgcgtgtca acacagtaca tccgggctgt atcaagaccc cgctggtcga tgatgatgaa | 600 |
| ggtgctgagg aaatgatgtc acagcgtacg agaaccccta tgggccacat tggcgaaccg | 660 |
| aatgacgtgg catggatctg tgtgtacctg gcatctgacg aatcgaaatt tgcgacgggt | 720 |

```
gcagaatttg tggtcgacgg cgggtatacc gcacagtga                         759
```

<210> SEQ ID NO 94
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 94

```
Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Asp Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Gln
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
130                 135                 140

Ser Gly Phe Val Gly Asp Pro Met Leu Gly Ala Tyr Asn Ala Ser Lys
145                 150                 155                 160

Gly Ala Ile Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Glu Gly Ala Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 95
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 95

```
atgaccgatc gtctgaagag caaagtagcc atcgtaaccg gcgggaccct gggtatcggt   60
ttggcaatcg ccgataaatt tgtagaggag ggtgcgaaag tagttattac tggtcgccac  120
gcggatgtag gtgaaaaggc cgccaaatca atcggcggta ctgatgttat tcgctttgtc  180
cagcacgatg catccgatga agcaggctgg acgaaactgt tcgacaccac cgaggaggca  240
```

```
ttcggcccgg ttacgaccgt cgtgaacaat gcagggattg cacttcagaa aagcgttgaa       300
gacactacca cggaggaatg gcacaaactg ctgtccgtta atctggatag tgttttttc        360 ggcacccgtc tgggcattca gcgcatgaag aataaaggct tgggcgctag catcatcaat      420
atgagcagta tcagtgggtt cgtaggcgat ccgatgctgg gggcatacaa tgcttccaag      480
ggggcggtac gtatcatgtc gaaaagcgca gcgctggatt gcgcactgaa ggactacgat      540
gtgcgtgtca acacagtaca tccgggctgt atcaagaccc cgctggtcga tgatgatgaa      600
ggtgctgagg aaatgatgtc acagcgtacg agaaccccta tgggccacat tggcgaaccg      660
aatgacgtgg catggatctg tgtgtacctg gcatctgacg aatcgaaatt tgcgacgggt      720
gcagaatttg tggtcgacgg cgggtatacc gcacagtga                            759
```

```
<210> SEQ ID NO 96
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 96
```

Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Gln
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Glu Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

```
<210> SEQ ID NO 97
<211> LENGTH: 759
```

```
<212> TYPE: DNA
<213> ORGANISM: Artificial Sequence
<220> FEATURE:
<223> OTHER INFORMATION: Synthetic Variant of L. kefir

<400> SEQUENCE: 97
atgaccgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagttcagaa aagcgttgaa     300
gacactacca cggaggaatg gaacaaactg ctgtccgtta atctggatag tgttttttc     360
ggcacccgtc tgggcattca gcgcatgaag aataaaggct gggcgctag catcatcaat      420
atgagcagta tcagtgggtt cgtaggcgat ccgatgctgg ggcatacaa tgcttccaag      480
ggggcggtac gtatcatgtc gaaaagcgca gcgctggatt gcgcactgaa ggactacgat     540
gtgcgtgtca acacagtaca tccgggctgt atcaagaccc cgctggtcga tgatgatgaa     600
ggtgctgagg aaatgatgtc acagcgtacg agaaccccta tgggccacat tggcgaaccg     660
aatgacgtgg catggatctg tgtgtacctg gcatctgacg aatcgaaatt tgcgacgggt     720
gcagaatttg tggtcgacgg cgggtatacc gcacagtga                            759
```

```
<210> SEQ ID NO 98
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 98

Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Gln
                85                  90                  95

Lys Ser Val Glu Asp Thr Thr Thr Glu Glu Trp Asn Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190
```

Thr Pro Leu Val Asp Asp Asp Glu Gly Ala Glu Met Met Ser Gln
            195                 200                 205

Arg Thr Arg Thr Pro Met Gly His Ile Gly Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 99
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 99

```
atgactgatc gtctgaagag caaagtagcc atcgtaaccg gcgggaccct gggtatcggt      60
ttggcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
caacacgatg catccgatga agcaggctgg acgaaactgt tcgacaccac cgaggaggca     240
ttcggcccgg ttacgaccgt cgtgaacaat gcagggattg cagttcagaa aagcgttgaa     300
ggcactacca cggaggaatg gcacaaactg ctgtccgtta atctggatag tgttttttc     360 ggcacccgtc tgggcattca gcgcatgaag aataaaggct gggcgctag catcatcaat     420 atgagcagta tcagtgggtt agtaggcgat ccgatgctgg gggcatacaa tgcttccaag     480
ggggcggtac gtatcatgtc gaaaagcgca gcgctggatt gcgcactgaa ggactacgat     540
gtgcgtgtca acacagtaca tccgggctgt atcaagaccc cgctggtcga tgatgatgaa     600
ggtgctgagg aaatgatgtc acagcgtacg agaaccccta tgggccacat tggcgaaccg     660
aatgacgtgg catggatctg tgtgtacctg gcatctgacg aatcgaaatt tgcgacgggt     720
gcagaatttg tggtcgacgg cgggtatacc gcacagtga                            759
```

<210> SEQ ID NO 100
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 100

Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Gln
                85                  90                  95

Lys Ser Val Glu Gly Thr Thr Thr Glu Glu Trp His Lys Leu Leu Ser
            100                 105                 110

```
Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Glu Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 101
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 101

```
atgaccgatc gtctgaagag caaagtagcc atcgtaaccg gcgggaccct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat cgctttgtc    180
cagcacgatg catccgatga agcaggatgg acgaaactgt cgacaccac cgaggaggca   240
ttcggcccgg ttacgaccgt cgtgaacaat gcagggattg cagttcagaa gagcgttgaa   300
gacactacca cggaggaatg gcacaaactg atgtccgtta atctggatag tgttttttc   360
ggcacccgtc tgggcattca gcgcatgaag aataaaggct gggcgctag catcatcaat   420
atgagcagta tcagtgggtt cgtaggcgat ccgatgctgg gggcatacaa tgcttccaag   480
ggggcggtac gtatcatgtc gaaaagcgca gcgctggatt gcgcactgaa ggactacgat   540
gtgcgtgtca acacagtaca tccgggctgt atcaagaccc cgctggtcga tgatgatgaa   600
ggtgctgagg aaatgatgtc acagcgtacg agaaccccta tggccacat ggcgaaccg    660
aatgacgtgg catggatctg tgtgtacctg gcatctgacg aatcgaaatt tgcgacgggt   720
gcagaatttg tggtcgacgg cgggtatacc gcacagtga                          759
```

<210> SEQ ID NO 102
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 102

```
Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30
```

```
Lys Val Val Ile Thr Gly Arg His Ala Asp Val Gly Glu Lys Ala Ala
             35                  40                  45
Lys Ser Ile Gly Gly Thr Asp Val Ile Arg Phe Val Gln His Asp Ala
 50                  55                  60
Ser Asp Glu Ala Gly Trp Thr Lys Leu Phe Asp Thr Thr Glu Glu Ala
 65                  70                  75                  80
Phe Gly Pro Val Thr Val Val Asn Asn Ala Gly Ile Ala Val Gln
                 85                  90                  95
Lys Ser Val Glu Asp Thr Thr Thr Glu Glu Trp His Lys Leu Met Ser
            100                 105                 110
Val Asn Leu Asp Ser Val Phe Phe Gly Thr Arg Leu Gly Ile Gln Arg
            115                 120                 125
Met Lys Asn Lys Gly Leu Gly Ala Ser Ile Ile Asn Met Ser Ser Ile
130                 135                 140
Ser Gly Phe Val Gly Asp Pro Met Leu Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Cys Ile Lys
            180                 185                 190
Thr Pro Leu Val Asp Asp Glu Gly Ala Glu Met Met Ser Gln
        195                 200                 205
Arg Thr Arg Thr Pro Met Gly His Ile Gly Glu Pro Asn Asp Val Ala
210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250

<210> SEQ ID NO 103
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 103
atgaccgatc gtctgaagag caaagtagcc atcgtaaccg gcgggaccct gggtatcggt      60
ttggcaatcg ccgataaatt tgtagaggag ggtgcgaaag tagttattac tggtcgacac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagttcagaa aagcgttgaa     300
gacactacca cggaggaatg gcacaaactg ctgtccgtta atctggatag tgttttttc      360
ggcacccgtc tgggcattca gcgcatgaag aataaaggct gggcgctag catcatcaat      420
atgagcagta tcagtgggtt cgtaggcgat ccgatgctgg ggcatacaa tgcttccaag      480
ggggcggtac gtatcatgtc gaaaagcgca gcgctggatt gcgcactgaa ggactatgat     540
gtgcgtgtca acacagtaca tccgggctgt atcaagaccc cgctggtcga tgatgatgaa     600
ggtgctgagg aaatgatgtc acagcgtacg agaaccccta tgggccacat tggcgaaccg     660
aatgacgtgg catggatctg tgtgtacctg gcatctgacg aatcgaaatt tgcgacgggt     720
gcagaatttg tggtcgacgg cgggtatatc gcacagtga                           759
```

```
<210> SEQ ID NO 104
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 104
```

Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Gln
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Asp Glu Gly Ala Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Ile Ala Gln
                245                 250

```
<210> SEQ ID NO 105
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 105
```
atgaccgatc gtctgaagag caaagtagcc atcgtaaccg gcgggaccct gggtatcggt      60
ttggcaatcg ccgataaatt tgtaggtgag ggtgcgaaag tagttattac tggtcgccac     120
gcggatgtag tgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagttcagaa aagcgttgag     300
aacactacca cggaggaatg gcacaaactg ctgtccgtta atctggatag tgttttttc     360

```
ggcacccgtc tgggcattca gcgcatgaag aataaaggct tgggcgctag catcatcaat    420
atgagcagta tcagtgggtt cgtaggcgat ccgatgctgg gggcatacaa tgcttccaag    480
ggggcggtac gtatcatgtc gaaaagcgca gcgctggatt gcgcactgaa ggactacgat    540
gtgcgtgtca acacagtaca tccgggctgt atcaagaccc cgctggtcga tgatgatcca    600
ggtgctgagg aaatgatgtc acagcgtacg agaaccccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                          759
```

<210> SEQ ID NO 106
<211> LENGTH: 252
<212> TYPE: PRT
<213> ORGANISM: Artificial Sequence
<220> FEATURE:
<223> OTHER INFORMATION: Synthetic Variant of L. kefir
<400> SEQUENCE: 106

Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Gly Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Gln
                85                  90                  95

Lys Ser Val Glu Asn Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Pro Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 107
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 107

```
atgaccgatc gtctgaagag caaagtagcc atcgtaaccg gcgggaccca gggtatcggt      60
ttggcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagttcagaa aagcgttgaa     300
gacactacca cggaggaatg gcacaaactg ctgtccgtta atctggatag tgttttttc      360
ggcacccgtc tgggcattca gcgcatgaag aataaaggct gggcgctag catcatcaat      420
atgagcagta tcagtgggtt cgtaggcgat ccgatgctgg gggcatacaa tgcttccaag     480
ggggcggtac gtatcatgtc gaaaagcgca gcgctggatt gcgcactgaa ggactacgat     540
gtgcgtgtca acacagtaca tccgggctgt atcaagaccc cgctggtcga tgatgatgaa     600
ggtgctgagg aaatgatgtc acagcgtacg agaaccccta tgggccacat ggcgaaccg      660
aatgacgtgg catggatctg tgtgtacctg gcatctgacg aatcgaaatt tgcgacgggt     720
gcagaatttg tggtcgacgg cgggtatacc gcacagtga                            759
```

<210> SEQ ID NO 108
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 108

```
Met Thr Asp Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Ala Val Gln
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Glu Gly Ala Glu Glu Met Met Ser Gln
        195                 200                 205

Arg Thr Arg Thr Pro Met Gly His Ile Gly Glu Pro Asn Asp Val Ala
```

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
            245                 250

<210> SEQ ID NO 109
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 109
atgaccgatc gtctgaagag caaagtagcc atcgtaaccg gcgggaccct gggtatcggt        60
ttggcaatcg ccgataaatt tgtagaggag ggtgcgaaag tagttattac tggtcgccac       120
gcggatgtag gtgaaaaggc cgccaaatca atcggcggta ctgatgttat tcgctttgtc       180
cagcacgatg catccgatga agcaggctgg acgaaactgt tcgacaccac cgaggaggca       240
ttcggcccgg ttacgaccgt cgtgaacaat gcaggattg cagttcagaa aagcgttgaa        300
gacactacca cggaggaatg gcacaaactg ctggatgtta atctggatag tgttttttc        360
ggcacccgtc tgggcattca gcgcatgaag aataaaggct gggcgctag catcatcaat        420
atgagcagta tcagtgggtt cgtaggcgat ccgatgctgg gggcatacaa tgcttccaag       480
ggggcggtac gtatcatgtc gaaaagcgca gcgctggatt gcgcactgaa ggactacgat       540
gtgcgtgtca acacagtaca tccgggctgt atcaagaccc cgctggtcga tggtgatgaa       600
ggtgctgagg aaatgatgtc acagcgtacg agaaacccta tgggccacat tggcgaaccg       660
aatgacgtgg catggatctg tgtgtacctg gcatctgacg aatcgaaatt tgcgacgggt       720
gcagaatttg tggtcgacgg cgggtatacc gcacagtga                             759

<210> SEQ ID NO 110
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 110

Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Gln
                85                  90                  95

Lys Ser Val Glu Asp Thr Thr Thr Glu Glu Trp His Lys Leu Leu Asp
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile

```
                130                 135                 140
Ser Gly Phe Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
                180                 185                 190

Thr Pro Leu Val Asp Gly Asp Glu Gly Ala Glu Glu Met Met Ser Gln
            195                 200                 205

Arg Thr Arg Thr Pro Met Gly His Ile Gly Glu Pro Asn Asp Val Ala
        210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 111
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 111

```
atgaccgatc gtctgaagag caaagtagcc atcgtaaccg gcgggaccct gggtatcggt    60
ttggcaatcg ccgataaatt tgtagaggag ggtgcgaaag tagttattac tggtcgccac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagttcagaa aagcgttgaa   300
gacactacca cggaggaatg gtctaaactg ctgtccgtta atctggatag tgttttttc    360
ggcacccgtc tgggcattca cgcatgaag aataaaggct gggcgctag catcatcaat    420
atgagcagta tcagtgggtt cgtaggcgat ccgatgctgg gggcatacaa tgcttccaag   480
ggggcggtac gtatcatgtc gaaaagcgca gcgctggatt gcgcactgaa ggactacgat   540
gtgcgtgtca acacagtaca tccgggctgt atcaagaccc cgctggtcga tgatgatgaa   600
ggtgctgagg aaatgatgtc acagcgtacg agaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                         759
```

<210> SEQ ID NO 112
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 112

```
Met Thr Asp Arg Leu Lys Ser Lys Val Ala Ile Val Thr Gly Gly Thr
1               5                  10                  15

Leu Gly Ile Gly Leu Ala Ile Ala Asp Lys Phe Val Glu Glu Gly Ala
                20                  25                  30

Lys Val Val Ile Thr Gly Arg His Ala Asp Val Gly Glu Lys Ala Ala
            35                  40                  45

Lys Ser Ile Gly Gly Thr Asp Val Ile Arg Phe Val Gln His Asp Ala
```

```
                50                  55                  60
Ser Asp Glu Ala Gly Trp Thr Lys Leu Phe Asp Thr Glu Glu Ala
 65                  70                  75                  80

Phe Gly Pro Val Thr Thr Val Asn Asn Ala Gly Ile Ala Val Gln
                 85                  90                  95

Lys Ser Val Glu Asp Thr Thr Thr Glu Glu Trp Ser Lys Leu Leu Ser
            100                 105                 110

Val Asn Leu Asp Ser Val Phe Phe Gly Thr Arg Leu Gly Ile Gln Arg
            115                 120                 125

Met Lys Asn Lys Gly Leu Gly Ala Ser Ile Ile Asn Met Ser Ser Ile
        130                 135                 140

Ser Gly Phe Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Glu Gly Ala Glu Glu Met Met Ser Gln
            195                 200                 205

Arg Thr Arg Thr Pro Met Gly His Ile Gly Glu Pro Asn Asp Val Ala
        210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 113
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 113

```
atgaccaacc gtctgaagag caaagtagcc atcgtaaccg gcgggaccca gggtatcggt     60
ttggcaatcg ccgataaatt tgtagaggag ggtgcgaaag tagttattac tggtcgccac    120
gcgggtgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcaggattg cagttcagaa aagcgttgaa    300
gacactacca cggaggaatg cacaaactg ctgtccgtta atctggatgg cgttttttc    360
ggcacccgtc tgggcattcg ccgcatgaag aataaaggct gggcgctag catcatcaat    420
atgagcagta tcagtgggtt cgtaggcgat ccgatgctgg gggcatacaa tgcttccaag    480
ggggcggtac gtatcatgtc gaaaagcgca gcgctggatt gcgcagtgaa ggactacgat    540
gtgcgtgtca acacagtaca tccgggctgt atcaagaccc gtctggtcga tgacgatcca    600
ggtgctgagg aaatgatgtc acagcgtacg agaaccccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                           759
```

<210> SEQ ID NO 114
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 114

```
Met Thr Asn Arg Leu Lys Ser Lys Val Ala Ile Val Thr Gly Gly Thr
1               5                   10                  15
Gln Gly Ile Gly Leu Ala Ile Ala Asp Lys Phe Val Glu Glu Gly Ala
            20                  25                  30
Lys Val Val Ile Thr Gly Arg His Ala Gly Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Ala Val Gln
                85                  90                  95
Lys Ser Val Glu Asp Thr Thr Thr Glu Glu Trp His Lys Leu Leu Ser
            100                 105                 110
Val Asn Leu Asp Gly Val Phe Phe Gly Thr Arg Leu Gly Ile Arg Arg
        115                 120                 125
Met Lys Asn Lys Gly Leu Gly Ala Ser Ile Ile Asn Met Ser Ser Ile
    130                 135                 140
Ser Gly Phe Val Gly Asp Pro Met Leu Gly Ala Tyr Asn Ala Ser Lys
145                 150                 155                 160
Gly Ala Val Arg Ile Met Ser Lys Ser Ala Ala Leu Asp Cys Ala Val
                165                 170                 175
Lys Asp Tyr Asp Val Arg Val Asn Thr Val His Pro Gly Cys Ile Lys
            180                 185                 190
Thr Arg Leu Val Asp Asp Pro Gly Ala Glu Glu Met Met Ser Gln
        195                 200                 205
Arg Thr Arg Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```

<210> SEQ ID NO 115
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 115

```
atgaccaacc gtctgaagag caaagtagcc atcgtaaccg gcgggaccca gggtatcggt      60
ttcgcaatcg ccgataaatt tgtagaggag ggtgcgaaag tagttattac tggtcgccac     120
gcggatgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagttcagaa aagcgttgaa     300
gacactacca cggaggaatg gcacaaactg ctgtccgtta atctggatgg cgttttttc      360 ggcacccgtc tgggcattca gcgcatgaag aataaaggct gggcgctag catcatcaat     420 atgagcagta tcagtgggct ggtaggcgat ccgatgctgg gggcatacaa tgcttccaag     480
```

-continued

```
ggggcggtac gtatcatgtc gaaaagcgca gcgctggatt gcgcagtgaa ggactacgat    540
gtgcgtgtca acacagtaca tccgggctgt atcaagaccc cgctggtcga tgatgatgaa    600
ggtgctgagg aaatgatgtc acagcgtacg agaaccccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                          759
```

<210> SEQ ID NO 116
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 116

```
Met Thr Asn Arg Leu Lys Ser Lys Val Ala Ile Val Thr Gly Gly Thr
 1               5                  10                  15

Gln Gly Ile Gly Phe Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Gln
                85                  90                  95

Lys Ser Val Glu Asp Thr Thr Thr Glu Glu Trp His Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Leu Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Val
                165                 170                 175

Lys Asp Tyr Asp Val Arg Val Asn Thr Val His Pro Gly Cys Ile Lys
            180                 185                 190

Thr Pro Leu Val Asp Asp Asp Glu Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 117
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 117

```
atgaccaacc gtctgaagag caaagtagcc atcgtaaccg gcgggaccca gggtatcggt    60
```

-continued

```
ttggcaatcg ccgataaatt tgtagccgag ggtgcgaaag tagttattac tggtcgccac    120
gcgggtgtag gtgaaaaggc cgccaaatca atcggcggta ctgatgttat tcgctttgtc    180
cagcacgatg catccgatga agcaggctgg acgaaactgt tcgacaccac cgaggaggca    240
ttcggcccgg ttacgaccgt cgtgaacaat gcagggattg cagttcagaa aagcgttgaa    300
gacactacca cgggggaatg gcacaaactg ttgtccgtta atctggatag tgttttttc    360 ggcacccgtc tgggcattca gcgcatgaag aataaaggct gggcgctag catcatcaat    420 atgagcagta tcagtgggtt cgtaggcgat ccgatgctgg gggcatacaa tgcttccaag    480
ggggcggtac gtatcatgtc gaaaagcgca gcgctggatt gcgcactgaa ggactacgat    540
gtgcgtgtca acacagtaca tccgggctgt atcaagaccc cgctggtcgt taaagatcca    600
ggtgctgagg aaatgatgtc acagcgtacg agaaccccta tgggccacat tggcgaaccg    660
aatgacgtgg catggatctg tgtgtacctg gcatctgacg aatcgaaatt tgcgacgggt    720
gcagaatttg tggtcgacgg cgggtatacc gcacagtga                          759
```

<210> SEQ ID NO 118
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 118

```
Met Thr Asn Arg Leu Lys Ser Lys Val Ala Ile Val Thr Gly Gly Thr
1               5                   10                  15

Gln Gly Ile Gly Leu Ala Ile Ala Asp Lys Phe Val Ala Glu Gly Ala
            20                  25                  30

Lys Val Val Ile Thr Gly Arg His Ala Gly Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Ala Val Gln
                85                  90                  95

Lys Ser Val Glu Asp Thr Thr Thr Gly Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Val Lys Asp Pro Gly Ala Glu Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240
```

Ala Glu Phe Val Val Asp Gly Gly Tyr Thr Ala Gln
            245                 250

<210> SEQ ID NO 119
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 119

```
atgaccgatc gtctgaagag caaagtagcc atcgtaaccg gcgggaccca gggtatcggt      60
ttggcaatcg ccgataaatt tgtagaggag ggtgcgaaag tagttattac tggtcgccac     120
gcgggtgtag gtgaaaaggc cgccaaatca atcggcggta ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagttcagaa aagcgttgaa     300
gacactacca cggaggaatg gcacaaactg ctgtccgtta atctggatag tgttttttc      360
ggcacccgtc tgggcattca gcgcatgaag aataaaggct gggcgctag catcatcaat      420
atgagcagta tcagtgggtt cgtaggcgat ccgatgctgg gggcatacaa tgcttccaag     480
ggggcgattc gtatcatgtc gaaaagcgca gcgctggatt gcgcactgaa ggactacgat     540
gtgcgtgtca acacagtaca tccgggctgt atcaagaccc cgctggtcga taaagatgag     600
ggtgctgagg aaatgatgtc acagcgtacg agaaccccta tgggccacat tggcgaaccg     660
aatgacgtgg catggatctg tgtgtacctg gcatctgacg aatcgaaatt tgcgacgggt     720
gcagaatttg tggtcgacgg cgggtatacc gcacagtga                             759
```

<210> SEQ ID NO 120
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 120

Met Thr Asp Arg Leu Lys Ser Lys Val Ala Ile Val Thr Gly Gly Thr
1               5                   10                  15

Gln Gly Ile Gly Leu Ala Ile Ala Asp Lys Phe Val Glu Glu Gly Ala
            20                  25                  30

Lys Val Val Ile Thr Gly Arg His Ala Gly Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Gln
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Met Leu Gly Ala Tyr Asn Ala Ser Lys
145                 150                 155                 160

```
Gly Ala Ile Arg Ile Met Ser Lys Ser Ala Ala Leu Asp Cys Ala Leu
            165                 170                 175

Lys Asp Tyr Asp Val Arg Val Asn Thr Val His Pro Gly Cys Ile Lys
        180                 185                 190

Thr Pro Leu Val Asp Lys Asp Glu Gly Ala Glu Glu Met Met Ser Gln
    195                 200                 205

Arg Thr Arg Thr Pro Met Gly His Ile Gly Glu Pro Asn Asp Val Ala
210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 121
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 121
atgaccgatc gtctgaagag caaagtagcc atcgtaaccg gcgggaccca gggtatcggt     60
ttggcaatcg ccgataaatt tgtagccgag ggtgcgaaag tagttattac tggtcgccac    120
gcggatgtag gtgaaaaggc cgccaaatca atcggcggta ctgatgttat cgctttgtc     180 cagcacgatg catccgatga agcaggctgg acgaaactgt tcgacaccac cgaggaggca    240
ttcggcccgg ttacgaccgt cgtgaacaat gcagggattg cagttcagaa aagcgttgaa    300
gacactacca cggaggaatg cacaaactg ctgtccgtta atctggatag tgttttttc     360 ggcacccgtc tgggcattca gcgcatgaag aataaaggct gggcgctag catcatcaat    420 atgagcagta tcagtgggtt cgtaggcgat ccgatgctgg gggcatacaa tgcttccaag    480
ggggcgattc gtatcatgtc gaaaagcgca gcgctggatt gcgcactgaa ggactacgat    540
gtgcgtgtca acacagtaca tccgggctgt atcaagaccc cgctggtcga taaagatcca    600
ggtgctgagg aaatgatgtc acagcgtacg agaaccccta tgggccacat tggtgaaccg    660
aatgacatcg catggatctg tgtgtacctg gcatctgacg aatcgaaatt tgcgacgggt    720
gcagaatttg tggtcgacgg cgggtatacc gcacagtga                          759

<210> SEQ ID NO 122
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 122

Met Thr Asp Arg Leu Lys Ser Lys Val Ala Ile Val Thr Gly Gly Thr
1               5                   10                  15

Gln Gly Ile Gly Leu Ala Ile Ala Asp Lys Phe Val Ala Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80
```

```
Phe Gly Pro Val Thr Thr Val Asn Asn Ala Gly Ile Ala Val Gln
                85                  90                  95
Lys Ser Val Glu Asp Thr Thr Thr Glu Glu Trp His Lys Leu Leu Ser
            100                 105                 110
Val Asn Leu Asp Ser Val Phe Phe Gly Thr Arg Leu Gly Ile Gln Arg
        115                 120                 125
Met Lys Asn Lys Gly Leu Gly Ala Ser Ile Ile Asn Met Ser Ser Ile
130                 135                 140
Ser Gly Phe Val Gly Asp Pro Met Leu Gly Ala Tyr Asn Ala Ser Lys
145                 150                 155                 160
Gly Ala Ile Arg Ile Met Ser Lys Ser Ala Ala Leu Asp Cys Ala Leu
                165                 170                 175
Lys Asp Tyr Asp Val Arg Val Asn Thr Val His Pro Gly Cys Ile Lys
            180                 185                 190
Thr Pro Leu Val Asp Lys Asp Pro Gly Ala Glu Glu Met Met Ser Gln
        195                 200                 205
Arg Thr Arg Thr Pro Met Gly His Ile Gly Glu Pro Asn Asp Ile Ala
210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```

<210> SEQ ID NO 123
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 123

```
atgaccgatc gtctgaagag caaagtagcc atcgtaaccg gcgggaccca gggtatcggt    60
ttggcaatcg ccgataaatt tgtagaggag ggtgcgaaag tagttattac tggtcgccac   120
gcgggtgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagttcagaa aagcgttgaa   300
gacactacca cggaggaatg cacaaactg ctgtccgtta atctggatag tgttttttc    360
ggcacccgtc tgggcattca gcgcatgaag aataaaggct gggcgctag catcatcaat   420
atgagcagta tcagtgggct ggtaggcgat ccgatgctgg gggcatacaa tgcttccaag   480
ggggcgattc gtatcatgtc gaaaagcgca gcgctggatt gcgcagtgaa ggactacgat   540
gtgcgtgtca acacagtaca tccgggctgt atcaagaccc cgctggtcga taaagatgag   600
ggtgctgagg aaatgatgtc acagcgtacg agaaccccta tgggccacat tggcgaaccg   660
aatgacgtgg catggatctg tgtgtacctg gcatctgacg aatcgaaatt tgcgacgggt   720
gcagaatttg tggtcgacgg cgggtatacc gcacagtga                          759
```

<210> SEQ ID NO 124
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 124

```
Met Thr Asp Arg Leu Lys Ser Lys Val Ala Ile Val Thr Gly Gly Thr
1               5                  10                  15

Gln Gly Ile Gly Leu Ala Ile Ala Asp Lys Phe Val Glu Glu Gly Ala
            20                  25                  30

Lys Val Val Ile Thr Gly Arg His Ala Gly Val Gly Glu Lys Ala Ala
            35                  40                  45

Lys Ser Ile Gly Gly Thr Asp Val Ile Arg Phe Val Gln His Asp Ala
50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Gln
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
            115                 120                 125

Met Lys Asn Lys Gly Leu Gly Ala Ser Ile Ile Asn Met Ser Ser Ile
130                 135                 140

Ser Gly Leu Val Gly Asp Pro Met Leu Gly Ala Tyr Asn Ala Ser Lys
145                 150                 155                 160

Gly Ala Ile Arg Ile Met Ser Lys Ser Ala Ala Leu Asp Cys Ala Val
                165                 170                 175

Lys Asp Tyr Asp Val Arg Val Asn Thr Val His Pro Gly Cys Ile Lys
            180                 185                 190

Thr Pro Leu Val Asp Lys Asp Glu Gly Ala Glu Met Met Ser Gln
            195                 200                 205

Arg Thr Arg Thr Pro Met Gly His Ile Gly Glu Pro Asn Asp Val Ala
210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 125
<211> LENGTH: 759
<212> TYPE: DNA
<213> ORGANISM: Artificial Sequence
<220> FEATURE:
<223> OTHER INFORMATION: Synthetic Variant of L. kefir

<400> SEQUENCE: 125
atgaccgatc gtctgaagag caaagtagcc atcgtaaccg gcgggaccca gggtatcggt      60
ttggcaatcg ccgataaatt tgtagccgag ggtgcgaaag tagttattac tggtcgccac     120
gcggatgtag gtgaaaaggc cgccaaatca atcggcggta ctgatgttat cgctttgtc      180 cagcacgatg catccgatga agcaggctgg acgaaactgt tcgacaccac cgaggaggca     240
ttcggcccgg ttacgaccgt cgtgaacaat gcagggattg cagttcagaa aagcgttgaa     300
gacactacca cggaggaatg gcacaaactg ctgtccgtta atctggatag tgttttttc      360 ggcacccgtc tgggcattca gcgcatgaag aataaaggct gggcgctag  catcatcaat     420 atgagcagta tcagtgggct ggtaggcgat ccgatgctgg ggcatacaa  tgcttccaag     480 ggggcgattc gtatcatgtc gaaagcgca gcgctggatt gcgcagtgaa ggactacgat      540
gtgcgtgtca acacagtaca tccgggctgt atcaagaccc cgctggtcga taaagatcca     600
```

```
ggtgctgagg aaatgatgtc acagcgtacg agaaccccta tgggccacat tggcgaacca    660
aacgatgtgg catggatctg tgtgtacctg gcatctgacg aatcgaaatt tgcgacgggt    720
gcagaatttg tggtcgacgg cgggtatacc gcacagtga                           759
```

<210> SEQ ID NO 126
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 126

```
Met Thr Asp Arg Leu Lys Ser Lys Val Ala Ile Val Thr Gly Gly Thr
1               5                   10                  15
Gln Gly Ile Gly Leu Ala Ile Ala Asp Lys Phe Val Ala Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Ala Val Gln
                85                  90                  95
Lys Ser Val Glu Asp Thr Thr Thr Glu Glu Trp His Lys Leu Leu Ser
            100                 105                 110
Val Asn Leu Asp Ser Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Ser Gly Leu Val Gly Asp Pro Met Leu Gly Ala Tyr Asn Ala Ser Lys
145                 150                 155                 160
Gly Ala Ile Arg Ile Met Ser Lys Ser Ala Ala Leu Asp Cys Ala Val
                165                 170                 175
Lys Asp Tyr Asp Val Arg Val Asn Thr Val His Pro Gly Cys Ile Lys
            180                 185                 190
Thr Pro Leu Val Asp Lys Asp Pro Gly Ala Glu Glu Met Met Ser Gln
        195                 200                 205
Arg Thr Arg Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```

<210> SEQ ID NO 127
<211> LENGTH: 762
<212> TYPE: DNA
<213> ORGANISM: Artificial Sequence
<220> FEATURE:
<223> OTHER INFORMATION: Synthetic Variant of L. Brevis

<400> SEQUENCE: 127

```
atgtctaacc gtctggatgg caaagtagcc atcattaccg gcgggactct gggtatcggt     60
ttggcaatcg ccacgaaatt tgtagaggag ggtgcgaaag taatgattac tggtcgtcac    120
tccgatgtag gtgaaaaggc cgccaaatca gtaggcactc cggatcagat tcagtttttt    180
```

-continued

```
cagcacgatt catccgatga agatggctgg acgaaactgt tcgacgccac cgagaaagca      240
ttcggcccgg ttagcacctt agtgaacaat gcagggattg cagttaacaa aagcgttgaa      300
gaaactacca cggccgaatg gcgtaaactg ctggccgtta atctggatgg tgttttttc       360 ggcacccgtc tgggcattca gcgcatgaaa aataaaggct gggcgctag catcatcaat       420 atgagcagta ttagcgggtt cgtaggcgat ccgagcctgg ggcatacaa cgcttccaag       480 ggggcggtac gtatcatgtc gaaaagcgca gcgctggatt gcgcactgaa ggactacgat      540
gtgcgtgtca acacagtaca tccgggctgc atcaagaccc cgctggtcga tgatctgccg      600
ggtgctgagg aagcgatgtc acagcgtacg aaaaccccta tgggccacat tggcgaaccg      660
aatgacatcg catatatctg tgtgtacctg gcatctaatg aatcgaaatt tgcgacgggt      720
tccgaatttg tggtcgacgg cgggtatacc gcacagtaat ga                        762
```

```
<210> SEQ ID NO 128
<211> LENGTH: 252
<212> TYPE: PRT
<213> ORGANISM: Artificial Sequence
<220> FEATURE:
<223> OTHER INFORMATION: Synthetic Variant of L. brevis

<400> SEQUENCE: 128

Met Ser Asn Arg Leu Asp Gly Lys Val Ala Ile Ile Thr Gly Gly Thr
1               5                   10                  15

Leu Gly Ile Gly Leu Ala Ile Ala Thr Lys Phe Val Glu Glu Gly Ala
                20                  25                  30

Lys Val Met Ile Thr Gly Arg His Ser Asp Val Gly Lys Ala Ala
            35                  40                  45

Lys Ser Val Gly Thr Pro Asp Gln Ile Gln Phe Phe Gln His Asp Ser
        50                  55                  60

Ser Asp Glu Asp Gly Trp Thr Lys Leu Phe Asp Ala Thr Glu Lys Ala
65                  70                  75                  80

Phe Gly Pro Val Ser Thr Leu Val Asn Asn Ala Gly Ile Ala Val Asn
                85                  90                  95

Lys Ser Val Glu Glu Thr Thr Thr Ala Glu Trp Arg Lys Leu Leu Ala
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
130                 135                 140

Ser Gly Phe Val Gly Asp Pro Ser Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Leu Pro Gly Ala Glu Glu Ala Met Ser Gln
        195                 200                 205

Arg Thr Lys Thr Pro Met Gly His Ile Gly Glu Pro Asn Asp Ile Ala
    210                 215                 220

Tyr Ile Cys Val Tyr Leu Ala Ser Asn Glu Ser Lys Phe Ala Thr Gly
225                 230                 235                 240

Ser Glu Phe Val Val Asp Gly Gly Tyr Thr Ala Gln
                245                 250
```

<210> SEQ ID NO 129
<211> LENGTH: 759
<212> TYPE: DNA
<213> ORGANISM: Artificial Sequence
<220> FEATURE:
<223> OTHER INFORMATION: Synthetic Variant of L. Kefir

<400> SEQUENCE: 129

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa aagcgttgaa     300
gacactacca cggaggaatg gcgtaaactg ctgtccgtta atctggatgg tgttttttc     360
ggcacccgtc tgggcattca gcgcatgaaa aataaaggct gggcgctag catcatcaat     420
atgagcagta ttagcgggtt cgtaggcgat ccgacgctgg gggcatacaa cgcttccaag     480
ggggcggtac gtatcatgtc gaaaagcgca gcgctggatt gcgcactgaa ggactacgat     540
gtgcgtgtca acacagtaca tccgggctgc atcaagaccc cgctggtcga tgatctggaa     600
ggtgctgagg aaatgatgtc acagcgtacg aaaacccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacagtga                           759
```

<210> SEQ ID NO 130
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 130

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175
```

Lys Asp Tyr Asp Val Arg Val Asn Thr Val His Pro Gly Cys Ile Lys
            180                 185                 190

Thr Pro Leu Val Asp Asp Leu Glu Gly Ala Glu Met Met Ser Gln
        195                 200                 205

Arg Thr Lys Thr Pro Met Gly His Ile Gly Glu Pro Asn Asp Ile Ala
        210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 131
<211> LENGTH: 852
<212> TYPE: DNA
<213> ORGANISM: Artificial Sequence
<220> FEATURE:
<223> OTHER INFORMATION: Synthetic ADH from Candida magnoliae

<400> SEQUENCE: 131
atggcaaaga attttagcaa tgtagagtat cccgcacccc ccccgcaca tacaaagaat      60 gagagcttac aagtattaga tttatttaag ttaaatggaa agtagcaag cataacagga    120 agcagcagcg gaataggata tgcattagca gaggcttttg cacaagtcgg agcagatgta   180
gcaatatggt ataatagcca tgatgcaaca ggaaaagcag aggcattagc aaagaagtat   240
ggagtaaagg taaaggcata taagcaaat gtaagcagca gcgatgcagt caagcaaaca    300
atagagcaac aaataaagga ttttggacat ttagatatag tagtagcaaa tgcaggaata   360
ccctggacaa agggagcata tatagatcaa gatgatgaca agcattttga ccaagtagta   420
gatgtagact taaggggagt aggatacgta gcaaagcatg caggaaggca ttttagggaa   480
aggtttgaga agagggaaa aaagggagca ttagtattta cagcaagcat gagcggacat   540
atagtaaatg tcccccaatt ccaagcaaca tataatgcag caaaggcagg agtaaggcat   600
tttgcaaaga gcttagcagt cgagtttgca ccctttgcaa gggtaaatag cgtaagcccc   660
ggatatataa atacagagat aagcgatttc gtcccccaag agacacaaaa taagtggtgg   720
agcttagtcc ccttaggaag gggaggagag acagcagagt tagtaggagc atatttattc   780
ttagcaagcg atgcaggaag ctatgcaaca ggaacagata taatagtaga tggaggatat   840
acattaccct aa                                                       852

<210> SEQ ID NO 132
<211> LENGTH: 283
<212> TYPE: PRT
<213> ORGANISM: Artificial Sequence
<220> FEATURE:
<223> OTHER INFORMATION: Synthetic ADH from Candida magnoliae

<400> SEQUENCE: 132

Met Ala Lys Asn Phe Ser Asn Val Glu Tyr Pro Ala Pro Pro Ala
1               5                   10                  15

His Thr Lys Asn Glu Ser Leu Gln Val Leu Asp Leu Phe Lys Leu Asn
            20                  25                  30

Gly Lys Val Ala Ser Ile Thr Gly Ser Ser Ser Gly Ile Gly Tyr Ala
        35                  40                  45

Leu Ala Glu Ala Phe Ala Gln Val Gly Ala Asp Val Ala Ile Trp Tyr
    50                  55                  60

Asn Ser His Asp Ala Thr Gly Lys Ala Glu Ala Leu Ala Lys Lys Tyr
65                  70                  75                  80

```
Gly Val Lys Val Lys Ala Tyr Lys Ala Asn Val Ser Ser Ser Asp Ala
             85                  90                  95

Val Lys Gln Thr Ile Glu Gln Gln Ile Lys Asp Phe Gly His Leu Asp
        100                 105                 110

Ile Val Val Ala Asn Ala Gly Ile Pro Trp Thr Lys Gly Ala Tyr Ile
        115                 120                 125

Asp Gln Asp Asp Asp Lys His Phe Asp Gln Val Asp Val Asp Leu
    130                 135                 140

Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
                165                 170                 175

Met Ser Gly His Ile Val Asn Val Pro Gln Phe Gln Ala Thr Tyr Asn
            180                 185                 190

Ala Ala Lys Ala Gly Val Arg His Phe Ala Lys Ser Leu Ala Val Glu
        195                 200                 205

Phe Ala Pro Phe Ala Arg Val Asn Ser Val Ser Pro Gly Tyr Ile Asn
    210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Glu Thr Ala Glu Leu Val Gly
                245                 250                 255

Ala Tyr Leu Phe Leu Ala Ser Asp Ala Gly Ser Tyr Ala Thr Gly Thr
            260                 265                 270

Asp Ile Ile Val Asp Gly Gly Tyr Thr Leu Pro
        275                 280

<210> SEQ ID NO 133
<211> LENGTH: 1047
<212> TYPE: DNA
<213> ORGANISM: Artificial Sequence
<220> FEATURE:
<223> OTHER INFORMATION: Synthetic ADH from Rhodococcus erythropolis

<400> SEQUENCE: 133
atgaaagcca ttcagtacac tcgtatcggt gcggaaccag aactgactga atcccgaag      60 ccggaaccgg gcccgggcga agtactgctg gaagtcacgg cagctggcgt gtgccattcc    120
gatgatttca ttatgtctct gccggaagaa cagtacacct acggcctgcc gctgaccctg    180
ggtcatgaag gtgctggtaa agttgccgca gttggcgaag gtgttgaagg ttggatatt    240 ggcaccaatg tggttgtgta cggcccatgg ggttgtggca actgttggca ttgcagtcag    300
ggcctggaga actattgctc ccgtgcgcag gaactgggta ttaacccgcc tggtctgggt    360
gctccggggg ctttggcaga atttatgatt gtcgactcac cacgtcattt ggtcccgatt    420
ggcgatttag accctgttaa aactgttccg ttgactgatg cgggcctgac cccataccat    480
gcaatcaaac gctccctgcc gaaactgcgc ggcggctctt atgcagtagt gatcggtacg    540
ggtggcctgg gccacgtggc tatccaactg ctgcgtcatt tatctgctgc aacggtgatc    600
gccttggaca tttctgccga taactggaa ctggctacca agtcggcgc acatgaagta      660 gtcctgtctg ataaagatgc agcggagaat gtgcgtaaaa ttactggtag ccaaggtgca    720
gctttggtgt tggattttgt gggctatcag cctaccattg acaccgccat ggcagtggcg    780
ggcgtgggct ctgacgtcac cattgttggt atcggtgatg ccaggcaca tgcgaaagtt     840 ggtttcttcc agagtcctta tgaggcatcg gttacggtac cttattgggg cgctcgtaat    900
```

```
gaactgatcg aattgatcga tctggcgcat gctggtattt tcgacattgc cgttgagacc      960
ttctctttgg ataatggtgc agaggcctat cgtcgcctgg ctgcgggcac actgtcaggc     1020
cgtgcggtag tcgtcccggg cctgtaa                                         1047
```

<210> SEQ ID NO 134
<211> LENGTH: 348
<212> TYPE: PRT
<213> ORGANISM: Artificial Sequence
<220> FEATURE:
<223> OTHER INFORMATION: Synthetic ADH from Rhodococcus erythropolis

<400> SEQUENCE: 134

```
Met Lys Ala Ile Gln Tyr Thr Arg Ile Gly Ala Glu Pro Glu Leu Thr
1               5                   10                  15

Glu Ile Pro Lys Pro Glu Pro Gly Pro Gly Glu Val Leu Leu Glu Val
            20                  25                  30

Thr Ala Ala Gly Val Cys His Ser Asp Asp Phe Ile Met Ser Leu Pro
        35                  40                  45

Glu Glu Gln Tyr Thr Tyr Gly Leu Pro Leu Thr Leu Gly His Glu Gly
    50                  55                  60

Ala Gly Lys Val Ala Ala Val Gly Glu Gly Val Glu Gly Leu Asp Ile
65                  70                  75                  80

Gly Thr Asn Val Val Val Tyr Gly Pro Trp Gly Cys Gly Asn Cys Trp
                85                  90                  95

His Cys Ser Gln Gly Leu Glu Asn Tyr Cys Ser Arg Ala Gln Glu Leu
            100                 105                 110

Gly Ile Asn Pro Pro Gly Leu Gly Ala Pro Gly Ala Leu Ala Glu Phe
        115                 120                 125

Met Ile Val Asp Ser Pro Arg His Leu Val Pro Ile Gly Asp Leu Asp
    130                 135                 140

Pro Val Lys Thr Val Pro Leu Thr Asp Ala Gly Leu Thr Pro Tyr His
145                 150                 155                 160

Ala Ile Lys Arg Ser Leu Pro Lys Leu Arg Gly Gly Ser Tyr Ala Val
                165                 170                 175

Val Ile Gly Thr Gly Gly Leu Gly His Val Ala Ile Gln Leu Leu Arg
            180                 185                 190

His Leu Ser Ala Ala Thr Val Ile Ala Leu Asp Val Ser Ala Asp Lys
        195                 200                 205

Leu Glu Leu Ala Thr Lys Val Gly Ala His Glu Val Val Leu Ser Asp
    210                 215                 220

Lys Asp Ala Ala Glu Asn Val Arg Lys Ile Thr Gly Ser Gln Gly Ala
225                 230                 235                 240

Ala Leu Val Leu Asp Phe Val Gly Tyr Gln Pro Thr Ile Asp Thr Ala
                245                 250                 255

Met Ala Val Ala Gly Val Gly Ser Asp Val Thr Ile Val Gly Ile Gly
            260                 265                 270

Asp Gly Gln Ala His Ala Lys Val Gly Phe Phe Gln Ser Pro Tyr Glu
        275                 280                 285

Ala Ser Val Thr Val Pro Tyr Trp Gly Ala Arg Asn Glu Leu Ile Glu
    290                 295                 300

Leu Ile Asp Leu Ala His Ala Gly Ile Phe Asp Ile Ala Val Glu Thr
305                 310                 315                 320

Phe Ser Leu Asp Asn Gly Ala Glu Ala Tyr Arg Arg Leu Ala Ala Gly
                325                 330                 335
```

Thr Leu Ser Gly Arg Ala Val Val Val Pro Gly Leu
                340                 345

<210> SEQ ID NO 135
<211> LENGTH: 1047
<212> TYPE: DNA
<213> ORGANISM: Artificial Sequence
<220> FEATURE:
<223> OTHER INFORMATION: Synthetic YGL ADH from Saccharomyces cervisiae

<400> SEQUENCE: 135

```
atgaccacgg aaaaaaccgt agtgttcgtg tcaggcgcga ccggtttat tgctctgcac      60
gtggtagatg acctgctgaa aactggttac aaagtaattg gttccggtcg ttctcaggaa    120
aaaaatgacg gtttgctgaa gaagttcaag tccaacccga atctgagcat ggaaattgtg    180
gaagatattg cggcaccaaa cgccttcgat aaagtattcc agaaacatgg taagaaaatt    240
aaagtggtcc tgcatatcgc gtccccggtc catttcaaca ctaccgattt cgaaaaagac    300
ttactgatcc cggcggtaaa cggtaccaaa tctattttgg aagcaattaa gaactatgcc    360
gcagacaccg tggaaaaagt ggttattact tcatctgttg ccgcgttggc ctctccgggt    420
gatatgaaag ataccagctt cgtggttaac gaagaatcct ggaataaaga cacctgggaa    480
tcgtgtcagg cgaatgctgt gtccgcttat tgcggttcta aaaaattcgc agagaaaacg    540
gcgtgggact tcttggaaga aaaccagagc agcattaaat ttactctgtc cacgattaac    600
ccaggcttcg tttttggtcc gcagctgttc gccgactcct tgcgcaatgg tattaactct    660
agcagtgcga ttattgcgaa cctggtgtcg tataaattag gggataactt ctacaattat    720
agcggcccgt ttatcgacgt ccgtgacgtt tccaaagctc atctgctggc atttgagaaa    780
cctgaatgcg ccggtcagcg cctgtttctg tgcgaggata tgttctgttc ccaggaagcc    840
ctggacattc tgaacgaaga atttccacag ctgaaggggca agatcgcaac gggcgaacct    900
ggcagcggct cgaccttcct gactaaaaat tgttgcaaat gcgacaatcg taaaactaaa    960
aacttgctgg gcttccagtt caacaaattc cgcgactgca ttgtcgatac tgcgtcccag   1020
ttgctggaag tgcaaagcaa aagctaa                                        1047
```

<210> SEQ ID NO 136
<211> LENGTH: 348
<212> TYPE: PRT
<213> ORGANISM: Artificial Sequence
<220> FEATURE:
<223> OTHER INFORMATION: Synthetic YGL ADH from Saccharomyces cervisiae

<400> SEQUENCE: 136

Met Thr Thr Glu Lys Thr Val Val Phe Val Ser Gly Ala Thr Gly Phe
1               5                   10                  15

Ile Ala Leu His Val Val Asp Asp Leu Leu Lys Thr Gly Tyr Lys Val
            20                  25                  30

Ile Gly Ser Gly Arg Ser Gln Glu Lys Asn Asp Gly Leu Leu Lys Lys
        35                  40                  45

Phe Lys Ser Asn Pro Asn Leu Ser Met Glu Ile Val Glu Asp Ile Ala
    50                  55                  60

Ala Pro Asn Ala Phe Asp Lys Val Phe Gln Lys His Gly Lys Glu Ile
65                  70                  75                  80

Lys Val Val Leu His Ile Ala Ser Pro Val His Phe Asn Thr Thr Asp
                85                  90                  95

Phe Glu Lys Asp Leu Leu Ile Pro Ala Val Asn Gly Thr Lys Ser Ile

|  |  | 100 |  |  | 105 |  |  | 110 |  |  |  |
|--|--|--|--|--|--|--|--|--|--|--|--|

Leu Glu Ala Ile Lys Asn Tyr Ala Ala Asp Thr Val Glu Lys Val Val
    115                      120                    125

Ile Thr Ser Ser Val Ala Ala Leu Ala Ser Pro Gly Asp Met Lys Asp
130                      135                    140

Thr Ser Phe Val Val Asn Glu Glu Ser Trp Asn Lys Asp Thr Trp Glu
145                      150                155                160

Ser Cys Gln Ala Asn Ala Val Ser Ala Tyr Cys Gly Ser Lys Lys Phe
            165                    170                    175

Ala Glu Lys Thr Ala Trp Asp Phe Leu Glu Glu Asn Gln Ser Ser Ile
            180                    185                    190

Lys Phe Thr Leu Ser Thr Ile Asn Pro Gly Phe Val Phe Gly Pro Gln
            195                    200                    205

Leu Phe Ala Asp Ser Leu Arg Asn Gly Ile Asn Ser Ser Ala Ile
            210                    215                    220

Ile Ala Asn Leu Val Ser Tyr Lys Leu Gly Asp Asn Phe Tyr Asn Tyr
225                      230                235                240

Ser Gly Pro Phe Ile Asp Val Arg Asp Val Ser Lys Ala His Leu Leu
            245                    250                    255

Ala Phe Glu Lys Pro Glu Cys Ala Gly Gln Arg Leu Phe Leu Cys Glu
            260                    265                    270

Asp Met Phe Cys Ser Gln Glu Ala Leu Asp Ile Leu Asn Glu Glu Phe
            275                    280                    285

Pro Gln Leu Lys Gly Lys Ile Ala Thr Gly Glu Pro Gly Ser Gly Ser
            290                    295                    300

Thr Phe Leu Thr Lys Asn Cys Cys Lys Cys Asp Asn Arg Lys Thr Lys
305                      310                315                320

Asn Leu Leu Gly Phe Gln Phe Asn Lys Phe Arg Asp Cys Ile Val Asp
            325                    330                    335

Thr Ala Ser Gln Leu Leu Glu Val Gln Ser Lys Ser
            340                    345

<210> SEQ ID NO 137
<211> LENGTH: 939
<212> TYPE: DNA
<213> ORGANISM: Artificial Sequence
<220> FEATURE:
<223> OTHER INFORMATION: Synthetic YDL ADH from Saccharomyces cervisiae

<400> SEQUENCE: 137

```
atgtcttttc caacagtt tttcacgctg aacaacggca ataaatccc ggcgattgcc      60 atcatcggca ctggtacacg ttggtataaa aatgaagaaa ctgacgcgac cttctccaat     120
agtctggttg aacaaatcgt gtatgcgttg aaactgccgg ggattatcca catcgacgcc     180
gcggagattt atcgcaccta cccggaagtg ggtaaagcac tgtccctgac cgaaaagcct     240
cgtaacgcga ttttctgac ggataaatat tctccgcaga ttaaaatgag tgactcccct     300
gcggacggtc tggatttagc attgaagaaa atgggtacag attatgttga tttatatctg     360
ttacattccc cgtttgtttc gaaggaagtg aatggcttaa gcttagaaga ggcttggaaa     420
gatatggagc agttatacaa aagtggtaaa gctaaaaaca tcggggtttc caatttcgca     480
gtggaagacc tgcaacgtat cctgaaagtc gctgaagtta accctcaggt caaccagatt     540
gagttctctc cgttcctgca aaaccaaaca ccaggcattt ataaattctg tcaggagcac     600
gatatcctgg tggaagcata ttctccgctg ggcccgctgc agaagaaaac cgcgcaggat     660
```

```
gacagccaac cattttttga gtacgtcaaa gaattgagcg aaaaatacat caaatccgag     720
gcccagatca tcctgcgctg ggtcactaaa cgcggtgtgc tgccagttac cacctcttca     780
aagcctcagc gcattagcga tgctcagaac ctgttttcct tcgacctgac agcggaagag     840
gttgataaaa tcacggagct gggtctggaa catgaaccgc tgcgcctgta ctggaataaa     900
ttgtatggca aatataacta cgccgcccag aaagtgtaa                             939
```

<210> SEQ ID NO 138
<211> LENGTH: 312
<212> TYPE: PRT
<213> ORGANISM: Artificial Sequence
<220> FEATURE:
<223> OTHER INFORMATION: Synthetic YDL ADH from Saccharomyces cervisiae

<400> SEQUENCE: 138

```
Met Ser Phe His Gln Gln Phe Phe Thr Leu Asn Asn Gly Asn Lys Ile
1               5                   10                  15

Pro Ala Ile Ala Ile Gly Thr Gly Thr Arg Trp Tyr Lys Asn Glu
            20                  25                  30

Glu Thr Asp Ala Thr Phe Ser Asn Ser Leu Val Glu Gln Ile Val Tyr
        35                  40                  45

Ala Leu Lys Leu Pro Gly Ile Ile His Ile Asp Ala Ala Glu Ile Tyr
    50                  55                  60

Arg Thr Tyr Pro Glu Val Gly Lys Ala Leu Ser Leu Thr Glu Lys Pro
65                  70                  75                  80

Arg Asn Ala Ile Phe Leu Thr Asp Lys Tyr Ser Pro Gln Ile Lys Met
                85                  90                  95

Ser Asp Ser Pro Ala Asp Gly Leu Asp Leu Ala Leu Lys Lys Met Gly
            100                 105                 110

Thr Asp Tyr Val Asp Leu Tyr Leu Leu His Ser Pro Phe Val Ser Lys
        115                 120                 125

Glu Val Asn Gly Leu Ser Leu Glu Gly Ala Trp Lys Asp Met Glu Gln
    130                 135                 140

Leu Tyr Lys Ser Gly Lys Ala Lys Asn Ile Gly Val Ser Asn Phe Ala
145                 150                 155                 160

Val Glu Asp Leu Gln Arg Ile Leu Lys Val Ala Glu Val Lys Pro Gln
                165                 170                 175

Val Asn Gln Ile Glu Phe Ser Pro Phe Leu Gln Asn Gln Thr Pro Gly
            180                 185                 190

Ile Tyr Lys Phe Cys Gln Glu His Asp Ile Leu Val Glu Ala Tyr Ser
        195                 200                 205

Pro Leu Gly Pro Leu Gln Lys Lys Thr Ala Gln Asp Ser Gln Pro
    210                 215                 220

Phe Phe Glu Tyr Val Lys Glu Leu Ser Glu Lys Tyr Ile Lys Ser Glu
225                 230                 235                 240

Ala Gln Ile Ile Leu Arg Trp Val Thr Lys Arg Gly Val Leu Pro Val
                245                 250                 255

Thr Thr Ser Ser Lys Pro Gln Arg Ile Ser Asp Ala Gln Asn Leu Phe
            260                 265                 270

Ser Phe Asp Leu Thr Ala Glu Glu Val Asp Lys Ile Thr Glu Leu Gly
        275                 280                 285

Leu Glu His Glu Pro Leu Arg Leu Tyr Trp Asn Lys Leu Tyr Gly Lys
    290                 295                 300

Tyr Asn Tyr Ala Ala Gln Lys Val
305                 310
```

<210> SEQ ID NO 139
<211> LENGTH: 939
<212> TYPE: DNA
<213> ORGANISM: Artificial Sequence
<220> FEATURE:
<223> OTHER INFORMATION: Synthetic YPR ADH from Saccharomyces cervisiae

<400> SEQUENCE: 139

```
atgccggcaa cgttaaaaaa cagcagtgct accttaaaat taaacacagg tgcgagcatt      60
cctgtcctgg ggttcggcac ctggcgctct gtcgataaca acggctatca tagtgtaatt     120
gcggcgctga aagcggggta ccgtcatatc gatgctgcgg ccatctatct gaatgaagaa     180
gaagtcggcc gtgcgatcaa ggactccggt gttcctcgtg aagaaatttt tattaccacc     240
aaactgtggg gcaccgaaca acgcgatcca gaagcagccc tgaacaaatc tctgaaacgt     300
ctgggtctgg actatgtgga cctgtatctg atgcactggc cggtccctct gaaaacagac     360
cgtgtaactg acggtaacgt cctgtgcatc ccgaccctgg aagatggcac cgtgacatc      420
gataccaaag agtggaattt tattaaaacc tgggaactga tgcaggaatt gccgaaaact     480
ggtaagacca aagccgtcgg tgtgtccaat ttttccatca acaatatcaa gaactgctg      540
gaatcgccaa ataacaaggt cgttccagca accaatcaga tcgagattca tccgttgctg     600
ccgcaggatg aattaatcgc cttttgtaaa gaaaaaggca ttgtggtcga agcatatagc     660
ccattcggct ccgctaacgc cccgctgctg aaagaacagg cgattatcga tatggccaaa     720
aagcacggcg tcgaaccggc gcaactgatt atcagctggt cgattcagcg cggttatgtg     780
gtattggcca agtccgtaaa tccggagcgt atcgtgtcga actttaagat ttttacccctg    840
ccagaggatg atttcaaaac catctctaac ctgagcaaag tgcacggtac caaacgtgtc    900
gttgacatga aatgggctc atttccgatt tttcaataa                            939
```

<210> SEQ ID NO 140
<211> LENGTH: 312
<212> TYPE: PRT
<213> ORGANISM: Artificial Sequence
<220> FEATURE:
<223> OTHER INFORMATION: Synthetic YPR ADH from Saccharomyces cervisiae

<400> SEQUENCE: 140

```
Met Pro Ala Thr Leu Lys Asn Ser Ser Ala Thr Leu Lys Leu Asn Thr
1               5                   10                  15

Gly Ala Ser Ile Pro Val Leu Gly Phe Gly Thr Trp Arg Ser Val Asp
            20                  25                  30

Asn Asn Gly Tyr His Ser Val Ile Ala Ala Leu Lys Ala Gly Tyr Arg
        35                  40                  45

His Ile Asp Ala Ala Ala Ile Tyr Leu Asn Glu Glu Val Gly Arg
    50                  55                  60

Ala Ile Lys Asp Ser Gly Val Pro Arg Glu Glu Ile Phe Ile Thr Thr
65                  70                  75                  80

Lys Leu Trp Gly Thr Glu Gln Arg Asp Pro Glu Ala Ala Leu Asn Lys
                85                  90                  95

Ser Leu Lys Arg Leu Gly Leu Asp Tyr Val Asp Leu Tyr Leu Met His
            100                 105                 110

Trp Pro Val Pro Leu Lys Thr Asp Arg Val Thr Asp Gly Asn Val Leu
        115                 120                 125

Cys Ile Pro Thr Leu Glu Asp Gly Thr Val Asp Ile Asp Thr Lys Glu
    130                 135                 140
```

```
Trp Asn Phe Ile Lys Thr Trp Glu Leu Met Gln Glu Leu Pro Lys Thr
145                 150                 155                 160

Gly Lys Thr Lys Ala Val Gly Val Ser Asn Phe Ser Ile Asn Asn Ile
                165                 170                 175

Lys Glu Leu Leu Glu Ser Pro Asn Asn Lys Val Val Pro Ala Thr Asn
            180                 185                 190

Gln Ile Glu Ile His Pro Leu Leu Pro Gln Asp Glu Leu Ile Ala Phe
        195                 200                 205

Cys Lys Glu Lys Gly Ile Val Val Glu Ala Tyr Ser Pro Phe Gly Ser
    210                 215                 220

Ala Asn Ala Pro Leu Leu Lys Glu Gln Ala Ile Ile Asp Met Ala Lys
225                 230                 235                 240

Lys His Gly Val Glu Pro Ala Gln Leu Ile Ile Ser Trp Ser Ile Gln
                245                 250                 255

Arg Gly Tyr Val Val Leu Ala Lys Ser Val Asn Pro Glu Arg Ile Val
                260                 265                 270

Ser Asn Phe Lys Ile Phe Thr Leu Pro Glu Asp Asp Phe Lys Thr Ile
            275                 280                 285

Ser Asn Leu Ser Lys Val His Gly Thr Lys Arg Val Val Asp Met Lys
        290                 295                 300

Trp Gly Ser Phe Pro Ile Phe Gln
305                 310
```

<210> SEQ ID NO 141
<211> LENGTH: 1029
<212> TYPE: DNA
<213> ORGANISM: Artificial Sequence
<220> FEATURE:
<223> OTHER INFORMATION: Synthetic GRE ADH from Saccharomyces cervisiae

<400> SEQUENCE: 141

```
atgtctgtgt tcgtgtcagg cgcgaatggt tttattgctc agcacatcgt agatctgctg      60
ctgaaagaag attacaaagt aattggttcc gcacgttctc aggaaaaagc tgaaaatttg     120
accgaagcct tcggtaacaa cccgaaattt agcatggaag tggtgcctga tattagcaaa     180
ctggatgcct tcgatcatgt attccagaaa catggtaaag atattaaaat cgtcctgcat     240
accgcgtccc cgttttgttt cgatattacc gattccgaac gtgacttact gatcccggcg     300
gtaaacggtg tcaaaggtat tttgcacagt attaagaaat atgccgcaga cagcgtggaa     360
cgcgtggttc tgacttcatc ttacgccgcg gtatttgata tggcgaagga aaacgataag     420
agcctgacct tcaacgaaga atcctggaat ccggcgacct gggaatcgtg tcagagtgat     480
ccggtgaacg cttattgcgg ttctaaaaaa ttcgcagaga aagcagcgtg gaattcttg     540
gaagaaaacc gtgatagcgt gaaatttgag ctgacagcgg tcaacccagt ttacgttttt     600
ggtccgcaga tgttcgataa agatgttaaa aaacacttga acaccagctg cgaactggtg     660
aactctctga tgcatctgag ccctgaagat aaaattccgg aactgtttgg cggttacatc     720
gacgtccgtg acgttgcgaa agctcatctg gttgcatttc agaaacgtga acaatcggt     780
cagcgcctga tcgtgtcgga ggcacgtttc acgatgcagg acgttctgga cattctgaac     840
gaagactttc cagtactgaa gggcaatatc ccggtcggca gcctggcag cggcgccacc      900
cataatactc tgggcgccac cctggacaat aaaaaaagca aaaaattgct gggcttcaaa      960
ttccgtaatc tgaagagac tattgacgat actgcgtccc agatcctgaa attcgaaggt    1020
cgcatttaa                                                          1029
```

```
<210> SEQ ID NO 142
<211> LENGTH: 342
<212> TYPE: PRT
<213> ORGANISM: Artificial Sequence
<220> FEATURE:
<223> OTHER INFORMATION: Synthetic GRE ADH from Saccharomyces cervisiae

<400> SEQUENCE: 142

Met Ser Val Phe Val Ser Gly Ala Asn Gly Phe Ile Ala Gln His Ile
1               5                   10                  15

Val Asp Leu Leu Lys Glu Asp Tyr Lys Val Ile Gly Ser Ala Arg
            20                  25                  30

Ser Gln Glu Lys Ala Glu Asn Leu Thr Glu Ala Phe Gly Asn Asn Pro
        35                  40                  45

Lys Phe Ser Met Glu Val Val Pro Asp Ile Ser Lys Leu Asp Ala Phe
    50                  55                  60

Asp His Val Phe Gln Lys His Gly Lys Asp Ile Lys Ile Val Leu His
65                  70                  75                  80

Thr Ala Ser Pro Phe Cys Phe Asp Ile Thr Asp Ser Glu Arg Asp Leu
                85                  90                  95

Leu Ile Pro Ala Val Asn Gly Val Lys Gly Ile Leu His Ser Ile Lys
            100                 105                 110

Lys Tyr Ala Ala Asp Ser Val Glu Arg Val Val Leu Thr Ser Ser Tyr
        115                 120                 125

Ala Ala Val Phe Asp Met Ala Lys Glu Asn Asp Lys Ser Leu Thr Phe
    130                 135                 140

Asn Glu Glu Ser Trp Asn Pro Ala Thr Trp Glu Ser Cys Gln Ser Asp
145                 150                 155                 160

Pro Val Asn Ala Tyr Cys Gly Ser Lys Lys Phe Ala Glu Lys Ala Ala
                165                 170                 175

Trp Glu Phe Leu Glu Glu Asn Arg Asp Ser Val Lys Phe Glu Leu Thr
            180                 185                 190

Ala Val Asn Pro Val Tyr Val Phe Gly Pro Gln Met Phe Asp Lys Asp
        195                 200                 205

Val Lys Lys His Leu Asn Thr Ser Cys Glu Leu Val Asn Ser Leu Met
    210                 215                 220

His Leu Ser Pro Glu Asp Lys Ile Pro Glu Leu Phe Gly Gly Tyr Ile
225                 230                 235                 240

Asp Val Arg Asp Val Ala Lys Ala His Leu Val Ala Phe Gln Lys Arg
                245                 250                 255

Glu Thr Ile Gly Gln Arg Leu Ile Val Ser Glu Ala Arg Phe Thr Met
            260                 265                 270

Gln Asp Val Leu Asp Ile Leu Asn Glu Asp Phe Pro Val Leu Lys Gly
        275                 280                 285

Asn Ile Pro Val Gly Lys Pro Gly Ser Gly Ala Thr His Asn Thr Leu
    290                 295                 300

Gly Ala Thr Leu Asp Asn Lys Lys Ser Lys Lys Leu Leu Gly Phe Lys
305                 310                 315                 320

Phe Arg Asn Leu Lys Glu Thr Ile Asp Asp Thr Ala Ser Gln Ile Leu
                325                 330                 335

Lys Phe Glu Gly Arg Ile
            340

<210> SEQ ID NO 143
```

<211> LENGTH: 1041
<212> TYPE: DNA
<213> ORGANISM: Artificial Sequence
<220> FEATURE:
<223> OTHER INFORMATION: Synthetic ADH from Streptomycel coelicolor

<400> SEQUENCE: 143

```
atgaaggcac tgcagtaccg caccatcggc gccccgcccg aggtcgtcac cgtcccggac    60
ccggagccgg gccccggcca ggtgctgttg aaggtgaccg cggccggagt ctgccactcc   120
gacatcgcgg tgatgagctg gcccgccgag ggcttcccgt acgagctgcc gctcaccctc   180
ggccacgagg gcgtcggcac cgtggccgcg ctcggcgccg gggtgacggg gctcgccgag   240
ggcgacgcgg tcgccgtgta cgggccctgg ggctgcggca cctgcgccaa gtgcgcggag   300
ggcaaggaga actactgcct gcgcgccgac gagctgggca tccgtccgcc ggggctcggg   360
cgtccggggt ccatggccga gtacctgctg atcgacgacc cccggcacct ggtcccgctg   420
gacgggctcg acccggtcgc ggcggtgccg ctcaccgacg ccggactgac gccgtaccac   480
gcgatcaagc ggtcgctgcc caagctggtc cccggctcca ccgcggtggt catcggcacc   540
ggtggtctcg gccacgtcgc catccagctg ctgcgcgccc tgacgtccgc ccgggtggtc   600
gccctggacg tcagcgagga aagctgcgc ctcgcccgtg cggtgggcgc gcacgaggcg   660
gtgctgtcgg acgcgaaggc cgcggacgcg gtgcgcgaga tcaccggcgg tctcggtgcc   720
gaggccgtgt cgacttcgt cggcgtgggc ccaccgtgc agaccgccgg agccgtcgcg   780
gccgtcgagg gcgatgtcac cctggtcggc atcggcggcg atcgctgcc cgtcggcttc   840
ggcatgctgc cgttcgaggt gtcggtcaac gcccctact ggggcagccg cagcgagctg   900
accgaggtgc tgaacctggc ccgctccggt gccgtgtcgg tgcacaccga acgtactcc   960
ctggacgacg cccgctcgc ctacgagcgg ctgcacgagg cagggtcaa cggccgcgcg  1020
gtgatcctgc cccacggctg a                                           1041
```

<210> SEQ ID NO 144
<211> LENGTH: 346
<212> TYPE: PRT
<213> ORGANISM: Artificial Sequence
<220> FEATURE:
<223> OTHER INFORMATION: Synthetic ADH from Streptomycel coelicolor

<400> SEQUENCE: 144

```
Met Lys Ala Leu Gln Tyr Arg Thr Ile Gly Ala Pro Pro Glu Val Val
1               5                   10                  15

Thr Val Pro Asp Pro Glu Pro Gly Pro Gly Gln Val Leu Leu Lys Val
            20                  25                  30

Thr Ala Ala Gly Val Cys His Ser Asp Ile Ala Val Met Ser Trp Pro
        35                  40                  45

Ala Glu Gly Phe Pro Tyr Glu Leu Pro Leu Thr Leu Gly His Glu Gly
    50                  55                  60

Val Gly Thr Val Ala Ala Leu Gly Ala Gly Val Thr Gly Leu Ala Glu
65                  70                  75                  80

Gly Asp Ala Val Ala Val Tyr Gly Pro Trp Gly Cys Gly Thr Cys Ala
                85                  90                  95

Lys Cys Ala Glu Gly Lys Glu Asn Tyr Cys Leu Arg Ala Asp Glu Leu
            100                 105                 110

Gly Ile Arg Pro Pro Gly Leu Gly Arg Pro Gly Ser Met Ala Glu Tyr
        115                 120                 125

Leu Leu Ile Asp Asp Pro Arg His Leu Val Pro Leu Asp Gly Leu Asp
```

|   |   |   |   |   |   |   |   |   |   |
|---|---|---|---|---|---|---|---|---|---|
| | | 130 | | | 135 | | | 140 | |
| Pro | Val | Ala | Ala | Val | Pro | Leu | Thr | Asp | Ala | Gly | Leu | Thr | Pro | Tyr | His |
| 145 | | | | 150 | | | | 155 | | | | 160 | | | |

Pro Val Ala Ala Val Pro Leu Thr Asp Ala Gly Leu Thr Pro Tyr His
145                 150                 155                 160

Ala Ile Lys Arg Ser Leu Pro Lys Leu Val Pro Gly Ser Thr Ala Val
            165                 170                 175

Val Ile Gly Thr Gly Leu Gly His Val Ala Ile Gln Leu Leu Arg
        180                 185                 190

Ala Leu Thr Ser Ala Arg Val Val Ala Leu Asp Val Ser Glu Glu Lys
            195                 200                 205

Leu Arg Leu Ala Arg Ala Val Gly Ala His Glu Ala Val Leu Ser Asp
    210                 215                 220

Ala Lys Ala Ala Asp Ala Val Arg Glu Ile Thr Gly Gly Leu Gly Ala
225                 230                 235                 240

Glu Ala Val Phe Asp Phe Val Gly Val Ala Pro Thr Val Gln Thr Ala
                245                 250                 255

Gly Ala Val Ala Ala Val Glu Gly Asp Val Thr Leu Val Gly Ile Gly
            260                 265                 270

Gly Gly Ser Leu Pro Val Gly Phe Gly Met Leu Pro Phe Glu Val Ser
        275                 280                 285

Val Asn Ala Pro Tyr Trp Gly Ser Arg Ser Glu Leu Thr Glu Val Leu
    290                 295                 300

Asn Leu Ala Arg Ser Gly Ala Val Ser Val His Thr Glu Thr Tyr Ser
305                 310                 315                 320

Leu Asp Asp Ala Pro Leu Ala Tyr Glu Arg Leu His Glu Gly Arg Val
                325                 330                 335

Asn Gly Arg Ala Val Ile Leu Pro His Gly
            340                 345

<210> SEQ ID NO 145
<211> LENGTH: 1032
<212> TYPE: DNA
<213> ORGANISM: Artificial Sequence
<220> FEATURE:
<223> OTHER INFORMATION: Synthetic ADH from Sporobolomyces salmonicolor

<400> SEQUENCE: 145

```
atggcaaaga tcgacaacgc agttctgccg gagggttctc tggtgctggt caccggcgcg    60
aacggctttg tcgctagcca tgtggtcgaa caactgctgg aacacggcta taaggtgcgc   120
ggcactgctc gctctgcctc caaactggcg aacctgcaga acgttggga cgccaaatac    180
cctggtcgtt tcgagactgc cgttgttgaa gacatgctga agcagggtgc atatgatgaa   240
gttattaaag cgcggcagg tgtcgcccac atcgcgtccg tggtcagctt ttctaacaaa   300
tatgatgagg tggtaactcc tgcgatcggt ggcacgctga atgccctgcg tgccgcagct   360
gctacgcctt ccgtgaaacg ttttgtgctg accagcagca ctgtttctgc actgattcca   420
aaacctaacg tcgaaggtat ttatctggat gagaagagct ggaacctgga agcattgat    480
aaggctaaaa ccctgcctga atctgatccg cagaaaagcc tgtgggtcta cgccgcaagc   540
aaaacggaag cggaactggc tgcctggaaa ttcatggacg aaaacaaacc gcactttact   600
ctgaatgccg ttctgccaaa ctacactatc ggtaccattt tgacccaga acccaatcc    660
ggttccactt ccggctggat gatgtctctg ttcaatggcg aagtatctcc ggcactggcg   720
ctgatgccgc gcagtacta tgtctctgca gttgatatcg gtctgctgca cctgggttgt   780
ctggttctgc gcaaatcga acgccgtcgt gtttacggca ccgcaggcac ctttgattgg   840
```

```
aacaccgttc tgcgacctt ccgtaaactg tatccgtcca agacgttccc ggctgacttt    900
ccggatcagg gccaggatct gtccaaattt gataccgccc cgagcctgga gattctgaaa    960
tccctgggcc gccctggctg gcgtagcatc gaggaatcta tcaaagatct ggtgggttcc   1020
gagaccgcct aa                                                      1032
```

```
<210> SEQ ID NO 146
<211> LENGTH: 343
<212> TYPE: PRT
<213> ORGANISM: Artificial Sequence
<220> FEATURE:
<223> OTHER INFORMATION: Synthetic ADH from Sporobolomyces salmonicolor

<400> SEQUENCE: 146
```

| | | | | | | | | | | | | | | |
|---|---|---|---|---|---|---|---|---|---|---|---|---|---|---|
| Met | Ala | Lys | Ile | Asp | Asn | Ala | Val | Leu | Pro | Glu | Gly | Ser | Leu | Val | Leu |
| 1 | | | | 5 | | | | | 10 | | | | | 15 | |
| Val | Thr | Gly | Ala | Asn | Gly | Phe | Val | Ala | Ser | His | Val | Val | Glu | Gln | Leu |
| | | | 20 | | | | | 25 | | | | | 30 | | |
| Leu | Glu | His | Gly | Tyr | Lys | Val | Arg | Gly | Thr | Ala | Arg | Ser | Ala | Ser | Lys |
| | | 35 | | | | | 40 | | | | | 45 | | | |
| Leu | Ala | Asn | Leu | Gln | Lys | Arg | Trp | Asp | Ala | Lys | Tyr | Pro | Gly | Arg | Phe |
| | 50 | | | | | 55 | | | | | 60 | | | | |
| Glu | Thr | Ala | Val | Val | Glu | Asp | Met | Leu | Lys | Gln | Gly | Ala | Tyr | Asp | Glu |
| 65 | | | | | 70 | | | | | 75 | | | | | 80 |
| Val | Ile | Lys | Gly | Ala | Ala | Gly | Val | Ala | His | Ile | Ala | Ser | Val | Val | Ser |
| | | | | 85 | | | | | 90 | | | | | 95 | |
| Phe | Ser | Asn | Lys | Tyr | Asp | Glu | Val | Thr | Pro | Ala | Ile | Gly | Gly | Thr | |
| | | | 100 | | | | | 105 | | | | | 110 | | |
| Leu | Asn | Ala | Leu | Arg | Ala | Ala | Ala | Thr | Pro | Ser | Val | Lys | Arg | Phe | |
| | | 115 | | | | | 120 | | | | | 125 | | | |
| Val | Leu | Thr | Ser | Ser | Thr | Val | Ser | Ala | Leu | Ile | Pro | Lys | Pro | Asn | Val |
| | 130 | | | | | 135 | | | | | 140 | | | | |
| Glu | Gly | Ile | Tyr | Leu | Asp | Glu | Lys | Ser | Trp | Asn | Leu | Glu | Ser | Ile | Asp |
| 145 | | | | | 150 | | | | | 155 | | | | | 160 |
| Lys | Ala | Lys | Thr | Leu | Pro | Glu | Ser | Asp | Pro | Gln | Lys | Ser | Leu | Trp | Val |
| | | | | 165 | | | | | 170 | | | | | 175 | |
| Tyr | Ala | Ala | Ser | Lys | Thr | Glu | Ala | Glu | Leu | Ala | Ala | Trp | Lys | Phe | Met |
| | | | 180 | | | | | 185 | | | | | 190 | | |
| Asp | Glu | Asn | Lys | Pro | His | Phe | Thr | Leu | Asn | Ala | Val | Leu | Pro | Asn | Tyr |
| | | 195 | | | | | 200 | | | | | 205 | | | |
| Thr | Ile | Gly | Thr | Ile | Phe | Asp | Pro | Glu | Thr | Gln | Ser | Gly | Ser | Thr | Ser |
| | 210 | | | | | 215 | | | | | 220 | | | | |
| Gly | Trp | Met | Met | Ser | Leu | Phe | Asn | Gly | Glu | Val | Ser | Pro | Ala | Leu | Ala |
| 225 | | | | | 230 | | | | | 235 | | | | | 240 |
| Leu | Met | Pro | Pro | Gln | Tyr | Tyr | Val | Ser | Ala | Val | Asp | Ile | Gly | Leu | Leu |
| | | | | 245 | | | | | 250 | | | | | 255 | |
| His | Leu | Gly | Cys | Leu | Val | Leu | Pro | Gln | Ile | Glu | Arg | Arg | Val | Tyr | |
| | | | 260 | | | | | 265 | | | | | 270 | | |
| Gly | Thr | Ala | Gly | Thr | Phe | Asp | Trp | Asn | Thr | Val | Leu | Ala | Thr | Phe | Arg |
| | | 275 | | | | | 280 | | | | | 285 | | | |
| Lys | Leu | Tyr | Pro | Ser | Lys | Thr | Phe | Pro | Ala | Asp | Phe | Pro | Asp | Gln | Gly |
| | 290 | | | | | 295 | | | | | 300 | | | | |
| Gln | Asp | Leu | Ser | Lys | Phe | Asp | Thr | Ala | Pro | Ser | Leu | Glu | Ile | Leu | Lys |
| 305 | | | | | 310 | | | | | 315 | | | | | 320 |
| Ser | Leu | Gly | Arg | Pro | Gly | Trp | Arg | Ser | Ile | Glu | Glu | Ser | Ile | Lys | Asp |

Leu Val Gly Ser Glu Thr Ala
                340

<210> SEQ ID NO 147
<211> LENGTH: 1050
<212> TYPE: DNA
<213> ORGANISM: Artificial Sequence
<220> FEATURE:
<223> OTHER INFORMATION: Synthetic ADH from Aspergillus flavus

<400> SEQUENCE: 147

```
atgtctattc cggaaatgca atgggctcaa gtagcggagc agaaaggcgg tccgctgatt      60
tacaaacaga ttccggttcc gaaaccgggc ccggacgaaa tcctggtaaa agtgcgttac     120
tctggtgtgt gccacacgga tctgcacgcg ctgaaaggtg actggccact gcctgtgaaa     180
atgccactgg tgggtggcca tgagggcgcg ggtgttgtcg tcgctcgtgg cgatctggtt     240
actgagttcg aaattggtga ccatgctggc ctgaaatggc tgaacggtag ctgcctggca     300
tgcgagttct gtaaacaggc tgacgaaccg ctgtgcccta acgcgagcct gtctggttat     360
actgtagatg gtactttcca gcagtatgcc attggcaaag ccacccatgc gagcaagctg     420
ccgaaaaacg tgcctctgga tgccgtggca ccggttctgt gcgcgggcat taccgtatac     480
aagggcctga agaaagcgg tgttcgtcct ggccaaaccg ttgcgatcgt aggtgcgggt     540
ggtggtctgg gctccctggc gctgcagtac gcgaaagcta tgggtattcg cgtggtggcg     600
attgatggcg gtgaagagaa acaagcgatg tgtgaacagc tgggcgcaga agcctacgtt     660
gactttacca aaacgcaaga tctggtagca gatgttaagg ccgccacccc tgaaggtctg     720
ggcgcgcatg cggtaattct gctggcggtc gccgaaaaac catttcagca ggcggccgaa     780
tatgtcagcc gtggtacggt ggttgccatt ggtctgccgg cgggcgcatt cctgcgcgcg     840
ccggtgttta acactgtggt tcgtatgatt aacattaagg gtagctacgt tgcaaccgc     900
caggacggcg ttgaggcagt ggacttcttc gcgcgcggcc tgatcaaagc gccgttcaaa     960
accgctcctc tgcaagatct gccgaaaatc ttcgaactga tggaacaagg taagattgca    1020
ggtcgctacg ttctggaaat cccggaatga                                      1050
```

<210> SEQ ID NO 148
<211> LENGTH: 349
<212> TYPE: PRT
<213> ORGANISM: Artificial Sequence
<220> FEATURE:
<223> OTHER INFORMATION: Synthetic ADH from Aspergillus flavus

<400> SEQUENCE: 148

Met Ser Ile Pro Glu Met Gln Trp Ala Gln Val Ala Glu Gln Lys Gly
1               5                   10                  15

Gly Pro Leu Ile Tyr Lys Gln Ile Pro Val Pro Lys Pro Gly Pro Asp
            20                  25                  30

Glu Ile Leu Val Lys Val Arg Tyr Ser Gly Val Cys His Thr Asp Leu
        35                  40                  45

His Ala Leu Lys Gly Asp Trp Pro Leu Pro Val Lys Met Pro Leu Val
    50                  55                  60

Gly Gly His Glu Gly Ala Gly Val Val Val Ala Arg Gly Asp Leu Val
65                  70                  75                  80

Thr Glu Phe Glu Ile Gly Asp His Ala Gly Leu Lys Trp Leu Asn Gly
                85                  90                  95

```
Ser Cys Leu Ala Cys Glu Phe Cys Lys Gln Ala Asp Glu Pro Leu Cys
            100                 105                 110

Pro Asn Ala Ser Leu Ser Gly Tyr Thr Val Asp Gly Thr Phe Gln Gln
        115                 120                 125

Tyr Ala Ile Gly Lys Ala Thr His Ala Ser Lys Leu Pro Lys Asn Val
    130                 135                 140

Pro Leu Asp Ala Val Ala Pro Val Leu Cys Ala Gly Ile Thr Val Tyr
145                 150                 155                 160

Lys Gly Leu Lys Glu Ser Gly Val Arg Pro Gly Gln Thr Val Ala Ile
                165                 170                 175

Val Gly Ala Gly Gly Leu Gly Ser Leu Ala Leu Gln Tyr Ala Lys
            180                 185                 190

Ala Met Gly Ile Arg Val Val Ala Ile Asp Gly Gly Glu Glu Lys Gln
        195                 200                 205

Ala Met Cys Glu Gln Leu Gly Ala Glu Ala Tyr Val Asp Phe Thr Lys
    210                 215                 220

Thr Gln Asp Leu Val Ala Asp Val Lys Ala Ala Thr Pro Glu Gly Leu
225                 230                 235                 240

Gly Ala His Ala Val Ile Leu Leu Ala Val Ala Glu Lys Pro Phe Gln
                245                 250                 255

Gln Ala Ala Glu Tyr Val Ser Arg Gly Thr Val Val Ala Ile Gly Leu
            260                 265                 270

Pro Ala Gly Ala Phe Leu Arg Ala Pro Val Phe Asn Thr Val Val Arg
        275                 280                 285

Met Ile Asn Ile Lys Gly Ser Tyr Val Gly Asn Arg Gln Asp Gly Val
    290                 295                 300

Glu Ala Val Asp Phe Phe Ala Arg Gly Leu Ile Lys Ala Pro Phe Lys
305                 310                 315                 320

Thr Ala Pro Leu Gln Asp Leu Pro Lys Ile Phe Glu Leu Met Glu Gln
                325                 330                 335

Gly Lys Ile Ala Gly Arg Tyr Val Leu Glu Ile Pro Glu
            340                 345

<210> SEQ ID NO 149
<211> LENGTH: 729
<212> TYPE: DNA
<213> ORGANISM: Artificial Sequence
<220> FEATURE:
<223> OTHER INFORMATION: Synthetic ADH from Oenococcus oeni

<400> SEQUENCE: 149
atgtttgatc gcctgaaggg taaggtggcg atcgtcaccg gcggtaatag cggtattggt     60
aaggcaatcg cggcagactt catcgccgag ggcgcgaaag tagtgattac cggtcgcaac    120
caagagaagg tcgccagac tgcgctggaa atcgccggtg acattctgtt cattcagcag    180
gacgtgagcc aggaggcgga ctggcagaaa gttatctcca aaaccatcga agttcgt      240 aagtttgata ttctggttaa caacgctggc gtcggcggcg tgggtaagcc actggcagaa    300
atgtccctgt ctgaattcaa ttggacccaa tccattaatc tgtccggtaa cttcctgggt    360
attcacttcg cgctgaacaa aatgaccgaa cctggtagca ttattgacgt aagcagcgcg    420
gctggcctgc gtggtttttcc gggcgcagcc gattatagcg cttccaaagg tggtacgcgt    480
ctgctgacgc gcgccgcggc gctggaagcg ctgcaaatgg gtaaaaagat ccgtgtaaac    540
tctattcacc aggttggat tgataccgat atcgtaccaa agatatgcg tgagcaggtt    600 atcgcgatga cccctatgca tcacctgggc caaccgaaag atattgccaa gctggcgacg    660
```

-continued

```
tatctggcat ctgacgagtc cgagtatact acgggctccg aactggcagc cgacggcggt    720
ctgatggca                                                            729
```

<210> SEQ ID NO 150
<211> LENGTH: 243
<212> TYPE: PRT
<213> ORGANISM: Artificial Sequence
<220> FEATURE:
<223> OTHER INFORMATION: Synthetic ADH from Oenococcus oeni

<400> SEQUENCE: 150

Met Phe Asp Arg Leu Lys Gly Lys Val Ala Ile Val Thr Gly Gly Asn
1               5                   10                  15

Ser Gly Ile Gly Lys Ala Ile Ala Ala Asp Phe Ile Ala Glu Gly Ala
            20                  25                  30

Lys Val Val Ile Thr Gly Arg Asn Gln Glu Lys Gly Arg Gln Thr Ala
        35                  40                  45

Leu Glu Ile Ala Gly Asp Ile Leu Phe Ile Gln Gln Asp Val Ser Gln
    50                  55                  60

Glu Ala Asp Trp Gln Lys Val Ile Ser Lys Thr Ile Glu Lys Phe Gly
65                  70                  75                  80

Lys Phe Asp Ile Leu Val Asn Asn Ala Gly Val Gly Val Gly Lys
                85                  90                  95

Pro Leu Ala Glu Met Ser Leu Ser Glu Phe Asn Trp Thr Gln Ser Ile
            100                 105                 110

Asn Leu Ser Gly Asn Phe Leu Gly Ile His Phe Ala Leu Asn Lys Met
        115                 120                 125

Thr Glu Pro Gly Ser Ile Ile Asp Val Ser Ser Ala Ala Gly Leu Arg
    130                 135                 140

Gly Phe Pro Gly Ala Ala Asp Tyr Ser Ala Ser Lys Gly Gly Thr Arg
145                 150                 155                 160

Leu Leu Thr Arg Ala Ala Ala Leu Glu Ala Leu Gln Met Gly Lys Lys
                165                 170                 175

Ile Arg Val Asn Ser Ile His Pro Gly Trp Ile Asp Thr Asp Ile Val
            180                 185                 190

Pro Lys Asp Met Arg Glu Gln Val Ile Ala Met Thr Pro Met His His
        195                 200                 205

Leu Gly Gln Pro Lys Asp Ile Ala Lys Leu Ala Thr Tyr Leu Ala Ser
    210                 215                 220

Asp Glu Ser Glu Tyr Thr Thr Gly Ser Glu Leu Ala Ala Asp Gly Gly
225                 230                 235                 240

Leu Met Ala

<210> SEQ ID NO 151
<211> LENGTH: 768
<212> TYPE: DNA
<213> ORGANISM: Artificial Sequence
<220> FEATURE:
<223> OTHER INFORMATION: Synthetic ADH from Ralstonia eutropha

<400> SEQUENCE: 151

```
atgcaggca aaattgcact ggttacgggc ggtgcgtctg gtatgggtct ggccttcacc     60
cgtcgcctgg cccaagaagg cgcacgtgtt tacttcaccg acattaacgg cgccgcgggt   120
cacgcgacga aaagcgagct gcagggtgct ggtctggcgg tcgtattcct gcgtcatgac   180
gtgacccagg aaaacgactg gctgcgcgtc ctggaacata ttggcgctgt tgacggtcgc   240
```

-continued

```
ctggatgtac tggtgaataa tgccggcatt gcgatttctc acaacattga gacttgtact    300
actgaggatt ttgatcgcac gctgaatgtt aacctgaagt ccgtgtttct gggctgcaaa    360
cacggtctgg ctctgatgaa acagaagggt ggcagcatca ttaacgttag ctctatcacc    420
gcgatttgcg gcgaacctgt ggcgctggcg tatagcgcta gcaaagccgg cgtccgtttt    480
ctgagcaagt ctgttgccct gcattgtgcg gagaagggct acgccatccg tgttaacagc    540
ctgcacccgg gttacattga tccccgctg ctggcaggca gcaacgcggg tggctccctg    600
accgctgacg aggtaaccgc gagccgtgta cgtattggcg gtgaaattcc gctgaaacgt    660
cgcggcaccc cggacgaagt tgcaggcgcg gttctgtacc tggctagcga tgaatccacc    720
tatgttactg gtactgagct ggtaattgat ggcggctacg catgtcat                768
```

<210> SEQ ID NO 152
<211> LENGTH: 256
<212> TYPE: PRT
<213> ORGANISM: Artificial Sequence
<220> FEATURE:
<223> OTHER INFORMATION: Synthetic ADH from Ralstonia eutropha

<400> SEQUENCE: 152

```
Met Gln Gly Lys Ile Ala Leu Val Thr Gly Ala Ser Gly Met Gly
1               5                  10                  15

Leu Ala Phe Thr Arg Arg Leu Ala Gln Glu Gly Ala Arg Val Tyr Phe
                20                  25                  30

Thr Asp Ile Asn Gly Ala Ala Gly His Ala Thr Glu Ser Glu Leu Gln
            35                  40                  45

Gly Ala Gly Leu Ala Val Val Phe Leu Arg His Asp Val Thr Gln Glu
        50                  55                  60

Asn Asp Trp Leu Arg Val Leu Glu His Ile Gly Ala Val Asp Gly Arg
65                  70                  75                  80

Leu Asp Val Leu Asn Asn Ala Gly Ile Ala Ile Ser His Asn Ile
                85                  90                  95

Glu Thr Cys Thr Thr Glu Asp Phe Asp Arg Thr Leu Asn Val Asn Leu
            100                 105                 110

Lys Ser Val Phe Leu Gly Cys Lys His Gly Leu Ala Leu Met Lys Gln
        115                 120                 125

Lys Gly Gly Ser Ile Ile Asn Val Ser Ser Ile Thr Ala Ile Cys Gly
    130                 135                 140

Glu Pro Val Ala Leu Ala Tyr Ser Ala Ser Lys Ala Gly Val Arg Phe
145                 150                 155                 160

Leu Ser Lys Ser Val Ala Leu His Cys Ala Glu Lys Gly Tyr Ala Ile
                165                 170                 175

Arg Val Asn Ser Leu His Pro Gly Tyr Ile Asp Thr Pro Leu Leu Ala
            180                 185                 190

Gly Ser Asn Ala Gly Gly Ser Leu Thr Ala Asp Glu Val Thr Ala Ser
        195                 200                 205

Arg Val Arg Ile Gly Gly Glu Ile Pro Leu Lys Arg Arg Gly Thr Pro
    210                 215                 220

Asp Glu Val Ala Gly Ala Val Leu Tyr Leu Ala Ser Asp Glu Ser Thr
225                 230                 235                 240

Tyr Val Thr Gly Thr Glu Leu Val Ile Asp Gly Gly Tyr Ala Cys His
                245                 250                 255
```

<210> SEQ ID NO 153

<211> LENGTH: 1056
<212> TYPE: DNA
<213> ORGANISM: Artificial Sequence
<220> FEATURE:
<223> OTHER INFORMATION: Synthetic ADH from Thermoanaerobium brockii

<400> SEQUENCE: 153

```
atgaaaggct tcgccatgct gagcatcggc aaagtgggtt ggattgaaaa agaaaaaccg      60
gcgccaggcc cgttcgatgc aattgtgcgc cctctggcag tagcgccgtg taccagcgat     120
attcatactg tgtttgaagg tgccattggc gagcgtcaca atatgattct gggccatgaa     180
gccgttggtg aagttgttga ggttggcagc gaagtgaagg atttcaaacc gggcgatcgc     240
gttgtcgttc cagcgattac cccggattgg cgcaccagcg aagtccagcg cggctaccat     300
cagcactctg gcggcatgct ggccggctgg aaattcagca atgtaaagga tggtgtgttc     360
ggtgaatttt ttcacgttaa cgacgcagac atgaatctgg cgcacctgcc gaaagaaatc     420
ccgctggaag cagcggttat gattccggat atgatgacca cgggttttca cggcgcagag     480
ctggcggaca ttgaactggg cgctacggta gccgtactgg catcggtcc ggtgggcctg      540
atggcagttg caggcgctaa gctgcgcggc gcaggtcgta ttattgccgt tggttctcgc     600
ccggtgtgtg tggacgccgc taagtattat ggtgcaacgg acattgtcaa ttacaaggac     660
ggcccaattg aatctcagat catgaacctg acggaaggta aaggcgttga cgccgcgatt     720
atcgctggcg caacgccga catcatggcg accgcagtta aaatcgtcaa gccaggtggt     780
actattgcta acgtcaacta cttcggcgaa ggtgaggtcc tgcctgtccc acgtctggaa     840
tggggttgcg gtatggcaca taaaaccatt aaaggtggcc tgtgcccagg cggccgtctg     900
cgtatggaac gcctgatcga tctggtcttc tacaaacgcg tggatcctag caaactggtg     960
actcacgttt tccgcggctt tgataacatc gaaaaagctt ttatgctgat gaaagataaa    1020
ccgaaagatc tgattaaacc ggttgtcatc ctggct                              1056
```

<210> SEQ ID NO 154
<211> LENGTH: 352
<212> TYPE: PRT
<213> ORGANISM: Artificial Sequence
<220> FEATURE:
<223> OTHER INFORMATION: Synthetic ADH from Thermoanaerobium brockii

<400> SEQUENCE: 154

```
Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
            20                  25                  30

Ala Val Ala Pro Cys Thr Ser Asp Ile His Thr Val Phe Glu Gly Ala
        35                  40                  45

Ile Gly Glu Arg His Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Val Val Pro Ala Ile Thr Pro Asp Trp Arg Thr Ser Glu Val Gln
                85                  90                  95

Arg Gly Tyr His Gln His Ser Gly Gly Met Leu Ala Gly Trp Lys Phe
            100                 105                 110

Ser Asn Val Lys Asp Gly Val Phe Gly Glu Phe Phe His Val Asn Asp
        115                 120                 125

Ala Asp Met Asn Leu Ala His Leu Pro Lys Glu Ile Pro Leu Glu Ala
```

```
                    130                 135                 140
Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
                165                 170                 175

Pro Val Gly Leu Met Ala Val Ala Gly Ala Lys Leu Arg Gly Ala Gly
                180                 185                 190

Arg Ile Ile Ala Val Gly Ser Arg Pro Val Cys Val Asp Ala Ala Lys
                195                 200                 205

Tyr Tyr Gly Ala Thr Asp Ile Val Asn Tyr Lys Asp Gly Pro Ile Glu
    210                 215                 220

Ser Gln Ile Met Asn Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
                245                 250                 255

Lys Pro Gly Gly Thr Ile Ala Asn Val Asn Tyr Phe Gly Glu Gly Glu
                260                 265                 270

Val Leu Pro Val Pro Arg Leu Glu Trp Gly Cys Gly Met Ala His Lys
                275                 280                 285

Thr Ile Lys Gly Gly Leu Cys Pro Gly Gly Arg Leu Arg Met Glu Arg
    290                 295                 300

Leu Ile Asp Leu Val Phe Tyr Lys Arg Val Asp Pro Ser Lys Leu Val
305                 310                 315                 320

Thr His Val Phe Arg Gly Phe Asp Asn Ile Glu Lys Ala Phe Met Leu
                325                 330                 335

Met Lys Asp Lys Pro Lys Asp Leu Ile Lys Pro Val Val Ile Leu Ala
                340                 345                 350

<210> SEQ ID NO 155
<211> LENGTH: 1125
<212> TYPE: DNA
<213> ORGANISM: Artificial Sequence
<220> FEATURE:
<223> OTHER INFORMATION: Synthetic ADH from Hore Liver E form

<400> SEQUENCE: 155
atgagcacag cagggaaagt aattaaatgc aaagcagctg tgctgtggga ggaaaagaaa      60
ccatttccca ttgaggaggt ggaggtcgca cctccgaagg cccatgaagt ccgtattaag    120
atggtggcca cagggatctg tcgctcagat gaccacgtgg ttagtgggac cctggtcaca    180
cctctgcctg tgatcgcagg ccatgaggca gctggcattg tggagagcat cggggaaggc    240
gtcactacag tacgtccagg tgataaagtc atcccactgt ttactcctca gtgtgggaaa    300
tgccgtgttt gtaaacaccc tgaaggcaac ttctgcttga aaaatgatct gagcatgcct    360
cgtgggacca tgcaggatgg taccagccgt ttcacctgcc gtgggaagcc tatccaccac    420
ttcctgggca ccagcacctt ctcccagtac accgtggtgg acgagatctc agtggccaag    480
atcgatgcgg cctcaccgct ggagaaagtc tgtctgattg gctgtgggtt ttctactggt    540
tatgggtctg cagtcaaggt tgccaaggtc acccagggct ccacctgtgc cgtgtttggc    600
ctgggggggg tgggcctgtc tgttatcatg ggctgtaaag cagccggggc ggcccgtatc    660
attggggtgg acatcaacaa agacaagttt gcaaaggcca agaagtgggg tgccactgag    720
tgtgtcaacc ctcaggacta caagaaacct atccaggagg tgctgacaga aatgagcaat    780
gggggcgtgg attttttcatt tgaagtcatt ggtcgtctgg acaccatggt gactgccttg    840
```

```
tcatgctgtc aagaagcata tggtgtgagc gtcatcgtag gggtacctcc tgattcccaa    900
aatctgtcta tgaatcctat gttgctgctg agtgggcgta cctggaaagg ggctattttt    960
ggtggtttta agagtaaaga ttctgtccct aaactggtgg ccgattttat ggctaaaaag    1020
tttgcactgg atcctttaat cacccatgtt ttacctttg aaaaaattaa tgaagggttt     1080
gacctgctgc gctctgggga gagtatccgt accatcctga cgttt                   1125
```

```
<210> SEQ ID NO 156
<211> LENGTH: 375
<212> TYPE: PRT
<213> ORGANISM: Artificial Sequence
<220> FEATURE:
<223> OTHER INFORMATION: Synthetic ADH from Hore Liver

<400> SEQUENCE: 156
```

| | | | | | | | | | | | | | | | |
|---|---|---|---|---|---|---|---|---|---|---|---|---|---|---|---|
| Met | Ser | Thr | Ala | Gly | Lys | Val | Ile | Lys | Cys | Lys | Ala | Ala | Val | Leu | Trp |
| 1 | | | | 5 | | | | | 10 | | | | | 15 | |
| Glu | Glu | Lys | Lys | Pro | Phe | Ser | Ile | Glu | Glu | Val | Glu | Val | Ala | Pro | Pro |
| | | | 20 | | | | | 25 | | | | | 30 | | |
| Lys | Ala | His | Glu | Val | Arg | Ile | Lys | Met | Val | Ala | Thr | Gly | Ile | Cys | Arg |
| | | 35 | | | | | 40 | | | | | 45 | | | |
| Ser | Asp | Asp | His | Val | Val | Ser | Gly | Thr | Leu | Val | Thr | Pro | Leu | Pro | Val |
| 50 | | | | | 55 | | | | | 60 | | | | | |
| Ile | Ala | Gly | His | Glu | Ala | Ala | Gly | Ile | Val | Glu | Ser | Ile | Gly | Glu | Gly |
| 65 | | | | 70 | | | | | 75 | | | | | 80 | |
| Val | Thr | Thr | Val | Arg | Pro | Gly | Asp | Lys | Val | Ile | Pro | Leu | Phe | Thr | Pro |
| | | | | 85 | | | | | 90 | | | | | 95 | |
| Gln | Cys | Gly | Lys | Cys | Arg | Val | Cys | Lys | His | Pro | Glu | Gly | Asn | Phe | Cys |
| | | | 100 | | | | | 105 | | | | | 110 | | |
| Leu | Lys | Asn | Asp | Leu | Ser | Met | Pro | Arg | Gly | Thr | Met | Gln | Asp | Gly | Thr |
| | | | 115 | | | | | 120 | | | | | 125 | | |
| Ser | Arg | Phe | Thr | Cys | Arg | Gly | Lys | Pro | Ile | His | His | Phe | Leu | Gly | Thr |
| | | | 130 | | | | | 135 | | | | | 140 | | |
| Ser | Thr | Phe | Ser | Gln | Tyr | Thr | Val | Val | Asp | Glu | Ile | Ser | Val | Ala | Lys |
| 145 | | | | | 150 | | | | | 155 | | | | | 160 |
| Ile | Asp | Ala | Ala | Ser | Pro | Leu | Glu | Lys | Val | Cys | Leu | Ile | Gly | Cys | Gly |
| | | | | 165 | | | | | 170 | | | | | 175 | |
| Phe | Ser | Thr | Gly | Tyr | Gly | Ser | Ala | Val | Lys | Val | Ala | Lys | Val | Thr | Gln |
| | | | 180 | | | | | 185 | | | | | 190 | | |
| Gly | Ser | Thr | Cys | Ala | Val | Phe | Gly | Leu | Gly | Gly | Val | Gly | Leu | Ser | Val |
| | | | 195 | | | | | 200 | | | | | 205 | | |
| Ile | Met | Gly | Cys | Lys | Ala | Ala | Gly | Ala | Ala | Arg | Ile | Ile | Gly | Val | Asp |
| | | 210 | | | | | 215 | | | | | 220 | | | |
| Ile | Asn | Lys | Asp | Lys | Phe | Ala | Lys | Ala | Lys | Glu | Val | Gly | Ala | Thr | Glu |
| 225 | | | | | 230 | | | | | 235 | | | | | 240 |
| Cys | Val | Asn | Pro | Gln | Asp | Tyr | Lys | Lys | Pro | Ile | Gln | Glu | Val | Leu | Thr |
| | | | | 245 | | | | | 250 | | | | | 255 | |
| Glu | Met | Ser | Asn | Gly | Gly | Val | Asp | Phe | Ser | Phe | Glu | Val | Ile | Gly | Arg |
| | | | 260 | | | | | 265 | | | | | 270 | | |
| Leu | Asp | Thr | Met | Val | Thr | Ala | Leu | Ser | Cys | Cys | Gln | Glu | Ala | Tyr | Gly |
| | | | 275 | | | | | 280 | | | | | 285 | | |
| Val | Ser | Val | Ile | Val | Gly | Val | Pro | Pro | Asp | Ser | Gln | Asn | Leu | Ser | Met |
| | | 290 | | | | | 295 | | | | | 300 | | | |
| Asn | Pro | Met | Leu | Leu | Leu | Ser | Gly | Arg | Thr | Trp | Lys | Gly | Ala | Ile | Phe |
| 305 | | | | | 310 | | | | | 315 | | | | | 320 |

```
Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
            340                 345                 350

Phe Glu Lys Ile Asn Glu Gly Phe Asp Leu Leu Arg Ser Gly Glu Ser
        355                 360                 365

Ile Arg Thr Ile Leu Thr Phe
    370             375

<210> SEQ ID NO 157
<211> LENGTH: 759
<212> TYPE: DNA
<213> ORGANISM: Lactobacillus Minor

<400> SEQUENCE: 157
atgaccgatc ggttgaaggg gaaagtagca attgtaactg gcggtaccct tgggaattggc      60 ttggcaatcg ctgataagtt tgttgaagaa ggcgcaaagg ttgttattac cggccgtcac     120
gctgatgtag gtgaaaaagc tgccagatca atcggcggca cagacgttat ccgttttgtc     180
caacacgatg cttctgatga accggctgg actaagttgt ttgatacgac tgaagaagca     240
tttggcccag ttaccacggt tgtcaacaat gccggaattg cggtcagcaa gagtgttgaa     300
gataccacaa ctgaagaatg cgcaagctg ctctcagtta acttggatgg tgtcttcttc     360
ggtacccgtc ttggaatcca acgtatgaag aataaaggac tcggagcatc aatcatcaat     420
atgtcatcta tcgaaggttt tgttggtgat ccagctctgg gtgcatacaa cgcttcaaaa     480
ggtgctgtca gaattatgtc taaatcagct gccttggatt gcgctttgaa ggactacgat     540
gttcgggtta acactgttca tccaggttat atcaagacac cattggttga cgatcttgaa     600
ggggcagaag aaatgatgtc acagcggacc aagacaccaa tgggtcatat cggtgaacct     660
aacgatatcg cttggatctg tgtttacctg gcatctgacg aatctaaatt tgccactggt     720
gcagaattcg ttgtcgacgg agggtacacc gcccaatag                            759

<210> SEQ ID NO 158
<211> LENGTH: 252
<212> TYPE: PRT
<213> ORGANISM: Lactobacillus Minor

<400> SEQUENCE: 158

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Arg Ser Ile Gly Gly Thr Asp Val Ile Arg Phe Val Gln His Asp Ala
    50                  55                  60

Ser Asp Glu Thr Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125
```

```
Met Lys Asn Lys Gly Leu Gly Ala Ser Ile Ile Asn Met Ser Ser Ile
    130                 135                 140
Glu Gly Phe Val Gly Asp Pro Ala Leu Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Tyr Ile Lys
            180                 185                 190
Thr Pro Leu Val Asp Asp Leu Glu Gly Ala Glu Met Met Ser Gln
        195                 200                 205
Arg Thr Lys Thr Pro Met Gly His Ile Gly Pro Asn Asp Ile Ala
    210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```

<210> SEQ ID NO 159
<211> LENGTH: 759
<212> TYPE: DNA
<213> ORGANISM: Artificial Sequence
<220> FEATURE:
<223> OTHER INFORMATION: Synthetic Variant of L. minor

<400> SEQUENCE: 159

```
atgaccgatc ggttgaaggg gaaagtagca attgtaactg gcggtacctt gggaattggc     60
ttggcaatcg ctgataagtt tgttgaagaa ggcgcaaagg ttgttattac cggccgtcac    120
gctgatgtag gtgaaaaagc tgccagatca atcgcggca cagacgttat ccgttttgtc    180
caacacgatg cttctgatga aaccggctgg actaagttgt tgatacgac tgaagaagca    240
tttggcccag ttaccacggt tgtcaacaat gccggaattg cggtcagcaa gagtgttgaa    300
gataccacaa ctgaagaatg cgcaagctg ctctcagtta acttggatgg tgtcttcttc    360
ggtacccgtc ttggaatcca acgtatgaag aataaaggac tcggagcatc aatcatcaat    420
atgtcatcta tcagtggttt tgttggtgat ccagctctgg gtgcatacaa cgcttcaaaa    480
ggtgctgtca gaattatgtc taaatcagct gccttggatt gcgctttgaa ggactacgat    540
gttcgggtta acactgttca tccaggttgt atcaagacac cattggttga cgatcttgaa    600
ggggcagaag aaatgatgtc acagcggacc aagacaccaa tgggtcatat cggtgaacct    660
aacgatatcg cttggatctg tgtttacctg gcatctgacg aatctaaatt tgccactggt    720
gcagaattcg ttgtcgacgg agggtacacc gcccaatag                           759
```

<210> SEQ ID NO 160
<211> LENGTH: 252
<212> TYPE: PRT
<213> ORGANISM: Artificial Sequence
<220> FEATURE:
<223> OTHER INFORMATION: Synthetic Variant of L. minor

<400> SEQUENCE: 160

```
Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
```

Arg Ser Ile Gly Gly Thr Asp Val Ile Arg Phe Val Gln His Asp Ala
 50                  55                  60

Ser Asp Glu Thr Gly Trp Thr Lys Leu Phe Asp Thr Thr Glu Glu Ala
 65                  70                  75                  80

Phe Gly Pro Val Thr Thr Val Asn Asn Ala Gly Ile Ala Val Ser
                 85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
             115                 120                 125

Met Lys Asn Lys Gly Leu Gly Ala Ser Ile Ile Asn Met Ser Ser Ile
130                 135                 140

Ser Gly Phe Val Gly Asp Pro Ala Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 161
<211> LENGTH: 252
<212> TYPE: PRT
<213> ORGANISM: Artificial Sequence
<220> FEATURE:
<223> OTHER INFORMATION: Engineered Ketoreductase Sequence Formula with
      L. brevis backbone Synthetic Construct
<220> FEATURE:
<221> NAME/KEY: MISC_FEATURE
<222> LOCATION: (3)..(3)
<223> OTHER INFORMATION: Xaa is an acidic polar or hydrophilic residue
<220> FEATURE:
<221> NAME/KEY: MISC_FEATURE
<222> LOCATION: (7)..(7)
<223> OTHER INFORMATION: Xaa is a polar or non-polar residue
<220> FEATURE:
<221> NAME/KEY: MISC_FEATURE
<222> LOCATION: (17)..(17)
<223> OTHER INFORMATION: Xaa is a non-polar, apliphatic or polar residue
<220> FEATURE:
<221> NAME/KEY: MISC_FEATURE
<222> LOCATION: (21)..(21)
<223> OTHER INFORMATION: Xaa is a non-polar, aromatic, or hydrophobic
      residue
<220> FEATURE:
<221> NAME/KEY: MISC_FEATURE
<222> LOCATION: (25)..(25)
<223> OTHER INFORMATION: Xaa is an acidic, nonpolar or polar residue
<220> FEATURE:
<221> NAME/KEY: MISC_FEATURE
<222> LOCATION: (29)..(29)
<223> OTHER INFORMATION: Xaa is an acidic, aliphatic or nonpolar residue
<220> FEATURE:
<221> NAME/KEY: MISC_FEATURE
<222> LOCATION: (40)..(40)
<223> OTHER INFORMATION: Xaa is a constrained, basic, or hydrophilic
      residue
<220> FEATURE:
<221> NAME/KEY: MISC_FEATURE

```
<222> LOCATION: (42)..(42)
<223> OTHER INFORMATION: Xaa is an acidic or a nonpolar residue
<220> FEATURE:
<221> NAME/KEY: MISC_FEATURE
<222> LOCATION: (53)..(53)
<223> OTHER INFORMATION: Xaa is a nonpolar or an acidic residue
<220> FEATURE:
<221> NAME/KEY: MISC_FEATURE
<222> LOCATION: (75)..(75)
<223> OTHER INFORMATION: Xaa is an acidic or polar residue
<220> FEATURE:
<221> NAME/KEY: MISC_FEATURE
<222> LOCATION: (94)..(94)
<223> OTHER INFORMATION: Xaa is a nonpolar or a polar residue
<220> FEATURE:
<221> NAME/KEY: MISC_FEATURE
<222> LOCATION: (95)..(95)
<223> OTHER INFORMATION: Xaa is an aliphatic, non-polar, or acidic
      residue
<220> FEATURE:
<221> NAME/KEY: MISC_FEATURE
<222> LOCATION: (95)..(95)
<223> OTHER INFORMATION: Xaa is a nonpolar or aliphatic residue
<220> FEATURE:
<221> NAME/KEY: MISC_FEATURE
<222> LOCATION: (96)..(96)
<223> OTHER INFORMATION: Xaa is polar residue
<220> FEATURE:
<221> NAME/KEY: MISC_FEATURE
<222> LOCATION: (101)..(101)
<223> OTHER INFORMATION: Xaa is an acidic, non-polar, or a polar
      residue
<220> FEATURE:
<221> NAME/KEY: MISC_FEATURE
<222> LOCATION: (105)..(105)
<223> OTHER INFORMATION: Xaa is an acidic or non-polar residue
<220> FEATURE:
<221> NAME/KEY: MISC_FEATURE
<222> LOCATION: (108)..(108)
<223> OTHER INFORMATION: Xaa is a hydrophilic, polar or constrained
      residue
<220> FEATURE:
<221> NAME/KEY: MISC_FEATURE
<222> LOCATION: (111)..(111)
<223> OTHER INFORMATION: Xaa is a non-polar or aliphatic residue
<220> FEATURE:
<221> NAME/KEY: MISC_FEATURE
<222> LOCATION: (112)..(112)
<223> OTHER INFORMATION: Xaa is an acidic or polar residue
<220> FEATURE:
<221> NAME/KEY: MISC_FEATURE
<222> LOCATION: (113)..(113)
<223> OTHER INFORMATION: Xaa is a nonpolar or aliphatic residue
<220> FEATURE:
<221> NAME/KEY: MISC_FEATURE
<222> LOCATION: (117)..(117)
<223> OTHER INFORMATION: Xaa s a nonpolar or polar residue
<220> FEATURE:
<221> NAME/KEY: MISC_FEATURE
<222> LOCATION: (127)..(127)
<223> OTHER INFORMATION: Xaa is a basic or polar residue
<220> FEATURE:
<221> NAME/KEY: MISC_FEATURE
<222> LOCATION: (145)..(145)
<223> OTHER INFORMATION: Xaa is a polar residue
<220> FEATURE:
<221> NAME/KEY: MISC_FEATURE
<222> LOCATION: (147)..(147)
<223> OTHER INFORMATION: Xaa is a nonpolar, aromatic, or hydrophobic
      residue
<220> FEATURE:
<221> NAME/KEY: MISC_FEATURE
<222> LOCATION: (152)..(152)
<223> OTHER INFORMATION: Xaa is a non polar, basic residue, or
      hydrophilic residue
<220> FEATURE:
<221> NAME/KEY: MISC_FEATURE
<222> LOCATION: (157)..(157)
<223> OTHER INFORMATION: Xaa is a polar residue
```

```
<220> FEATURE:
<221> NAME/KEY: MISC_FEATURE
<222> LOCATION: (163)..(163)
<223> OTHER INFORMATION: Xaa is a nonpolar or aliphatic residue
<220> FEATURE:
<221> NAME/KEY: MISC_FEATURE
<222> LOCATION: (176)..(176)
<223> OTHER INFORMATION: Xaa is a nonpolar or aliphatic residue
<220> FEATURE:
<221> NAME/KEY: MISC_FEATURE
<222> LOCATION: (190)..(190)
<223> OTHER INFORMATION: Xaa is a cysteine
<220> FEATURE:
<221> NAME/KEY: MISC_FEATURE
<222> LOCATION: (194)..(194)
<223> OTHER INFORMATION: Xaa is a constrained, basic, or polar residue
<220> FEATURE:
<221> NAME/KEY: MISC_FEATURE
<222> LOCATION: (197)..(197)
<223> OTHER INFORMATION: Xaa is a hydrophilic, acidic, basic, aliphatic
      or nonpolar residue
<220> FEATURE:
<221> NAME/KEY: MISC_FEATURE
<222> LOCATION: (198)..(198)
<223> OTHER INFORMATION: Xaa is an acidic, basic, hydrophilic, or
      nonpolar residue
<220> FEATURE:
<221> NAME/KEY: MISC_FEATURE
<222> LOCATION: (199)..(199)
<223> OTHER INFORMATION: Xaa is an acidic, aliphatic, or nonpolar
      residue
<220> FEATURE:
<221> NAME/KEY: MISC_FEATURE
<222> LOCATION: (200)..(200)
<223> OTHER INFORMATION: Xaa is an acidic or constrained residue
<220> FEATURE:
<221> NAME/KEY: MISC_FEATURE
<222> LOCATION: (202)..(202)
<223> OTHER INFORMATION: Xaa is a nonpolar or aliphatic residue
<220> FEATURE:
<221> NAME/KEY: MISC_FEATURE
<222> LOCATION: (206)..(206)
<223> OTHER INFORMATION: Xaa is a nonpolar, aromatic, or hydrophobic
      residue
<220> FEATURE:
<221> NAME/KEY: MISC_FEATURE
<222> LOCATION: (211)..(211)
<223> OTHER INFORMATION: Xaa is a basic residue
<220> FEATURE:
<221> NAME/KEY: MISC_FEATURE
<222> LOCATION: (223)..(223)
<223> OTHER INFORMATION: Xaa is a nonpolar or aliphatic residue
<220> FEATURE:
<221> NAME/KEY: MISC_FEATURE
<222> LOCATION: (250)..(250)
<223> OTHER INFORMATION: Xaa is a polar or nonpolar residue

<400> SEQUENCE: 161

Met Ser Xaa Arg Leu Asp Xaa Lys Val Ala Ile Ile Thr Gly Gly Thr
1               5                   10                  15

Xaa Gly Ile Gly Xaa Ala Ile Ala Xaa Lys Phe Val Xaa Glu Gly Ala
            20                  25                  30

Lys Val Met Ile Thr Gly Arg Xaa Ser Xaa Val Gly Glu Lys Ala Ala
        35                  40                  45

Lys Ser Val Gly Xaa Pro Asp Gln Ile Gln Phe Phe Gln His Asp Ser
    50                  55                  60

Ser Asp Glu Asp Gly Trp Thr Lys Leu Phe Xaa Ala Thr Glu Lys Ala
65                  70                  75                  80

Phe Gly Pro Val Ser Thr Leu Val Asn Asn Ala Gly Ile Xaa Xaa Xaa
                85                  90                  95

Lys Ser Val Glu Xaa Thr Thr Thr Xaa Glu Trp Xaa Lys Leu Xaa Xaa
            100                 105                 110
```

-continued

```
Xaa Asn Leu Asp Xaa Val Phe Phe Gly Thr Arg Leu Gly Ile Xaa Arg
        115                 120                 125

Met Lys Asn Lys Gly Leu Gly Ala Ser Ile Ile Asn Met Ser Ser Ile
    130                 135                 140

Xaa Gly Xaa Val Gly Asp Pro Xaa Leu Gly Ala Tyr Xaa Ala Ser Lys
145                 150                 155                 160

Gly Ala Xaa Arg Ile Met Ser Lys Ser Ala Ala Leu Asp Cys Ala Xaa
                165                 170                 175

Lys Asp Tyr Asp Val Arg Val Asn Thr Val His Pro Gly Xaa Ile Lys
            180                 185                 190

Thr Xaa Leu Val Xaa Xaa Xaa Gly Xaa Glu Glu Ala Xaa Ser Gln
        195                 200                 205

Arg Thr Xaa Thr Pro Met Gly His Ile Gly Glu Pro Asn Asp Xaa Ala
    210                 215                 220

Tyr Ile Cys Val Tyr Leu Ala Ser Asn Glu Ser Lys Phe Ala Thr Gly
225                 230                 235                 240

Ser Glu Phe Val Val Asp Gly Gly Tyr Xaa Ala Gln
                245                 250

<210

```
<221> NAME/KEY: MISC_FEATURE
<222> LOCATION: (94)..(94)
<223> OTHER INFORMATION: Xaa is a nonpolar or a polar residue
<220> FEATURE:
<221> NAME/KEY: MISC_FEATURE
<222> LOCATION: (95)..(95)
<223> OTHER INFORMATION: Xaa is an aliphatic, non-polar, or acidic
      residue
<220> FEATURE:
<221> NAME/KEY: MISC_FEATURE
<222> LOCATION: (95)..(95)
<223> OTHER INFORMATION: Xaa is a nonpolar or aliphatic residue
<220> FEATURE:
<221> NAME/KEY: MISC_FEATURE
<222> LOCATION: (96)..(96)
<223> OTHER INFORMATION: Xaa is polar residue
<220> FEATURE:
<221> NAME/KEY: MISC_FEATURE
<222> LOCATION: (101)..(101)
<223> OTHER INFORMATION: Xaa is an acidic, non-polar, or a polar residue
<220> FEATURE:
<221> NAME/KEY: MISC_FEATURE
<222> LOCATION: (105)..(105)
<223> OTHER INFORMATION: Xaa is an acidic or non-polar residue
<220> FEATURE:
<221> NAME/KEY: MISC_FEATURE
<222> LOCATION: (108)..(108)
<223> OTHER INFORMATION: Xaa is a hydrophilic, polar or constrained
      residue
<220> FEATURE:
<221> NAME/KEY: MISC_FEATURE
<222> LOCATION: (111)..(111)
<223> OTHER INFORMATION: Xaa is a non-polar or aliphatic residue
<220> FEATURE:
<221> NAME/KEY: MISC_FEATURE
<222> LOCATION: (112)..(112)
<223> OTHER INFORMATION: Xaa is an acidic or polar residue
<220> FEATURE:
<221> NAME/KEY: MISC_FEATURE
<222> LOCATION: (113)..(113)
<223> OTHER INFORMATION: Xaa is a nonpolar or aliphatic residue
<220> FEATURE:
<221> NAME/KEY: MISC_FEATURE
<222> LOCATION: (117)..(117)
<223> OTHER INFORMATION: Xaa s a nonpolar or polar residue
<220> FEATURE:
<221> NAME/KEY: MISC_FEATURE
<222> LOCATION: (127)..(127)
<223> OTHER INFORMATION: Xaa is a basic or polar residue
<220> FEATURE:
<221> NAME/KEY: MISC_FEATURE
<222> LOCATION: (145)..(145)
<223> OTHER INFORMATION: Xaa is a polar residue
<220> FEATURE:
<221> NAME/KEY: MISC_FEATURE
<222> LOCATION: (147)..(147)
<223> OTHER INFORMATION: Xaa is a nonpolar, aromatic, or hydrophobic
      residue
<220> FEATURE:
<221> NAME/KEY: MISC_FEATURE
<222> LOCATION: (152)..(152)
<223> OTHER INFORMATION: Xaa is a non polar, basic residue, or
      hydrophilic residue
<220> FEATURE:
<221> NAME/KEY: MISC_FEATURE
<222> LOCATION: (157)..(157)
<223> OTHER INFORMATION: Xaa is a polar residue
<220> FEATURE:
<221> NAME/KEY: MISC_FEATURE
<222> LOCATION: (163)..(163)
<223> OTHER INFORMATION: Xaa is a nonpolar or aliphatic residue
<220> FEATURE:
<221> NAME/KEY: MISC_FEATURE
<222> LOCATION: (176)..(176)
<223> OTHER INFORMATION: Xaa is a nonpolar or aliphatic residue
<220> FEATURE:
<221> NAME/KEY: MISC_FEATURE
<222> LOCATION: (190)..(190)
<223> OTHER INFORMATION: Xaa is a cysteine
```

```
<220> FEATURE:
<221> NAME/KEY: MISC_FEATURE
<222> LOCATION: (194)..(194)
<223> OTHER INFORMATION: Xaa is a constrained, basic, or polar residue
<220> FEATURE:
<221> NAME/KEY: MISC_FEATURE
<222> LOCATION: (197)..(197)
<223> OTHER INFORMATION: Xaa is a hydrophilic, acidic, basic, aliphatic
      or nonpolar residue
<220> FEATURE:
<221> NAME/KEY: MISC_FEATURE
<222> LOCATION: (198)..(198)
<223> OTHER INFORMATION: Xaa is an acidic, basic, hydrophilic, or
      nonpolar residue
<220> FEATURE:
<221> NAME/KEY: MISC_FEATURE
<222> LOCATION: (199)..(199)
<223> OTHER INFORMATION: Xaa is an acidic, aliphatic, or nonpolar
      residue
<220> FEATURE:
<221> NAME/KEY: MISC_FEATURE
<222> LOCATION: (200)..(200)
<223> OTHER INFORMATION: Xaa is an acidic or constrained residue
<220> FEATURE:
<221> NAME/KEY: MISC_FEATURE
<222> LOCATION: (202)..(202)
<223> OTHER INFORMATION: Xaa is a nonpolar or aliphatic residue
<220> FEATURE:
<221> NAME/KEY: MISC_FEATURE
<222> LOCATION: (206)..(206)
<223> OTHER INFORMATION: Xaa is a nonpolar, aromatic, or hydrophobic
      residue
<220> FEATURE:
<221> NAME/KEY: MISC_FEATURE
<222> LOCATION: (211)..(211)
<223> OTHER INFORMATION: Xaa is a basic residue
<220> FEATURE:
<221> NAME/KEY: MISC_FEATURE
<222> LOCATION: (223)..(223)
<223> OTHER INFORMATION: Xaa is a nonpolar or aliphatic residue
<220> FEATURE:
<221> NAME/KEY: MISC_FEATURE
<222> LOCATION: (250)..(250)
<223> OTHER INFORMATION: Xaa is a polar or nonpolar residue

<400> SEQUENCE: 162

Met Thr Xaa Arg Leu Lys Xaa Lys Val Ala Ile Val Thr Gly Gly Thr
1               5                   10                  15

Xaa Gly Ile Gly Xaa Ala Ile Ala Xaa Lys Phe Val Xaa Glu Gly Ala
            20                  25                  30

Lys Val Val Ile Thr Gly Arg Xaa Ala Xaa Val Gly Glu Lys Ala Ala
        35                  40                  45

Lys Ser Ile Gly Xaa Thr Asp Val Ile Arg Phe Val Gln His Asp Ala
    50                  55                  60

Ser Asp Glu Ala Gly Trp Thr Lys Leu Phe Xaa Thr Thr Glu Glu Ala
65                  70                  75                  80

Phe Gly Pro Val Thr Thr Val Val Asn Asn Ala Gly Ile Xaa Xaa Xaa
                85                  90                  95

Lys Ser Val Glu Xaa Thr Thr Thr Xaa Glu Trp Xaa Lys Leu Xaa Xaa
            100                 105                 110

Xaa Asn Leu Asp Xaa Val Phe Phe Gly Thr Arg Leu Gly Ile Xaa Arg
        115                 120                 125

Met Lys Asn Lys Gly Leu Gly Ala Ser Ile Ile Asn Met Ser Ser Ile
    130                 135                 140

Xaa Gly Xaa Val Gly Asp Pro Xaa Leu Gly Ala Tyr Xaa Ala Ser Lys
145                 150                 155                 160

Gly Ala Xaa Arg Ile Met Ser Lys Ser Ala Ala Leu Asp Cys Ala Xaa
            165                 170                 175
```

```
Lys Asp Tyr Asp Val Arg Val Asn Thr Val His Pro Gly Xaa Ile Lys
                180                 185                 190

Thr Xaa Leu Val Xaa Xaa Xaa Gly Xaa Glu Glu Met Xaa Ser Gln
        195                 200                 205

Arg Thr Xaa Thr Pro Met Gly His Ile Gly Glu Pro Asn Asp Xaa Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Xaa Ala Gln
                245                 250

<210> SEQ ID NO 163
<211> LENGTH: 252
<212> TYPE: PRT
<213> ORGANISM: Artificial Sequence
<220> FEATURE:
<223> OTHER INFORMATION: Engineered Ketoreductase Sequence Formula with
      L. minor backbone Synthetic Construct
<220> FEATURE:
<221> NAME/KEY: MISC_FEATURE
<222> LOCATION: (3)..(3)
<223> OTHER INFORMATION: Xaa is an acidic polar or hydrophilic residue
<220> FEATURE:
<221> NAME/KEY: MISC_FEATURE
<222> LOCATION: (7)..(7)
<223> OTHER INFORMATION: Xaa is a polar or non-polar residue
<220> FEATURE:
<221> NAME/KEY: MISC_FEATURE
<222> LOCATION: (17)..(17)
<223> OTHER INFORMATION: Xaa is a non-polar, apliphatic or polar residue
<220> FEATURE:
<221> NAME/KEY: MISC_FEATURE
<222> LOCATION: (21)..(21)
<223> OTHER INFORMATION: Xaa is a non-polar, aromatic, or hydrophobic
      residue
<220> FEATURE:
<221> NAME/KEY: MISC_FEATURE
<222> LOCATION: (25)..(25)
<223> OTHER INFORMATION: Xaa is an acidic, nonpolar or polar residue
<220> FEATURE:
<221> NAME/KEY: MISC_FEATURE
<222> LOCATION: (29)..(29)
<223> OTHER INFORMATION: Xaa is an acidic, aliphatic or nonpolar residue
<220> FEATURE:
<221> NAME/KEY: MISC_FEATURE
<222> LOCATION: (40)..(40)
<223> OTHER INFORMATION: Xaa is a constrained, basic, or hydrophilic
      residue
<220> FEATURE:
<221> NAME/KEY: MISC_FEATURE
<222> LOCATION: (42)..(42)
<223> OTHER INFORMATION: Xaa is an acidic or a nonpolar residue
<220> FEATURE:
<221> NAME/KEY: MISC_FEATURE
<222> LOCATION: (53)..(53)
<223> OTHER INFORMATION: Xaa is a nonpolar or an acidic residue
<220> FEATURE:
<221> NAME/KEY: MISC_FEATURE
<222> LOCATION: (75)..(75)
<223> OTHER INFORMATION: Xaa is an acidic or polar residue
<220> FEATURE:
<221> NAME/KEY: MISC_FEATURE
<222> LOCATION: (94)..(94)
<223> OTHER INFORMATION: Xaa is a nonpolar or a polar residue
<220> FEATURE:
<221> NAME/KEY: MISC_FEATURE
<222> LOCATION: (95)..(95)
<223> OTHER INFORMATION: Xaa is an aliphatic, non-polar, or acidic
      residue
<220> FEATURE:
<221> NAME/KEY: MISC_FEATURE
<222> LOCATION: (95)..(95)
<223> OTHER INFORMATION: Xaa is a nonpolar or aliphatic residue
```

```
<220> FEATURE:
<221> NAME/KEY: MISC_FEATURE
<222> LOCATION: (96)..(96)
<223> OTHER INFORMATION: Xaa is polar residue
<220> FEATURE:
<221> NAME/KEY: MISC_FEATURE
<222> LOCATION: (101)..(101)
<223> OTHER INFORMATION: Xaa is an acidic, non-polar, or a polar residue
<220> FEATURE:
<221> NAME/KEY: MISC_FEATURE
<222> LOCATION: (105)..(105)
<223> OTHER INFORMATION: Xaa is an acidic or non-polar residue
<220> FEATURE:
<221> NAME/KEY: MISC_FEATURE
<222> LOCATION: (108)..(108)
<223> OTHER INFORMATION: Xaa is a hydrophilic, polar or constrained
      residue
<220> FEATURE:
<221> NAME/KEY: MISC_FEATURE
<222> LOCATION: (111)..(111)
<223> OTHER INFORMATION: Xaa is a non-polar or aliphatic residue
<220> FEATURE:
<221> NAME/KEY: MISC_FEATURE
<222> LOCATION: (112)..(112)
<223> OTHER INFORMATION: Xaa is an acidic or polar residue
<220> FEATURE:
<221> NAME/KEY: MISC_FEATURE
<222> LOCATION: (113)..(113)
<223> OTHER INFORMATION: Xaa is a nonpolar or aliphatic residue
<220> FEATURE:
<221> NAME/KEY: MISC_FEATURE
<222> LOCATION: (117)..(117)
<223> OTHER INFORMATION: Xaa s a nonpolar or polar residue
<220> FEATURE:
<221> NAME/KEY: MISC_FEATURE
<222> LOCATION: (127)..(127)
<223> OTHER INFORMATION: Xaa is a basic or polar residue
<220> FEATURE:
<221> NAME/KEY: MISC_FEATURE
<222> LOCATION: (145)..(145)
<223> OTHER INFORMATION: Xaa is a polar residue
<220> FEATURE:
<221> NAME/KEY: MISC_FEATURE
<222> LOCATION: (147)..(147)
<223> OTHER INFORMATION: Xaa is a nonpolar, aromatic, or hydrophobic
      residue
<220> FEATURE:
<221> NAME/KEY: MISC_FEATURE
<222> LOCATION: (152)..(152)
<223> OTHER INFORMATION: Xaa is a non polar, basic residue, or
      hydrophilic residue
<220> FEATURE:
<221> NAME/KEY: MISC_FEATURE
<222> LOCATION: (157)..(157)
<223> OTHER INFORMATION: Xaa is a polar residue
<220> FEATURE:
<221> NAME/KEY: MISC_FEATURE
<222> LOCATION: (163)..(163)
<223> OTHER INFORMATION: Xaa is a nonpolar or aliphatic residue
<220> FEATURE:
<221> NAME/KEY: MISC_FEATURE
<222> LOCATION: (176)..(176)
<223> OTHER INFORMATION: Xaa is a nonpolar or aliphatic residue
<220> FEATURE:
<221> NAME/KEY: MISC_FEATURE
<222> LOCATION: (190)..(190)
<223> OTHER INFORMATION: Xaa is a cysteine
<220> FEATURE:
<221> NAME/KEY: MISC_FEATURE
<222> LOCATION: (194)..(194)
<223> OTHER INFORMATION: Xaa is a constrained, basic, or polar residue
<220> FEATURE:
<221> NAME/KEY: MISC_FEATURE
<222> LOCATION: (197)..(197)
<223> OTHER INFORMATION: Xaa is a hydrophilic, acidic, basic, aliphatic
      or nonpolar residue
<220> FEATURE:
<221> NAME/KEY: MISC_FEATURE
<222> LOCATION: (198)..(198)
```

<223> OTHER INFORMATION: Xaa is an acidic, basic, hydrophilic, or
nonpolar residue
<220> FEATURE:
<221> NAME/KEY: MISC_FEATURE
<222> LOCATION: (199)..(199)
<223> OTHER INFORMATION: Xaa is an acidic, aliphatic, or nonpolar
residue
<220> FEATURE:
<221> NAME/KEY: MISC_FEATURE
<222> LOCATION: (200)..(200)
<223> OTHER INFORMATION: Xaa is an acidic or constrained residue
<220> FEATURE:
<221> NAME/KEY: MISC_FEATURE
<222> LOCATION: (202)..(202)
<223> OTHER INFORMATION: Xaa is a nonpolar or aliphatic residue
<220> FEATURE:
<221> NAME/KEY: MISC_FEATURE
<222> LOCATION: (206)..(206)
<223> OTHER INFORMATION: Xaa is a nonpolar, aromatic, or hydrophobic
residue
<220> FEATURE:
<221> NAME/KEY: MISC_FEATURE
<222> LOCATION: (211)..(211)
<223> OTHER INFORMATION: Xaa is a basic residue
<220> FEATURE:
<221> NAME/KEY: MISC_FEATURE
<222> LOCATION: (223)..(223)
<223> OTHER INFORMATION: Xaa is a nonpolar or aliphatic residue
<220> FEATURE:
<221> NAME/KEY: MISC_FEATURE
<222> LOCATION: (250)..(250)
<223> OTHER INFORMATION: Xaa is a polar or nonpolar residue

<400> SEQUENCE: 163

```
Met Thr Xaa Arg Leu Lys Xaa Lys Val Ala Ile Val Thr Gly Gly Thr
1               5                   10                  15

Xaa Gly Ile Gly Xaa Ala Ile Ala Xaa Lys Phe Val Xaa Glu Gly Ala
                20                  25                  30

Lys Val Val Ile Thr Gly Arg Xaa Ala Xaa Val Gly Glu Lys Ala Ala
            35                  40                  45

Arg Ser Ile Gly Xaa Thr Asp Val Ile Arg Phe Val Gln His Asp Ala
        50                  55                  60

Ser Asp Glu Thr Gly Trp Thr Lys Leu Phe Xaa Thr Thr Glu Glu Ala
65                  70                  75                  80

Phe Gly Pro Val Thr Thr Val Asn Asn Ala Gly Ile Xaa Xaa Xaa
                85                  90                  95

Lys Ser Val Glu Xaa Thr Thr Xaa Glu Trp Xaa Lys Leu Xaa Xaa
            100                 105                 110

Xaa Asn Leu Asp Xaa Val Phe Phe Gly Thr Arg Leu Gly Ile Xaa Arg
        115                 120                 125

Met Lys Asn Lys Gly Leu Gly Ala Ser Ile Ile Asn Met Ser Ser Ile
130                 135                 140

Xaa Gly Xaa Val Gly Asp Pro Xaa Leu Gly Ala Tyr Xaa Ala Ser Lys
145                 150                 155                 160

Gly Ala Xaa Arg Ile Met Ser Lys Ser Ala Ala Leu Asp Cys Ala Xaa
                165                 170                 175

Lys Asp Tyr Asp Val Arg Val Asn Thr Val His Pro Gly Xaa Ile Lys
            180                 185                 190

Thr Xaa Leu Val Xaa Xaa Xaa Xaa Gly Xaa Glu Glu Met Xaa Ser Gln
        195                 200                 205

Arg Thr Xaa Thr Pro Met Gly His Ile Gly Glu Pro Asn Asp Xaa Ala
    210                 215                 220

Trp Ile Cys Val Tyr Leu Ala Ser Asp Glu Ser Lys Phe Ala Thr Gly
225                 230                 235                 240
```

Ala Glu Phe Val Val Asp Gly Gly Tyr Xaa Ala Gln
              245                 250

<210> SEQ ID NO 164
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 164

Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Asn Asn Ala Gly Ile Asn Val Ser
                85                  90                  95

Lys Ser Val Glu Asp Thr Thr Thr Glu Glu Trp His Lys Leu Leu Ser
            100                 105                 110

Val Asn Leu Asp Ser Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Ser Gly Phe Val Gly Asp Pro Thr Leu Gly Ala Tyr Thr Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Leu Glu Gly Ala Glu Met Met Ser Gln
        195                 200                 205

Arg Thr Arg Thr Pro Met Gly His Ile Gly Glu Pro Asn Asp Val Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 165
<211> LENGTH: 252
<212> TYPE: PRT
<213> ORGANISM: Artificial Sequence
<220> FEATURE:
<223> OTHER INFORMATION: Synthetic Variant of L. kefir

<400> SEQUENCE: 165

Met Thr Asp Arg Leu Lys Ser Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala

-continued

```
                35                  40                  45
Lys Ser Ile Gly Gly Thr Asp Val Ile Arg Phe Val Gln His Asp Ala
        50                  55                  60
Ser Asp Glu Ala Gly Trp Thr Lys Leu Phe Asp Thr Thr Glu Glu Ala
65                  70                  75                  80
Phe Gly Pro Val Thr Thr Val Val Asn Asn Ala Gly Ile Ala Val Ser
                85                  90                  95
Lys Ser Val Glu Asp Thr Thr Thr Glu Glu Trp His Lys Leu Leu Ser
            100                 105                 110
Val Asn Leu Asp Ser Val Phe Phe Gly Thr Arg Leu Gly Ile Gln Arg
            115                 120                 125
Met Lys Asn Lys Gly Leu Gly Ala Ser Ile Ile Asn Met Ser Ser Ile
            130                 135                 140
Ser Gly Phe Val Gly Asp Pro Thr Leu Gly Ala Tyr Thr Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Cys Ile Lys
                180                 185                 190
Thr Pro Leu Val Asp Asp Leu Glu Gly Ala Glu Glu Met Gly Ser Gln
            195                 200                 205
Arg Thr Arg Thr Pro Met Gly His Ile Gly Glu Pro Asn Asp Val Ala
    210                 215                 220
Trp Ile Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```